US012385915B2

(12) United States Patent
Hu et al.

(10) Patent No.: US 12,385,915 B2
(45) Date of Patent: Aug. 12, 2025

(54) DETECTION OF ANTIGENS

(71) Applicant: ARIZONA BOARD OF REGENTS ON BEHALF OF ARIZONA STATE UNIVERSITY, Scottsdale, AZ (US)

(72) Inventors: Ye Hu, Scottsdale, AZ (US); Xiangxing Kong, Scottsdale, AZ (US); Tanxi Cai, Scottsdale, AZ (US); Qingbo Shu, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 296 days.

(21) Appl. No.: 17/617,802

(22) PCT Filed: Jun. 15, 2020

(86) PCT No.: PCT/US2020/037785
§ 371 (c)(1),
(2) Date: Dec. 9, 2021

(87) PCT Pub. No.: WO2020/252474
PCT Pub. Date: Dec. 17, 2020

(65) Prior Publication Data
US 2023/0314427 A1    Oct. 5, 2023

Related U.S. Application Data

(60) Provisional application No. 62/861,896, filed on Jun. 14, 2019.

(51) Int. Cl.
*G01N 33/68*    (2006.01)
*G01N 33/543*    (2006.01)
*G01N 33/569*    (2006.01)

(52) U.S. Cl.
CPC ..... *G01N 33/569* (2013.01); *G01N 33/54326* (2013.01); *G01N 33/6848* (2013.01); *G01N 2333/35* (2013.01); *G01N 2446/00* (2013.01); *G01N 2458/15* (2013.01)

(58) Field of Classification Search
None
See application file for complete search history.

(56) References Cited

U.S. PATENT DOCUMENTS

| 8,354,234 B2 | 1/2013 | Chen et al. |
| 2015/0024960 A1 | 1/2015 | Lee et al. |
| 2015/0260715 A1* | 9/2015 | Hu ..................... G01N 33/5695 436/527 |

FOREIGN PATENT DOCUMENTS

WO    WO2018151930 A1    8/2018

OTHER PUBLICATIONS

"The Global Plan to Stop TB", WHO, Geneva, 2011, 12 www.stoptb.org/global/plan/.
Böni, Jürg, et al. "Simple monitoring of antiretroviral therapy with a signal-amplification-boosted HIV-1 p24 antigen assay with heat-denatured plasma." Aids 11.6 (1997): F47-F52.
Cavanaugh, Joseph S., et al. "Comparative yield of different diagnostic tests for tuberculosis among people living with HIV in Western Kenya." PloS one 11.3 (2016): e0152364.
Donovan, Margery, and Paul Palumbo. "Diagnosis of HIV: challenges and strategies for HIV prevention and detection among pregnant women and their infants." Clinics in perinatology 37.4 (2010): 751-763.
Evans, Carlton A. "GeneXpert—a game-changer for tuberculosis control?." PLoS medicine 8.7 (2011): e1001064.
Fan, Jia, et al. "Rapid diagnosis of new and relapse tuberculosis by quantification of a circulating antigen in HIV-infected adults in the Greater Houston metropolitan area." BMC Med 15, 188 (2017). https://doi.org/10.1186/s12916-017-0952-z.
Hemelaar, Joris, et al. "Global and regional molecular epidemiology of HIV-1, 1990-2015: a systematic review, global survey, and trend analysis." The Lancet infectious diseases 19.2 (2019): 143-155.
http://chemistry.emory.edu/msc/tutorial/mass-spectrometry-ionization.html) Retrieved Aug. 2022.
https://en.wikipedia.org/wiki/Data-independent_acquisition Retrieved Aug. 2022.
https://en.wikipedia.org/wiki/Selected_reaction_monitoring) Retrieved Aug. 2022.
https://en.wikipedia.org/wiki/Subtypes_of_HIV Retrieved Aug. 2022.
https://planetorbitrap.com/orbitrap-eclipse-tribrid-ms#tab:specifications Retrieved Aug. 2022.
International Preliminary Report on Patentability; PCT/US2020/037785; issued Dec. 14, 2021.
International Search Report; PCT/US2020/037785; mailed Dec. 3, 2020.
Kigozi, N. Gladys, et al. "Tuberculosis knowledge, attitudes and practices of patients at primary health care facilities in a South African metropolitan: research towards improved health education." BMC public health 17, 795(2017).
Liu, Chang, et al. "Quantification of circulating Mycobacterium tuberculosis antigen peptides allows rapid diagnosis of active disease and treatment monitoring." Proceedings of the National Academy of Sciences Apr. 11, 2017;114(15):3969-3974. doi: 10.1073/pnas.1621360114. Epub Mar. 27, 2017. PMID: 28348223; PMCID: PMC5393254.
Osmanov, Saladin, et al. "Estimated global distribution and regional spread of HIV-1 genetic subtypes in the year 2000." Journal of acquired immune deficiency syndromes (1999) 29.2 (2002): 184-190.

(Continued)

*Primary Examiner* — Jennifer E Graser
(74) *Attorney, Agent, or Firm* — Baker, Donelson, Bearman, Caldwell & Berkowitz, P.C.

(57) ABSTRACT

Provided herein are methods for detecting and identifying disease-specific biomarkers, such as target antigens associated with infection.

35 Claims, 57 Drawing Sheets

Specification includes a Sequence Listing.

(56) References Cited

OTHER PUBLICATIONS

Pai, Madhukar, and Marco Schito. "Tuberculosis diagnostics in 2015: landscape, priorities, needs, and prospects." The Journal of infectious diseases Apr. 1, 2015;211 Suppl 2(Suppl 2):S21-8. doi: 10.1093/infdis/jiu803. PMID: 25765103; PMCID: PMC4366576.

Read, Jennifer S., and Committee on Pediatric AIDS. "Diagnosis of HIV-1 infection in children younger than 18 months in the United States." Pediatrics 120.6 (2007): e1547-e1562.

Schüpbach, Jörg. "Viral RNA and p24 antigen as markers of HIV disease and antiretroviral treatment success." International archives of allergy and immunology 132.3 (2003): 196-209.

Theron, Grant, et al. "Evaluation of the Xpert MTB/RIF assay for the diagnosis of pulmonary tuberculosis in a high HIV prevalence setting." American journal of respiratory and critical care medicine 184.1 (2011): 132-140.

Ulintz, Peter J., et al. "Comparison of MS2-only, MSA, and MS2/MS3 methodologies for phosphopeptide identification." Journal of proteome research 8.2 (2009): 887-899.

World Health Organization (2013) Policy Update: Xpert MTB/RIF Assay for the Diagnosis of Pulmonary and Extrapulmonary TB in Adults and Children. (WHO, Geneva). ISBN: 978-92-4-150633-5.

World Health Organization (2014) High-Priority Target Product Profiles for New Tuberculosis Diagnostics: Report of a Consensus Meeting. World Health Organization, Geneva, Switzerland, Apr. 28-29, 2014. who.int/iris/bitstream/handle/10665/135617/WHO_HTM_TB_2014.18_eng.pdf?sequence=1&isAllowed=y ISBN: 978-92-4-003236-1.

World Health Organization (WHO). Global tuberculosis report Sep. 18, 2018. https://apps.who.int/iris/bitstream/handle/10665/274453/9789241565646-eng.pdf?ua=1. ISBN 9789241565646.

World Health Organization Policy on Collaborative TB/HIV Activities. Guidelines for National Programmes and Other Stakeholders. Geneva: World Health Organization; 2012. who.int/iris/bitstream/10665/44789/1/9789241503006_eng.pdf; ISBN: 978-92-4-150300-6.

World Health Organization. (2013). Global tuberculosis report 2013. World Health Organization. ISBN: 978-92-4-156465-6.

Written Opinion of International Searching Authority; PCT/US2020/037785; mailed Dec. 3, 2020.

Zeka, Arzu N., Sezai Tasbakan, and Cengiz Cavusoglu. "Evaluation of the GeneXpert MTB/RIF assay for rapid diagnosis of tuberculosis and detection of rifampin resistance in pulmonary and extrapulmonary specimens." Journal of clinical microbiology 49.12 (2011): 4138-4141.

Zhang, W., Shu, Q., Zhao, Z. et al. Antigen 85B peptidomic analysis allows species-specific mycobacterial identification. Clin Proteom 15, 1 (2018). https://doi.org/10.1186/s12014-017-9177-6.

* cited by examiner

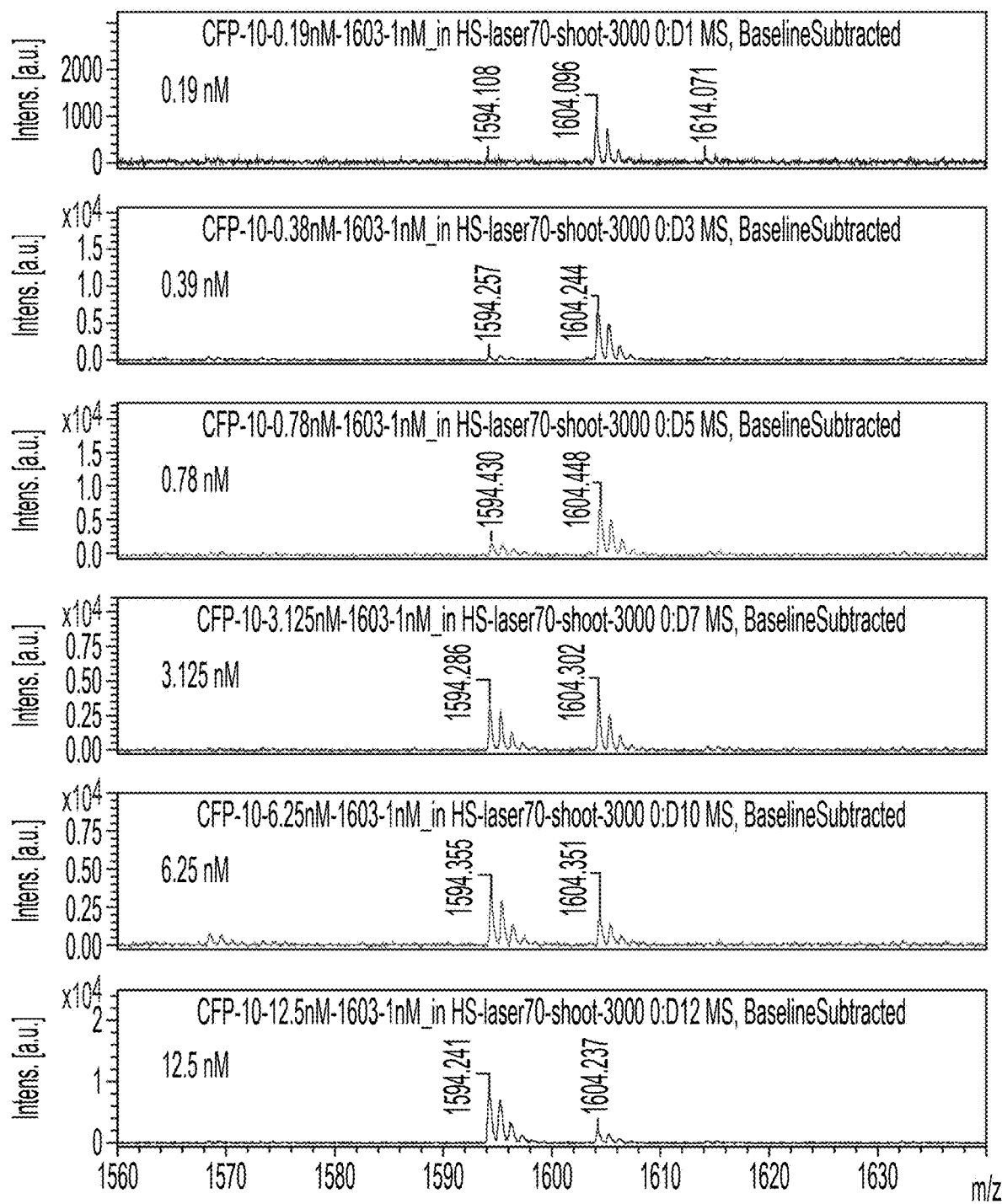
FIG. 3 – CONT.

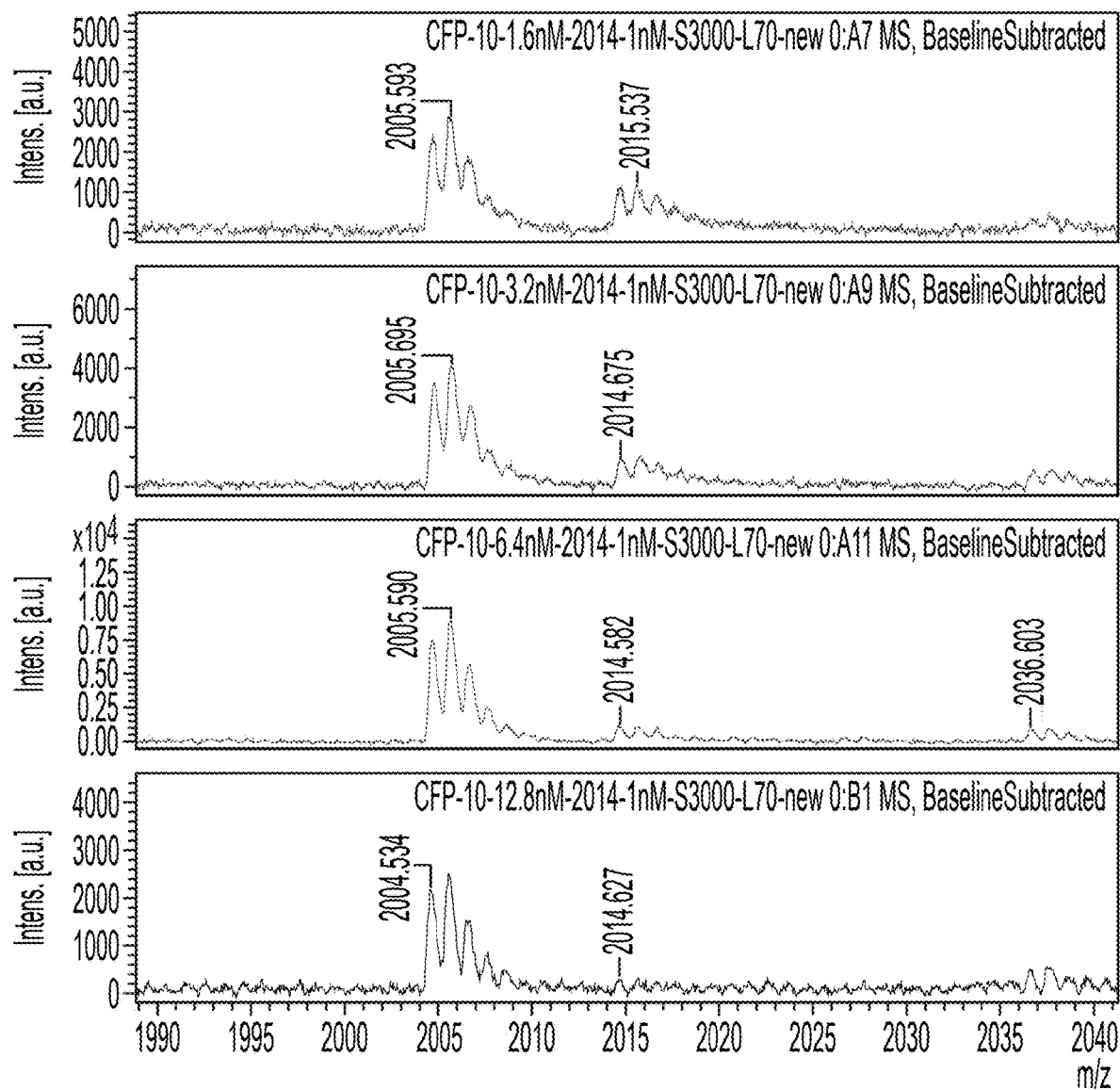
FIG. 4 – CONT.

(A) Peptide 1594 with a sequence of TDAATLAQEAGNFER from CFP-10

(B) Peptide 2004 with a sequence of TQIDQVESTAGSLQGQWR from CFP-10

(C) Peptide 1901 with a sequence of WDATATELNNALQNLAR from ESat-6

(D) Peptide 2032 with a sequence of TQIDQVESTAASLQAQWR from CFP-10

FIG. 8A
Transition Overview

| Transition | Q3 | Interferences |
|---|---|---|
| ○ y13 | 1377.68 | 4 |
| ○ y10 | 1134.55 | 8 |
| ○ y12 | 1306.64 | 9 |
| b8 | 772.38 | 10 |
| b9 | 901.43 | 11 |
| b10 | 972.46 | 11 |
| ○ y9 | 1021.47 | 12 |
| ○ y6 | 693.33 | 12 |
| ○ y7 | 822.37 | 13 |
| b13 | 1290.6 | 13 |
| ○ y8 | 950.43 | 14 |
| b12 | 1143.53 | 14 |
| ○ y14 | 1492.7 | 15 |
| ○ y11 | 1235.6 | 19 |
| ○ y5 | 622.29 | 19 |
| b11 | 1029.49 | 19 |
| y3 | 451.23 | 25 |
| y4 | 565.27 | 26 |
| b7 | 644.33 | 28 |
| b6 | 573.29 | 31 |
| y2 | 304.16 | 34 |
| b5 | 460.2 | 37 |
| b4 | 359.16 | 40 |
| b14 | 1419.64 | 57 |

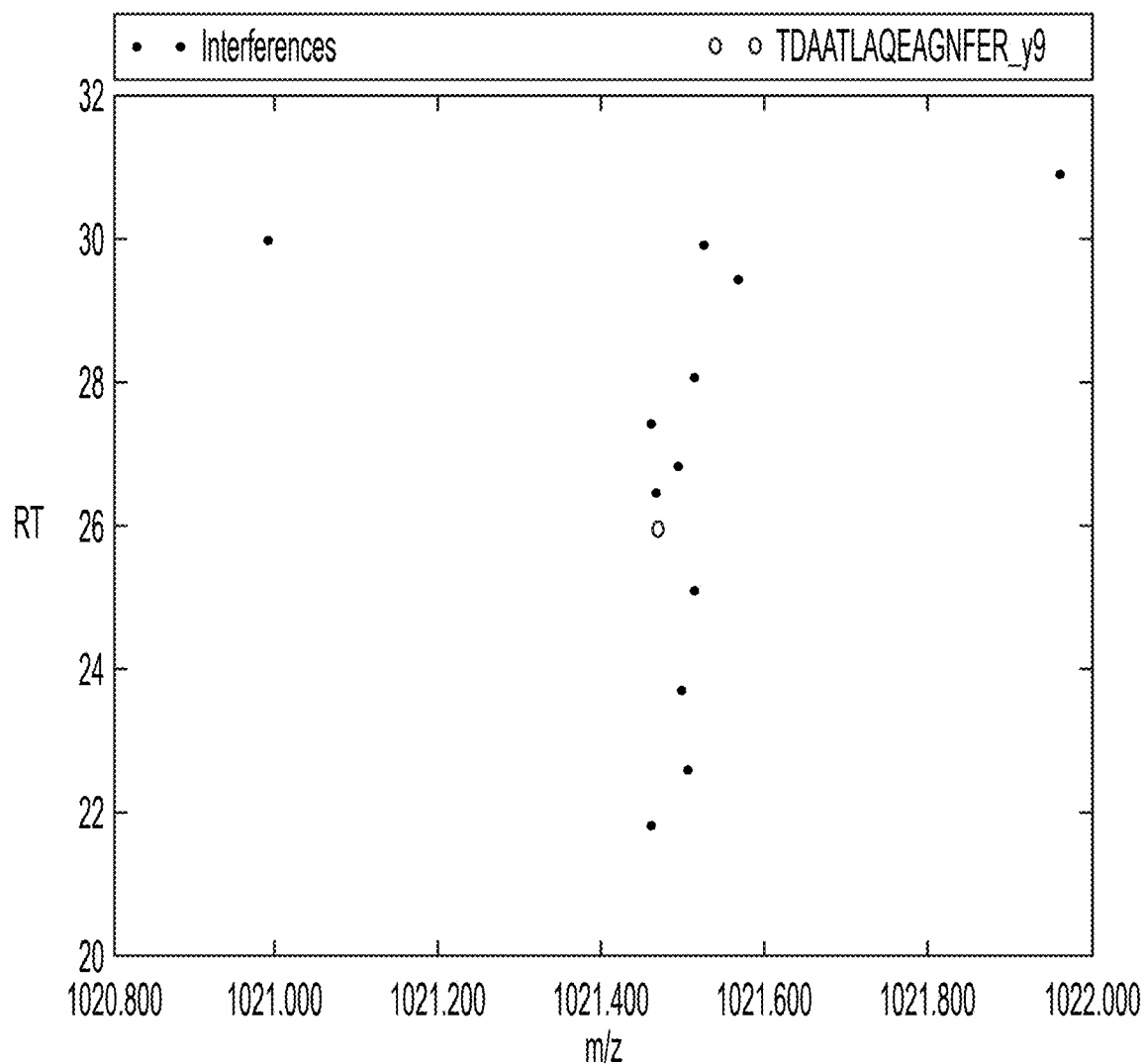
*FIG. 8C – CONT.*

| [M+H]+ | Peptide name | Sequence | m/z | Percentage of Strains in Protein database covered by Target peptides |
|---|---|---|---|---|
| HIV-1 | pep1462 | ETINEEAAEWDR | 1462.64 | > 95% |
| | pep1447 | DTINEEAAEWDR | 1447.62 | |
| | pep1293 | MYSPVSILDIR | 1293.54 | |
| | pep1295 | MYSPTSILDIR | 1295.67 | |
| | pep1321 | MYNPTNILDIK | 1321.68 | |
| HIV-2 | pep958 | AEQTDPAVK | 958.04 | > 98% |

FIG. 14

```
Thermo Scientific SII for Xcalibur Method

---- Overview ----
Name: New Instrument Method
Comment:
Run time: 35.000 [min]
Instrument: MININT-O59MG6C_Nano on minint-o59mg6c
Description:
---- Script ----
initial    Instrument Setup
           PumpModule.LoadingPump.%A.Equate: "98% water/2%ACN/0.1%FA"
           PumpModule.LoadingPump.%B.Equate: "%B"
           PumpModule.LoadingPump.%C.Equate: "%C"
           PumpModule.LoadingPump.Pressure.LowerLimit: 0 [bar]
           PumpModule.LoadingPump.Pressure.UpperLimit: 620 [bar]
           PumpModule.LoadingPump.MaximumFlowRampUp: 10 [µl/min²]
           PumpModule.LoadingPump.MaximumFlowRampDown: 10 [µl/min²]
           PumpModule.NC_Pump.%A.Equate: "water"
           PumpModule.NC_Pump.%B.Equate: "100% ACN/0.1%FA"
           PumpModule.NC_Pump.Pressure.LowerLimit: 0 [bar]
           PumpModule.NC_Pump.Pressure.UpperLimit: 900 [bar]
           PumpModule.NC_Pump.MaximumFlowRampUp: 0.300 [µl/min²]
           PumpModule.NC_Pump.MaximumFlowRampDown: 0.300 [µl/min²]
           ColumnOven.TempCtrl: Off
           Sampler.LowDispersionMode: Off
           Sampler.WashSpeed: 4.000 [µl/s]
           Sampler.WashVolume: 50.000 [µl]
           Sampler.PunctureDepth: 7.000 [mm]
           Sampler.SampleHeight: 1.000 [mm]
           Sampler.WasteSpeed: 4.000 [µl/s]
           Sampler.DispenseDelay: 2.000 [s]
           Sampler.DispSpeed: 2.000 [µl/s]
           Sampler.DrawSpeed: 0.050 [µl/s]
           Sampler.DrawDelay: 5.000 [s]
           Sampler.RinseBetweenReinjections: No
           Sampler.FlushVolume: 3.000 [µl]
           Sampler.TransVialPunctureDepth: 10.000 [mm]
           Sampler.TransLiquidHeight: 3.000 [mm]
           Sampler.TransportVialCapacity: Unlimited
           Sampler.LastTransportVial: R1
           Sampler.FirstTransportVial: R1
           Sampler.InjectMode: ulPickUp
           Sampler.LoopWashFactor: 2.000
           Sampler.PumpDevice: "NC_Pump"
           Sampler.TempCtrl: On
           Sampler.Temperature.Nominal: 4.0 [°C]
           Sampler.ReadyTempDelta: None
           Sampler.Temperature.LowerLimit: 4.0 [°C]
           Sampler.Temperature.UpperLimit: 45.0 [°C]
           ColumnOven.ValveRight: 1_2
```

FIG. 14 Continued

```
Thermo Scientific SII for Xcalibur Method 0.000 [min] Equilibration
            PumpModule.LoadingPump.Flow.Nominal: 5.000 [µl/min]
            PumpModule.LoadingPump.%B.Value: 0.0 [%]
            PumpModule.LoadingPump.%C.Value: 0.0 [%]
            PumpModule.LoadingPump.Curve: 5
            PumpModule.NC_Pump.Flow.Nominal: 0.300 [µl/min]
            PumpModule.NC_Pump.%B.Value: 2.0 [%]
            PumpModule.NC_Pump.Curve: 5
0.000 [min] Inject Preparation
            Wait PumpModule.LoadingPump.Ready And PumpModule.NC_Pump.Ready And ColumnOven.Ready And Samp
0.000 [min] Inject
            Sampler.Inject
0.000 [min] Start Run
            ColumnOven.ColumnOven_Temp.AcqOn
            PumpModule.LoadingPump.LoadingPump_Pressure.AcqOn
            PumpModule.NC_Pump.NC_Pump_Flow.AcqOn
            PumpModule.NC_Pump.NC_Pump_Pressure.AcqOn
0.000 [min] Run
            PumpModule.LoadingPump.Flow.Nominal: 5.000 [µl/min]
            PumpModule.LoadingPump.%B.Value: 0.0 [%]
            PumpModule.LoadingPump.%C.Value: 0.0 [%]
            PumpModule.LoadingPump.Curve: 5
            PumpModule.NC_Pump.Flow.Nominal: 0.300 [µl/min]
            PumpModule.NC_Pump.%B.Value: 2.0 [%]
            PumpModule.NC_Pump.Curve: 5
            ColumnOven.ValveRight: 1_2
5.000 [min]
            PumpModule.NC_Pump.Flow.Nominal: 0.300 [µl/min]
            PumpModule.NC_Pump.%B.Value: 2.0 [%]
            PumpModule.NC_Pump.Curve: 5
            ColumnOven.ValveRight: 10_1
22.000 [min]
            PumpModule.NC_Pump.Flow.Nominal: 0.300 [µl/min]
            PumpModule.NC_Pump.%B.Value: 38.0 [%]
            PumpModule.NC_Pump.Curve: 5
24.000 [min]
            PumpModule.NC_Pump.Flow.Nominal: 0.300 [µl/min]
            PumpModule.NC_Pump.%B.Value: 95.0 [%]
            PumpModule.NC_Pump.Curve: 5
28.000 [min]
            PumpModule.NC_Pump.Flow.Nominal: 0.300 [µl/min]
            PumpModule.NC_Pump.%B.Value: 95.0 [%]
            PumpModule.NC_Pump.Curve: 5
30.000 [min]
            PumpModule.NC_Pump.Flow.Nominal: 0.300 [µl/min]
            PumpModule.NC_Pump.%B.Value: 5.0 [%]
            PumpModule.NC_Pump.Curve: 5
35.000 [min]
```

FIG. 14 Continued

```
Thermo Scientific SII for Xcalibur Method

PumpModule.LoadingPump.Flow.Nominal: 5.000 [µl/min]
          PumpModule.LoadingPump.%B.Value: 0.0 [%]
          PumpModule.LoadingPump.%C.Value: 0.0 [%]
          PumpModule.LoadingPump.Curve: 5
          PumpModule.NC_Pump.Flow.Nominal: 0.300 [µl/min]
          PumpModule.NC_Pump.%B.Value: 5.0 [%]
          PumpModule.NC_Pump.Curve: 5
35.000 [min] Stop Run
          ColumnOven.ColumnOven_Temp.AcqOff
          PumpModule.LoadingPump.LoadingPump_Pressure.AcqOff
          PumpModule.NC_Pump.NC_Pump_Flow.AcqOff
          PumpModule.NC_Pump.NC_Pump_Pressure.AcqOff
```

FIG. 14 Continued

Method Summary

Method Settings

Method Duration (min): 35

Global Parameter

Ion Source

Ion Source Type: NSI
Spray Voltage: Static
Positive Ion (V): 1800
Negative Ion (V): 600

Positive Ion

| Time (min) | Voltage (V) |
|---|---|

Negative Ion

| Time (min) | Voltage (V) |
|---|---|

Sweep Gas (Arb): 0
Ion Transfer Tube Temp (°C): 200

Experiment 1

Start Time (min): 0
End Time (min): 35

Master Scan:

SRM

Use Cycle Time: False
Dwell Time (ms): 40
Use Calibrated RF Lens: True

FIG. 14 Continued

Q1 Resolution (FWHM): 1.2
Q3 Resolution (FWHM): 1.2
CID Gas (mTorr): 1.5
Source Fragmentation (V): 0
Chromatographic Peak Width (sec): 6
Use Chromatographic Filter: True
Use Retention Time Reference: False
Display Retention Time: False
Use Quan Ion: False
Show Visualization: False SRM Table

| Compound | Start Time (min) | End Time (min) | Polarity | Precursor (m/z) | Product (m/z) | Collision Energy (V) |
|---|---|---|---|---|---|---|
| short | 0 | 35 | Positive | 746.85 | 622.29 | 30 |
| short | 0 | 35 | Positive | 746.85 | 693.33 | 30 |
| short | 0 | 35 | Positive | 746.85 | 822.37 | 30 |
| short | 0 | 35 | Positive | 746.85 | 950.43 | 30 |
| short | 0 | 35 | Positive | 746.85 | 1021.47 | 30 |
| short | 0 | 35 | Positive | 746.85 | 1134.55 | 30 |
| short | 0 | 35 | Positive | 746.85 | 1235.6 | 30 |
| 1593 | 0 | 35 | Positive | 797.38 | 622.29 | 30 |
| 1593 | 0 | 35 | Positive | 797.38 | 693.33 | 30 |
| 1593 | 0 | 35 | Positive | 797.38 | 822.37 | 30 |
| 1593 | 0 | 35 | Positive | 797.38 | 950.43 | 30 |
| 1593 | 0 | 35 | Positive | 797.38 | 1021.47 | 30 |
| 1593 | 0 | 35 | Positive | 797.38 | 1134.55 | 30 |
| 1593 | 0 | 35 | Positive | 797.38 | 1235.6 | 30 |
| 1603 | 0 | 35 | Positive | 802.37 | 632.3 | 30 |
| 1603 | 0 | 35 | Positive | 802.37 | 703.34 | 30 |
| 1603 | 0 | 35 | Positive | 802.37 | 832.38 | 30 |
| 1603 | 0 | 35 | Positive | 802.37 | 960.44 | 30 |
| 1603 | 0 | 35 | Positive | 802.37 | 1031.48 | 30 |

FIG. 14 Continued

| 1603 | 0 | 35 | Positive | 802.37 | 1144.56 | 30 |
| 1603 | 0 | 35 | Positive | 802.37 | 1245.61 | 30 |

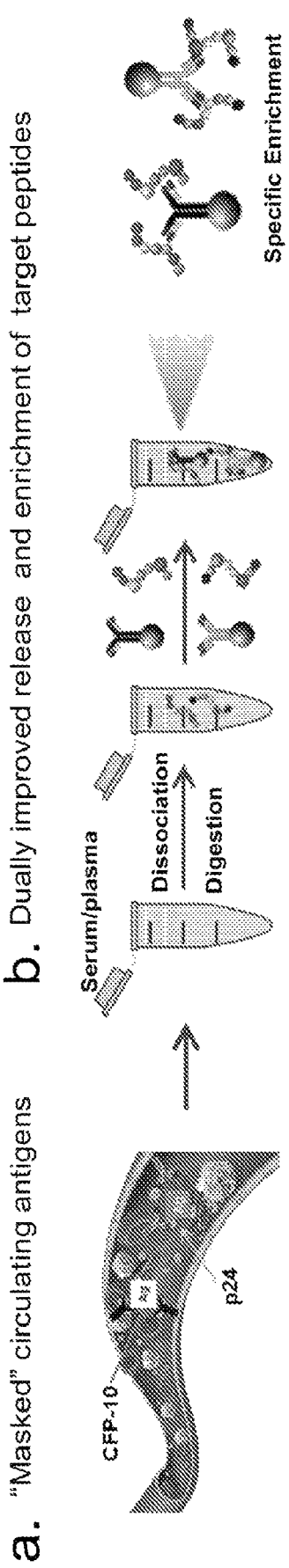
FIG. 18A-B

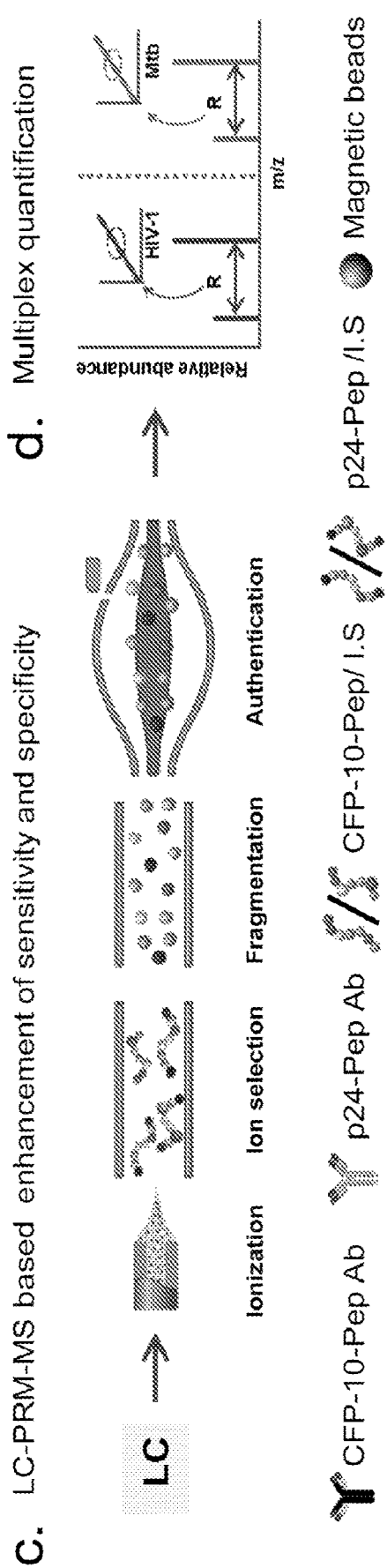
FIG. 18C-D

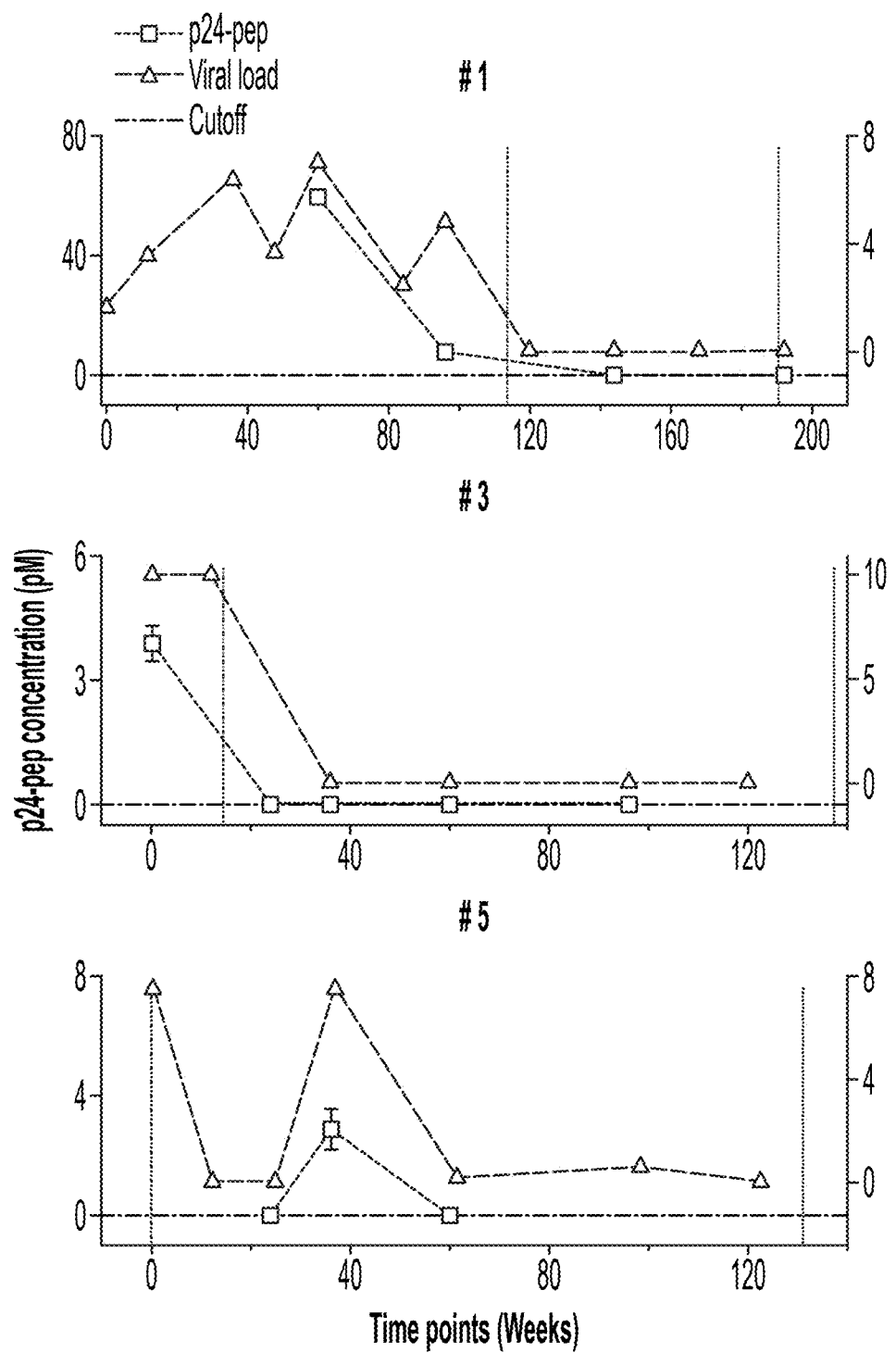

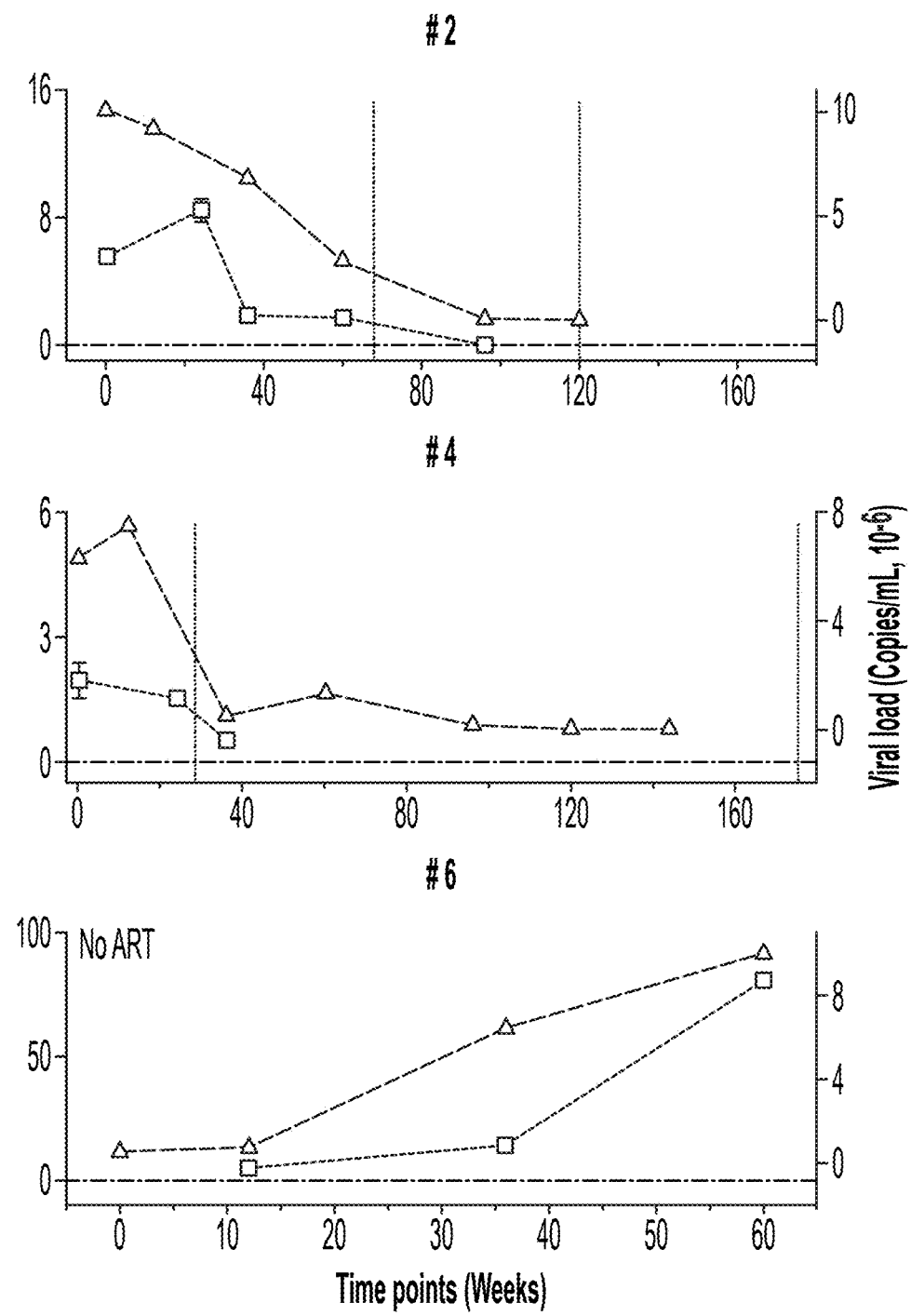
FIG. 19C – CONT.

FIG. 20B – CONT.
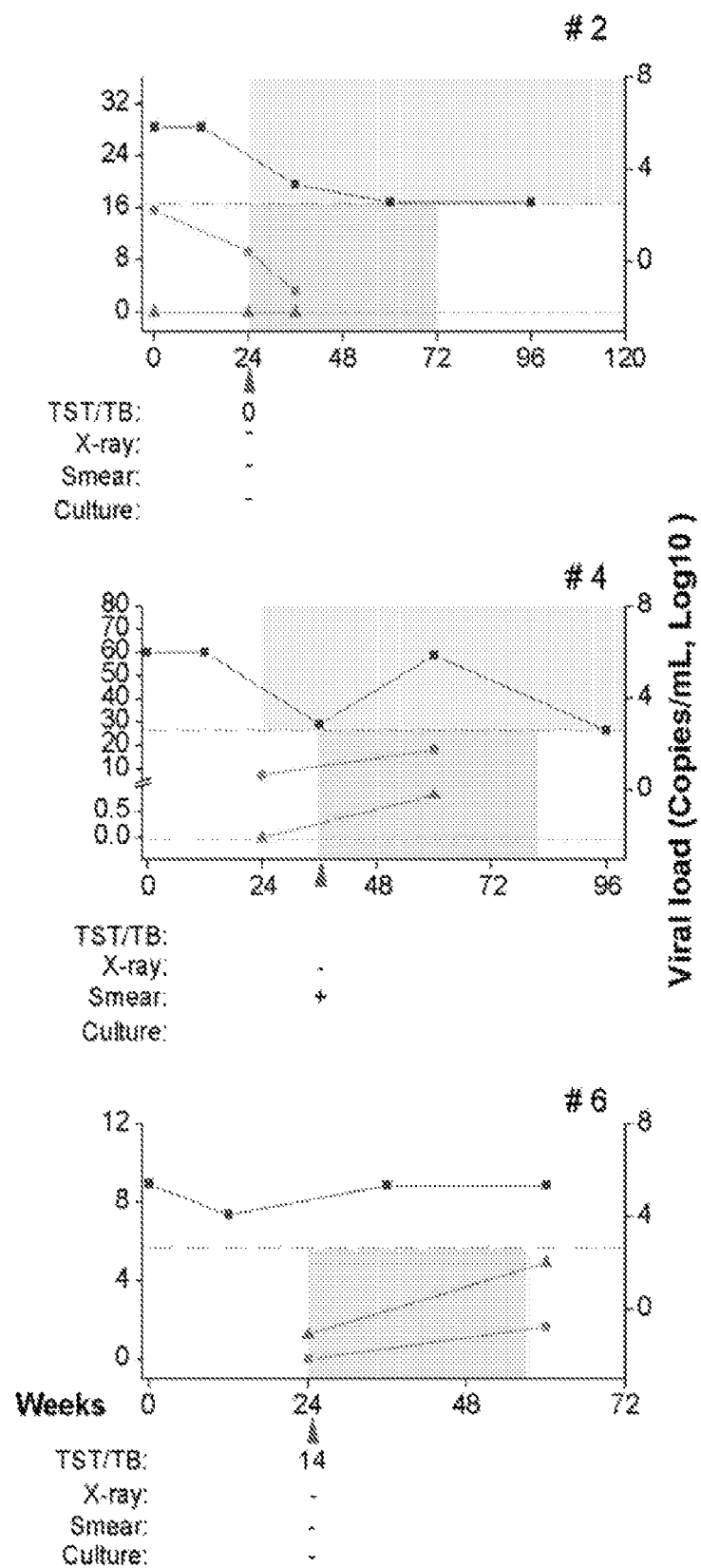

*FIG. 21B*

| [M+H]⁺ | Sequence |
|---|---|
| 1566.8321 | VHPVHAGPIAPGQMR |
| 1462.6444 | ETINEEAAEWDR |
| 1356.6430 | PEPTAPPEESFR |
| 1295.6664 | MYSPTSILDIR |
| 1144.5844 | SGVETTTPPQK |

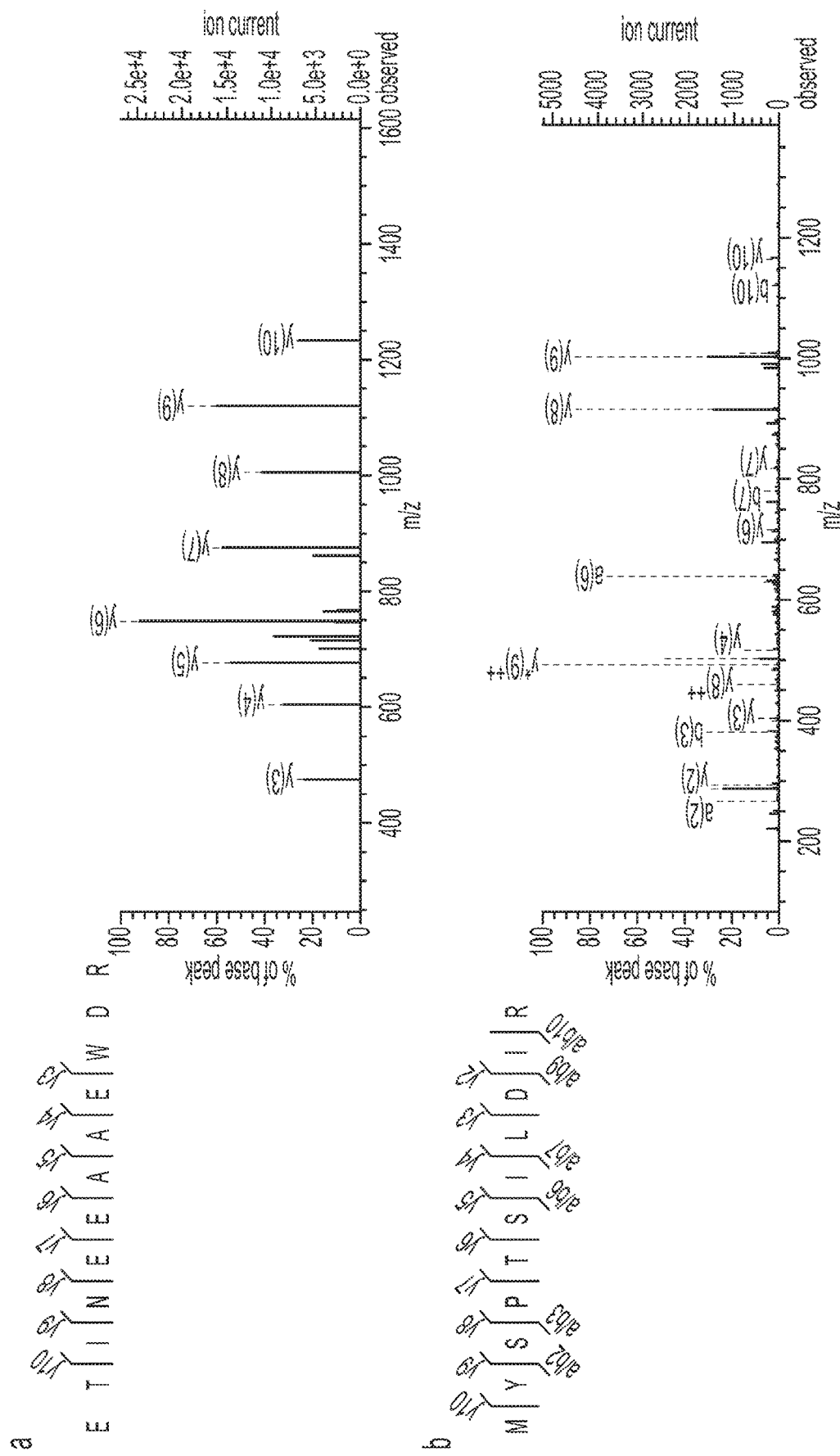
FIGS. 22A-B

| [M+H]+ | Peptide name | Sequence | m/z | Percentage of Strains in Protein database covered by Target peptides |
|---|---|---|---|---|
| HIV-1 | pep1462 | ETINEEAAEWDR | 1462.64 | >95% |
| | pep1447 | DTINEEAAEWDR | 1447.62 | |
| | pep1293 | MYSPVSILDIR | 1293.54 | |
| | pep1295 | MYSPTSILDIR | 1295.67 | |

FIG. 24
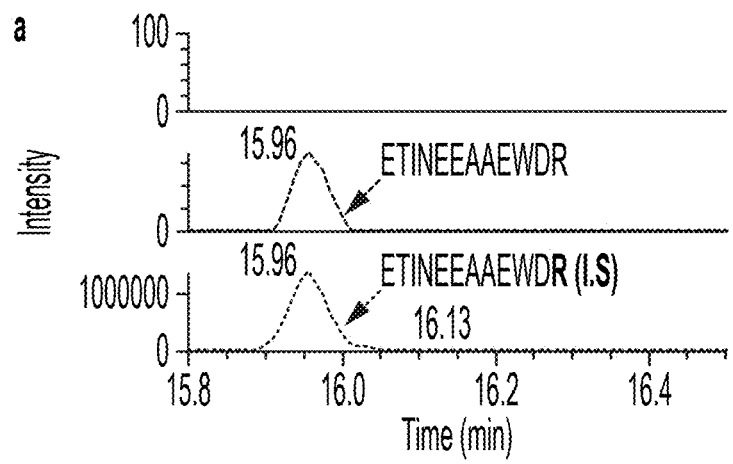
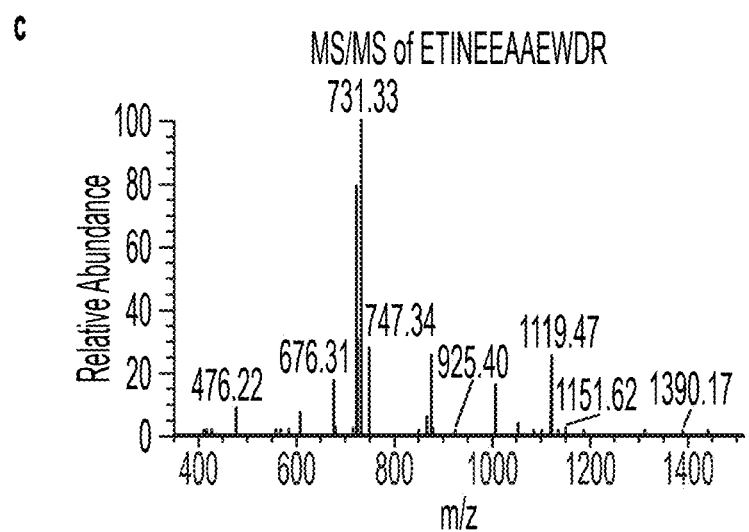
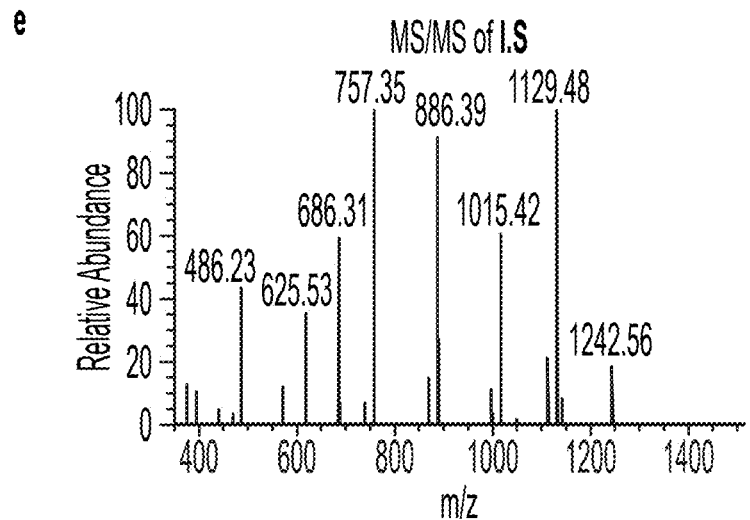

FIG. 24 – CONT.
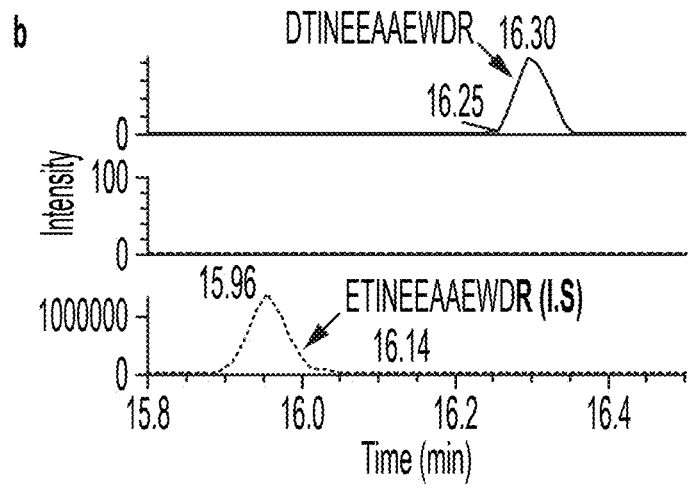
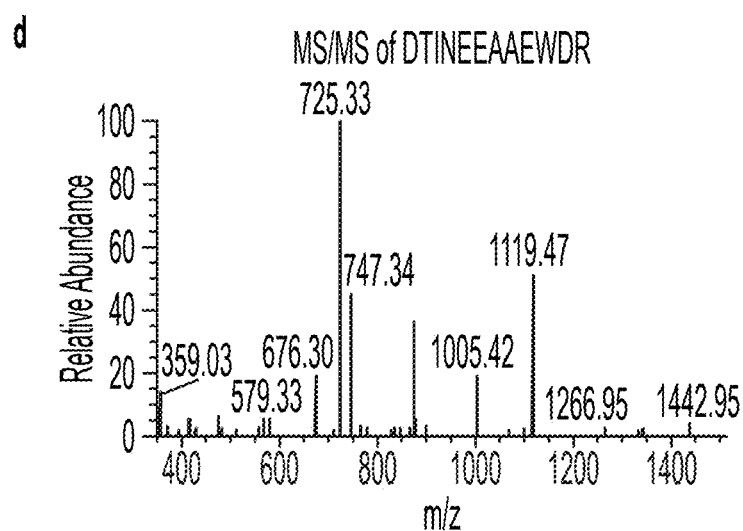
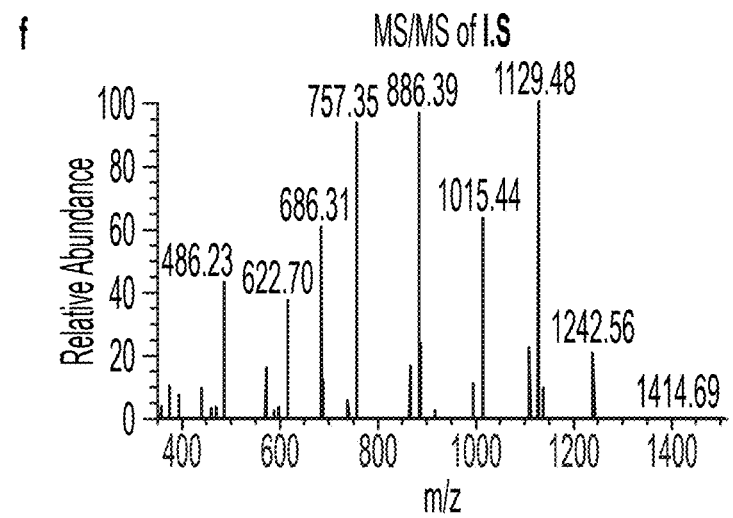

| | | TIC Signal | Signal/Noise | Peak Area | Significance |
|---|---|---|---|---|---|
| Immobilized Trypsin & 2 PM CFP-10 | Overnight | 8E3 | 8.9e2 | 3.3E4 | Save money $0.4/Sample |
| | 2hrs | 1.8E4 | 6.4e2 | 9.3E4 | Save money & Save Time |
| Immobilized Trypsin & 0.5 PM CFP-10 | Overnight | 8.9E3 | 4.8e2 | 5.4E4 | Save money & Detection of Low abundant peptide |
| | 2hrs | 1.8E4 | 6.4e2 | 9.3E4 | Save money & Save Time & Detection of Low abundant peptide |
| sequencing Trypsin & 2 PM CFP-10 | Overnight | 2.3e4 | 9.7e2 | 1.2e5 | Cost money $20/Sample & Consume Time |
| | 2hrs | 1.2e3 | 8.9e1 | 1.9e3 | Cost money & Save Time |

* The "f" in "safe" should be replaced with "v"

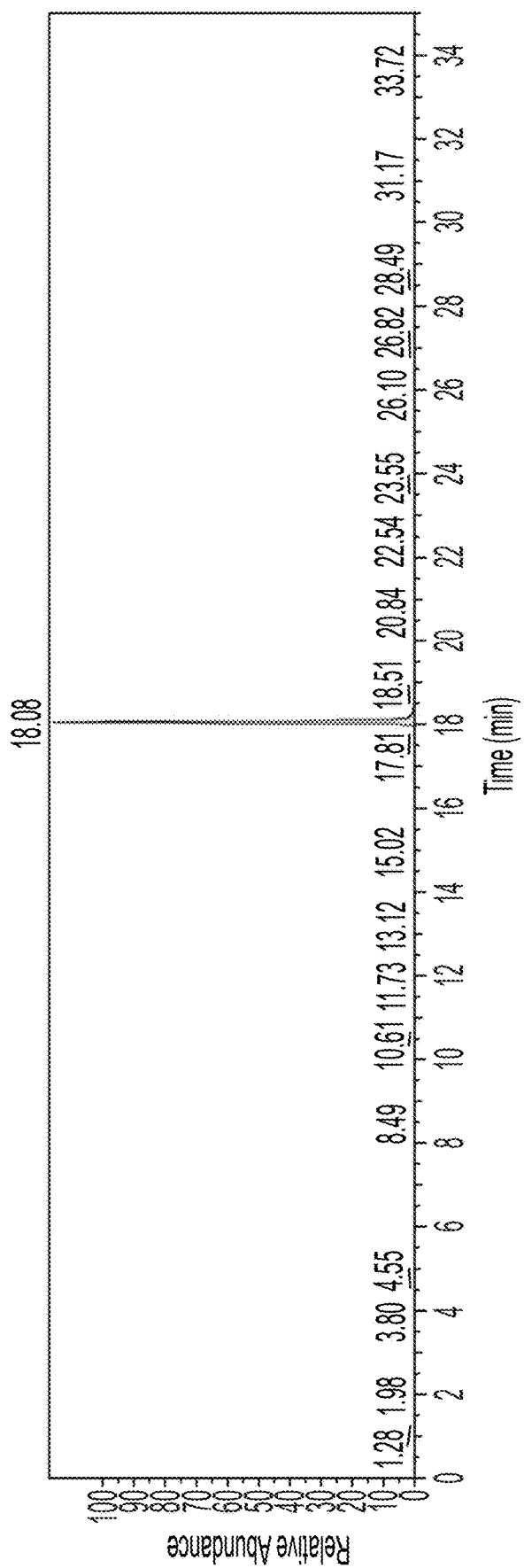
FIG. 28 - CONT.

US 12,385,915 B2

DETECTION OF ANTIGENS

This application is a national phase application of PCT Application PCT/US2020/037785 filed on 15 Jun. 2020, which claims priority from U.S. Provisional Patent Application No. 62/861,896, filed on Jun. 14, 2019, the contents of each of which are incorporated herein by reference in their entireties.

GOVERNMENT INTERESTS

This invention was made with government support under R01 AI113725, R01 AI122932, and R01 HD090927 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Aug. 7, 2020, is named 2952332-002WO1_SL.txt and is 193,197 bytes in size.

FIELD OF THE INVENTION

This invention is directed to methods for detecting and identifying target antigens associated with infection.

BACKGROUND OF THE INVENTION

Conventional methods of detecting pathogen proteins in human biological samples down are incapable of detecting sub-nanomolar levels, which is critical for accurate infection diagnosis. Accordingly, there is a need for improved methods for infection diagnosis. The problems addressed by this disclosure include providing such improved methods.

SUMMARY OF THE INVENTION

An aspect of the invention is directed towards a method for detection and identification of a disease-specific biomarker. In one embodiment, the method comprises contacting an enzyme-digested biological sample with an antibody-modified solid support (AMSS) under conditions that promote binding of the AMSS to its target if present in the contacted biological sample, wherein the antibodies bind specifically to a disease-specific biomarker; sensing the disease-specific biomarker in a concentration comprising the range of about 0.1 pM to about 6 µM; subjecting the sample to a mass spectrometry-based analytical technique; detecting m/z peaks in the mass spectrum; and identifying the subject from which biological sample was obtained as having the disease based on the m/z peaks in the mass spectrum. An aspect of the invention is directed towards a method of detecting and identifying a disease in a subject. In one embodiment, the method comprises identifying the disease-specific biomarker according to the technique described herein; identifying the similarities and differences between disease-specific biomarker spectrum and the spectrum obtained from the sample from the subject; identifying a subject who has contracted a disease or disorder, or who are at risk of developing an active disease or disorder, based on the m/z peaks in the mass spectrum; and treating the subject with a therapeutically effective amount of a medicament. In an embodiment, the disease is caused by an infectious pathogen comprising a bacterium, a fungus, or a virus. In a further embodiment, the bacterial disease comprises tuberculosis, nontuberculosis mycobacterial (NTM) disease, or gut microbial perturbations. In another embodiment the viral disease comprises a human immunodeficiency virus (HIV) disease or Ebola disease. In an embodiment, the disease-specific biomarker comprises a disease-specific antigen, a disease-specific protein, a disease-specific peptide, or a fragment thereof. In an embodiment, the disease-specific target biomarker has a molecular weight in the range of about 500 Daltons (Da) to about 5000 Da. In an embodiment, disease-specific biomarker is a *Mycobacterium* peptide comprising the sequence TDAATLAQEAGNFER (SEQ ID NO:1), TQIDQVESTAGSLQGQWR (SEQ ID NO:2), WDATATELNNALQNLAR (SEQ ID NO:3), TQIDQVESTAASLQAQWR (SEQ ID NO:4), or a combination thereof. In an embodiment, disease-specific biomarker is a HIV-1 specific peptide comprising the sequence ETINEEAAEWDR (SEQ ID NO: 5), DTINEEAAEWDR (SEQ ID NO: 6), MYSPTSILDIR (SEQ ID NO: 7), MYSPVSILDIK (SEQ ID NO: 8), MYSPVSILDIR (SEQ ID NO: 9), or a combination thereof. In an embodiment, the disease-specific biomarker is a HIV-2 specific peptide comprising the sequence MYNPTNILDIK (SEQ ID NO: 10), AEQTDPAVK (SEQ ID NO: 11), or a combination thereof. In an embodiment, the enzyme-digested biological sample comprises one or more internal reference standards. In a further embodiment, the internal reference standard comprises an isotopically labeled sample. In an embodiment, the biological sample is obtained from a human subject. In a further embodiment, the biological sample is blood, serum, cerebrospinal fluid, semen, urine, plasma, or a biological culture media. In an embodiment, the method further comprising generating a reference mass spectrum in which a peak corresponding to a disease-specific biomarker of interest is present in the reference mass spectrum.

In an embodiment, the AMSS is a non-porous support or a porous support. In an embodiment, the AMSS comprises a bead, a nanodisk, a microdisk, a film, rod, nanoparticle or a microparticle. In an embodiment, the AMSS is etched for structure. In an embodiment, the AMSS comprises a magnetic bead.

In an embodiment, the mass spectrometry-based analytical technique is applied to the disease-specific biomarker bound to the AMSS or is applied to an eluted disease-specific biomarker. In an embodiment, the mass spectrometry-based analytical technique comprises a hard ionization technique or a soft ionization technique. In an embodiment, the hard ionization technique comprises electronic ionization (EI). In an embodiment, the soft ionization technique comprises: matrix-assisted laser desorption/ionization (MALDI), electrospray ionization (ESI), fast atom bombardment (FAB), chemical ionization (CI), atmospheric-pressure chemical ionization (APCI), desorption electrospray ionization (DESI), atmospheric pressure photoionization (APPI), or secondary ion mass spectrometry (SIMS). In an embodiment, the hard ionization technique or the soft ionization technique is coupled with at least two mass analyzers and at least one technique to induce fragmentation comprises tandem mass spectrometry (MS²). In an embodiment, the at least one technique to induce fragmentation comprises collision-induced dissociation (CID), electron capture dissociation (ECD), electron transfer dissociation (ETD), negative electron transfer dissociation (NETD), electron-detachment dissociation (EDD), charge transfer dissociation (CTD), photodissociation, infrared multiphoton dissociation (IRMPD), blackbody infrared radiative dissociation (BIRD), or surface induced dissociation (SID). In an embodiment, the tandem mass spectrometry (MS²) technique comprises data-independent acquisition (DIA) or data-dependent acquisition (DDA).

In an embodiment, the mass spectrometry-based analytical technique comprises at least one mass analyzer. In a further embodiment, the at least one mass analyzer comprises a quadrupole mass analyzer, a time of flight (TOF) mass analyzer, a magnetic sector mass analyzer, an electrostatic sector mass analyzer, a quadrupole ion trap mass analyzer, an orbitrap mass analyzer, or ion cyclotron resonance mass analyzer. In an embodiment, the method comprises MS²/MS³ data dependent neutral loss method. In an embodiment, the method comprises nanoelectrospray-tandem mass spectrometry (iNanoESI-MS/MS). In an embodiment, the hard ionization technique or the soft ionization technique is coupled with at least two mass analyzers and at least one technique to induce fragmentation comprises tandem mass spectrometry (MS²).

In an embodiment, the mass spectrometry-based analytical technique is combined with a separation technique. In a further embodiment, the mass spectrometry-based analytical technique combined with a separation technique comprises liquid chromatography mass spectrometry (LC-MS), liquid chromatography with tandem mass spectrometry (LC-MS-MS or LC-MS²), liquid chromatography scheduled parallel reaction monitoring mass spectrometry (LC-sPRM-MS), NanoLC-ESI-MS/MS or immunoprecipitation coupled liquid chromatography scheduled parallel reaction monitoring mass spectrometry (LC-iSPRM-MS).

In an embodiment, the m/z peaks [M+H]⁺ identified by MALDI-TOF MS comprise: a m/z peak at 1594 is indicative of a disease-specific target antigen TDAATLAQEAGNFER (SEQ ID NO: 1) associated with co-infection by *Mycobacterium tuberculosis* complex subspecies and one or more of *M. kansasii, M. marinum,* and *M. ulcerans* infection; a m/z peak at 1901 (ESAT-6) is indicative of a disease-specific target antigen WDATATELNNALQNLAR (SEQ ID NO: 3) associated with infection by *Mycobacterium tuberculosis* complex species; a m/z peak at 2004 is indicative of a disease-specific target antigen TQIDQVESTAGSLQGQWR (SEQ ID NO: 2) associated with infection by *Mycobacterium tuberculosis* complex subspecies; a m/z peak at 2032 is indicative of a disease-specific target antigen associated with infection by *M. kansasii*; or a combination thereof.

In another embodiment, m/z peaks [M+H]⁺ identified by MALDI-TOF MS comprise: a m/z peak at 1463 Da is indicative of a disease-specific peptide ETINEEAAEWDR (SEQ ID NO: 5) of HIV-1 infection; a m/z peak at 1448 Da is indicative of a disease-specific peptide DTINEEAAEWDR (SEQ ID NO: 6) of HIV-1 infection; a m/z peak at 1294 is indicative of a disease-specific peptide MYSPVSILDIR (SEQ ID NO: 9) of HIV-1 infection; a m/z peak at 1296 Da is indicative of a disease-specific peptide MYSPTSILDIR (SEQ ID NO: 7) of HIV-1 infection; or a combination thereof.

In another embodiment, m/z peaks [M+H]⁺ identified by MALDI-TOF MS comprise: a m/z peak at 1322 Da is indicative of a disease specific peptide MYNPTNILDIK (SEQ ID NO: 10) of HIV-2 infection; a m/z peak at 958 Da is indicative of a disease specific peptide AEQTDPAVK (SEQ ID NO: 11) indicative of HIV-2 infection; or a combination thereof.

An aspect of the invention is directed towards a kit for the detection and identification of a biomarker of disease or disorder, the kit comprising one or more of antibody-modified solid supports, wherein the antibodies bind specifically to a disease or disorder peptide or fragment thereof and instructions for use.

BRIEF DESCRIPTION OF THE DRAWINGS

(FIG. 6A) Sample processing prior to MS analysis. (FIG. 6B) Scheme of LC-MRM MS system and the flow setting. Buffers that are used for eluting peptides from analytical column are colored red. Buffer that is used for sample loading is colored orange. This is cited from the instrument manual of Thermo Scientific UltiMate 3000 RSLCnano system with minor modification. (FIG. 6C) The MRM-MS signal that is generated from the targeted peptide (red) and its internal standard with stable isotopic labeling (green), which causes 10 Da of mass shift in its product fragments.

(FIG. 7A) The intensity of each MRM transitions selected for a targeted CFP-10 peptide (upper panel) and its internal standard (lower panel) are presented, and their m/z are labeled on each centroid peak. (FIG. 7B) The extracted ion chromatograph of the targeted CFP-10 peptide exported from Skyline. (FIG. 7C) The extracted ion chromatograph of internal standard peptide that is generated by stable isotopic labeling of targeted CFP-10 peptide. All monitored fragments are presented with different colors and their m/z and charge are listed in the box legend.

FIGS. 8A-8C present Selection of MRM transitions. (FIG. 8A) Overview of all theoretical b and y ions of the targeted CFP-10 peptide with m/z in the range of 300-1,500, and their human proteome interferences provided by SRM Collider. All ions selected in the final assay are marked with green circles, and some ions that are not selected due to the criteria setting illustrated in FIG. 10 are marked with red circles. (FIG. 8B) The MS/MS spectrum of targeted peptide are identified after database search and used for spectral library build-up in Skyline. (FIG. 8C) The retention times and mass-to-charge ratios of y13 (left panel, red dot) and y9 (right panel, red dot) fragment ions from targeted peptide and their interferences (blue dots). FIGS. 8B and 8C disclose "TDAATLAQEAGNFER" as SEQ ID NO: 1.

Figure 12:
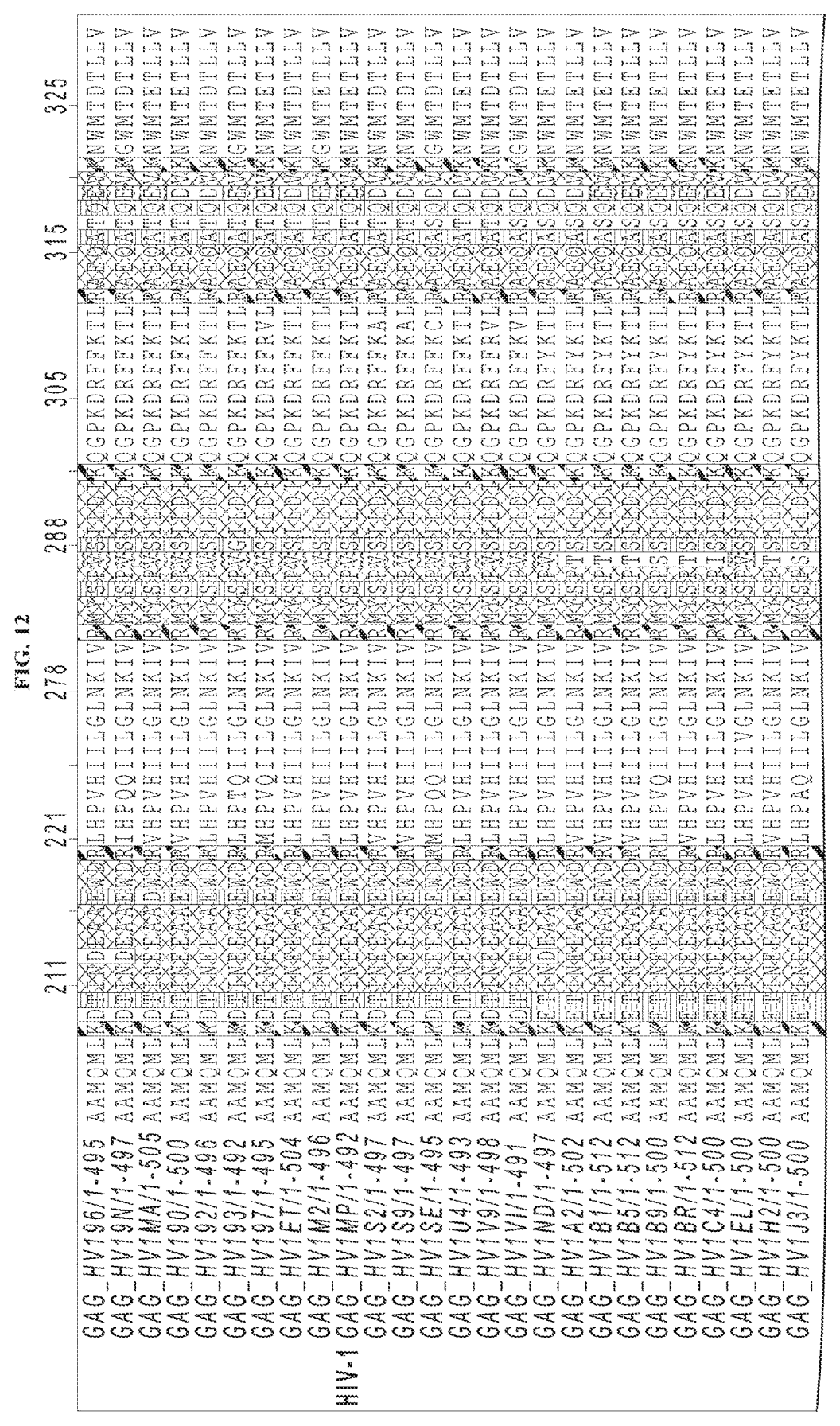
Figure 12:
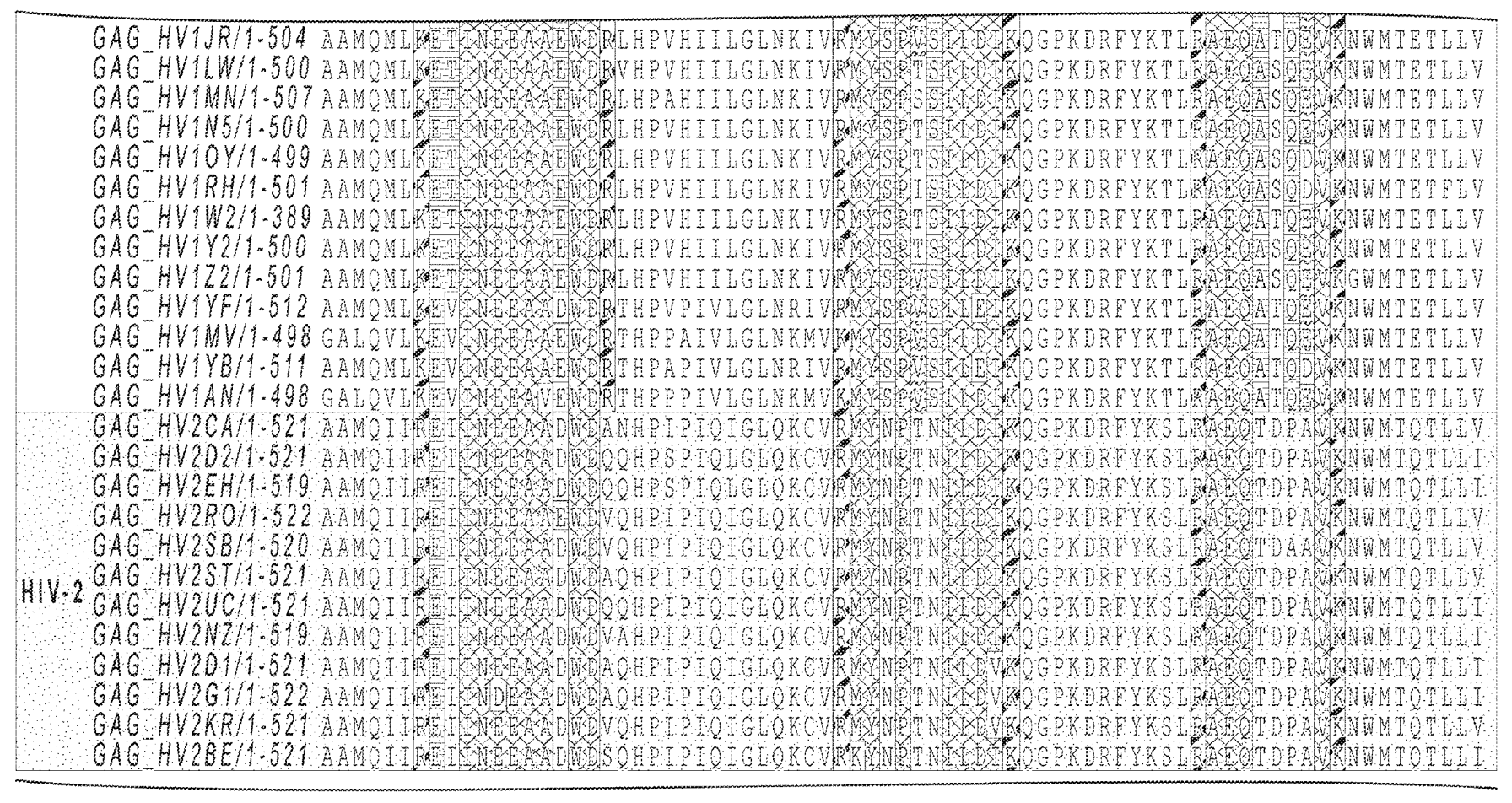

FIG. 12 shows a sequence alignment of Gap proteins from different HIV-1 and HIV-2 strains (SEQ ID NOS 605-757, respectively, in order of appearance). Sequences of HIV-1 and HIV-2 from the UniProtKB database were aligned by CLUSTAL Omega (1.2.4) multiple sequence alignment (http://www.uniprot.org/align/). 4 peptides the target peptides with corresponding sequence regions in from HIV-1 (SEQ ID NOS 5, 6, 9, and 7, respectively, in order of appearance) and 2 peptides from HIV-2 (SEQ ID NOS 10 and 11, respectively, in order of appearance) are selected to be our target peptides used for the detection and quantification of HIV-1 and HIV-2, respectively, based on their specificity. The combination of 4 peptides from HIV-1 allows for the detection of more than 95% of HIV-1 strains, while the combination of 2 peptides can cover more than 98% percent of HIV-2 strains. Red text (R and K) in the aligned sequence indicates tryptic cleavage sites.

FIG. 14 shows an instrument method.

FIG. 18 shows LC-iSPRM-MS platform for simultaneous detection and quantification of HIV and TB. Panel a: serum from HIV-1- and TB-free human subjects was spiked with recombinant p24 and CFP-10 protein, then trypsin digested, spiked with stable isotope-labeled internal standards, antibody-enriched for the two target peptides, and analyzed by LC-SPRM-MS. Multiplex quantification of target peptides are determined by MS intensity ratio of target and isotope labeled internal standard peptides. Panel b: p24- and CFP-10-specific peptides can be simultaneously enriched and sensitively detected from spiked serum samples with high specificity due to the multiple confirmations provided by the mass spectrometer, including the retention time, mass-over-charge (m/z) and MS/MS spectrum of the target peptides.

FIG. 22 shows LC-MS/MS spectra of target peptides from recombinant p24. The p24 precursor ions of the target peptides corresponding to 2+ charge state (m/z of 648.34 and 731.82) were chosen for MS/MS fragmentation. The b- and y-ion series indicate the sequence of (a) ETINEE-AAEWDR (SEQ ID NO: 5), $[M+H]^{2+}$ at m/z of 731.82; (b) DTINEEAAEWDR (SEQ ID NO: 6), $[M+H]^{2+}$ at m/z of 724.82. FIG. 22B discloses SEQ ID NO: 7.

FIG. 23 shows HIV-1 and HIV-2 sequence alignment (SEQ ID NOS 605-757, respectively, in order of appearance). Sequence alignment of the p24 protein region from HIV-1 and HIV-2 UniProtKB database entries, where highlighted text indicates tryptic cleavage sites (red, R and K residues), and regions of sequence identity (dark blue) and amino acid conservation (light blue). FIG. 23 discloses the four peptide sequences in the panel beneath the alignment as SEQ ID NOS 5, 6, 9, and 7, respectively, in order of appearance.

FIG. 24 shows simultaneous enrichment of p24-specific peptide ETINEEAAEWDR (SEQ ID NO: 5) and its variant DTINEEAAEWDR (SEQ ID NO: 6) by an antibody raised against ETINEEAAEWER (SEQ ID NO: 13) after both peptides were spiked into serum (6 pM each) and subjected to antibody enrichment. A 0.3 min of time shift was found between the two peptides of ETINEEAAEWDR (SEQ ID NO: 5) (a) and DTINEEAAEWDR (SEQ ID NO: 6) (b), which produced similar intensities. (c), (d), (e) and (f) MS/MS spectra of (c) ETINEEAAEWDR (SEQ ID NO: 5), (d) DTINEEAAEWDR (SEQ ID NO: 6), and their respective (e)(f) isotopic labeled internal standards (I. S).

DETAILED DESCRIPTION

Figures 1A, 1B, 1C, 1D:
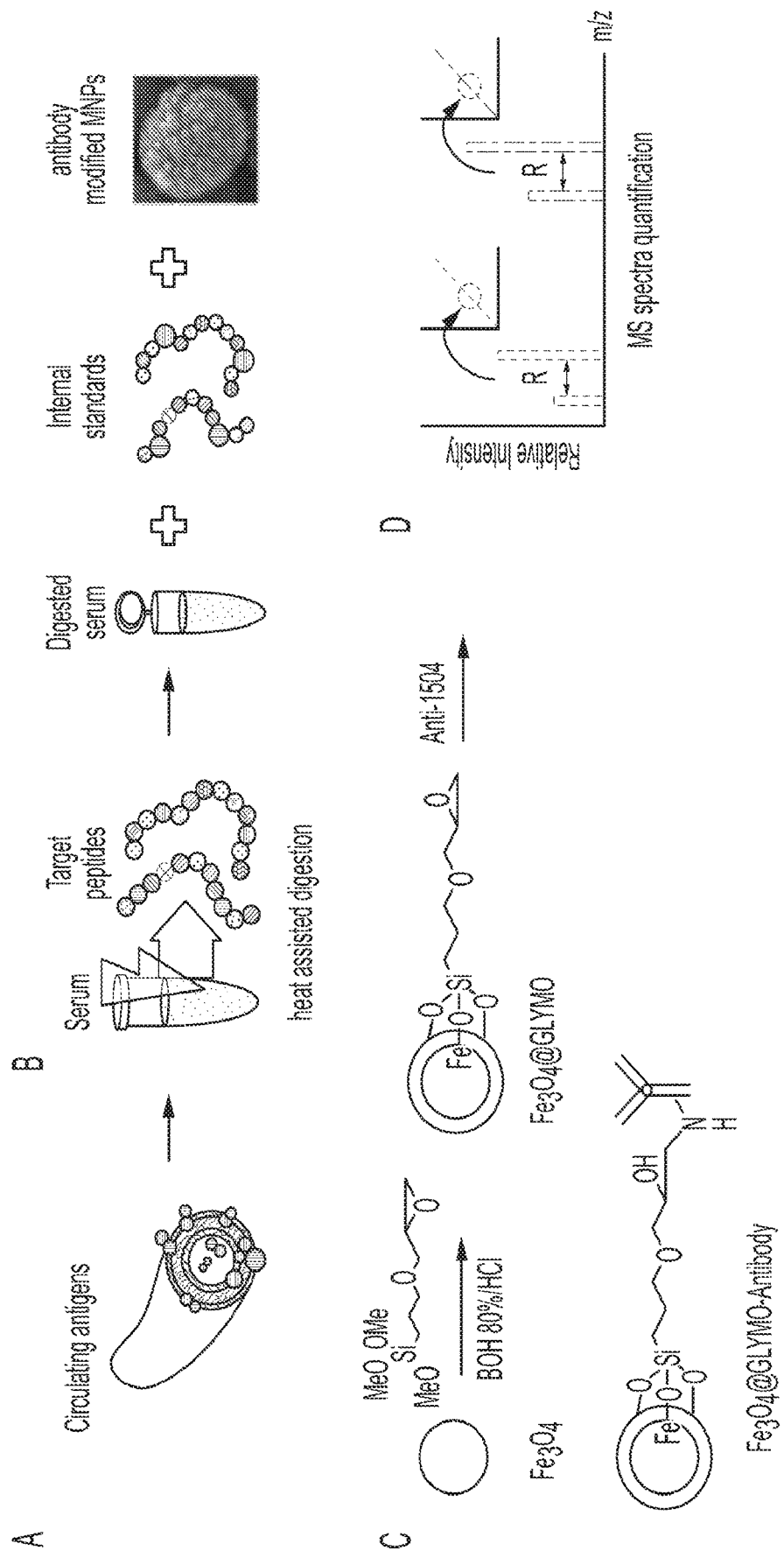
FIG. 1 is a schematic illustration of an exemplary magnetic NS MALDI-MS platform to detect peptide sequences from tryptic digestion of CFP10 in human serum or plasma.
Figure 2:
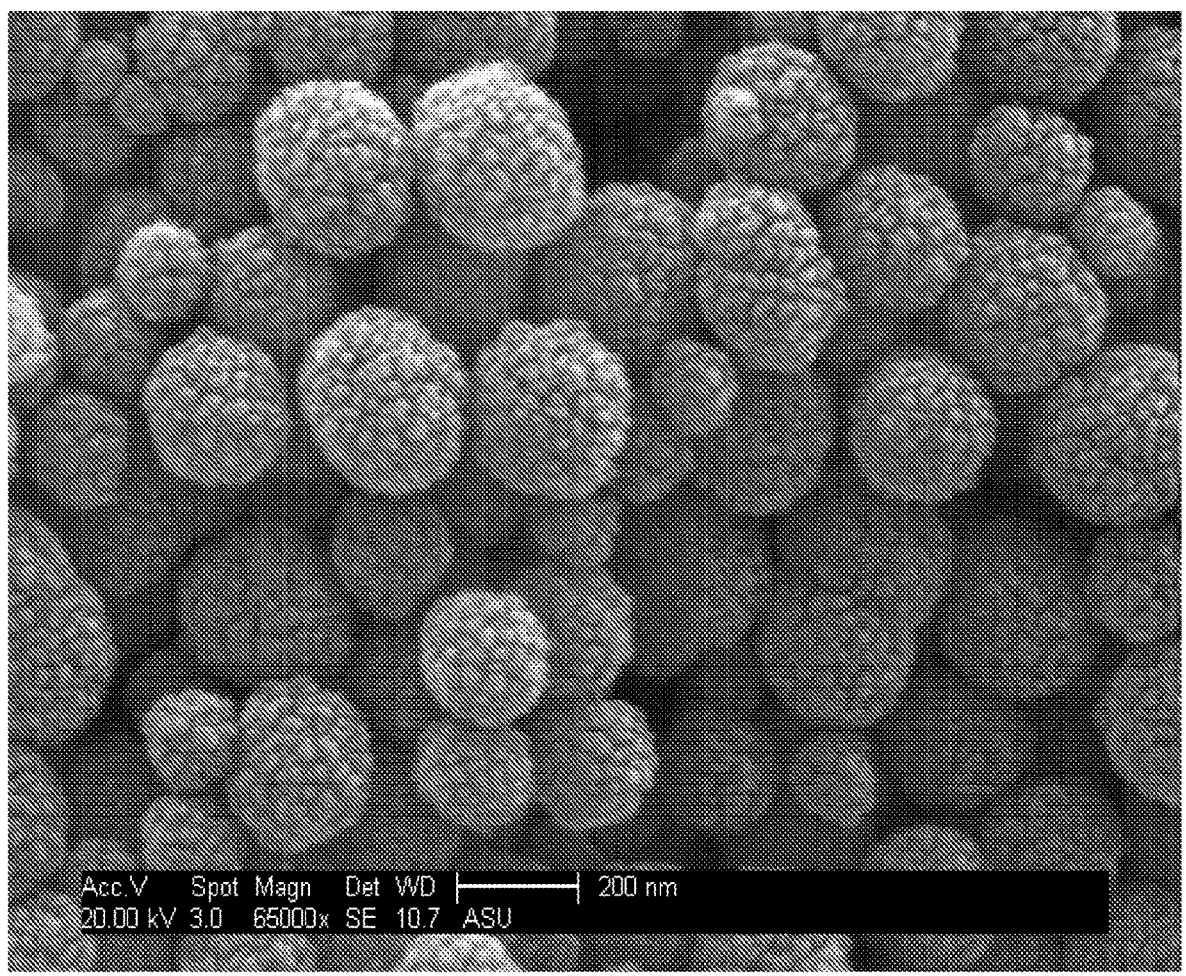
FIG. 2 is a SEM image of magnetic nanoparticles (NPs).
Figure 3:
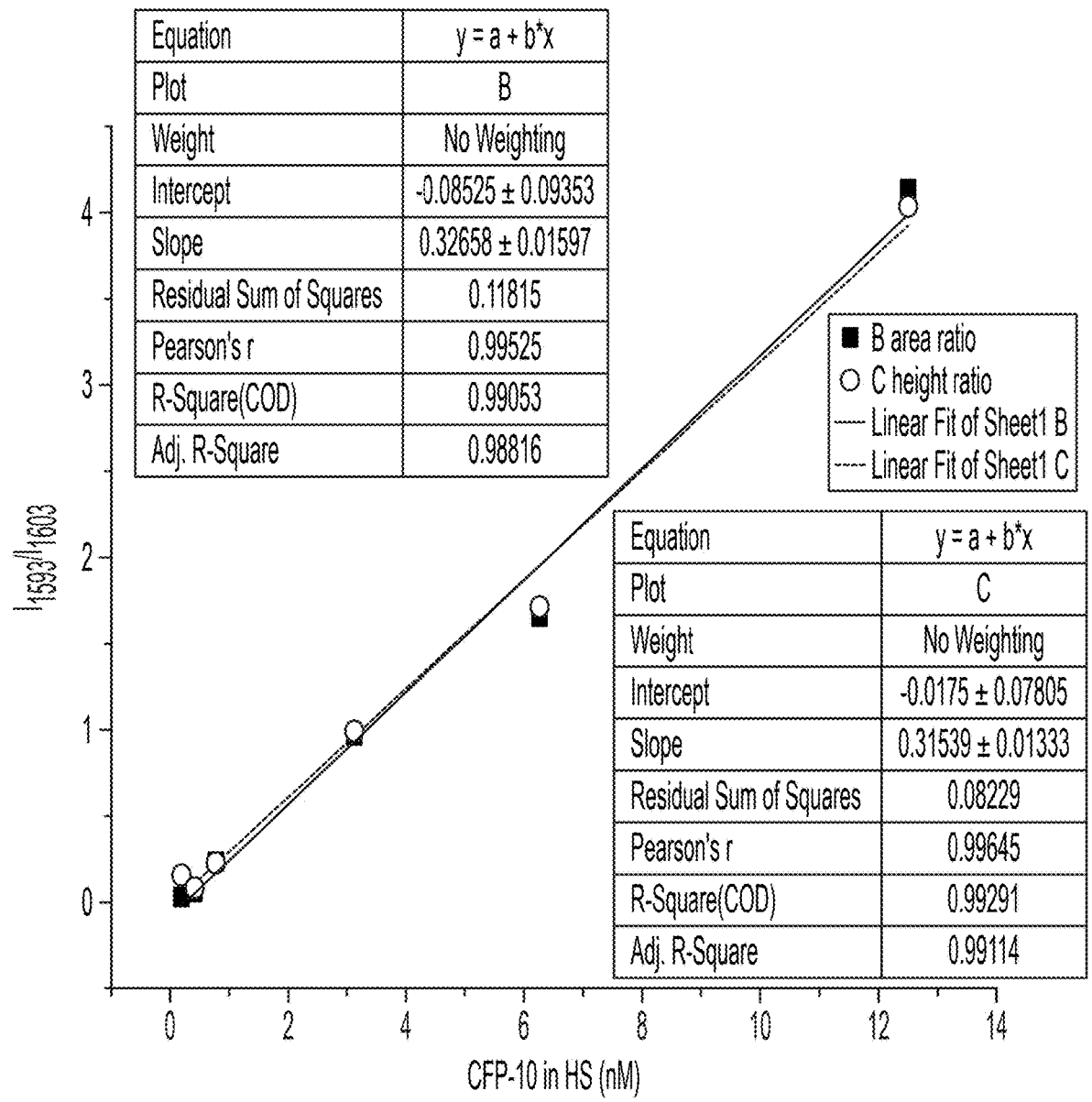
FIG. 3 presents titration curves for CFP-10 (peptide 1593) quantitation in serum. MALDI-TOF MS spectra of healthy serum spiked with CFP-10 after microwave-assisted trypsin digestion. Peptide 1593 was captured by anti-1593 antibody modified NPs. The Limit of Detection was 0.26 nM in serum. Internal isotope peptide (MW: 1604), reference: 1 nM, relative to 100 uL serum, added after tryptic digestion.
Figure 4:
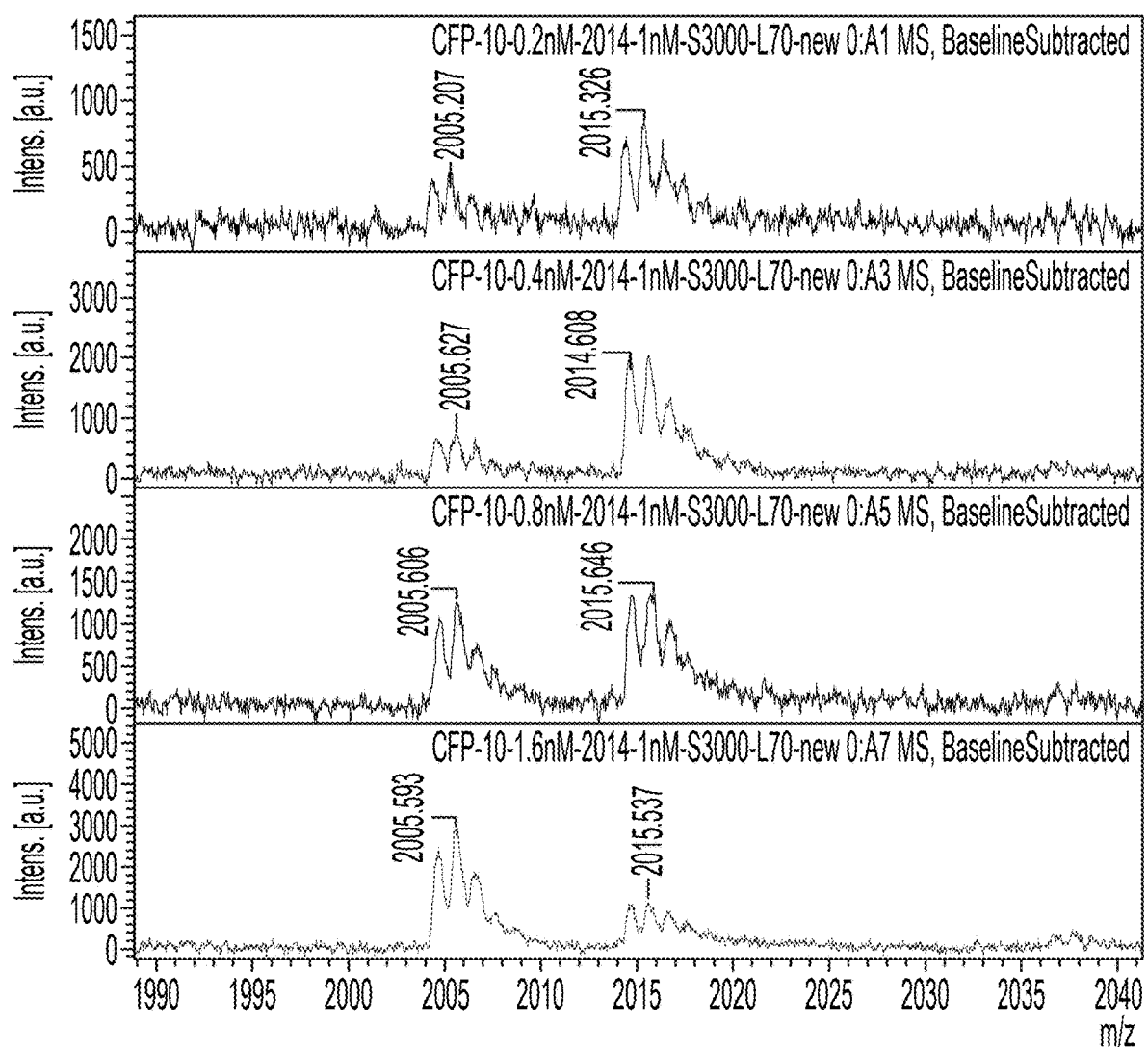
FIG. 4 presents MALDI-TOF MS spectra of healthy serum spiked with CFP-10 after microwave-assisted trypsin digestion. Peptide 2004 were captured by antibody-2004 modified NPs. The Limit of Detection was 0.4 nM in serum. Internal isotope peptide (MW: 2014), reference: 1 nM, relative to 100 uL serum, added after tryptic digestion.
Figure 5A:
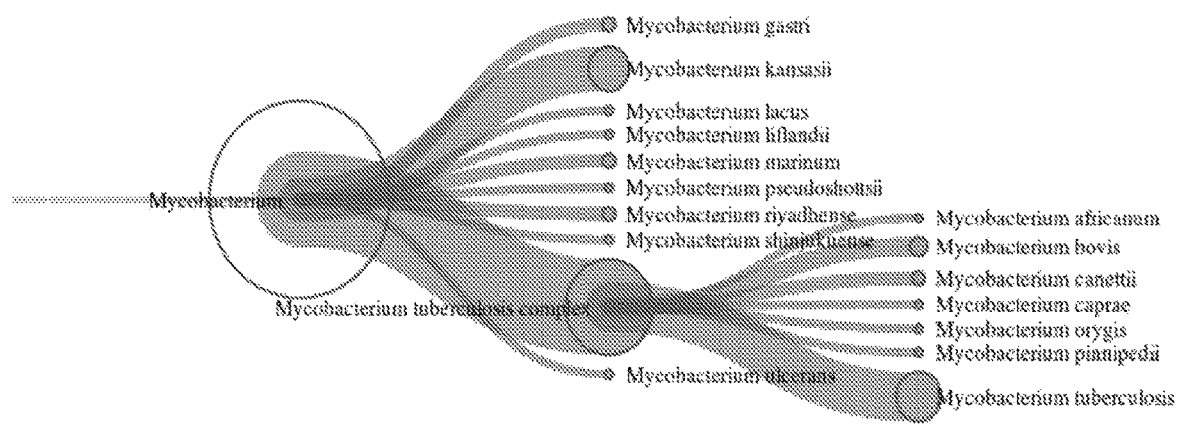
FIGS. 5A-5D demonstrate origination of selected peptide sequences after tryptic digestion of CFP-10 and ESat-6, obtained at unipept.ugent.be on the World Wide Web. Figures disclose SEQ ID NOS 1-4, respectively, in order of appearance.
Figure 5B:
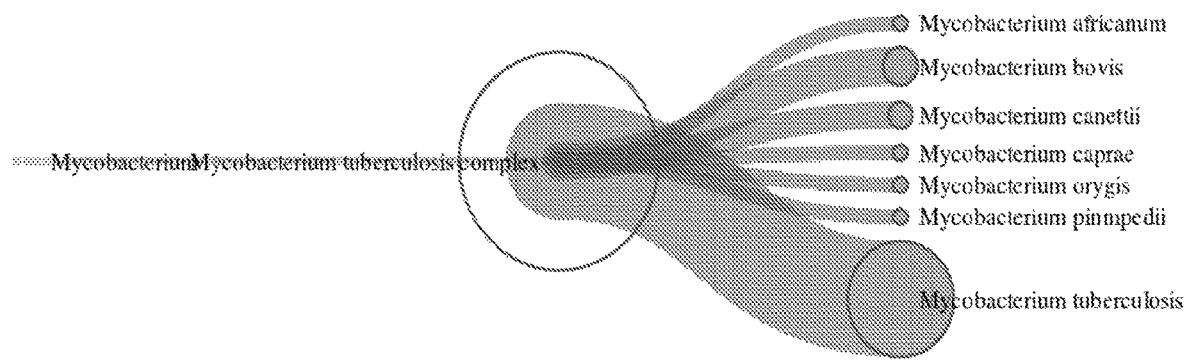
Figure 5C:
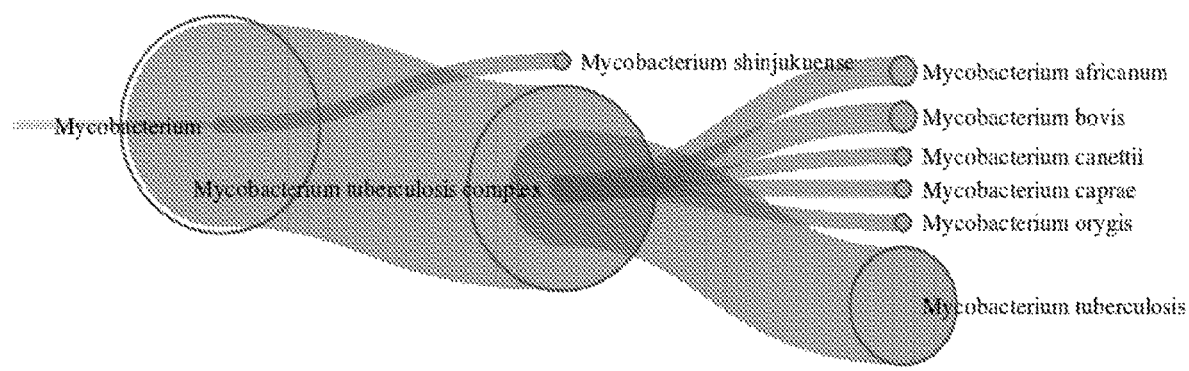
Figure 5D:
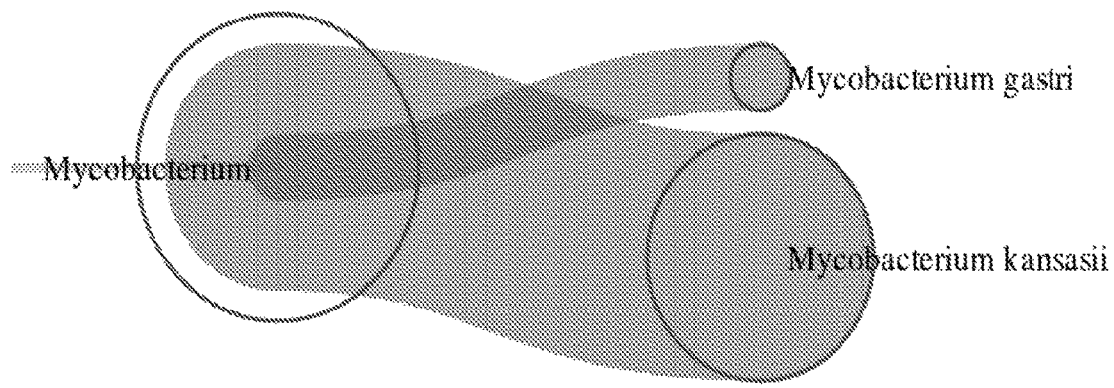

The methods and compositions provided herein are based at least in part on the inventors' development of mass spectrometry-based methods for the detection and identification of a disease-specific biomarker (for example, pathogenic antigens) in a biological sample (such as serum or plasma). As described herein, the presence of particular disease-associated target antigens in the sample provides infection information. In some embodiments, the information is pertinent for tuberculosis (TB) diagnosis. In some embodiments, the information is pertinent for monitoring TB therapy. In some embodiments, the information is pertinent for HIV diagnosis. In some embodiments, the information is pertinent for monitoring HIV treatment.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Methods of Detection and Identification

Aspects described herein are directed towards methods of detection and identification of a disease-specific biomarker using the MS methodologies described herein. Aspects described herein are also directed towards methods of detecting and identifying a disease in a subject using the MS methodologies described herein. The term "disease-specific biomarker" can refer to any marker that indicates the presence of a disease. In some embodiments, the disease-specific biomarker comprises a disease-specific antigen, a disease-specific protein, a disease-specific peptide, or a fragment thereof. In some embodiments, the disease-specific biomarker can be 5, 6, 7, 8, 9, 10, 11, 12, 13, 14, 15, 16, 17, 18, 19, 20, 25, or 30 amino acids in length. For example, as described herein, a disease-specific biomarker can be selected based on a combination of the marker's signal intensity when analyzed by MALDI-TOF MS (for example) and the marker's ability to detect and/or discriminate HIV-1 subtypes and HIV-2. Without wishing to be bound by theory, a disease-specific biomarker (for example, a disease-specific peptide) contains a region of significant sequence conservation among the different species or strains (such as bacterial species or viral strains) that will be analyzed in the assay described herein in order for the peptide to be bound and precipitated by the peptide-specific approach, resulting in enrichment of the peptide from the peptide background that is produced during sample digestion. Without wishing to be bound by theory, the length of the peptide and its composition can influence its m/z value and thus its detectability during MS analysis. For example, the peptide VHPVHAGPIPPGQMR (SEQ ID NO: 14) was detected according to the methods described herein, but VHPVHAG-PIPPGQMR (SEQ ID NO: 14) peptide appeared more variable among and within the various HIV-1 subtypes than the two peptides (e.g., (E/D)TINEEAAEWDR (SEQ ID NO: 15) or MYSPTSILDI(R/K) (SEQ ID NO: 16)) elected to pursue. Without wishing to be bound by theory, using the VHPVHAGPIPPGQMR (SEQ ID NO: 14) peptide as a target biomarker would have made it more difficult to identify an antibody that could detect most of the HIV-1 subtypes due to the variability. For example, HIV shows a high mutation on its genome, and the mutations can be identified in the peptide sequence region targeted. Here, to cover all HIV-1 strains, multiple peptide sequences with amino acid variations can be used to achieve the highest coverage. Unless the patient is infected with multiple HIV-1 strains, the combination of these peaks may not be observed.

This disease-specific biomarker as described herein can be indicative of an infection or disease. The disease-specific biomarker can also be used to detect infectious pathogens (such as bacterial pathogens, fungal pathogen, and/or viral pathogens). In embodiments, the disease comprises a bacterial disease or a viral disease. Non-limiting examples of a pathogenic bacterium, of which can cause disease/infection in a mammal (such as humans) include: *Streptococcus* (e.g., *S. pneumoniae, S. sanguinis, S. bovis*), *Pseudomonas* (e.g., *P. aeruginosa, P. oryzihabitans*), *Salmonella* (e.g., *S. enterica, S. bongori*), *Shigella* (e.g., *S. dysenteriae, S. flexneri*), *Mycoplasma* (e.g., *M. pneumoniae, M. genitalium*), *Mycobacterium* (e.g., *M. tuberculosis, M. leprae, M. kansasii, M. marinum, M. ulcerans*). Non-limiting examples of a pathogenic fungus, of which can cause disease/infection in a mammal (such as humans) include: *Pneumocystis* (e.g., *P. carinii, P. jirovecii*). For example, *M. tuberculosis* can cause tuberculosis. For example, nontuberculous mycobacterial (NTM) infection can cause NTM lung disease. Non-limiting examples of a pathogenic virus which can cause disease/infection include Orthomyxoviridae family viruses (e.g. Influenza A and B), Paramyxoviridae family viruses (e.g. respiratory syncytial virus and Parainfluenza viruses 1-4), Filoviridae family viruses (e.g. Bundibugyo virus, Reston virus, Sudan virus, Taï Forest virus, Zaire ebolavirus (Ebola virus), Marburg virus (Marburg hemorrhagic fevers)), Bunyaviridae family viruses (e.g. hantaviruses, Rift Valley fever and Crimean-Congo hemorrhagic fever), Arenaviridae family viruses (e.g. Lassa fever virus), Retroviridae family viruses (e.g., HIV, FIV), and Flaviviridae family viruses (e.g. dengue and yellow fever).

For example, the diseases associated with the above pathogens comprises tuberculosis, Ebola virus disease (EVD), nontuberculous mycobacterial (NTM) lung disease, human immune deficiency virus (HIV) infection (such as AIDS and Kaposi's Sarcoma), or gut microbial perturbations. In an embodiment, the disease is not solely nontuberculous mycobacterial (NTM) lung disease. In an embodiment, the methods of detection and identification of a disease-specific biomarker comprise subjecting the sample to a mass spectrometry-based analytical technique and detecting m/z peaks in the mass spectrum. In an embodiment the method comprises identifying the subject from which the biological sample was obtained as having a disease based on the m/z peaks in the mass spectrum. In one embodiment, the disease-specific biomarker has a molecular weight in the range of about 500 Da to about 5000 Da. For example, the molecular weight comprises less than 500 Da, about 500, about 600 Da, about 700 Da, about 800 Da, about 900 Da, about 1000 Da, about 1500 Da, about 2000 Da, about 2500 Da, about 3000 Da, about 3500 Da, about 4000 Da, about 4500 Da, about 5000 Da, and greater than 5000 Da.

Aspects of the invention are drawn towards contacting an enzyme-digested sample with an antibody-modified solid support (AMSS). For example, an enzyme-digested sample comprises a trypsin digested sample. In some embodiments, the contacting can occur under conditions that promote binding of the AMSS to disease specific antibodies if present in the contacted biological sample. The term antibody-modified solid support (AMSS) refers to any solid support that can be porous or non-porous. In some embodiments, the AMSS can be any solid phase substance for which an antibody can be bound. In further embodiments, the surface of the AMSS can be modified to produce textured surfaces, for example as described in PCT Publication No. WO/2018/151930, which is hereby incorporated by reference in its entirety, for defining features such as pores, ridges and valleys or other similar morphologies. In further embodiments, a non-porous support can be transparent, such as glass, or alternatively, plastic, polystyrene, polyethylene, dextran, polypropylene and the like. In other embodiments, the porous support can be nitrocellulose, porous glass, or agarose (such as sephadex). Non-limiting examples of the AMSS include: a bead (such as plastic, glass, silica, magnetic, agarose, and the like), a nanoparticle (such as a nanodisk), a microparticle (such as a microdisk or a magnetic bead), a film, a rod. In some embodiments, the nanoparticle is about 10 nm to about 1000 nm in size. For example, the nanodisk is about 800 nm. In some embodiments, the nanodisk can be about 50 nm, about 100 nm, about 200 nm, about 300 nm, about 400 nm, about 500 nm, about 600 nm, about 700 nm, about 800 nm, about 900 nm, or about 1000 nm. For example, the AMSS comprises a magnetic bead. In some embodiments the magnetic bead is about 1 micron to about 100 microns in size. For example, the magnetic bead is about 1 micron to about 2.8 microns. For example, the magnetic bead can be about 0.5 µm, about 1 µm, about 1.25 µm, about 1.50 µm, about 1.75 µm, about 2 µm, about 2.25 µm, about 2.5 µm, about 2.75 µm, about 3 µm, about 3.25 µm, about 3.50 µm, about 3.75 µm, about 4 µm, about 4.25 µm, about 4.5 µm, about 4.75 µm, about 5 µm, about 5.25 µm, about 5.50 µm, about 5.75 µm, about 6 µm, about 6.5 µm, about 7 µm, about 7.5 µm, about 8 µm, about 8.5 µm, about 9 µm, about 9.5 µm, about 10 µm, about 11 µm, about 12 µm, about 13 µm, about 14 µm, about 15 µm, about 16 µm, about 17 µm, about 18 µm, about 19 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the AMSS can be etched for structure or made porous. For example, etching or increasing porosity can increase surface area giving more area for antibody attachment and/or decreasing unwanted binding. Other non-limiting examples include the matrix in a chromatographic column, a filter, or a surface. Without wishing to be bound by theory, the AMSS can be conjugated with an antibody directed to a target antigen, which serves as a marker for the desired disease or infection.

The method further comprises sensing the disease-specific biomarker in a concentration comprising the range of less than 0.1 pM, about 0.1 pm, about 0.2 pM, about 0.3 pM, about 0.4 pM, about 0.5 pm, about 0.6 pM, about 0.7 pM, about 0.8 pM, about 0.9 pM, about 1.0 pM, about 2.0 pM, about 5 pM, about 10 pM, about 20 pM, about 30 pM, about 50 pM, bout 60 pM, about 70 pM, about 80 pM, about 90 pM, about 0.1 nM, about 0.2 nM, about 0.3 nM, about 0.4 nM, about 0.5 nM, about 0.6 nM, about 0.7 nM, about 0.8 nM, about 0.9 nM, about 1.0 nM, about 2.0 nM, about 5 nM, about 10 nM, about 20 nM, about 30 nM, about 50 nM, about 60 nM, about 70 nM, about 80 nM, about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 2.0 µM, about 3.0 µM, about 4.0 µM, about 5.0 µM, about 10 µM, about 20 µM, about 30 µM, about 50 µM, about 60 µM, about 70 µM, about 80 µM, about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, or greater than 1.0 mM. For example, in tuberculosis patient blood, the disease specific biomarker is in a concentration of about 0.1 pm to about 200 pM. For example, the Ebola disease-specific biomarker VP40 is in a concentration of about 1 µM to about 6 µM.

In an embodiment, the disease-specific biomarker concentration range will vary depending upon the disease application. Without wishing to be bound by theory, the approach is designed to work with low abundance biomarkers. For example, the biomarkers comprise protein biomarkers in blood. In another embodiment, the method is drawn towards measuring the absolute concentration of the biomarker in a sample relative to a spiked-in internal standard peptide. Without wishing to be bound by theory, the pretreatment biomarker can be used to evaluate the relative severity of the infection. For example, the difference between biomarker levels at time points before and after treatment initiation can be useful as a measure of disease progression or response to treatment.

Aspects of the invention are drawn towards methods of detecting or identifying a disease-specific biomarker by subjecting a biological sample to a mass spectrometry-based analytical technique. In an embodiment, the mass spectrometry technique comprises at least one hard ionization technique or at least one soft ionization technique. The phrase "soft ionization technique" refers to an ionization technique that produces little to no fragmention ions. For example, soft ionization techniques can comprise matrix-assisted laser desorption/ionization (MALDI), electrospray ionization (ESI), fast atom bombardment (FAB), chemical ionization (CI), atmospheric-pressure chemical ionization (APCI), desorption electrospray ionization (DESI), atmospheric pressure photoionization (APPI), or secondary ion mass spectrometry (SIMS). The pharse "hard ionization technique" refers to an ionization technique that produces ions with greater fragmentation compared to soft ionization techniques. For example, the hard ionization technique comprises electronic ionization (EI). In an embodiment, the mass spectrometry-based analytical technique comprises selected reaction monitoring (SRM), parallel reaction monitoring (PRM), scheduled parallel reaction monitoring (sPRM), multiple reaction monitoring (MRM), scheduled multiple reaction monitoring (sMRM), immunoprecipitation scheduled parallel reaction monitoring (iSPRM), or nanoelectrospray-tandem mass spectrometry (NanoES-MS/MS).

In another embodiment, the mass spectrometry-based analytical technique comprises tandem mass spectrometry ($MS^2$). The term "tandem mass spectrometry" refers to a mass spectrometry based analytical technique where an analyte is ionized to generate ions which are then separated by a mass analyzer and subsequently undergo further fragmentation and are subjected to at least one other mass analyzer before detection. Herein, the term "tandem mass spectrometry" can also refer to multi-stage or sequential mass spectrometry ($MS^n$), where n is a number greater than 2 and n–1 is the generation of product ion spectra. The term "product ion" refers to an ion that is the product of a fragmentation of a parent ion. For example, the tandem mass spectrometry ($MS^2$) technique comprises selected reaction monitoring (SRM), parallel reaction monitoring (PRM), scheduled parallel reaction monitoring (sPRM), multiple reaction monitoring (MRM), scheduled multiple reaction monitoring (sMRM), immunoprecipitation scheduled parallel reaction monitoring (iSPRM), or nanoelectrospray-tandem mass spectrometry (NanoES-MS/MS). Additionally, the $MS^2$ technique can comprise data-independent acquisition (DIA) or data-dependent acquisition (DDA). For example, $MS^n$ can be $MS^2$, $MS^3$, $MS^4$, $MS^5$, or sequential generations of the target ions. For example, to conduct a relative quantification of markers between two samples, a labeling tag such as TMT will be applied, and $MS^3$ is used to generate quantitative results.

In an embodiment, tandem mass spectrometry ($MS^2$) comprises a technique to induce fragmentation comprises collision-induced dissociation (CID), electron capture dissociation (ECD), electron transfer dissociation (ETD), negative electron transfer dissociation (NETD), electron-detachment dissociation (EDD), charge transfer dissociation (CTD), photodissociation, infrared multiphoton dissociation (IRMPD), blackbody infrared radiative dissociation (BIRD), or surface induced dissociation (SID).

In addition to an ionization technique, the mass spectrometry technique utilizes at least one mass analyzer comprising a quadrupole mass analyzer, a time of flight (TOF) mass analyzer, a magnetic sector mass analyzer, an electrostatic sector mass analyzer, a quadrupole ion trap mass analyzer, an orbitrap mass analyzer, or ion cyclotron resonance mass analyzer.

In a further embodiment, the invention is drawn towards a mass spectrometry-based analytical technique applied to the disease-specific biomarker bound to the AMSS. In another embodiment, the invention is drawn towards a mass spectrometry-based analytical technique applied to an eluted disease-specific biomarker.

In some embodiments, the methods use MALDI-TOF-MS based methods, but in other embodiments, other mass spectrometry techniques can be applied by one skilled in the art. In MALDI (matrix assisted laser desorption ionization) TOF (time-of-flight) mass spectrometry, a sample/matrix mixture is placed on a defined location ("spot", or "sample spot" herein) on a metal plate, known as a MALDI plate. A laser beam is directed onto a location on the spot for a very brief instant, causing desorption and ionization of molecules or other components of the sample. The sample components "fly" to an ion detector. The instrument measures mass to charge ratio (m/z) and relative intensity of the components (molecules) in the sample in the form of a mass spectrum. The term mass to charge ratio (m/z) refers to the ratio of the mass of the species to the charge state of the species. Described herein, it is understood that a m/z peak refers to the [M+H]$^+$ ion. It is understood by one skilled in the art that the hydrogen ion can be replaced with another ion. For example, the ion can be a cation or an anion. Non-limiting examples of cations include sodium (Na$^+$), potassium (K$^+$), and cesium (Cs$^+$). It is also understood by one skilled in the art that the nominal or exact mass of the analyte will not change, but the m/z will change based upon the counter ion used. For example, the m/z for an [M+H]$^+$ peak will be different than the m/z for [M+Na]$^+$ peak, while the mass of M remains the same. An m/z peak can also refer to multiply charged species. As described herein the presence of particular disease-associated target antigens in the sample provides infection information, for example for tuberculosis (TB) diagnosis and for monitoring TB therapy.

In some embodiments, the method uses the mass spectrometry-based analytical technique combined with a separation technique. In some embodiments, the mass spectrometry-based analytical technique combined with a separation technique comprises LC-MS based methods or gas chromatography-mass spectrometry (GC-MS). For example, the mass-spectrometry-based analytical technique comprises column chromatography with liquid-solid interaction (forward and/or reverse phase interactions) coupled to a mass spectrometry technique. Liquid chromatography (LC) coupled mass spectrometry (MS) is an accurate analytical method for biomarker analysis when used with targeted MS approaches multiple reaction monitoring (MRM), selective reaction monitoring (SRM) and parallel reaction monitoring (PRM) modes. In LC-MS, target protein identification is enhanced by detection of target peptides with characteristic LC column elution times and charge-to-mass ratios. Multiple biomarker-derived peptides can be analyzed to provide improved detection specificity and the precursor ions of these peptides can also be fragmented in the MS collision cell to allow direct determination of their amino acid sequences. In some embodiments, the method uses LC-MRM-MS based methods. In some embodiments, the method uses LC-iSPRM-MS based methods. In some embodiments, the LC-MS based method comprises liquid chromatography mass spectrometry (LC-MS), liquid chromatography with tandem mass spectrometry (LC-MS-MS or LC-MS$^2$), liquid chromatography scheduled parallel reaction monitoring mass spectrometry (LC-sPRM-MS), or immunoprecipitation coupled liquid chromatography scheduled parallel reaction monitoring mass spectrometry (LC-iSPRM-MS). In some embodiments, the method uses immunoprecipitation (IP) with nanoelectrospray-tandem MS (NanoES-MS/MS).

Accordingly, in another aspect, provided herein is a method of detecting and identifying pathogen-associated peptides in a sample. In some embodiments, MALDI-TOF-MS-based detection methods where specific *Mycobacterium*-associated peptides are detected and identified in enzyme-digested human serum or plasma samples using antibody-modified iron oxide nanoparticles. Unlike conventional uses of magnetic dynabeads, where the enriched and bound target peptides are eluted out after enrichment, the present methods include spotting antibody-modified NPs directly onto a MALDI plate after capturing target peptide if present in the sample. In this manner, the process is simplified and has a lower detection limit. By combining different peptides digested from *Mycobacterium* proteins, infection caused by *Mycobacterium tuberculosis* can be distinguished from *M. kansasii* and other mycobacteria. As described herein, the methods provide a new tool for diagnosing a subject as having a particular *Mycobacterium* infection or co-infection with two or more mycobacteria species.

In some cases, the method comprises contacting a trypsin-digested biological sample with antibody-modified magnetic nanoparticles (NPs) under conditions that promote binding of the antibody-modified magnetic NPs to its target if present in the contacted biological sample, where the antibodies bind specifically to a disease-specific target antigen; spotting the contacted antibody-modified magnetic NPs to a MALDI plate; performing MALDI-TOF-MS analysis of the spotted NPs, whereby a mass spectrum of a molecule is obtained; and detecting m/z [M+H]$^+$ peaks in the mass spectrum, where a m/z peak at 1594 is indicative of a disease-specific target antigen associated with co-infection by *Mycobacterium tuberculosis* complex subspecies and one or more of *M. kansasii*, *M. marinum*, and *M. ulcerans* infection, where a m/z peak at 1901 or 2004 is indicative of a disease-specific target antigen associated with infection by *Mycobacterium tuberculosis* complex subspecies, and where a m/z peak at 2032 is indicative of a disease-specific target antigen associated with infection by *M. kansasii*. This mass target can also be observed from *M. gordonae*, which is another NTM species causing human infection.

The magnetic nanoparticles can be $Fe_3O_4$, $MnFe_2O_4$, $CoFe_2O_4$, $NiFe_2O_4$, or $ZnFe_2O_4$. In some cases, the antibody-modified magnetic nanoparticles are prepared by the steps of: surface functionalizing magnetic nanoparticles by contacting (3-Glycidyloxypropyl)trimethoxysilane (GLYMO) to a monodispersed preparation of magnetic nanoparticles; and conjugating antibodies that bind specifically to the disease-specific target antigen to the GLYMO contacted magnetic nanoparticles.

In some cases, wherein, prior to conjugating antibodies, the GLYMO contacted magnetic nanoparticles are contacted to a blocking solution selected from Tris-NaCl buffer (pH>8.0), (2-aminoethyl)ethanol, or $NH_2(CH_2CH_2O)nCH_3$; where n is a number from 1 to 100.

In some embodiments, *Mycobacterium*-specific peptides are peptides detected following trypsin digestion of mycobacterial proteins such as 10-KDa culture filtrate proteins (CFP-10), which are early secretory antigens. In some cases, the disease-specific target antigen has a molecular weight in the range of about 500 Daltons (Da) to about 5000 Daltons (Da). In particular, the disease-associated antigens include two segments of CFP-10 detected following trypsin digestion: peptide 1594 (TDAATLAQEAGNFER, MW: 1593.75; SEQ ID NO:1) and peptide 2004 (TQIDQVE-STAGSLQGQWR, MW:2003.98; SEQ ID NO:2). Peptide 2004 is only found in *Mycobacterium tuberculosis* complex subspecies (M. Tb, *M. africanum, M. bovis, M. canettii, M. caprae, M. orysis, M. pinnipedii*); while peptide 1594 is found in *Mycobacterium tuberculosis* complex subspecies (M. Tb) as well as *M. kansasii, M. marinum, M. ulcerans*, and/or *M. gastrii*. Accordingly, by detecting the presence or absence of particular peptides in a trypsin-digested patient serum or plasma sample, it is possible to distinguish between infection by *Mycobacterium tuberculosis* complex subspecies and by *M. kansasii, M. marinum, M. ulcerans*, and/or *M. gastrii*. See Table 1.

TABLE 1

| Diagnosis of infection based on the detection of peptide sequence after serum digestion | | | | |
|---|---|---|---|---|
| Peptide 1594 | Peptide 1901 | Peptide 2004 | Peptide 2032 | Diagnosis |
| + | − | + | − | Co-infection with *M. Tb* and *M. kansasii*, *M. marinum*, *M. ulcerans*, and/or *M. gastrii* |
| − | + | + | − | Infected with *M. Tb* complexes |
| − | − | − | + | Infected with *M. kansasii*, *M. marinum*, *M. ulcerans*, and/or *M. gastrii*. |
| − | − | − | − | No infection with *M. Tb* complexes or *M. kansasii*, *M. marinum*, *M. ulcerans*, and/or *M. gastrii* |

A m/z $[M+H]^+$ peak at 1594 is indicative of a disease-specific target antigen associated with co-infection by *Mycobacterium tuberculosis* complex subspecies and one or more of *M. kansasii, M. marinum*, and *M. ulcerans* infection. A m/z $[M+H]^+$ peak at 1901 or 2004 is indicative of a disease-specific target antigen associated with infection by *Mycobacterium tuberculosis* complex subspecies. A m/z $[M+H]^+$ peak at 2032 is indicative of a disease-specific target antigen associated with infection by *M. kansasii* and/or *M. gastrii*.

TABLE 12

| The VP40 peptide targets for five Ebola species identification | | | | | | | |
|---|---|---|---|---|---|---|---|
| Peptide Sequence | SEQ ID NO: | M + H⁺ | EBOV | SUDV | BDBV | TAFV | RESTV |
| LGPGIPDHPLR* | 17 | 1171.7 | + | | + | + | + |
| LGQGIPDHPLR | 18 | 1202.7 | | + | | | |
| LRPILLPNK | 19 | 1063.7 | + | | | | |
| LRPILLPGK* | 20 | 1006.7 | | | + | | + |
| LRPILLPGR | 21 | 1034.7 | | | | + | |
| LRPVLLPGK | 22 | 992.7 | | + | | | |

Table 12 shows a m/z $[M+H]^+$ peak at 1171.7 is indicative of a disease-specific peptide sequence LGPGIPDHPLR* (SEQ ID NO: 17) which indicates infection with Ebola virus (EBOV), Budibugyo virus (BDBV), Taï Forest virus (TAFV), and/or Reston virus (RESTV). A m/z $[M+H]^+$ peak at 1202.7 is indicative of the disease specific peptide sequence LGQGIPDHPLR (SEQ ID NO: 18) which indicates infection with Sudan virus (SUDV). A m/z $[M+H]^+$ peak at 1063.7 is indicative of the disease specific peptide sequence LRPILLPNK (SEQ ID NO: 19) which indicates infection with Ebola virus (EBOV). A m/z $[M+H]^+$ peak at 1006.7 is indicative of the disease specific peptide sequence LRPILLPGK* (SEQ ID NO: 20) which indicates infection with Bundibugyo virus (BDBV) and/or Reston virus (RESTV). A m/z $[M+H]^+$ peak at 1034.7 is indicative of the disease-specific peptide LRPILLPGR (SEQ ID NO: 21) which indicates infection with Taï Forest virus (TAFV). A m/z $[M+H]^+$ peak at 992.7 is indicative of the disease-specific peptide sequence LRPVLLPGK (SEQ ID NO: 22) which indicates infection with Sudan virus (SUDV).

In some embodiments, HIV-1/2 specific peptides are peptides detected following trypsin digestion. For example, HIV-1 specific peptides include ETINEEAAEWDR (SEQ ID NO: 5) (m/z peak at 1462.64); DTINEEAAEWDR (SEQ ID NO: 6) (m/z peak at 1447.62); MYSPVSILDIR (SEQ ID NO: 9) (m/z peak at 1293.54); and MYSPTSILDIR (SEQ ID NO: 7) (m/z peak at 1295.54), which collectively cover 95% of HIV-1 stains. HIV-2 specific peptides include MYNPTNILDIK (SEQ ID NO: 23) (m/z peak at 1321.68), MYNPPTNILDIK (SEQ ID NO: 12) (m/z peak at 1321.68), and AEQTDPAVK (SEQ ID NO: 11) (m/z peak at 958.04) which collectively cover 98% of HIV-2 strains. See FIG. 12.

For example, with HIV-2, multiple strains are covered. Without wishing to be bound by theory, more than one sequence is targeted here due to the natural mutation.

In some cases, the trypin-digested biological sample comprises one or more internal reference standards. In an embodiment, the internal reference standard comprises an isotopically labed sample. In one embodiment, the sample is an synthetic peptide that has the same sequence as the disease-specific biomarker, but is labeled with a stable heavy isotope to shift its m/z ratio by a fixed amount. For example, the isotopically labeled synthetic peptide is spiked into the sample in a known amount so that its signal can be compared to the biomarker target signal to allow the absolute quantification of an unknown amount of biomarker present in a sample.

In some cases, the method further comprises generating a reference mass spectrum in which a peak corresponding to one or more microorganism antigens of interest is reliably present in the reference mass spectrum.

In some embodiments, the method used to detect serum/plasma biomarkers is integration of immunoprecipitation (IP) with nanoelectrospray-tandem MS (NanoES-MS/MS).

This approach is used to detect the circulating level of a virulence factor secreted by *Mycobacterium tuberculosis* (Mtb), the 10 kDa culture filtrate protein (CFP-10) described above. Before one can perform such targeted MS analyses, patient serum/plasma samples need to be digested to liberate target peptides from their respective biomarkers. This process is complicated by the high abundance, diversity and dynamic range of the proteins present in serum. To address this issue, a sample denaturation and protein chromatography protocol is used to reduce the abundance of off-target proteins in these samples, after which the protein depleted samples are trypsin digested and subjected to IP without a buffer exchange step. This process reduces the amount of trypsin required to efficiently and reproducibly generate target peptides used for biomarker identification and quantitation. This process has several advantages over standard approaches, as it: 1) avoids sample dilution and can be scaled as-needed to account for the observed concentration of the target biomarker in the sample; 2) permits efficient liberation of trace amount of target peptide even at low enzyme-to-substrate mass ratios (i.e., 1:500-1:1,000); and 3) does not require the time-consuming reduction and alkylation of disulfide bonds, as many pathogen-derived biomarkers do not contain these features. This workflow allows a target biomarker to be detected down to sub-pM lower limits of detection and allows multiplex enrichment and detection of target peptides from one or more biomarkers of interest.

In some embodiments, the method used to detect serum/plasmid biomarkers is LC-PRM-MS.

As used herein, the term "sample" means non-biological samples and biological sample and encompasses clinical specimens (diagnostic samples collected as part of standard clinical procedures). Non-biological samples include those prepared in vitro comprising varying concentrations of a target molecule of interest in solution. Biological samples include, without limitation, whole blood, lymph, serum, plasma, urine, saliva, sputum, breath extract (meaning exhaled air captured in a solution), bone marrow, aspirates (nasal, lung, bronchial, tracheal), eye fluid, amniotic fluid, feces other bodily fluids and secretions, cells, and tissue specimens and dilutions of them. Any suitable biological sample ("biosample") can be used. For example, a biological sample can be a specimen obtained from a subject or can be derived from such a subject. A subject can provide a plurality of biological samples, including a solid biological sample, from for example, a biopsy or a tissue. In some cases, a sample can be a tissue section or cells that are placed in or adapted to tissue culture. A biological sample also can be a biological fluid such as urine, blood, plasma, serum, saliva, tears, cerebrospinal fluid, semen, bile, lymph, or mucus, or such a sample absorbed onto a paper or polymer substrate. A biological sample can be further fractionated, if desired, to a fraction containing particular cell types. In some embodiments, a sample can be a combination of samples from a subject (e.g., a combination of a tissue and fluid sample). In some cases, serum or plasma is obtained from the subject using techniques known in the art. For example, the sample is a liquid biopsy sample.

By "subject" or "individual" or "animal" or "patient" or "mammal," is meant any subject, for example a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on. Thus, in addition to being useful for human diagnostic and prognostic applications (e.g., diagnosing a disease in a human patient), the methods and devices of the present invention may also be useful for veterinary treatment of mammals, including companion animals.

In another aspect, provided herein is an article of manufacture such as a kit comprising materials and reagents that can be used to determine whether a subject has a *Mycobacterium* infection and to identify the *Mycobacterium* species. An article of manufacture can include, for example, one or more of antibody-modified solid supports (such as magnetic nanoparticles), antibodies, a MALDI-TOF matrix, and sampling materials (e.g., swabs, elution buffer). The article of manufacture can also include instructions for use in practicing a method for detecting and identifying a target antigen associated with infection by one or more *Mycobacterium* species or virus as provided herein.

In some cases, the kit comprises antibody-modified magnetic nanoparticles (NPs), wherein the antibodies bind specifically to a *Mycobacterium* or viral peptide. The *Mycobacterium* or viral peptide can have a sequence comprising TDAATLAQEAGNFER (SEQ ID NO:1), TQIDQVESTAGSLQGQWR (SEQ ID NO:2), WDATATELNNALQNLAR (SEQ ID NO:3), or TQIDQVESTAASLQAQWR (SEQ ID NO:4).

The kits described herein also can optionally include instructions for treating a patient based on the presence or absence of particular mycobacterial antigens in the patient's sample as described herein.

The terms "determining", "measuring", "evaluating", "assessing," "assaying," and "analyzing" can be used interchangeably herein to refer to any form of measurement and include determining if an element is present or not. These terms can include both quantitative and/or qualitative determinations. Assessing may be relative or absolute. "Assessing the presence of" includes determining the amount of something present, as well as determining whether it is present or absent.

In yet other embodiments, the instructions are not themselves present in the kit, but means for obtaining the instructions from a remote source, e.g., via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Identifying Target Antigens Associated with *Mycobacterium* Infection Selection of Tryptic Digested Peptides Segment from CFP-10

10-KDa culture filtrate proteins (CFP-10) are a series early secretory antigens from mycobacteria. Two CFP-10 segments from CFP-10 resulting from trypsin digestion (peptide 1594: TDAATLAQEAGNFER (SEQ ID NO: 1), MW: 1593.75, and peptide 2004: TQIDQVE-STAGSLQGQWR (SEQ ID NO: 2), MW:2003.98) were selected as targets. Peptide 2004 is found only in *Mycobacterium tuberculosis* complex subspecies (MTb, *M. africanum, M. bovis, M. canettii, M. caprae, M. orysis, M. Pinnipedii*, etc); while peptide 1594 can be found in CFP-10 secreted from *M. kansasii, M. marinum, M. ulcerans*, etc, as well as the *Mycobacterium tuberculosis* complexes. Therefore, by detecting presence or absence of two peptides in patient serum/plasma, we can distinguish the infection of *Mycobacterium tuberculosis* from infection of *M. kansasii* or *M. marinum*, and thus provide reasonable information for physicians to medically treat patients.

Synthesis of Monodispersed Iron Oxide $Fe_3O_4$ NPs

Monodispersed iron oxide nanoparticles ($Fe_3O_4$) were synthesized by solvothermal method using $FeCl_3 \cdot 7H_2O$ in ethylene glycol. After separation using a NdFeB magnet, the NPs were washed with ethanol.

After drying the washed NPs in vacuum overnight, the iron oxide NPs were ultrasonically washed with diluted HCl acid, followed by ethanol washing two additional times following by drying overnight under a vacuum.

Bioconjugation of Superparamagnetic Nanoparticles with Anti-1593 Antibody 10 mg of iron oxide NPs were dispersed in 800 uL of PBS buffer (pH: 8.3, adjusted by using 1.0 M NaOH), followed by adding in anti-1593 antibody, with an antibody/iron oxide ratio of 7 μg/mg. The mixture were incubated at room temperature for 3 hours. The antibody modified NPs were separated by DynaMag2. The NPs were dispersed in 1 mL of Tris-NaCl buffer (Tris: 0.2 M; NaCl 0.1 M; pH: 8.0) which is used to block excess epoxy group on the NPs surface. The mixture was incubated on Hula mixer for another 30 minutes (min.). The antibody modified NPs were separated by Dynamag2 and washed using deionized (DI) water trice. The final antibody modified NPs were dispersed in 500 μL DI water, and stored at −4 C for further use.

Bioconjugation of Superparamagnetic Nanoparticles with Anti-2004 Antibody 10 mg of iron oxide NPs were dispersed in 800 uL of PBS buffer (pH: 8.3, adjusted by using 1.0 M NaOH), followed by adding in anti-2004 antibody, with an antibody/iron oxide ratio of 7 μg/mg. The mixture were incubated at room temperature for 3 hours. The antibody modified NPs were separated by DynaMag2. The NPs were dispersed in 1 mL of Tris-NaCl buffer (Tris: 0.2 M; NaCl 0.1 M; pH: 8.0) which is used to block excess epoxy groups on the NPs surface. The mixture was incubated on Hula mixer for another 30 min. The antibody-modified NPs were separated by Dynamag2 and washed using deionized water trice. The final antibody-modified NPs were dispersed in 500 μL DI water, and stored at −4° C. for further use.

Tryptic Digestion of Patient's Serum/Plasma

To 100 μL of serum/plasma were added 400 μL of $NH_4HCO_3$ (100 mM), followed by 10 uL of trypsin (1 μg/μl). The mixture was digested at 20% microwave power for 5 min in water bath, the water was changed then repeat the microwave digestion for total 6 times. The mixture was incubated in a Hula mixer overnight at 37° C., and then centrifuged at 10,000 rcf for 5 min. The top clear supernatant was transferred to a new EP tube.

Capture of Peptide 1594 from CFP-10

Isotopic peptide 1603 (50 nM, 2 μL, total 100 fmol) was added into a trypsin digested plasma/serum sample. The sample was then vortexed for about 10 seconds to mix the sample. Five microliters of antibody-modified NPs were added to the mixture. The mixture was then incubated with Hula mixer for 3 hours at room temperature. The mixture was centrifuged for less than 10 seconds to retain liquid to the bottom of the tube. A magnet (or DynaMag 2) was used to separate supernatant from antibody-modified NPs. The NPs were washed 3 times in a washing buffer (50 mM Tris HCl, 150 mM NaCl, 0.2% triton x-100, pH: 7.4~7.5, approximately 80 μL/tube). Before the supernatant was removed, the tube was centrifuged for fewer than 10 seconds to keep liquid down to the tube bottom. 100 μL of DI water was used to wash the NPs. Wash the NPs until no bubbles are visible in the solution. The tube of washed NPs was centrifuged and NPs were separated with a magnet. Washed NPs were dispered in about 4 μL of DI water, and then spotted onto a MS 96-well MALDI plate (2 μL per spot). Onto each spot, α-Cyano-4-hydroxycinnamic acid (CHCA) (6 mg/mL in $CH_3CN/H_2O=6/4$ (v/v) in 0.1% TFA; 0.7 μL per spot) was spotted.

Capture of Peptide 1594 from CFP-10

Repeat procedure in example 5, in which isotopic peptide 2014 were used to replace isotopic peptide 1604.

Example 2: Immunoprecipitation and Targeted MS Detection of Proteolytic Peptides Derived from Human Pathogen in Serum/Plasma MS analyses have shown promise for improved understanding and diagnosis of several important human diseases, including tuberculosis, Alzheimer's, and multiple cancers, to name just a few. MS offers greater potential for the specific detection of a target biomarker than enzyme linked immunoassays (ELISAs), a common approach for clinical biomarker analysis. ELISA relies on the ability of two assay antibodies to recognize two distinct epitopes on a biomarker of interest. ELISA specificity is determined by the restriction of these epitopes to the target protein and by the fact that both regions must be recognized on the same protein to produce a positive signal.

LC-MS analyses can demonstrate greater specificity for a biomarker target, since they identify a target protein by the detection of target peptides with characteristic LC column elution times and charge-to-mass ratios. Multiple biomarker-derived peptides can be analyzed to provide improved detection specificity and the precursor ions of these peptides can also be fragmented in the MS collision cell to allow direct determination of their amino acid sequence. The SISCAPA (Stable Isotope Standards and Capture by Anti-Peptide Antibodies) approach allows immunoprecipitation (IP) of proteolytic peptides of interest using target peptide antibodies prior to MS analysis of selected MRM transitions.

At least five factors need to be considered in developing a specific IP-MS workflow targeting a pathogen-derived peptide. These are 1) the affinity and specificity of the antibody to the target peptide, 2) the selection criteria for the diagnostic pathogen-derived protein and its signature peptides, 3) the abundance of the protein of interest in the circulation and its limit of detection in the assay, 4) the ability to efficiently separate the target peptide from interfering factors, and 5) the MS signal quality of the selected peptide. Most IP-based assays focus on the first four factors.

SISCAPA employs an addition-only trypsin digestion approach capable of automation, employs a wash step with 3-((3-cholamidopropyl) dimethylammonio)-1-propanesulfonate (CHAPS) buffer to reduce nonspecific binding events, and optimizes the transition for each targeted peptide. Even with these efforts, low abundance peptide species are frequently under-sampled compared to high abundance peptide species and cannot be identified easily by the MS detector. More effort is still required to improve MS assay workflows to overcome this bias.

To address this issue, a new protocol was to produce and isolate target peptides from pathogen-derived proteins present in serum or plasma samples. This method employs a heat- and detergent-based denaturing step suitable for use with a wide range of sample volumes, and which allows a subsequent addition-only trypsin digestion procedure for the generation of target peptides.

This denaturation process involves a simple addition and mixing step with a solution containing phosphate buffered saline (PBS), triton X-100 and sodium dodecyl sulphate (SDS) to achieve a define final concentration, followed by a 5-minute heating step. This procedure has previously been employed to dissociate protein complexes, including antigen-antibody complexes generated as part of the normal immune response to a pathogen, prior to ELISA. This streamlined process also efficiently denatures sample proteins to enhance their efficient cleavage during a subsequent trypsin digestion step. Notably, this procedure does not use reducing and alkylation reagents employed in most proteomic sample processing workflows, and which can interfere with trypsin activity during a subsequent digestion step required to release target peptides for MS analysis. Eliminating this step may improve assay sensitivity if the target protein does not contain one or more disulfide bond, as is the case for many pathogen-derived biomarkers. Detergents present in the denaturing buffer can also suppress nonspecific binding during the antibody capture step.

The process used to conjugate an affinity molecule (e.g. a biomarker peptide-specific antibody) to an enrichment matrix is another significant consideration for methods based on affinity capture of target biomarkers. This process can determine the orientation of the affinity molecule on the matrix and thus its ability to interact with its biomarker target. It can also determine the stability of this interaction, which can directly and indirectly influence biomarker detection. Any significant loss of the affinity molecule during the binding step directly decreases the detection sensitivity for the target biomarker as it is not captured on the affinity matrix for subsequent analysis. Release of the affinity molecule during the elution phase, however, can reduce biomarker detection since its binding to the LC column may significantly reduce the binding capacity of the column for the biomarker peptides of interest.

Protein G is used for antibody capture in the SISCAPA workflow, since antibodies captured by interaction with protein G are situated so that both their antigen recognition sites are available for antigen binding. However, this is an affinity interaction, not a covalent interaction, and antibodies can dissociate during both the biomarker binding and elution steps. This is a particular concern during biomarker elution where conditions that disrupt the antigen-antibody complex may also disrupt the antibody-protein G complex, although potential was an issue not described in the SISCPA workflow. Epoxy functional group have also been used to bind biomarker-specific antibodies to an IP matrix. This is a covalent binding and thus there should be very little antibody loss during either the antigen binding or elution procedure, but antibodies are not bound to the affinity matrix in a defined orientation, which may reduce the number of antigen recognition sites available for antigen binding.

We selected protein G magnetic beads as the solid surface for our protocol, since this approach requires less antibody and is faster than the procedure employed to conjugate antibodies to an epoxy-functionalized matrix. However, to prevent the loss of LC column binding capacity through binding of antibody released during the elution of the target peptide, we employed StageTips to bind and antibodies present in the eluate and to capture any large particulates (e.g. capture bead contamination) present in this sample. This clean-up step, which is not part of the SISCAPA workflow, markedly increased the quality of the antibody-associated MS signal, as reflected the reduction in the number and intensity of off-target peaks in the LC spectrum. The ability to rapidly remove particulate contaminants prior to LC analysis is particularly important, since such particles can rapidly obstruct a LC column, leading to a pressure increase that can rapidly destroy it.

MS signal quality relies on the sequence of the target peptides and the parameter settings used for MS data acquisition, which influence MS scanning speed, mass resolution and sensitivity due to the fixed nature of the MS detector. Matrix assisted laser desorption ionization-time of flight MS (MALDI-TOF MS) permits rapid analysis since samples are not first separated on an LC column. MALDI-TOF MS is not sensitive to minor particulate carryover that can destroy LC columns, but is less sensitive than LC-MS and is subject to reduced specificity by contaminating peptides.

LC-based targeted MS workflows offer additional separation of peptides in the upstream of MS analysis, which improves assay specificity. More importantly, optimum MRM transitions of the targeted peptide ion and standardized data processing and interpretation algorithm provide confirmation of its source protein in the analyzed serum sample. We have developed a biomarker specific protocol to optimize the detection of these transitions to improve detection specificity.

Figures 6A, 6B, 6C:
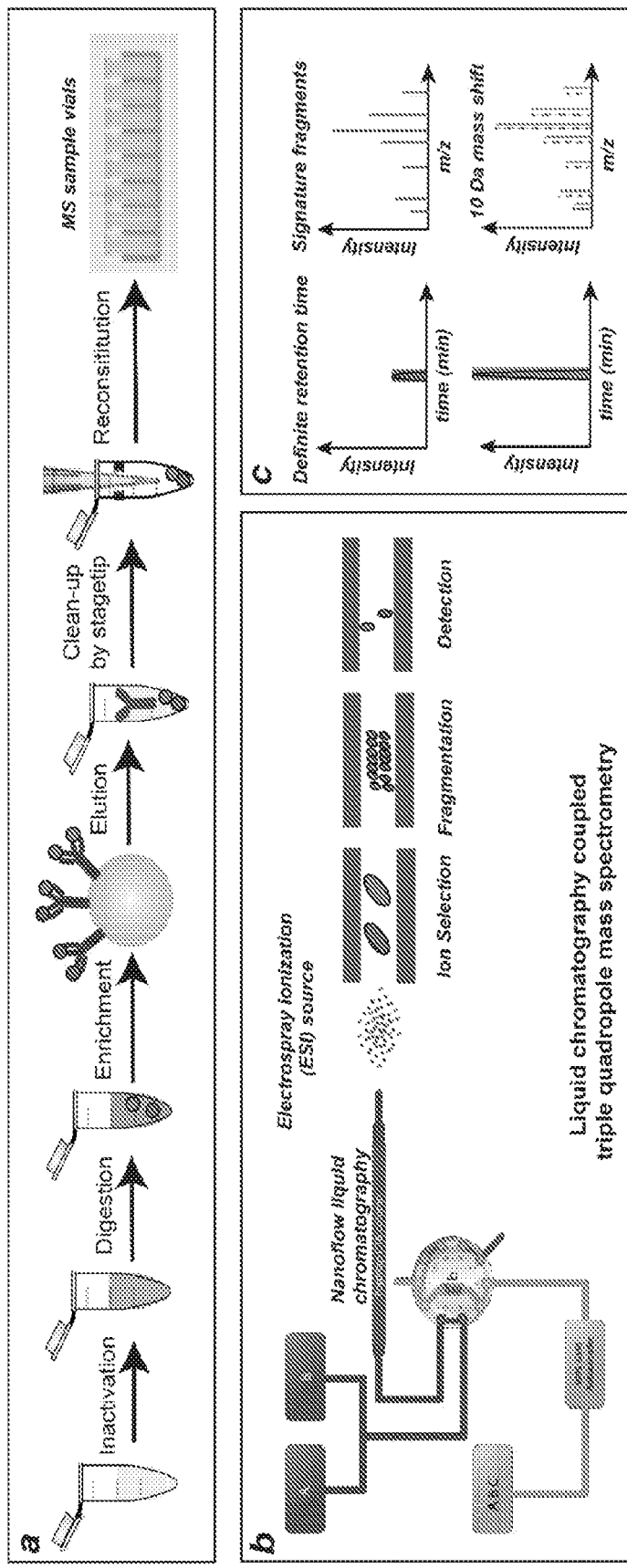
FIGS. 6A-6C show the workflow for MRM-MS detection of CFP-10 peptide in serum.

By changing the denaturing buffer, addition of a clean-up step, selection of optimum MRM transitions and better interpreting MS signal, this workflow showed an improved sensitivity and specificity in clinical samples Sample Pre-Treatment Using a Protein Denaturing Buffer Serum samples are diluted 10× with denaturing buffer, as this was determined to be the optimum dilution for subsequent trypsin digestion and IP. Standard assays utilize 100 µL of serum that is mixed with 900 µL of denaturing buffer in a 1.5 mL of centrifuge tube, which is then sealed and incubated for 5 min in a 100° C. heat block. Caution! When moving the samples from heat block, it is recommended that the assay operator wear thermal insulation gloves. The total volume of serum processed for a sample analysis can be scaled to comply with assay requirements reflecting to serum concentration range of the biomarker of interest. Scaled sample volumes should be processed in 1 mL total aliquots in 1.5 mL centrifuge tubes to ensure consistent heat transfer, which would differ if scaled sample volumes are processed in larger tubes. For example, in an assay for serum detection of the Mtb antigen CFP10, which used 200 µL of serum, two aliquots were prepared for each sample. The schematic present in FIGS. 6A-6C depicts an overview of this workflow.

After this 5 min denaturation step, samples are transferred to a 25° C. Branson 2800 sonicating water bath (2.84 L) and sonicated for 5 minutes at 40 KHz, then transferred to a suitable centrifuge tube rack to stabilize the tubes for subsequent sample processing steps.

After the sonication/cooling step, the tube is pulse-centrifuged (SCILOGEX D1008, 5 s at 1,340 g and 25° C.) to spin down any liquid trapped in its cap and 20 µL of 1M Tris (hydroxymethyl) aminomethane buffer (pH 10) is added to 1 mL of the denatured serum sample to adjust its pH to ~8.5. This sample is then vortexed to thoroughly mix its contents and pulse-centrifuged again.

Protein Digestion

After pH adjustment, denatured serum samples are mixed with 10 µg/mL of sequence grade trypsin, placed on a Hulamixer® and incubated at 20 RPM for 16 hours at 37° C.

After overnight digestion, samples are adjusted to pH ~7 by the addition of 10 µL of 10% trifluoroacetic acid (TFA), vortexed to clarify the solution of precipitates that may form after adding TFA, and then pulse-centrifuged as above to spin down any liquid present in the tube lid.

Binding of Peptide-Specific Antibody to Protein G Magnetic Beads

The optimum amounts of magnetic beads and antibody vary among different peptide targets. For the antibody we generated to CFP-10 peptide TDAATLAQEAGNFER (SEQ ID NO: 1), these parameters were determined to be 3 mg of protein G-conjugated magnetic beads and 50 of the CFP-10 peptide-specific antibody. Magnetic beads need to be washed with 200 µL of PBS one time to remove any buffer remnant. Beads and antibody are incubated for 1 hour at 25° C. in 400 µL of binding buffer on Hulamixer® set to 20 RPM. After binding, the beads are washed 2× with 200 µL of binding buffer to remove unbound antibody.

Antibody-conjugated beads are suspended in 400 µL of binding buffer and stored at 4° C. for <2 weeks in order to maintain antibody activity.

Immunoprecipitation (IP) of the Target Peptide

In order to capture CFP-10 peptide TDAATLAQEAGNFER (SEQ ID NO: 1) from serum, 100 µL of trypsin-digested serum is mixed with 0.15 mg of antibody-conjugated magnetic beads at 25° C. on a Hulamixer® set to 20 RPM. This amount of beads/antibody was determined empirically by assessing the MS signal intensity of the target peptide upon analysis of a serum sample spiked with a set amount of CFP-10 protein. The optimum amount of beads/antibody required to analyze another peptide must be determined by this method prior to testing clinical samples.

The beads are combined from two aliquot and suspended in 200 µL of PBS buffer. The beads are transferred into a new centrifuge tube and washed 2× with 200 µL of PBS buffer, and then washed 1× with 100 µL of LC-grade water.

Captured peptides are eluted by incubating the beads with 100 µL of 1% formic acid at 25° C. for 30 minutes on a Hulamixer® set to 20 RPM.

After incubation, microcentrifuge tubes containing the capture beads in elution buffer are transferred to a rare earth magnet and incubated for 20 minutes at 25° C. to allow complete capture of the antigen-depleted beads on the magnet before transfer of the eluate.

Clean-Up of IP Eluent by StageTips

StageTips packed with a C8 disk are conditioned by the addition of 50 µL of 0.1% TFA in acetonitrile followed by 50 µL of 0.1% TFA in water. Added buffer is remove by centrifuging tips placed in adaptor-filled centrifuge tubes for 3 minutes at 2,000 g and 25° C. Caution! Due to the changed height of tubes containing StageTips, the rotor lid cannot be attached during this centrifugation step. Centrifuge tubes must also be placed into the rotor in an ordered fashion so that their will not contact the inner wall of the centrifuge.

After the conditioning process described above, StageTips are loaded with the IP eluent and centrifuged using the same conditions as in step 12.

StageTips are then loaded with 50 µL of 0.1% TFA in acetonitrile and centrifuged under as in step 12 to permit completed recovery of the target peptide.

StageTips are removed from these tubes and the StageTip elutate is evaporated under vacuum, and then reconstituted in 1% formic acid.

After centrifuging the reconstituted samples at 25° C. and 21,000 g for 15 minutes to remove any residual particulates that might escape the StageTip filter, the supernatant is transfer into an MS sample vial. Caution! Prevent contacting the bottom of tube and picking up any invisible particle by leaving one µL of solution.

MRM Analysis of the Targeted Peptide

To set up the LC and MS methods for a targeted peptide, it is better to prepare a various concentrations of internal standard of that peptide solutions and get the gradient of organic solvent and collision energy optimized based on the MS signal of these solutions. The gradient of organic solvent and MS parameters used here is listed in Document for LC-MRM method.

After loading the sample onto LC column, the MS spectra are collected using the optimum MS method setting.

MS Data Analysis Using Skyline

MRM data can be processed by a number of available software tools. Based on the design of these tools, they may require the MS/MS spectra of targeted peptide as a reference in order to build a spectral library for peak recognition and evaluation. Here we recommend Skyline as the tool of MRM data processing, due to its compatibility with multiple MS instruments. Skyline needs MS/MS spectrum of targeted CFP-10 peptide to build the library. In this regard, a tryptic digest of Mtb culture filtrates was analyzed by LC-MS/MS and the MS/MS spectra were searched against Mtb protein sequence database through PEAKS Studio. One MS/MS spectrum was identified as the targeted CFP-10 peptide after search and was imported into Skyline. Skyline utilizes it to construct the spectral library.

Algorithm Development for Data Interpretation

Figure 7A:
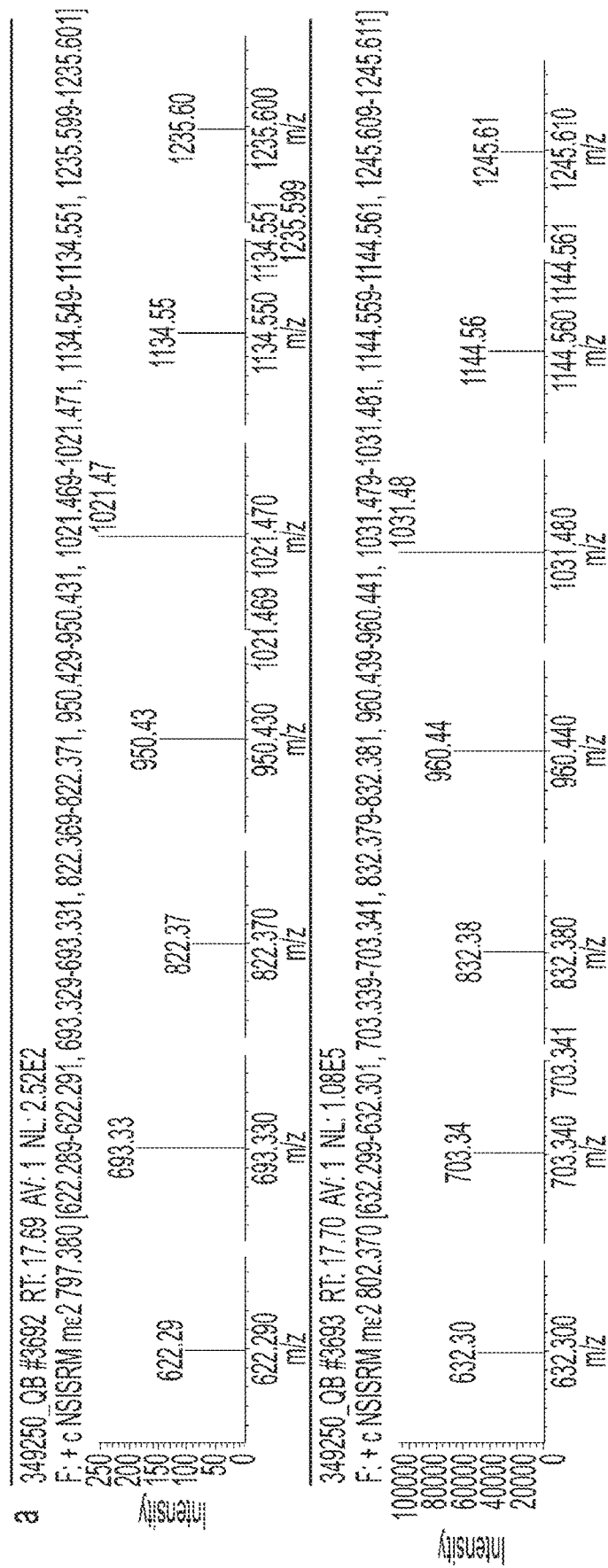
FIGS. 7A-7C show representative MS signal from a positive clinical sample.
Figure 7B:
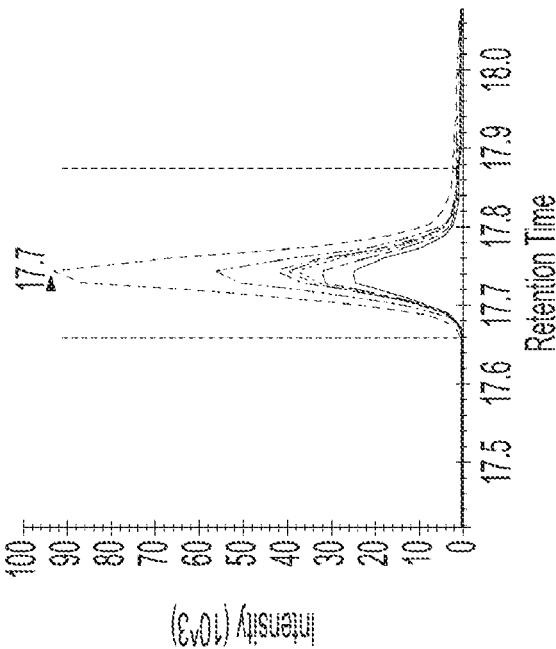
Figure 7C:
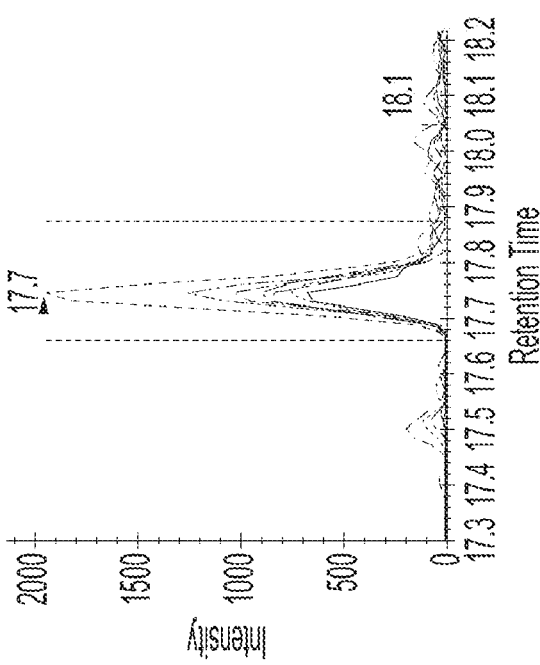

Using the Thermo Xcalibur software, the MRM signal can be reviewed in a transition fashion (FIG. 7a). However, it needs further evaluation of the MS signal quality in order to interpret the result appropriately. When checking the peaks in the ion chromatography, there are numerous peaks which are formed by some transitions (FIG. 7b). The important task is to define the unique peak that belongs to the targeted CFP-10 peptide (light peptide). Since the internal standard (IS) peptide (heavy peptide) was spiked into the sample before IP (FIGS. 6A-6C), we can observe the peak of heavy peptide in a definitive retention time among all samples.

By setting the retention time of heavy IS peptide as a reference, many interfering peaks can be directly filtered out of the MS spectrum. However, some false positive peaks caused by instrumental or chemical noise cannot be filtered out by retention time, since this noise is stochastically distributed across the entire LC gradient.

To evaluate the validity of the target MS signal, it is therefore important to evaluate the relative intensities of each fragment that appears to derive from the target peptide and its matching IS peptide and calculate the similarity between the light (serum) and heavy (IS) peptide fragments. Similar light and heavy peptide signals provide greater confident for the positive detection of the target biomarker signal. The Skyline program returns a dot product (rdotp) to reflect this similarity, where an rdtop value equal to 1 denotes identical signal.

Adjusting the rdotp cutoff produces a corresponding change in the area under the curve (AUC) of the receiver operating characteristic (ROC) curve, which denotes the ability to distinguish positive from false-positive signals. However, the accuracy of this analysis heavily depends on the accuracy of the reference method, which is not well established in tuberculosis diagnosis. To discriminate possible Mtb-infected patients from subjects without TB, more parameters are needed to interpret the MS signal. The number of observed fragments from a target peptide, and their intensities, are useful indicators.

The baseline of the background noise in an MS spectrum must be subtracted from target peaks to determine if these peaks represent artifacts or real signal. Skyline performs this task before exporting the peak area, so values greater than zero can be interpreted as positive signal for that fragment ion.

When multiple fragments of the target peptide are observed, each fragment can theoretically function as a surrogate signal for the targeted peptide ion. Each fragment can be evaluated through SRM collider, after setting the human proteome as background, under the assumption that fragments with fewer interfering fragments from the human proteome may be more specific indicators of valid CFP-10 peptide signal. We restricted ion types to b/y ions and within the 200-1,500 m/z range that represent the best resolution region of the MRM-MS instrument. This analysis indicated that there were 24 fragments of our target peptide that were suitable for MRM detection. In practice, however, only some of these ions can be observed in the MS spectrum due to incomplete fragmentation.

Figure 8B:
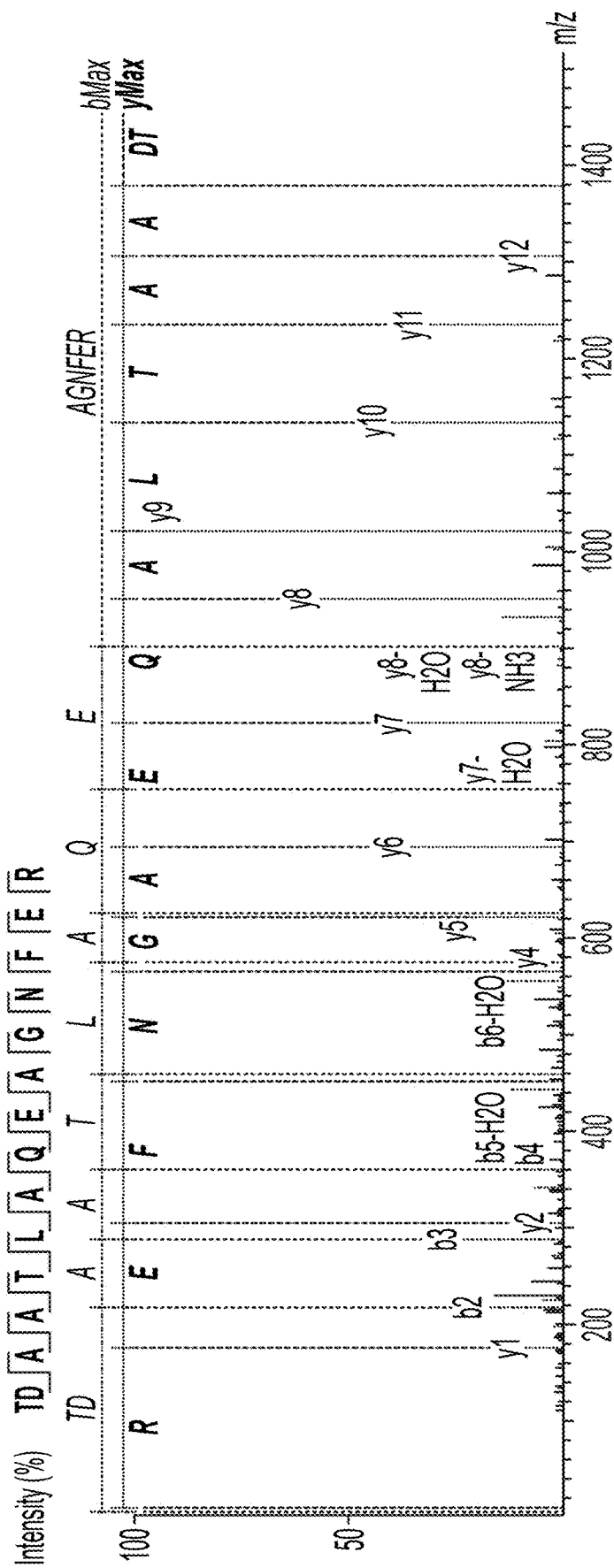
Figure 8C:
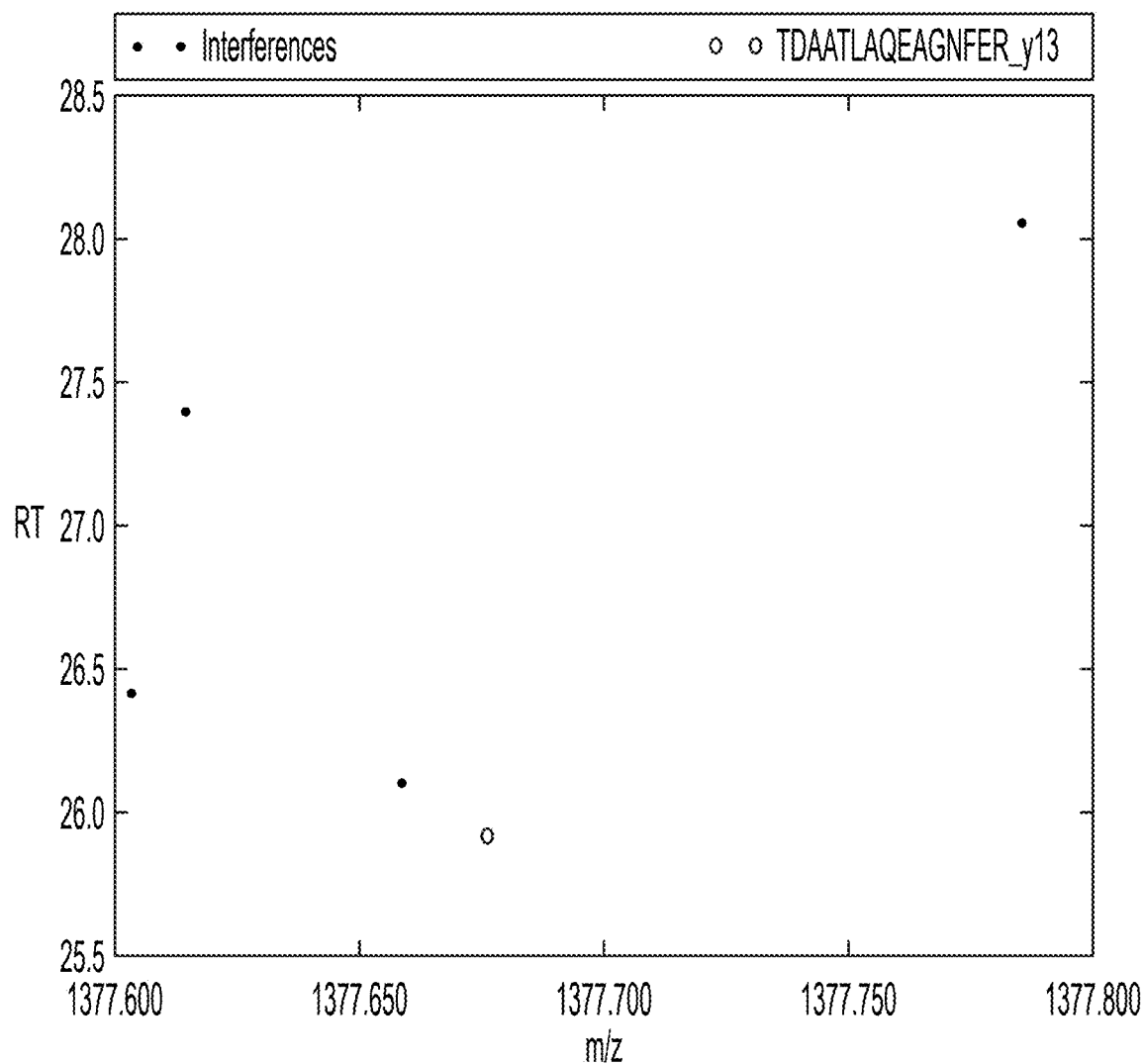
Figure 9:
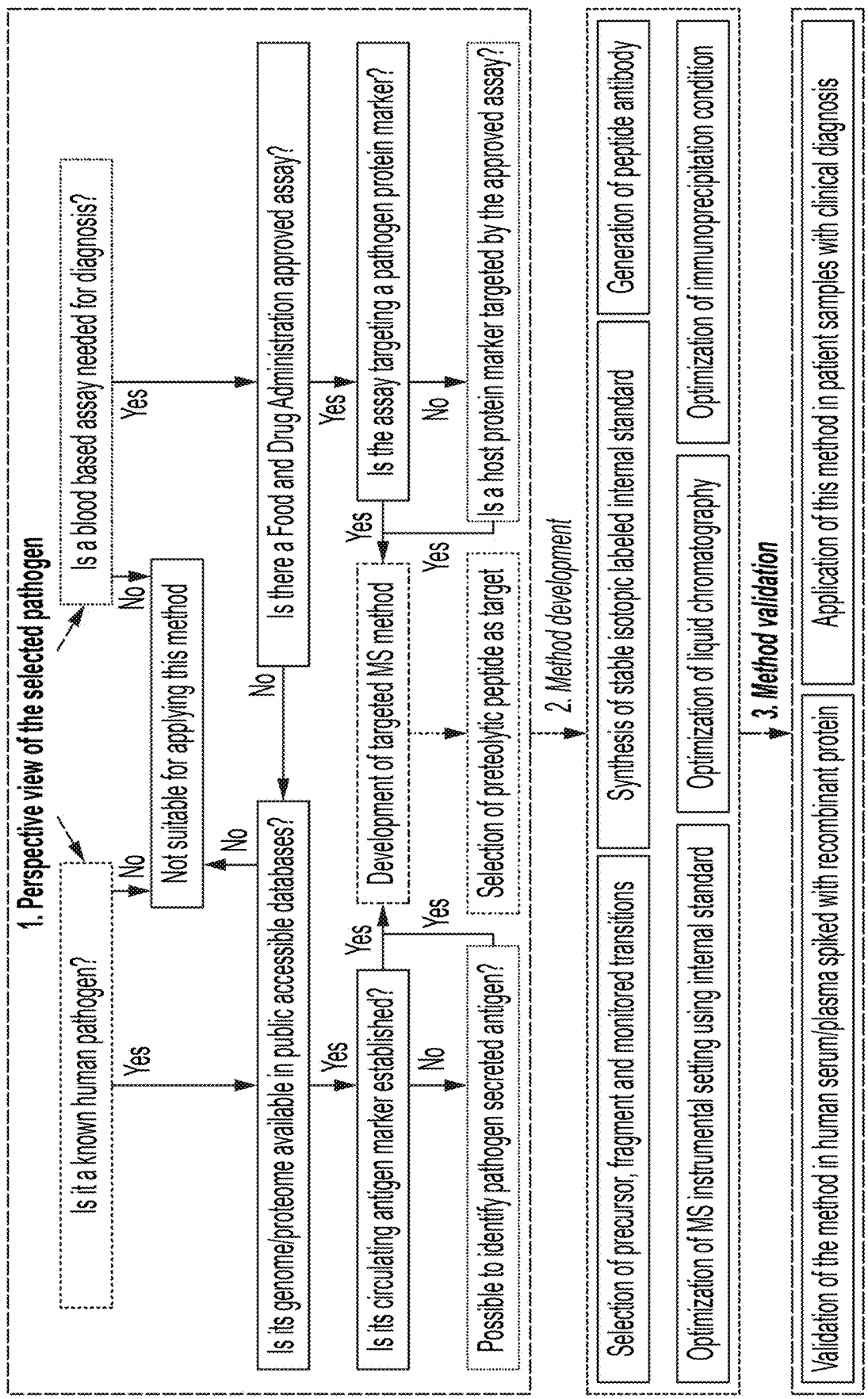
FIG. 9 presents Scheme 1 for pathogen selection, method development, and method validation.

As shown in FIGS. 8A-8C, y9 is the most intense fragment ion produced by the CFP-10 peptide TDAATLAQEAGNFER (SEQ ID NO: 1), and this ion peak has 100-fold greater intensity than that of y13. Some fragments (e.g, y14 and y3) were not found on the MS/MS spectrum by the peak picking and scoring algorithm. After evaluation by SRM Collider, there are more interferences with y9 than that with y13 (FIG. 8c). However, most of the interferences of y9 are distant in their retention times, which means they are quite different in their hydrophobicity and can be easily separated by the nanoflow LC employed in this analysis. Further, only five of the examples matching the interference peptide sequence (Table 3-Exhibit B) did not have a carbamidomethylated cysteine, which was present in the remaining seven peptides.

This example indicates an advantage of our modified workflow, since its omission of the standard reduction/akylation step, removes 60% of the interference for y9 (7 of 12 instances). The y9 ion is the most intense fragment produced by our target CFP-10 peptide and is highly specific for it, and therefore represent an optimal diagnostic fragment. The detection specificity for the CFP-10 target peptide can be further increased by the selection of additional product ions using the same approach.

We have developed an algorithm of how to evaluate MRM transitions and interpret their MS signal as shown in Box 1. It is based on the intensities and uniqueness of observed MRM transitions as well as their rdotp values. This approach indicates a clear rationale for evaluating whether or not an MS signal for a target peptide (e.g. our CFP-10 target peptide) can be called a true positive based on its score from this approach.

Algorithm Optimization Based on ROCC

A training set and a validation set of MS signals from two clinical cohorts are used to further improve the algorithm for data interpretation (Box 1).

Table 2 shows MRM transition list for Mtb antigens.

| Compound | SEQ ID NO: | Start Time (min) | End Time (min) | Polarity | Precursor (m/z) | Product (m/z) | Collision Energy (V) |
|---|---|---|---|---|---|---|---|
| LYASAEATDSK_Mpt32 | 24 | 9.4 | 11.4 | Positive | 578.28 | 650.3 | 30 |
| LYASAEATDSK_Mpt32 | 24 | 9.4 | 11.4 | Positive | 578.28 | 721.34 | 30 |
| LYASAEATDSK_Mpt32 | 24 | 9.4 | 11.4 | Positive | 578.28 | 808.37 | 30 |
| LYASAEATDSK_Mpt32 | 24 | 9.4 | 11.4 | Positive | 578.28 | 879.41 | 30 |
| LYASAEATDSK_Mpt32 | 24 | 9.4 | 11.4 | Positive | 578.28 | 1042.47 | 30 |
| NDPTQQIPK_Ag85b | 25 | 13.5 | 15.5 | Positive | 520.77 | 230.08 | 30 |
| NDPTQQIPK_Ag85b | 25 | 13.5 | 15.5 | Positive | 520.77 | 244.17 | 30 |
| NDPTQQIPK_Ag85b | 25 | 13.5 | 15.5 | Positive | 520.77 | 406.24 | 30 |
| NDPTQQIPK_Ag85b | 25 | 13.5 | 15.5 | Positive | 520.77 | 613.37 | 30 |

-continued

| Compound | SEQ ID NO: | Start Time (min) | End Time (min) | Polarity | Precursor (m/z) | Product (m/z) | Collision Energy (V) |
|---|---|---|---|---|---|---|---|
| NDPTQQIPK_Ag85b | 25 | 13.5 | 15.5 | Positive | 520.77 | 714.41 | 30 |
| NDPTQQIPK_Ag85b | 25 | 13.5 | 15.5 | Positive | 520.77 | 811.47 | 30 |
| EsxN_AQAASLEAEHQAIVR | 26 | 15.3 | 17.3 | Positive | 797.42 | 697.87 | 30 |
| EsxN_AQAASLEAEHQAIVR | 26 | 15.3 | 17.3 | Positive | 797.42 | 723.43 | 30 |
| EsxN_AQAASLEAEHQAIVR | 26 | 15.3 | 17.3 | Positive | 797.42 | 923.51 | 30 |
| EsxN_AQAASLEAEHQAIVR | 26 | 15.3 | 17.3 | Positive | 797.42 | 1052.55 | 30 |
| EsxN_AQAASLEAEHQAIVR | 26 | 15.3 | 17.3 | Positive | 797.42 | 1165.63 | 30 |
| FLSAATSSTPR_Mpt64 | 27 | 15.4 | 17.4 | Positive | 569.3 | 547.28 | 30 |
| FLSAATSSTPR_Mpt64 | 27 | 15.4 | 17.4 | Positive | 569.3 | 648.33 | 30 |
| FLSAATSSTPR_Mpt64 | 27 | 15.4 | 17.4 | Positive | 569.3 | 719.37 | 30 |
| FLSAATSSTPR_Mpt64 | 27 | 15.4 | 17.4 | Positive | 569.3 | 790.41 | 30 |
| FLSAATSSTPR_Mpt64 | 27 | 15.4 | 17.4 | Positive | 569.3 | 877.44 | 30 |
| VEYVDVR_GlnA | 28 | 15.8 | 17.8 | Positive | 440.23 | 274.19 | 30 |
| VEYVDVR_GlnA | 28 | 15.8 | 17.8 | Positive | 440.23 | 389.21 | 30 |
| VEYVDVR_GlnA | 28 | 15.8 | 17.8 | Positive | 440.23 | 488.28 | 30 |
| VEYVDVR_GlnA | 28 | 15.8 | 17.8 | Positive | 440.23 | 651.35 | 30 |
| VEYVDVR_GlnA | 28 | 15.8 | 17.8 | Positive | 440.23 | 780.39 | 30 |
| IESENPDAVANVQAR_AcpM | 29 | 16.4 | 18.4 | Positive | 806.9 | 658.36 | 30 |
| IESENPDAVANVQAR_AcpM | 29 | 16.4 | 18.4 | Positive | 806.9 | 757.43 | 30 |
| IESENPDAVANVQAR_AcpM | 29 | 16.4 | 18.4 | Positive | 806.9 | 828.47 | 30 |
| IESENPDAVANVQAR_AcpM | 29 | 16.4 | 18.4 | Positive | 806.9 | 943.5 | 30 |
| IESENPDAVANVQAR_AcpM | 29 | 16.4 | 18.4 | Positive | 806.9 | 1040.55 | 30 |
| IESENPDAVANVQAR_AcpM | 29 | 16.4 | 18.4 | Positive | 806.9 | 1154.6 | 30 |
| GVTEETTTGVLR_SahH | 30 | 17.05 | 19.05 | Positive | 631.83 | 545.27 | 30 |
| GVTEETTTGVLR_SahH | 30 | 17.05 | 19.05 | Positive | 631.83 | 747.44 | 30 |
| GVTEETTTGVLR_SahH | 30 | 17.05 | 19.05 | Positive | 631.83 | 876.48 | 30 |
| GVTEETTTGVLR_SahH | 30 | 17.05 | 19.05 | Positive | 631.83 | 1005.52 | 30 |
| GVTEETTTGVLR_SahH | 30 | 17.05 | 19.05 | Positive | 631.83 | 1106.57 | 30 |
| LEEENPEAAQALR_AcpM | 31 | 17.2 | 19.2 | Positive | 735.365 | 629.37 | 30 |
| LEEENPEAAQALR_AcpM | 31 | 17.2 | 19.2 | Positive | 735.365 | 758.415 | 30 |
| LEEENPEAAQALR_AcpM | 31 | 17.2 | 19.2 | Positive | 735.365 | 855.47 | 30 |
| LEEENPEAAQALR_AcpM | 31 | 17.2 | 19.2 | Positive | 735.365 | 969.51 | 30 |
| LEEENPEAAQALR_AcpM | 31 | 17.2 | 19.2 | Positive | 735.365 | 1098.55 | 30 |
| LEEENPEAAQALR_AcpM | 31 | 17.2 | 19.2 | Positive | 735.365 | 1227.6 | 30 |
| NQAETLVYQTEK_DnaK | 32 | 17.3 | 19.3 | Positive | 712.357 | 668.33 | 30 |
| NQAETLVYQTEK_DnaK | 32 | 17.3 | 19.3 | Positive | 712.357 | 767.39 | 30 |
| NQAETLVYQTEK_DnaK | 32 | 17.3 | 19.3 | Positive | 712.357 | 981.53 | 30 |

-continued

| Compound | SEQ ID NO: | Start Time (min) | End Time (min) | Polarity | Precursor (m/z) | Product (m/z) | Collision Energy (V) |
|---|---|---|---|---|---|---|---|
| NQAETLVYQTEK_DnaK | 32 | 17.3 | 19.3 | Positive | 712.357 | 1110.57 | 30 |
| NQAETLVYQTEK_DnaK | 32 | 17.3 | 19.3 | Positive | 712.357 | 1181.6 | 30 |
| GSLVEGGIGGTEAR_cfp2 | 33 | 17.6 | 19.6 | Positive | 651.84 | 590.29 | 30 |
| GSLVEGGIGGTEAR_cfp2 | 33 | 17.6 | 19.6 | Positive | 651.84 | 703.37 | 30 |
| GSLVEGGIGGTEAR_cfp2 | 33 | 17.6 | 19.6 | Positive | 651.84 | 760.39 | 30 |
| GSLVEGGIGGTEAR_cfp2 | 33 | 17.6 | 19.6 | Positive | 651.84 | 817.42 | 30 |
| GSLVEGGIGGTEAR_cfp2 | 33 | 17.6 | 19.6 | Positive | 651.84 | 946.46 | 30 |
| EsxO_AQAGLLEAEHQAIVR | 34 | 19.8 | 21.8 | Positive | 803.44 | 703.9 | 30 |
| EsxO_AQAGLLEAEHQAIVR | 34 | 19.8 | 21.8 | Positive | 803.44 | 723.43 | 30 |
| EsxO_AQAGLLEAEHQAIVR | 34 | 19.8 | 21.8 | Positive | 803.44 | 852.47 | 30 |
| EsxO_AQAGLLEAEHQAIVR | 34 | 19.8 | 21.8 | Positive | 803.44 | 923.51 | 30 |
| EsxO_AQAGLLEAEHQAIVR | 34 | 19.8 | 21.8 | Positive | 803.44 | 1052.55 | 30 |
| EsxO_AQAGLLEAEHQAIVR | 34 | 19.8 | 21.8 | Positive | 803.44 | 1165.63 | 30 |
| SLADPNVSFANK_cfp2 | 35 | 19.9 | 21.9 | Positive | 631.82 | 479.26 | 30 |
| SLADPNVSFANK_cfp2 | 35 | 19.9 | 21.9 | Positive | 631.82 | 566.29 | 30 |
| SLADPNVSFANK_cfp2 | 35 | 19.9 | 21.9 | Positive | 631.82 | 665.36 | 30 |
| SLADPNVSFANK_cfp2 | 35 | 19.9 | 21.9 | Positive | 631.82 | 876.46 | 30 |
| SLADPNVSFANK_cfp2 | 35 | 19.9 | 21.9 | Positive | 631.82 | 1062.52 | 30 |
| IALFGNHAPK_PpiA | 36 | 20 | 22 | Positive | 534.3 | 452.26 | 30 |
| IALFGNHAPK_PpiA | 36 | 20 | 22 | Positive | 534.3 | 566.3 | 30 |
| IALFGNHAPK_PpiA | 36 | 20 | 22 | Positive | 534.3 | 623.33 | 30 |
| IALFGNHAPK_PpiA | 36 | 20 | 22 | Positive | 534.3 | 770.39 | 30 |
| IALFGNHAPK_PpiA | 36 | 20 | 22 | Positive | 534.3 | 883.48 | 30 |
| cfp10_QELDEISTNIR | 37 | 20.65 | 22.65 | Positive | 659.34 | 503.29 | 30 |
| cfp10_QELDEISTNIR | 37 | 20.65 | 22.65 | Positive | 659.34 | 590.33 | 30 |
| cfp10_QELDEISTNIR | 37 | 20.65 | 22.65 | Positive | 659.34 | 703.41 | 30 |
| cfp10_QELDEISTNIR | 37 | 20.65 | 22.65 | Positive | 659.34 | 832.45 | 30 |
| cfp10_QELDEISTNIR | 37 | 20.65 | 22.65 | Positive | 659.34 | 947.48 | 30 |
| cfp10_QELDEISTNIR | 37 | 20.65 | 22.65 | Positive | 659.34 | 1060.56 | 30 |
| SLENYIAQTR_Mpt64 | 38 | 20.7 | 22.7 | Positive | 597.81 | 475.26 | 30 |
| SLENYIAQTR_Mpt64 | 38 | 20.7 | 22.7 | Positive | 597.81 | 588.35 | 30 |
| SLENYIAQTR_Mpt64 | 38 | 20.7 | 22.7 | Positive | 597.81 | 751.41 | 30 |
| SLENYIAQTR_Mpt64 | 38 | 20.7 | 22.7 | Positive | 597.81 | 865.45 | 30 |
| SLENYIAQTR_Mpt64 | 38 | 20.7 | 22.7 | Positive | 597.81 | 994.5 | 30 |
| TTGDPPFPGQPPPVANDTR_Mpt32 | 39 | 21.4 | 23.4 | Positive | 655.32 | 483.75 | 30 |
| TTGDPPFPGQPPPVANDTR_Mpt32 | 39 | 21.4 | 23.4 | Positive | 655.32 | 772.39 | 30 |
| TTGDPPFPGQPPPVANDTR_Mpt32 | 39 | 21.4 | 23.4 | Positive | 655.32 | 795.41 | 30 |
| TTGDPPFPGQPPPVANDTR_Mpt32 | 39 | 21.4 | 23.4 | Positive | 655.32 | 869.45 | 30 |

-continued

| Compound | SEQ ID NO: | Start Time (min) | End Time (min) | Polarity | Precursor (m/z) | Product (m/z) | Collision Energy (V) |
|---|---|---|---|---|---|---|---|
| TTGDPPFPGQPPPVANDTR_Mpt32 | 39 | 21.4 | 23.4 | Positive | 655.32 | 966.5 | 30 |
| TTGDPPFPGQPPPVANDTR_Mpt32 | 39 | 21.4 | 23.4 | Positive | 655.32 | 998.46 | 30 |
| IPDEDLAGLR_AcpM | 40 | 21.6 | 23.6 | Positive | 549.79 | 493.25 | 30 |
| IPDEDLAGLR_AcpM | 40 | 21.6 | 23.6 | Positive | 549.79 | 529.35 | 30 |
| IPDEDLAGLR_AcpM | 40 | 21.6 | 23.6 | Positive | 549.79 | 644.37 | 30 |
| IPDEDLAGLR_AcpM | 40 | 21.6 | 23.6 | Positive | 549.79 | 773.415 | 30 |
| IPDEDLAGLR_AcpM | 40 | 21.6 | 23.6 | Positive | 549.79 | 888.44 | 30 |
| IPDEDLAGLR_AcpM | 40 | 21.6 | 23.6 | Positive | 549.79 | 985.49 | 30 |
| TVANFVGLAQGTK_PpiA | 41 | 23.2 | 25.2 | Positive | 653.36 | 504.28 | 30 |
| TVANFVGLAQGTK_PpiA | 41 | 23.2 | 25.2 | Positive | 653.36 | 674.38 | 30 |
| TVANFVGLAQGTK_PpiA | 41 | 23.2 | 25.2 | Positive | 653.36 | 773.44 | 30 |
| TVANFVGLAQGTK_PpiA | 41 | 23.2 | 25.2 | Positive | 653.36 | 1034.56 | 30 |
| TVANFVGLAQGTK_PpiA | 41 | 23.2 | 25.2 | Positive | 653.36 | 1105.6 | 30 |
| LVFLTGPK_GarA | 42 | 23.5 | 25.5 | Positive | 437.77 | 301.19 | 30 |
| LVFLTGPK_GarA | 42 | 23.5 | 25.5 | Positive | 437.77 | 402.22 | 30 |
| LVFLTGPK_GarA | 42 | 23.5 | 25.5 | Positive | 437.77 | 515.32 | 30 |
| LVFLTGPK_GarA | 42 | 23.5 | 25.5 | Positive | 437.77 | 662.39 | 30 |
| LVFLTGPK_GarA | 42 | 23.5 | 25.5 | Positive | 437.77 | 761.46 | 30 |
| MPAVTDLVK_DnaK | 43 | 23.5 | 25.5 | Positive | 487.27 | 421.75 | 30 |
| MPAVTDLVK_DnaK | 43 | 23.5 | 25.5 | Positive | 487.27 | 575.34 | 30 |
| MPAVTDLVK_DnaK | 43 | 23.5 | 25.5 | Positive | 487.27 | 674.41 | 30 |
| MPAVTDLVK_DnaK | 43 | 23.5 | 25.5 | Positive | 487.27 | 745.45 | 30 |
| MPAVTDLVK_DnaK | 43 | 23.5 | 25.5 | Positive | 487.27 | 842.5 | 30 |
| AFDWDQAYR_Mpt64 | 44 | 24 | 26 | Positive | 586.26 | 409.22 | 30 |
| AFDWDQAYR_Mpt64 | 44 | 24 | 26 | Positive | 586.26 | 537.28 | 30 |
| AFDWDQAYR_Mpt64 | 44 | 24 | 26 | Positive | 586.26 | 652.3 | 30 |
| AFDWDQAYR_Mpt64 | 44 | 24 | 26 | Positive | 586.26 | 838.38 | 30 |
| AFDWDQAYR_Mpt64 | 44 | 24 | 26 | Positive | 586.26 | 953.41 | 30 |
| TVGDVVAYIQK_AcpM | 45 | 24 | 26 | Positive | 596.832 | 551.32 | 30 |
| TVGDVVAYIQK_AcpM | 45 | 24 | 26 | Positive | 596.832 | 622.36 | 30 |
| TVGDVVAYIQK_AcpM | 45 | 24 | 26 | Positive | 596.832 | 721.42 | 30 |
| TVGDVVAYIQK_AcpM | 45 | 24 | 26 | Positive | 596.832 | 820.49 | 30 |
| TVGDVVAYIQK_AcpM | 45 | 24 | 26 | Positive | 596.832 | 935.52 | 30 |
| TVGDVVAYIQK_AcpM | 45 | 24 | 26 | Positive | 596.832 | 992.54 | 30 |
| cfp10_TDAATLAQEAGNFER | 46 | 24.3 | 26.3 | Positive | 797.379 | 693.33 | 30 |
| cfp10_TDAATLAQEAGNFER | 46 | 24.3 | 26.3 | Positive | 797.379 | 822.37 | 30 |
| cfp10_TDAATLAQEAGNFER | 46 | 24.3 | 26.3 | Positive | 797.379 | 950.43 | 30 |

-continued

| Compound | SEQ ID NO: | Start Time (min) | End Time (min) | Polarity | Precursor (m/z) | Product (m/z) | Collision Energy (V) |
|---|---|---|---|---|---|---|---|
| cfp10_TDAATLAQEAGNFER | 46 | 24.3 | 26.3 | Positive | 797.379 | 1021.47 | 30 |
| cfp10_TDAATLAQEAGNFER | 46 | 24.3 | 26.3 | Positive | 797.379 | 1134.55 | 30 |
| cfp10_TDAATLAQEAGNFER | 46 | 24.3 | 26.3 | Positive | 797.379 | 1235.6 | 30 |
| VVDWLVDK_DnaK | 47 | 24.5 | 26.5 | Positive | 487.27 | 361.21 | 30 |
| VVDWLVDK_DnaK | 47 | 24.5 | 26.5 | Positive | 487.27 | 474.29 | 30 |
| VVDWLVDK_DnaK | 47 | 24.5 | 26.5 | Positive | 487.27 | 660.37 | 30 |
| VVDWLVDK_DnaK | 47 | 24.5 | 26.5 | Positive | 487.27 | 775.4 | 30 |
| VVDWLVDK_DnaK | 47 | 24.5 | 26.5 | Positive | 487.27 | 874.47 | 30 |
| cfp10_TQIDQVESTAGSLQGQWR | 48 | 25.3 | 27.3 | Positive | 1002.493 | 787.42 | 30 |
| cfp10_TQIDQVESTAGSLQGQWR | 48 | 25.3 | 27.3 | Positive | 1002.493 | 931.47 | 30 |
| cfp10_TQIDQVESTAGSLQGQWR | 48 | 25.3 | 27.3 | Positive | 1002.493 | 1103.56 | 30 |
| cfp10_TQIDQVESTAGSLQGQWR | 48 | 25.3 | 27.3 | Positive | 1002.493 | 1190.61 | 30 |
| cfp10_TQIDQVESTAGSLQGQWR | 48 | 25.3 | 27.3 | Positive | 1002.493 | 1319.63 | 30 |
| AADMWGPSSDPAWER_Ag85B | 49 | 25.4 | 27.4 | Positive | 838.36 | 389.15 | 30 |
| AADMWGPSSDPAWER_Ag85B | 49 | 25.4 | 27.4 | Positive | 838.36 | 575.23 | 30 |
| AADMWGPSSDPAWER_Ag85B | 49 | 25.4 | 27.4 | Positive | 838.36 | 658.33 | 30 |
| AADMWGPSSDPAWER_Ag85B | 49 | 25.4 | 27.4 | Positive | 838.36 | 1044.47 | 30 |
| AADMWGPSSDPAWER_Ag85B | 49 | 25.4 | 27.4 | Positive | 838.36 | 1101.5 | 30 |
| AADMWGPSSDPAWER_Ag85B | 49 | 25.4 | 27.4 | Positive | 838.36 | 1287.58 | 30 |
| IPLDVAEGDTVIYSK_GroS | 50 | 26.2 | 28.2 | Positive | 810.43 | 882.46 | 30 |
| IPLDVAEGDTVIYSK_GroS | 50 | 26.2 | 28.2 | Positive | 810.43 | 1011.5 | 30 |
| IPLDVAEGDTVIYSK_GroS | 50 | 26.2 | 28.2 | Positive | 810.43 | 1082.54 | 30 |
| IPLDVAEGDTVIYSK_GroS | 50 | 26.2 | 28.2 | Positive | 810.43 | 1181.6 | 30 |
| IPLDVAEGDTVIYSK_GroS | 50 | 26.2 | 28.2 | Positive | 810.43 | 1296.63 | 30 |
| FSDPSKPNGQIWTGVIGSPAANAPDAGPPQR_Mpt32 | 51 | 27.2 | 29.2 | Positive | 1044.85 | 625.34 | 30 |
| FSDPSKPNGQIWTGVIGSPAANAPDAGPPQR_Mpt32 | 51 | 27.2 | 29.2 | Positive | 1044.85 | 837.42 | 30 |
| FSDPSKPNGQIWTGVIGSPAANAPDAGPPQR_Mpt32 | 51 | 27.2 | 29.2 | Positive | 1044.85 | 1022.5 | 30 |
| FSDPSKPNGQIWTGVIGSPAANAPDAGPPQR_Mpt32 | 51 | 27.2 | 29.2 | Positive | 1044.85 | 1164.58 | 30 |
| FSDPSKPNGQIWTGVIGSPAANAPDAGPPQR_Mpt32 | 51 | 27.2 | 29.2 | Positive | 1044.85 | 1261.63 | 30 |
| FLLDQAITSAGR_GarA | 52 | 27.7 | 29.7 | Positive | 646.35 | 604.34 | 30 |
| FLLDQAITSAGR_GarA | 52 | 27.7 | 29.7 | Positive | 646.35 | 675.38 | 30 |
| FLLDQAITSAGR_GarA | 52 | 27.7 | 29.7 | Positive | 646.35 | 803.44 | 30 |
| FLLDQAITSAGR_GarA | 52 | 27.7 | 29.7 | Positive | 646.35 | 918.47 | 30 |
| FLLDQAITSAGR_GarA | 52 | 27.7 | 29.7 | Positive | 646.35 | 1031.55 | 30 |
| EAPYELNITSATYQSAIPPR_Mpt64 | 53 | 28.4 | 30.4 | Positive | 1111.06 | 931.5 | 30 |

| Compound | SEQ ID NO: | Start Time (min) | End Time (min) | Polarity | Precursor (m/z) | Product (m/z) | Collision Energy (V) |
|---|---|---|---|---|---|---|---|
| EAPYELNITSATYQSAIPPR_Mpt64 | 53 | 28.4 | 30.4 | Positive | 1111.06 | 1032.55 | 30 |
| EAPYELNITSATYQSAIPPR_Mpt64 | 53 | 28.4 | 30.4 | Positive | 1111.06 | 1103.58 | 30 |
| EAPYELNITSATYQSAIPPR_Mpt64 | 53 | 28.4 | 30.4 | Positive | 1111.06 | 1190.62 | 30 |
| EAPYELNITSATYQSAIPPR_Mpt64 | 53 | 28.4 | 30.4 | Positive | 1111.06 | 1291.66 | 30 |
| EAPYELNITSATYQSAIPPR_Mpt64 | 53 | 28.4 | 30.4 | Positive | 1111.06 | 1404.75 | 30 |
| GFQSIHESDMLLLPDPETAR_GlnA | 54 | 29 | 31 | Positive | 752.7 | 573.3 | 30 |
| GFQSIHESDMLLLPDPETAR_GlnA | 54 | 29 | 31 | Positive | 752.7 | 785.38 | 30 |
| GFQSIHESDMLLLPDPETAR_GlnA | 54 | 29 | 31 | Positive | 752.7 | 898.46 | 30 |
| GFQSIHESDMLLLPDPETAR_GlnA | 54 | 29 | 31 | Positive | 752.7 | 1011.43 | 30 |
| GFQSIHESDMLLLPDPETAR_GlnA | 54 | 29 | 31 | Positive | 752.7 | 1132.47 | 30 |
| GFQSIHESDMLLLPDPETAR_GlnA | 54 | 29 | 3 | Positive | 752.7 | 1245.56 | 30 |
| SVFDDGLAFDGSSIR_GlnA | 55 | 30.1 | 32.1 | Positive | 793.378 | 781.38 | 30 |
| SVFDDGLAFDGSSIR_GlnA | 55 | 30.1 | 32.1 | Positive | 793.378 | 852.42 | 30 |
| SVFDDGLAFDGSSIR_GlnA | 55 | 30.1 | 32.1 | Positive | 793.378 | 965.51 | 30 |
| SVFDDGLAFDGSSIR_GlnA | 55 | 30.1 | 32.1 | Positive | 793.378 | 1022.53 | 30 |
| SVFDDGLAFDGSSIR_GlnA | 55 | 30.1 | 32.1 | Positive | 793.378 | 1137.55 | 30 |
| SVFDDGLAFDGSSIR_GlnA | 55 | 30.1 | 32.1 | Positive | 793.378 | 1252.58 | 30 |
| PGLPVEYLQVPSPSMGR_Ag85B | 56 | 31.1 | 33.1 | Positive | 913.97 | 731.87 | 30 |
| PGLPVEYLQVPSPSMGR_Ag85B | 56 | 31.1 | 33.1 | Positive | 913.97 | 830.42 | 30 |
| PGLPVEYLQVPSPSMGR_Ag85B | 56 | 31.1 | 33.1 | Positive | 913.97 | 958.48 | 30 |
| PGLPVEYLQVPSPSMGR_Ag85B | 56 | 31.1 | 33.1 | Positive | 913.97 | 1071.56 | 30 |
| PGLPVEYLQVPSPSMGR_Ag85B | 56 | 31.1 | 33.1 | Positive | 913.97 | 1234.62 | 30 |
| PGLPVEYLQVPSPSMGR_Ag85B | 56 | 31.1 | 33.1 | Positive | 913.97 | 1363.67 | 30 |
| ESAT6_WDATATELNNALQNLAR | 57 | 33.6 | 35.6 | Positive | 950.98 | 601.34 | 30 |
| ESAT6_WDATATELNNALQNLAR | 57 | 33.6 | 35.6 | Positive | 950.98 | 899.51 | 30 |
| ESAT6_WDATATELNNALQNLAR | 57 | 33.6 | 35.6 | Positive | 950.98 | 1013.55 | 30 |
| ESAT6_WDATATELNNALQNLAR | 57 | 33.6 | 35.6 | Positive | 950.98 | 1126.63 | 30 |
| ESAT6_WDATATELNNALQNLAR | 57 | 33.6 | 35.6 | Positive | 950.98 | 1255.68 | 30 |
| AGANLFELENFVAR_Bfrb | 58 | 33.7 | 35.7 | Positive | 775.9 | 735.39 | 30 |
| AGANLFELENFVAR_Bfrb | 58 | 33.7 | 35.7 | Positive | 775.9 | 848.46 | 30 |
| AGANLFELENFVAR_Bfrb | 58 | 33.7 | 35.7 | Positive | 775.9 | 977.51 | 30 |
| AGANLFELENFVAR_Bfrb | 58 | 33.7 | 35.7 | Positive | 775.9 | 1124.57 | 30 |
| AGANLFELENFVAR_Bfrb | 58 | 33.7 | 35.7 | Positive | 775.9 | 1237.66 | 30 |
| WETFLTSELPGWLQANR_Ag85A | 59 | 38.1 | 40.1 | Positive | 1024.52 | 417.1 | 30 |
| WETFLTSELPGWLQANR_Ag85A | 59 | 38.1 | 40.1 | Positive | 1024.52 | 941.5 | 30 |
| WETFLTSELPGWLQANR_Ag85A | 59 | 38.1 | 40.1 | Positive | 1024.52 | 1054.58 | 30 |
| WETFLTSELPGWLQANR_Ag85A | 59 | 38.1 | 40.1 | Positive | 1024.52 | 1183.62 | 30 |
| WETFLTSELPGWLQANR_Ag85A | 59 | 38.1 | 40.1 | Positive | 1024.52 | 1270.65 | 30 |

-continued

| Compound | SEQ ID NO: | Start Time (min) | End Time (min) | Polarity | Precursor (m/z) | Product (m/z) | Collision Energy (V) |
|---|---|---|---|---|---|---|---|
| Cfp2_DPASAPDVPTAAQLTSLLNSLADPNVSFANK | 60 | 38.9 | 40.9 | Positive | 1042.2 | 566.29 | 30 |
| Cfp2_DPASAPDVPTAAQLTSLLNSLADPNVSFANK | 60 | 38.9 | 40.9 | Positive | 1042.2 | 753.34 | 30 |
| Cfp2_DPASAPDVPTAAQLTSLLNSLADPNVSFANK | 60 | 38.9 | 40.9 | Positive | 1042.2 | 876.46 | 30 |
| Cfp2_DPASAPDVPTAAQLTSLLNSLADPNVSFANK | 60 | 38.9 | 40.9 | Positive | 1042.2 | 991.48 | 30 |
| Cfp2_DPASAPDVPTAAQLTSLLNSLADPNVSFANK | 60 | 38.9 | 40.9 | Positive | 1042.2 | 1062.52 | 30 |

TABLE 3 interference ions for each transition.

| Q1 | RT | Sequence | SEQ ID NO: | Transitions |
|---|---|---|---|---|
| 797.42 | 27.45 | TNLTTEQIANYVAR | 61 | y14 y6 y5 y3 b9 b10 b14 |
| 796.41 | 26.68 | DPALC[160]QHKPLTPQGDELSKPR | 62 | y8 y7 y3 b8 b9 b11 |
| 797.42 | 26.7 | LGGLSAPPWAKPEDR | 63 | y8 y6 y3 b7 b9 b14 |
| 796.89 | 22.32 | DLEVETLTASSEGNK | 64 | y11 y3 b6 b9 b10 |
| 797.44 | 27.7 | TTLPGVVNGANNPAIR | 65 | y14 y12 y11 b4 b14 |
| 797.4 | 28.15 | YSDIEPSTGGEVVLK | 66 | y11 y8 y2 b4 b7 |
| 797.38 | 29.01 | QYHVQFFGDAPER | 67 | y8 y2 b7 b13 b14 |
| 796.4 | 29.5 | MTSEIETNIVAVER | 68 | y3 y2 b6 b9 b12 |
| 797.39 | 21.07 | MEPGPDGPAASGPAAIR | 69 | y12 y11 b4 b14 |
| 796.04 | 21.36 | VNDPTESQQEDQLIAGAQDEAK | 70 | y7 y5 b11 b12 |
| 797.41 | 22.49 | EQVQIGAHSPPQFR | 71 | y8 b6 b7 b14 |
| 797.38 | 24.24 | TEQEVVEGMDISTR | 72 | y14 y11 b4 b14 |
| 796.39 | 25.46 | VVC[160]TESWPLAHHR | 73 | y14 b4 b5 b12 |
| 797.43 | 26.45 | EPGPIAPSTNSSPVLK | 74 | y11 y4 b4 b11 |
| 795.88 | 26.57 | AHFNAMFQPSSPTR | 75 | y11 b5 b7 b8 |
| 797.37 | 26.75 | MDQFGNGLEIDQAR | 76 | y6 y3 b9 b14 |
| 796.73 | 28.69 | DPALC[160]QHKPLTPQGDELSEPR | 77 | y8 y7 y3 b8 |
| 797.07 | 29.06 | METRPTALMSSTVAAAAPAAGAASR | 78 | y12 y3 b4 b11 |
| 796.43 | 29.4 | TRPTDLVFVVDSSR | 79 | y9 y5 y4 b11 |

TABLE 3-continued interference ions for each transition.

| Q1 | RT | Sequence | SEQ ID NO: | Transitions |
|---|---|---|---|---|
| 796.89 | 29.92 | ELGFVQPSGVTDGMR | 80 | y7 b5 b6 b7 |
| 795.88 | 30.82 | MLTDPDLPQEFER | 81 | y3 y2 b5 b7 |
| 795.89 | 20.98 | C[160]STPLLHQQYTSR | 82 | y5 b5 b6 |
| 796.4 | 21.15 | ISC[160]GPPAHVENAIAR | 83 | b4 b5 b8 |
| 797.41 | 22.12 | LLEAVGSSSGTPNAPPP | 84 | y6 y3 b9 |
| 797.71 | 22.51 | TPTQHSPVPPEEVTGPSQMDTR | 85 | y7 y4 b8 |
| 797.42 | 22.79 | TTYVSQSGQVISAPR | 86 | y14 y4 b14 |
| 797.4 | 22.98 | SFPQSSQLSQETVR | 87 | y10 b5 b14 |
| 795.87 | 23.43 | MNGDHMVLGSSVTDK | 88 | y6 y4 b7 |
| 797.38 | 23.66 | EYPLVINQTC[160]HR | 89 | y9 b6 b14 |
| 797.37 | 24.12 | GEGAIGSLDYTPEER | 90 | y2 b13 b14 |
| 797.39 | 24.58 | DVVHPLGGEEPSMAR | 91 | y3 b12 b14 |
| 797.38 | 25.1 | VYQPFLTTC[160]DGHR | 92 | y8 b7 b14 |
| 797.36 | 25.19 | AFDC[160]PSSFQIHER | 93 | y2 b13 b14 |
| 796.4 | 26.1 | TLAPQVC[160]SSFATGPR | 94 | y13 y12 y7 |
| 797.37 | 26.24 | SEPC[160]DDLQIPNTNVHLSHDAK | 95 | y11 b9 b11 |
| 796.39 | 26.39 | FNNVQLNLTDEER | 96 | y2 b4 b7 |
| 796.39 | 26.48 | QLVDEFQASGGVGER | 97 | y2 b5 b7 |
| 797.04 | 26.88 | EDASGQLSC[160]IQLPVDSQGGDANK | 98 | b5 b9 b11 |
| 797.34 | 26.92 | FTSDMSNTEWGYR | 99 | y3 b12 b14 |
| 797.36 | 27.1 | MAFMAATDHSDQLR | 100 | y12 y5 b14 |
| 797.41 | 27.17 | LEIGPVYSSVSSEAR | 101 | y7 b8 b14 |
| 796.38 | 27.4 | TIGMPATEEVDC[160]IR | 102 | y13 y9 b11 |
| 797.41 | 27.63 | LLETVEYNISGAER | 103 | y2 b13 b14 |
| 797.38 | 27.99 | SQGDNNVSLVEEFR | 104 | y3 b12 b14 |
| 796.46 | 28.05 | TIQAPTQVPVVVSPR | 105 | y13 y10 b4 |
| 797.41 | 28.06 | C[160]TLHLGIEFPDSVR | 106 | y9 b6 b14 |
| 796.41 | 28.21 | SEITNQLSVSDINSQSVGGARPK | 107 | b7 b10 b11 |
| 797.72 | 29.09 | WAGGPPGTGGHGPLSLNSPDPYEK | 108 | y7 y5 y4 |
| 796.39 | 29.1 | GC[160]FTPVVTDPITER | 109 | y2 b7 b11 |
| 797.37 | 30.38 | GSIDDVFNC[160]NLSPR | 110 | y11 b4 b14 |
| 796.37 | 30.43 | TFISLSSTDVSPNQSNTSNEMK | 111 | y11 y2 b12 |
| 796.07 | 30.61 | HVLTSHIDEPPTQNQSDLLNK | 112 | y8 y4 y3 |
| 795.89 | 30.85 | STLGPALEAVSMDGDK | 113 | y7 y4 b4 |
| 797.4 | 21.2 | VWTHC[160]QTQHGIVK | 114 | y11 b4 |
| 795.88 | 21.4 | QSGQC[160]LDGVSLSSPR | 115 | b4 b6 |
| 797.35 | 21.54 | ENYGSITSMGYESR | 116 | y4 b14 |
| 797.37 | 21.58 | EGDYIVSVNGQPC[160]R | 117 | y4 b14 |

TABLE 3-continued interference ions for each transition.

| Q1 | RT | Sequence | SEQ ID NO: | Transitions |
|---|---|---|---|---|
| 796.41 | 21.7 | EGYLQIGANTQAAQK | 118 | y5 y4 |
| 795.88 | 21.78 | TNGVPTTEEVDC[160]IR | 119 | y9 b12 |
| 797.44 | 22.47 | VQTDKPHLVSLGSGR | 120 | b5 b14 |
| 796.36 | 22.49 | YSSNLGNFNYEQR | 121 | y5 y4 |
| 796.72 | 22.54 | VVAGDHNLSQNDGTEQVVSVQK | 122 | y9 y6 |
| 797.39 | 22.71 | ILDETQEAVEYQR | 123 | y4 b14 |
| 797.02 | 22.83 | DDSC[160]SGDSSAQLSSGEHLLGPNR | 124 | y5 y4 |
| 795.88 | 23.03 | SVQWC[160]AVSQPEATK | 125 | b5 b12 |
| 795.88 | 23.36 | NTSSEQEEVVEALR | 126 | b4 b7 |
| 796.9 | 23.42 | TTTWQRPTMESVR | 127 | y2 b10 |
| 797.4 | 23.55 | TASESISNLSEAGSIK | 128 | y14 b5 |
| 797.41 | 23.71 | TPSTTTSSHYLGTLK | 129 | y14 b5 |
| 797.42 | 24.1 | TVGFNHLTLGHNQR | 130 | y14 b14 |
| 796.34 | 24.12 | GGHINDAFMTEDER | 131 | y2 b7 |
| 797.3 | 24.31 | GFGC[160]C[160]FPC[160]C[160]SVDK | 132 | y2 b6 |
| 796.41 | 24.31 | WTC[160]SKPKPSTMLR | 133 | y2 b6 |
| 796.86 | 24.36 | MPAYHSSLMDPDTK | 134 | y4 b5 |
| 797.36 | 24.44 | SSLGLDNSLSTSSEDPHSGC[160]PSR | 135 | b4 b6 |
| 797.7 | 24.88 | GSEC[160]WHLSSGSVHPSPGSAPAQR | 136 | b7 b13 |
| 796.91 | 25.05 | C[160]QPLGSALPPQAPTR | 137 | y9 y8 |
| 797.42 | 25.15 | NIQHLNSQIHSFR | 138 | y2 b14 |
| 795.9 | 25.18 | VTTSDEDIGINAISR | 139 | b5 b6 |
| 797.38 | 25.36 | FVELQVC[160]DHYQR | 140 | b4 b14 |
| 797.37 | 25.65 | HFITSSSSKPC[160]EPEEHYVQK | 141 | b8 b11 |
| 797.38 | 25.71 | TTGSTQSNFNFYVK | 142 | y14 b6 |
| 797.03 | 25.82 | GLHGAATVVLGQGQHGGC[160]APEEED | 143 | y2 b5 |
| 796.86 | 25.85 | TLTAEEAEEEWER | 144 | y2 b4 |
| 796.93 | 26.14 | FGGTPIHFPGGRPPR | 145 | b5 b6 |
| 796.37 | 26.41 | TLDENSDSAGLWQR | 146 | y13 b6 |
| 797.04 | 26.42 | LNVAGAGGGGDSGGGPGAATDGNFTAGLA | 147 | y6 b11 |
| 795.91 | 26.52 | VFSQNAYLIDHQR | 148 | y4 b7 |
| 796.92 | 26.66 | EGSGNPTPLINPLAGR | 149 | y8 b13 |
| 797.41 | 26.69 | TFAQTTYLIDHQR | 150 | y14 b14 |
| 796.89 | 26.73 | VASMAPVTAEGFQER | 151 | y2 b5 |
| 796.42 | 26.79 | SVLPPDGNGSPVLPDK | 152 | y9 64 |
| 797.45 | 26.98 | VNPDLQVEVKPSIR | 153 | y12 b14 |
| 797.71 | 27.08 | TSETNTPQGNQEQLVTVMEER | 154 | y2 b7 |

TABLE 3-continued interference ions for each transition.

| Q1 | RT | Sequence | SEQ ID NO: | Transitions |
|---|---|---|---|---|
| 797.41 | 27.36 | QIQGTETEFNSLVK | 155 | y11 b4 |
| 796.89 | 27.47 | DEIYIPLQEEDTK | 156 | y11 b10 |
| 795.87 | 27.53 | VEDESLDNTWLNR | 157 | y3 b5 |
| 797.37 | 27.67 | C[160]VPRPGGAVC[160]EC[160]PGGFQLDASR | 158 | y8 b11 |
| 796.85 | 27.67 | MGGGGALQWNC[160]SGGIQ | 159 | b10 b13 |
| 796.41 | 27.77 | DVEEKPAHAPARPEAPVDSMLK | 160 | y5 b6 |
| 795.9 | 27.91 | MAGSYPEGAPAILADK | 161 | y2 b6 |
| 796.37 | 28.35 | LDC[160]ASAIQNYLSGTHGGSPGPER | 162 | y2 b5 |
| 796.91 | 28.68 | HALPSPLEGSFQPGR | 163 | y6 b4 |
| 797.38 | 28.69 | HC[160]PSTFFSSPGLTR | 164 | b4 b14 |
| 796.87 | 28.81 | ISDDTPLEMMTSPR | 165 | b4 b5 |
| 796.32 | 28.9 | ELC[160]DC[160]EQC[160]GEVFSEHSC[160]LK | 166 | y11 b7 |
| 797.41 | 29.06 | EGVYEISLSPTGVSR | 167 | b6 b14 |
| 795.89 | 29.13 | SESEVHFDVETAIK | 168 | y2 b7 |
| 796.43 | 29.18 | LIGTNC[160]IIYPVNSK | 169 | b6 b8 |
| 795.9 | 29.42 | C[160]DVVVGGGISGMAAAK | 170 | b5 b6 |
| 796.91 | 29.6 | EEVYIVQASNVDVK | 171 | y11 b5 |
| 797.4 | 29.62 | QEAASTGPGMEPETTATTILASVK | 172 | y6 b11 |
| 796.4 | 29.71 | VVETMQSTLDAEIR | 173 | y14 b4 |
| 797.45 | 29.92 | INSELQVPPTQVLR | 174 | y12 b14 |
| 796.4 | 29.96 | QQNAQGGFSSTQDTVVALHALSK | 175 | y9 b5 |
| 796.41 | 30.08 | FPSLLTQNENMVAK | 176 | y3 b9 |
| 796.07 | 30.14 | QHHHQSSFPGSLPQETNLTLK | 177 | y5 b12 |
| 796.72 | 30.18 | SGGEALAVANDSTSTPQNANGLWK | 178 | y4 b11 |
| 797.34 | 30.31 | SSC[160]SDMDLLHSWR | 179 | b6 b14 |
| 796.38 | 20.94 | AGSVHYGHYTALC[160]R | 180 | b10 |
| 796.37 | 21.03 | C[160]NTQAELLAAGC[160]QR | 181 | y4 |
| 795.85 | 21.1 | GVLVC[160]DEC[160]C[160]SVHR | 182 | b7 |
| 795.8 | 21.1 | TFMDMDQDSEDEK | 183 | y2 |
| 796.85 | 21.18 | LTWHSYPSEDDDK | 184 | b10 |
| 796.91 | 21.19 | FAVVENNSSAVTAQR | 185 | b13 |
| 796.85 | 21.19 | VEDTC[160]VEWDPTGGK | 186 | y10 |
| 795.89 | 21.32 | AFSQNSQFIQHQR | 187 | b7 |
| 795.9 | 21.34 | C[160]LPNPTPEGGAVPGPK | 188 | b13 |
| 796.84 | 21.35 | GEGQGLVC[160]DLC[160]NDR | 189 | b11 |
| 796.86 | 21.44 | SSTNTSLPDDNGAWK | 190 | y3 |
| 795.91 | 21.46 | LGEVVNTHGPVEPDK | 191 | b4 |

TABLE 3-continued interference ions for each transition.

| Q1 | RT | Sequence | SEQ ID NO: | Transitions |
|---|---|---|---|---|
| 796.38 | 21.49 | QSSNRPAHNISHILGHDC[160]SSAV | 192 | b6 |
| 796.73 | 21.54 | GPQGPTGSEGTPGLPGGVGQPGAVGEK | 193 | b14 |
| 797.39 | 21.61 | QGTLSTAAPTTSPAPC[160]LSNHHNK | 194 | b11 |
| 795.87 | 21.63 | ENSENTTAPEVFPR | 195 | b5 |
| 796.38 | 21.64 | EQQMVPGIPQGAHEA | 196 | y7 |
| 797.38 | 21.67 | LVAAC[160]PESC[160]VVC[160]TK | 197 | y2 |
| 795.88 | 21.89 | ASC[160]GQDQAAAETLLR | 198 | b10 |
| 796.37 | 21.9 | SMNDISLTPNTDQR | 199 | b6 |
| 796.71 | 21.91 | EDGTVSTANQNGVSSNGPGEILNK | 200 | y6 |
| 796.88 | 22.14 | SNPEDQILYQTER | 201 | y2 |
| 796.39 | 22.23 | LEGMNETVSNLTQR | 202 | b5 |
| 796.38 | 22.3 | KPSSETDIENWASK | 203 | b7 |
| 796.88 | 22.31 | MSESLDTADPAVTGAK | 204 | y8 |
| 796.38 | 22.39 | VTLYEC[160]HSQGEIR | 205 | y14 |
| 797.41 | 22.43 | VHSHEVAAYLASPGR | 206 | b14 |
| 797.35 | 22.46 | AGC[160]QVVAPSDMMDGR | 207 | b14 |
| 796.37 | 22.52 | SISGTSTSEKPNSMDTANTSPFK | 208 | y6 |
| 795.89 | 22.6 | NFQSESVPALGGQEK | 209 | y6 |
| 797.36 | 22.64 | DSPVC[160]PSYSPTMPR | 210 | b14 |
| 797.42 | 22.71 | DRPSLPQERPGWR | 211 | b14 |
| 797.7 | 22.97 | EDGEVVQEEEVC[160]AKPSVTEEK | 212 | y5 |
| 795.89 | 23 | DAETGEEVTHYLVK | 213 | b4 |
| 795.92 | 23.2 | TGSLPHSSEQLLGHK | 214 | b4 |
| 797.39 | 23.31 | ASSVLPEHHEAFNR | 215 | b14 |
| 797.68 | 23.41 | LSGAMC[160]TSC[160]ASQTTANDPYTVR | 216 | b5 |
| 795.91 | 23.5 | VSTAQDVIQQTLC[160]K | 217 | b4 |
| 795.9 | 23.61 | VSSSSESEPELAQLK | 218 | b12 |
| 796.62 | 23.61 | TSC[160]SNC[160]TSNGMEC[160]MWC[160]SSTK | 219 | b12 |
| 796.89 | 23.77 | ESSQPPVAFSSSIEK | 220 | y2 |
| 797.35 | 23.82 | NC[160]QTVLAPC[160]SPNPC[160]ENAAVC[160]K | 221 | b4 |
| 797.36 | 23.83 | GQDTQFWAGHYGAR | 222 | b14 |
| 796.89 | 23.92 | MTENVVC[160]TGAVNAVK | 223 | b5 |
| 797.41 | 23.94 | YPSTSEAVNIQGISK | 224 | b6 |
| 795.9 | 24.04 | AGFPC[160]FKPSGAAPQR | 225 | b7 |
| 796.41 | 24.06 | STLEEQGLHVHSVR | 226 | b13 |
| 796.9 | 24.06 | GTANTC[160]IPSISSIGSK | 227 | y3 |
| 797.42 | 24.19 | SFNQNSHLIIHQR | 228 | b14 |

TABLE 3-continued interference ions for each transition.

| Q1 | RT | Sequence | SEQ ID NO: | Transitions |
|---|---|---|---|---|
| 795.87 | 24.23 | IPIDNMTNEMEQR | 229 | b7 |
| 796.42 | 24.31 | INLPAPNPDHVGGYK | 230 | y2 |
| 796.93 | 24.48 | SPGTHLGALAQTVQGR | 231 | y10 |
| 797.04 | 24.48 | LSNC[160]DPPPTYEEATGQVNLQR | 232 | b6 |
| 795.87 | 24.76 | EDISAC[160]LQGTHGFR | 233 | b6 |
| 796.37 | 24.76 | EDC[160]C[160]PGKPLNVFR | 234 | y4 |
| 795.82 | 24.82 | EC[160]DMC[160]FSQASSLR | 235 | y4 |
| 795.84 | 24.91 | DC[160]AANTFIEDSGYK | 236 | y5 |
| 796.4 | 24.93 | LQESGQVTISELC[160]K | 237 | y10 |
| 795.88 | 24.95 | SQAC[160]GGNLGSIEELR | 238 | b6 |
| 797.08 | 25.01 | GPHPQALPGHLPGAGDSGAGAGGGVVR | 239 | b9 |
| 795.89 | 25.08 | LEYSGAISAHC[160]NLR | 240 | b11 |
| 797.38 | 25.1 | MGVTC[160]VSQMPVAEGK | 241 | y12 |
| 797.33 | 25.14 | TC[160]DFFSPYENGEK | 242 | y14 |
| 796.84 | 25.16 | FGYYGDALQQDC[160]R | 243 | b12 |
| 797.41 | 25.26 | LLSLHSPNSYYGSR | 244 | b14 |
| 796.91 | 25.27 | YQVSEEVPSGTVIGK | 245 | y2 |
| 796.9 | 25.38 | ESTATLLGC[160]NASIQK | 246 | b4 |
| 796.9 | 25.48 | TSVTTSISEPWTQR | 247 | b13 |
| 795.83 | 25.52 | MSYSC[160]C[160]LPSLGC[160]R | 248 | y3 |
| 796.36 | 25.56 | SEYSSYPDINFNR | 249 | b4 |
| 795.91 | 25.71 | HSHGLALQPSFPGSR | 250 | b4 |
| 796.43 | 25.74 | LPYSGRPAPAPAAAPGV | 251 | b5 |
| 795.9 | 25.75 | AEQDITTLEQSISR | 252 | y4 |
| 796.89 | 25.83 | VMSPENFPTASVEGK | 253 | y3 |
| 796.43 | 25.99 | GGNQEIGPLPPTGNLK | 254 | y11 |
| 796.86 | 26.03 | GAEVTYMNMTAYNK | 255 | b10 |
| 797.47 | 26.05 | SPAARPPVPAPPALPR | 256 | b14 |
| 797.4 | 26.12 | C[160]LVPGYYSTHLQR | 257 | b14 |
| 797.45 | 26.16 | LAPISEEGKPQLVGR | 258 | b14 |
| 795.86 | 26.18 | DEDLQEMENLAQR | 259 | b7 |
| 795.89 | 26.26 | WIHFGTEVTNSSGR | 260 | y8 |
| 796.44 | 26.37 | VLPMVPAPPGSSAAAAR | 261 | y14 |
| 796.38 | 26.41 | SNFSPHFASSNQLR | 262 | y5 |
| 796.34 | 26.42 | C[160]LHC[160]LYSC[160]HWR | 263 | y9 |
| 795.9 | 26.47 | VGNIPYEATEEQLK | 264 | b7 |
| 797.36 | 26.48 | HPDEAAFFDTASTGK | 265 | y5 |
| 795.89 | 26.58 | SSLTQEEAPVSWEK | 266 | y4 |

TABLE 3-continued interference ions for each transition.

| Q1 | RT | Sequence | SEQ ID NO: | Transitions |
|---|---|---|---|---|
| 796.92 | 26.58 | VLNQYTDTIIQER | 267 | y2 |
| 796.4 | 26.64 | LEQGENVFLQATDK | 268 | y7 |
| 796.87 | 26.64 | MAFMAATDHSNQLR | 269 | y5 |
| 796.7 | 26.7 | MNSPSQSSPGMNPGQPTSMLSPR | 270 | b4 |
| 796.93 | 26.9 | FVYPVPYTTRPPR | 271 | y2 |
| 797.36 | 26.94 | WDSNIC[160]ELHYTR | 272 | b14 |
| 796.39 | 27.02 | YPAEEPASAWTPSPPPVTTSSSK | 273 | b8 |
| 795.89 | 27.07 | TSANPETLLGEMEAK | 274 | y2 |
| 796.4 | 27.15 | MTQPFPTQFAPQAK | 275 | y10 |
| 796.89 | 27.18 | TFSQMSSLVYHHR | 276 | y4 |
| 795.91 | 27.21 | VGQC[160]VVVFSQAPSGR | 277 | y12 |
| 797.41 | 27.35 | NPSTNVSVVVFDSTK | 278 | b6 |
| 795.9 | 27.37 | VLMVETHNEIYDK | 279 | b5 |
| 795.87 | 27.41 | MDNC[160]LAAAALNGVDR | 280 | b6 |
| 796.4 | 27.45 | LVIEC[160]GADC[160]NILSK | 281 | b5 |
| 795.85 | 27.52 | FC[160]C[160]EDGTTIVNFK | 282 | y7 |
| 796.41 | 27.55 | YHYAEISSQVPLGK | 283 | y4 |
| 797.43 | 27.55 | LQTLSIQQC[160]LPHR | 284 | b14 |
| 795.91 | 27.57 | LVMVSTLDTSSQPGR | 285 | y10 |
| 796.44 | 27.62 | QPPPGIVAPAAMLSSR | 286 | y5 |
| 796.94 | 27.63 | SPLQAVEPISTSVHK | 287 | y7 |
| 797.4 | 27.8 | IVETDESQGIFVEK | 288 | y3 |
| 795.9 | 27.92 | LSWPQSTGIC[160]SNIK | 289 | y4 |
| 795.91 | 27.97 | SVLDLGSGC[160]GATAIAAK | 290 | b5 |
| 796.88 | 28.05 | AAGFDEIEQDLTQR | 291 | b13 |
| 796.89 | 28.06 | QTVMTSATWPDTVR | 292 | b5 |
| 797.4 | 28.07 | TAFTNHQIYELEK | 293 | y14 |
| 797.44 | 28.17 | APSSPALQALAGQAGVR | 294 | b14 |
| 796.93 | 28.21 | MEPAVGGPGPLIVNNK | 295 | y11 |
| 796.94 | 28.21 | QVHILQQNC[160]IALR | 296 | b4 |
| 796.36 | 28.31 | VEVSGDASC[160]C[160]SPDPISPEDLPR | 297 | y11 |
| 797.39 | 28.33 | EGFPTDAPYPTTLGK | 298 | b4 |
| 796.9 | 28.4 | SAYALGGLGSGIC[160]PNR | 299 | b4 |
| 796.9 | 28.51 | ASSLC[160]HHASLPWVK | 300 | b4 |
| 797.38 | 28.69 | FLNDTSLPHSC[160]FR | 301 | b14 |
| 796.92 | 28.7 | FLIDSNGQVITTER | 302 | y2 |
| 796.41 | 28.77 | IEGENYLPQPIYR | 303 | y3 |
| 796.89 | 28.89 | VTGLIENHDYEFR | 304 | y3 |

TABLE 3-continued interference ions for each transition.

| Q1 | RT | Sequence | SEQ ID NO: | Transitions |
|---|---|---|---|---|
| 796.43 | 28.9 | ILFVSQGSEIASQGR | 305 | b6 |
| 797.42 | 28.93 | DLDQVQLHLEEVR | 306 | b14 |
| 796.87 | 28.98 | FNDITADVYSEYR | 307 | b4 |
| 796.95 | 29.03 | LC[160]VPGIVALQSPPNK | 308 | y11 |
| 797.07 | 29.36 | IEETC[160]QVGMKPPVPGGYTLQGK | 309 | b11 |
| 797.42 | 29.42 | VWPQATAPEQAPAPARPYQGVR | 310 | y5 |
| 796.9 | 29.54 | LGVEMLSESQLSDGK | 311 | y8 |
| 797.72 | 29.55 | QNEHHLEGGFSIGSVGPDGQLGR | 312 | y5 |
| 796.39 | 29.62 | NFLETDNEGNGILR | 313 | y10 |
| 796.41 | 29.64 | GILFVGSGVSGGEEGAR | 314 | b5 |
| 797.41 | 29.69 | VTDATETTITISWR | 315 | b14 |
| 796.37 | 29.81 | EWDILETEEHYK | 316 | b6 |
| 796.72 | 29.88 | QVRPPSC[160]PVPFPETFNGESSR | 317 | y9 |
| 796.94 | 29.96 | VVFHLHESFPRPK | 318 | b7 |
| 795.91 | 30 | MYQGHMQVVGVTLK | 319 | b5 |
| 796.03 | 30.05 | SPGDGGPHDVFTSLPSDC[160]QLGSR | 320 | b5 |
| 797.42 | 30.22 | WAAGAMAAPEPLRPR | 321 | b14 |
| 796.89 | 30.25 | AQLEEEIIAYEER | 322 | y2 |
| 796.87 | 30.39 | MSEDSSALPWSINR | 323 | b8 |
| 796.84 | 30.46 | LMNEDPMYSMYAK | 324 | b4 |
| 797.41 | 30.55 | GLGAFVIDSDHLGHR | 325 | b14 |
| 795.92 | 30.6 | ADANTAAIQAVLYNR | 326 | y4 |
| 797.39 | 30.69 | EDIVTEQIDFSAAR | 327 | b14 |
| 796.71 | 30.71 | MVRPQDTVAYEDLSEDYTQK | 328 | b13 |
| 796.87 | 30.72 | DYFQHPHFSTWK | 329 | y3 |
| 796.4 | 30.73 | IVESMQSTLDAEIR | 330 | b4 |
| 796.7 | 30.74 | SLSNENYGVYNC[160]SIINEAGAGR | 331 | y3 |
| 796.38 | 30.75 | QSWNPFPDFTPQK | 332 | b10 |
| 797.71 | 30.87 | LTWPTDAGPDDAAVDTSSEITTK | 333 | y9 |

FIG. 14 presents the LC-MRM instrument method.

Example 3—LC-PRM-MS Based Diagnostic Methods and Proteotypic Peptide Biomarkers Specific to HIV-1/2 p24 Antigen Human immunodeficiency virus (HIV) testing and counseling is an essential first step in controlling the virus, but the World Health Organization (WHO) reports that only about half of people currently infected with HIV worldwide are aware of their status. Even though the chief rationale for the situations may include socioeconomic factors associated with HIV, such as poverty, the low level of population's knowledge and attitudes about HIV infections, as well as the patient's behaviors, the diagnostic and treatment monitoring challenges in patients with HIV infection, especially those also infected with Tuberculosis (TB), are major contributors for the missed or delayed of HIV diagnosis or treatment.

Currently, the diagnosis of HIV seems to be much straightforward because of the availability of rapid diagnostic tests (RDTs), Ab/Ag Combination Assays (ELISA) and Nucleic Acid Amplification Test (NAT) for HIV infection.

However, the low sensitivity and specificity of RDTs remains to be a major concern, even though it is fast and cost effective ($2.0 per test) for low resource setting.

For Ab/Ag Combination Assays, further validation of the results by western blot and extensive performance evaluation are still needed for Ab/Ag Combination Assay in diverse field settings, even though they are more sensitive and specific than RDTs and with low requirement on equipment and operator. Moreover, due to the presence of antigen-specific host antibodies and immunoglobulin-specific, rheumatoid-factor-like antibodies, as well as the existence of homologs of target antigen proteins, Ab/Ag Combination assay that designed to test the intact antigen protein was confronted with several problems such as false positives, false negatives and other interferences.

More importantly, both of RDTs and Ab/Ag Combination assay are not suitable for infant (<18 months) HIV screening (due to the presence of maternal antibodies) or antiretroviral treatment (ART) monitoring, since the RDTs are mainly designed to test for HIV antibodies, and most of the currently available Ab/Ag combination assays gave only a single result and did not differentiate whether a positive result was due to the presence of the HIV-1 p24 antigen or due to the presence of antibody to HIV-1 or -2. Therefore, infant HIV screening or the standard of care to monitor ART are typically achieved by NAT based on plasma HIV RNA concentration.

However, the NAT is a highly technically demanding, involving the issues of high costs ($160.07 per test), dedicated infrastructure facility, equipment, consumables and technical expertise. Moreover, most of the commercially marketed NAAT test for HIV are monoplex-PCRs, which are bound to miss out the detection of both HIV-1 and HIV-2 in a single NAT test. Furthermore, no commercial NAT test for HIV-2 are available based on our best knowledge.

To address the issues, an LC-iSPRM-MS diagnostic platform for single step, rapid and quantitative detection of HIV-1 and HIV-2 antigens with multiple enhancement of sensitivity and specificity was developed.

We identified a panel of new proteotypic peptide biomarkers specific to HIV-1/2 p24 antigen and developed an LC-iSPRM-MS diagnostic platform for single assay, rapid and quantitative detection of HIV-1 and HIV-2 antigens with multiple enhancement of sensitivity and specificity. LC-iSPRM-MS can not only sensitively and specifically identify and measure pathogen burden directly from clinical samples, including serum, plasma, or whole blood obtained from a human, but also provide one step confirmation and discrimination of HIV-1 or HIV-2 infections based on peptide sequence, and further allows assess treatment response in patients infected with HIV-1 or HIV-2. The detection methods include but not limited to mass spectrometry, chromatography, electrochemistry and chemical sensors, electrophoresis, immunochemical techniques, nanotechnology and microfabrication, and dipstick point of care assays.

Pretreatment of Serum/Plasma

Serum samples (50 µL) were added with 450 µL of Viral Lysis Buffer (0.4% TritonX-100, 0.2% SDS in PBS, pH=7.4), heating at 100° C. for 5 min, then cooling down the temperature into room temperature. Add 10 µl 1M Tris. Microwave digested (P4 level microwave power, 6*5 min) with 10 µg (25 µl) sequence grade Trypsin (sequence grade modified, Promega, more trypsin may be needed (40-50 µg) if aggregation appeared), then 37° C. for 1 h.

Protein G-Dynabeads Coupling

Prepare protein G Dynabeads®: Resuspend Dynabeads® in the vial (vortex >30 sec or tilt and rotate 5 min). Transfer 100 µL (3 mg) Dynabeads® to a tube. Place the tube on the magnet to separate the beads from the solution and remove the supernatant. Wash the beads once with 400 µL of PBS with 0.2% Tween®-20 and remove the supernatant from the beads.

Binding of Antibody: Add monoclonal HIV-1/2 antibody (Ab) (50 µg) diluted in 400 µL PBS with 0.2% Tween®-20, to the Dynabeads® from above. Incubate with rotation for 1 h at room temperature. Place the tube on the magnet and wash the beads twice with 400 µL PBS with Tween®-20. Remove the tube from the magnet and resuspend the beads-Ab complex in 400 µL PBS with Tween®-20. Wash by gentle pipetting.

Immunoprecipitate Target Antigen

After added TFA to a final concentration of 0.1% (5 µL), the digested serum samples were spiked with 1.0 µL of 50 nmol/L stable isotope labeled internal standard peptide. Added 25 µL of HIV-1/2 antibody conjugated beads into each serum samples. For each sample, the antibody is 50/16=3.1 ug, and the beads is 3/16=0.1875 mg. Incubate with rotation for 1 hour at room temperature. Place the tube on the magnet and remove the supernatant. Wash the beads-Ab complex 2 times with 400 ul PBS, and once with 100 µL of LC grade water. Place the tube on the magnet and remove the supernatant. Add 20 µL Elution Buffer (1% Formic Acid) and incubated at RT for 15 min at HulaMixer. Place the tube on the magnet and transfer the supernatant containing eluted Ab and Ag to an Eppendorf LoBind tube. Transfer 16 µL of the supernatant to sample vial for LC-MS analysis (15 µL injection).

LC-PM-MS Analysis

Eluates were loaded on a C18 trap column, eluted onto a C18 analytical column, and fractionated with a 0.3 µL/min acetonitrile/formic acid gradient (5-40%) and analyzed using the PRM Mode on a nano-LC UltiMate 3000 high performance liquid chromatography (HPLC) system coupled with an Orbitrap Fusion™ Lumos™ Tribrid™ Mass Spectrometer (Thermo Fisher Scientific). Skyline software version 4.1.0.18169 (MacCoss Lab Software) was used to analyze serum MS and MS/MS spectra against a library produced using recombinant p24 and CFP-10 digests.

Example 4—HIV Peptide Alignment

Figure 15:
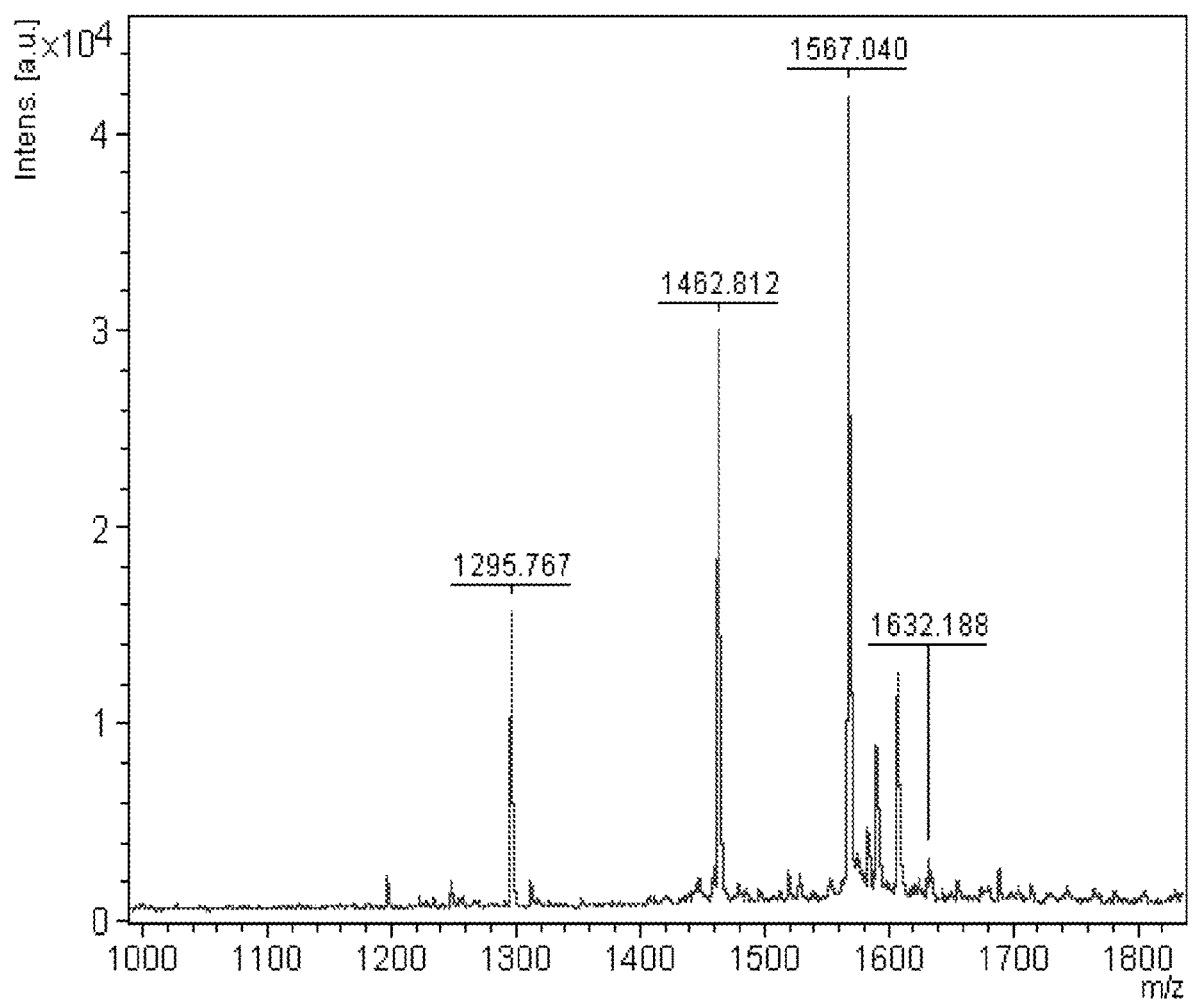
FIG. 15 shows a MALDI-TOF MS spectrum of recombinant p24 tryptic digestion products.

FIG. 15 shows a mass spectrum of a trypsin digest of recombinant p24, which generated only three major peaks that matched those provided by a bioinformatic analysis of this sequence (Table 4).

TABLE 4

List of [M + H]⁺ values for p24 trypic peptides provided by Skyline analysis (table discloses SEQ ID NOS 334, 5, 335, 7, and 336, respectively, in order of appearance).

| [M + H]⁺ | SEQUENCE | Peptide ID | Sequence variation within the HIV-1 M group |
|---|---|---|---|
| 1566.8321 | VHPVHAGPIAPGQMR | (PEPTIDE2) | [6 Class M variant aa positions; 6/15: 40.0%] |
| 1462.6444 | ETINEEAAEWDR | (PEPTIDE1) | [2 Class M variant aa positions; 2/12: 16.6%] |
| 1356.6430 | PEPTAPPEESFR | (ND) | |
| 1295.6664 | MYSPTSILDIR | (PEPTIDE3) | [3 Class M variant aa positions; 3/11: 27.2%] |
| 1144.5844 | SGVETTTPPQK | (ND) | |

Peptide IDs were assigned based on their order of appearance in the p24 aa sequence. Variable aa positions in the p24 sequence of HIV-1 group M viruses were identified after alinging all reviewed p24 gag entries in the UniProtKB virus database (January 2020).

All the HIV p24 sequences found in the UniProtKB database were aligned that had reviewed entries and identified two peptides regions that were completely conserved among the aligned sequences of all these p24 entries (GSDIAGTTS (SEQ ID NO: 337) and QGPKEPFRDYVDRF (SEQ ID NO: 338)). In addition, the alignments of all three Skyline entries with matching tryptic peaks were obtained.

A search of the UniProtKB database with the two completely conserved peptides gave an estimate of the total number of UniProtKB HIV-1 entries that contained this region (Table 5: 60,000), which were subsequently used to estimate the relative frequency of the amino acid variants of our target peptides among all HIV-1 p24 entries with the corresponding sequence.

TABLE 5

Estimate of HIV-1 gag sequence entries in the UniProKB database that contain the target peptide regions. Table discloses SEQ ID NOS 337 and 338, respectively, in order of appearance.

| AA SEQUENCE | HIV-1 ENTRIES | TOTAL UNIPROTKB ENTRIES |
|---|---|---|
| GSDIAGTTS | ~60,829 | [62,996 total: including 48 HIV2 + 2,119 SIV] |
| QGPKEPFRDYVDRF | 60,443 | [no HIV-2 or SIV] |

Alignment of all reviewed HIV-1 p24 entries in the UniProtKB virus database (January 2020) identified two aa sequence regions adjacent to the target peptides that were completely conserved among all HIV-1 p24 entries: GSDIAGTTS (SEQ ID NO: 337) and QGPKEPFRDYVDRF (SEQ ID NO: 338). Peptide searches of the UniProtKB virus database were performed to identify the number of entries that matched these sequences and entries that did not have HIV-1 identifiers were excluded from the estimate of HIV-1 p24 entries.

Figure 16:
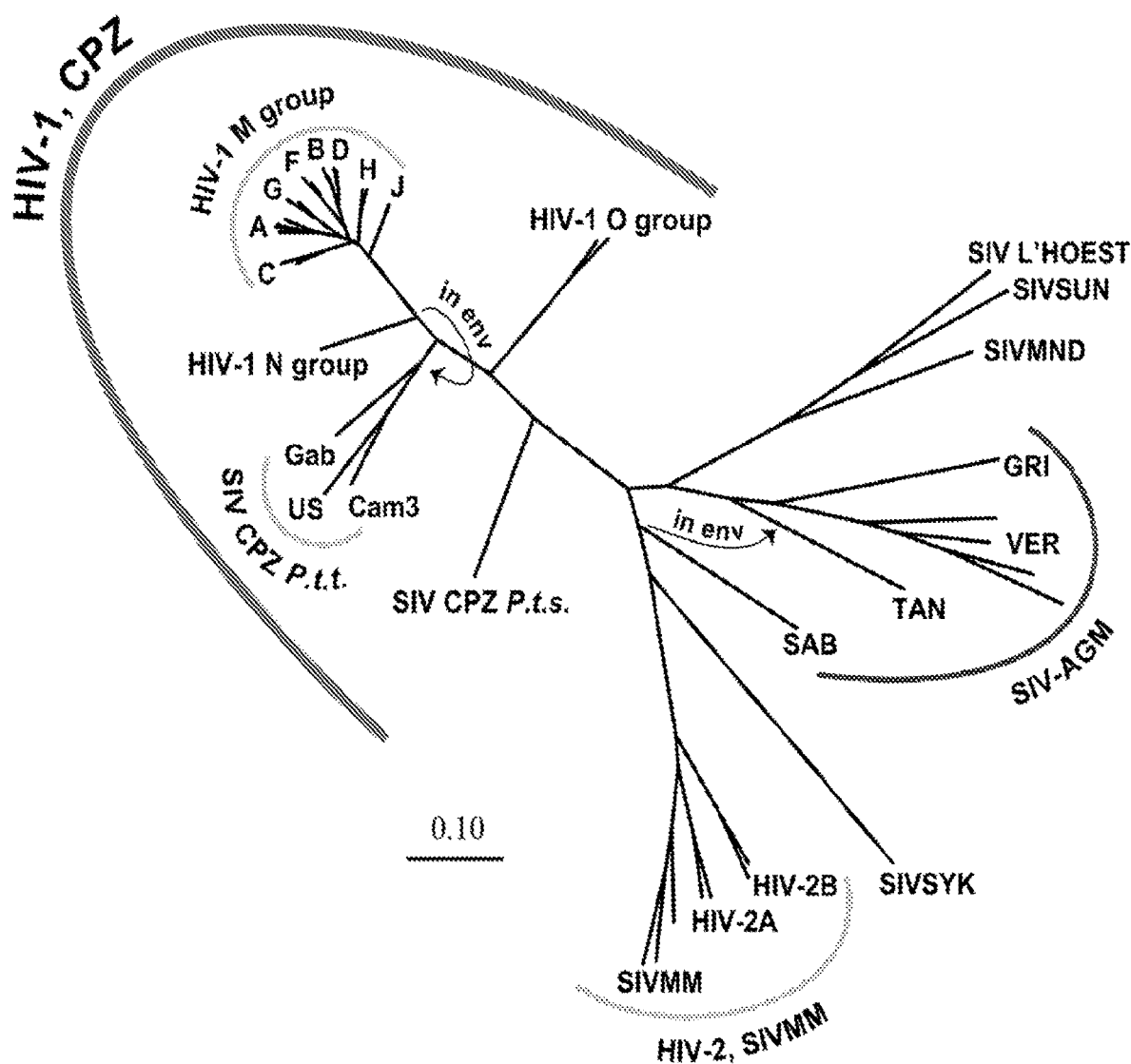
FIG. 16 shows a phylogenic tree of the HIV and SIV viruses. The image indicates the major groupings of HIV and SIV viruses. The HIV-1 M ("major") group contains HIV-1 subtypes responsible for most human infections, with the subtypes in this group accounting for >90% of reported HIV/AIDS cases, although the prevalence of these subtypes and their circulating recombinant forms (CRFs) varies by geographical locale (see FIG. 17).
Figure 17:
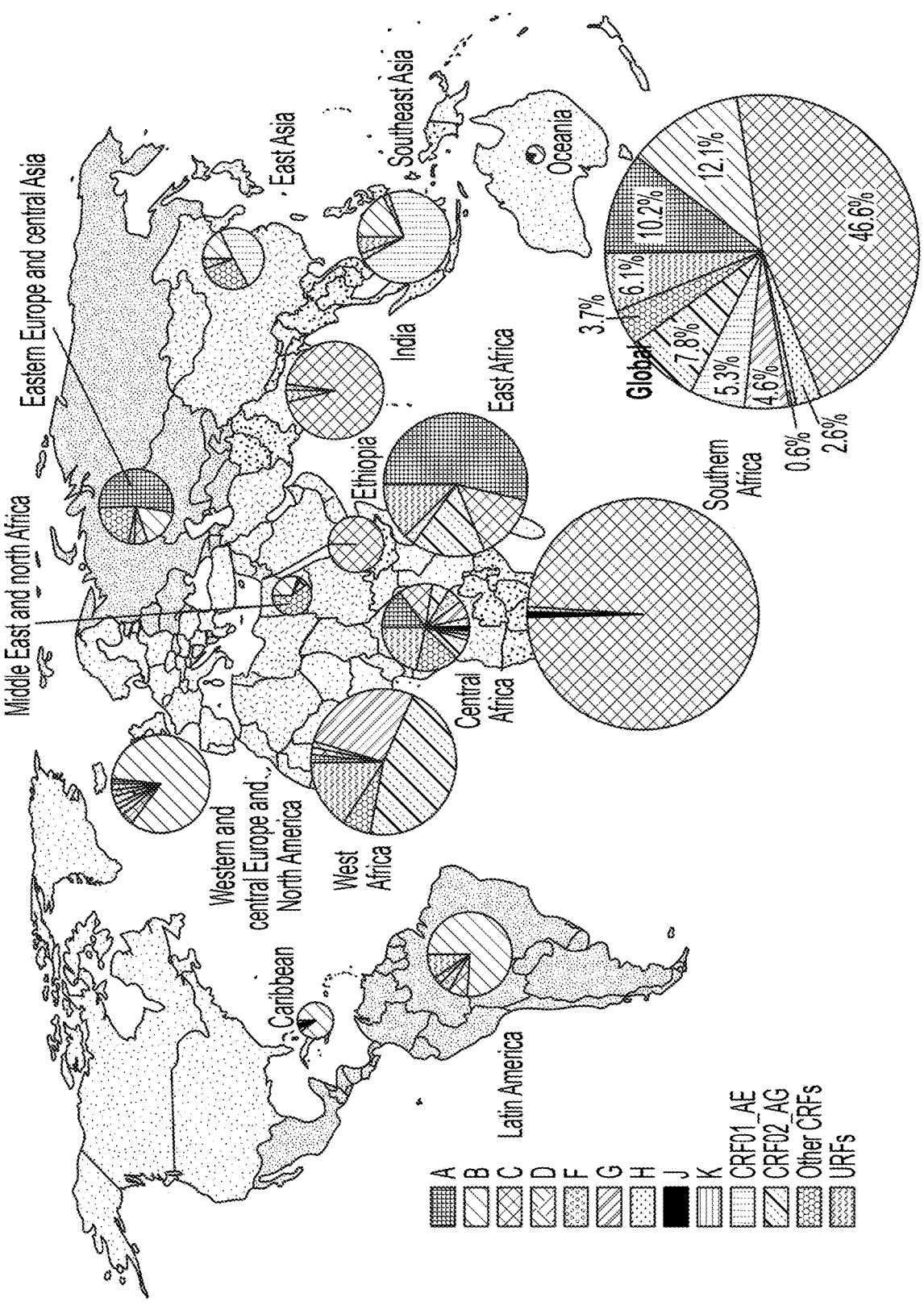
FIG. 17 shows Global and regional molecular epidemiology of HIV-1, 1990-2015: a systematic review, global survey, and trend analysis (Hemelaar, J. et al., The Lancet Infectious Diseases, 2018, 19 (2), p. 143-155. HIV-1 M subtypes A, B and C appear to be responsible for most (72.9%) global HIV-1 infections, with HIV-1 subtype C accounting for almost half (46.6%) of all cases. Circulating recombinant forms (CRFs; subtype A derivatives), and unique recombinant forms (URFs) of HIV-1 M and were responsible for most of the remaining global HIV-1 infections (22.8% of the total). Rough distributions and prevalence of each virus are as follows: HIV-1 M Subtype A (common in Eastern Africa, Eastern Europe and Central Asia), Subtype B (major form found in North and South America, Europe, the Middle East, North Africa, Japan, and Australia), Subtype C (dominant in Southern Africa, Eastern Africa, and India), Subtype D (primarily found in Eastern and Central Africa), Subtype F (detected in Central Africa, South America and Eastern Europe) Subtype G (detected in Africa and Central Europe), Subtype H (restricted to Central Africa), and Subtype J (primarily detected in North, Central and West Africa, and the Caribbean). For the three other subtypes, while Subtype K (restricted to the Democratic Republic of Congo (DRC) and Cameroon) and Subtype L (limited to the DRC), can be new subtypes. Non-group M virus infections are rare and geographically restricted: all known HIV-1 N cases are restricted (<20 cases as of 2015), while HIV-1 O cases are primarily detected in West Central Africa (<2% of HIV-1 cases in Cameroon). Most (>80%) HIV-2 cases are detected in West Africa, and only Subtypes A and B are considered to be pandemic. (Summary adapted from S, Pattou C, Walker N, Schwardlander B, Esparza J; WHO-UNAIDS Network for HIV Isolation and Characterization. (2002) Estimated global distribution and regional spread of HIV-1 genetic subtypes in the year 2000. *J Acquir Immune Defic Syndr.* 29(2):184-90).

Table 6 depicts the alignment of all three target peptides according to their species, group, subtype and viral isolate, where the evolutionary relationship amongst these groups is shown in FIG. 16. Note that Group M is estimated to account for >90% of HIV/AIDS cases, with the breakdown of the contribution of individual HIV-1 groups shown in FIG. 17.

TABLE 6

Alignment of PEPTIDE1, PEPTIDE2 and PEPTIDE3 in reviewed HIV-1/2 p24 and SIV p247 sequences found in the UniproKB virus database. Table 6 discloses "PEPTIDE1", "PEPTIDE2", and "PEPTIDE3" sequences as SEQ ID NOS 349-540, respectively, in order of appearance. Table discloses "PEPTIDE1 and PEPTIDE2" sequences as SEQ ID NOS 541-604, respectively, in order of appearance.

| ENTRY | PEPTIDE1 (1462) | PEPTIDE2 (1566) | PEPTIDE3 (1295) | GROUP:SUBTYPE (ISOLATE) |
|---|---|---|---|---|
| P24740 | MQMLKDTINEEAADWDR | VHPVHAGPIPPGQMREPRGS | NKIVRMYSPVSILDIRQGPKE | M:A (MAL) |
| | MQMLKDTINEEAAEWDR | LHPVHAGPIPPGQMREPRGS | NKIVRMYSPVSILDIRQGPKE | M:A (U455) |
| Q73367 | MQMLKETINEEAAEWDR | LHPVQAGPVAPGQMREPRGS | NKIVRMYSPSSILDIKQGPKE | M:B (89.6) |
| O12158 | MQMLKDTINEEAAEWDR | LHPVHAGPVAPGQMREPRGS | NKIVRMYSPVSILDIKQGPKE | M:B (92BR025) |

TABLE 6-continued

Alignment of PEPTIDE1, PEPTIDE2 and PEPTIDE3 in reviewed HIV-1/2
p24 and SIV p247 sequences found in the UniproKB virus database. Table 6 discloses
"PEPTIDE1", "PEPTIDE2", and "PEPTIDE3" sequences as SEQ ID NOS 349-540,
respectively, in order of appearance. Table discloses "PEPTIDE1 and PEPTIDE2"
sequences as SEQ ID NOS 541-604, respectively, in order of appearance.

| | | | | |
|---|---|---|---|---|
| P03349 | MQMLKETINEEAAEWDR | VHPVHAGPIAPGQMREPRGS | NKIVRMYSPTSILDIRQGPKE | M:B (ARV2/SF2) |
| P03347 | MQMLKETINEEAAEWDR | VHPVHAGPIAPGQMREPRGS | NKIVRMYSPTSILDIRQGPKE | M:B (BH10) |
| P04593 | MQMLKETINEEAAEWDR | VHPVHAGPIAPGQMREPRGS | NKIVRMYSPTSILDIRQGPKE | M:B (BH5) |
| P03348 | MQMLKETINEEAAEWDR | VHPVHAGPIAPGQMREPRGS | NKIVRMYSPTSILDIRQGPKE | M:B (BRU/LAI) |
| P05887 | MQMLKETINEEAAEWDR | LHPVHAGPIAPGQMREPRGS | NKIVRMYSPISILDIRQGPKE | M:B (CDC-451) |
| Q75001 | MQMLKDTINEEAAEWDR | LHPVHAGPVAPGQMRDPRGS | NKIVRMYSPVSILDIKQGPKE | M:B (ETH2220) |
| P04591 | MQMLKETINEEAAEWDR | VHPVHAGPIAPGQMREPRGS | NKIVRMYSPTSILDIRQGPKE | M:B (HXB2) |
| P12494 | MQMLKETINEEAAEWDR | LHPAQAGPIAPGQMREPRGS | NKIVRMYSPSSILDIRQGPKE | M:B (JH32) |
| P20873 | MQMLKETINEEAAEWDR | LHPVHAGPIAPGQMREPRGS | NKIVRMYSPVSILDIRQGPKE | M:B (JRCSF) |
| Q70622 | MQMLKETINEEAAEWDR | VHPVHAGPIAPGQMREPRGS | NKIVRMYSPTSILDIRQGPKE | M:B (LW123) |
| P05888 | MQMLKETINEEAAEWDR | LHPAHAGPIAPGQMREPRGS | NKIVRMYSPSSILDIRQGPKE | M:B (MN) |
| P12493 | MQMLKETINEEAAEWDR | LHPVHAGPIAPGQMREPRGS | NKIVRMYSPTSILDIRQGPKE | M:B (NY5) |
| P20889 | MQMLKETINEEAAEWDR | LHPVHAGPIAPGQMREPRGS | NKIVRMYSPTSILDIRQGPKE | M:B (OYI) |
| P05890 | MQMLKETINEEAAEWDR | LHPVHAGPIAPGQMREPRGS | NKIVRMYSPISILDIRQGPKE | M:B (RF/HAT3) |
| P24736 | MQMLKDTINEEAAEWDR | LHPVHAGPIPPGQMREPRGS | NKIVRMYSPVSILDIKQGPKE | M:B (U455) |
| P05889 | MQMLKETINEEAAEWDR | LHPVHAGPIAPGQMREPRGS | NKIVRMYSPTSILDIRQGPKE | M:B (WMJ22) |
| P35962 | MQMLKETINEEAAEWDR | LHPVHAGPIAPGQMREPRGS | NKIVRMYSPTSILDIRQGPKE | M:B (YU-2) |
| O12157 | MQMLKDTINEEAAEWDR | LHPVHAGPVAPGQMREPRGS | NKIVRMYSPVSILDIKQGPKE | M:C (92BR025) |
| Q75002 | MQMLKDTINEEAAEWDR | LHPVHAGPVAPGQMRDPRGS | NKIVRMYSPVSILDIKQGPKE | M:C (ETH2220) |
| P04592 | MQMLKETINEEAAEWDR | LHPVHAGPIAPGQMREPRGS | NKIVRMYSPVSILDIRQGPKE | M:D (ELI) |
| P18800 | MQMLKETINDEAAEWDR | LHPVHAGPVAPGQMREPRGS | NKIVRMYSPVSILDIRQGPKE | M:D (NDK) |
| P12495 | MQMLKETINEEAAEWDR | LHPVHAGPIAPGQMREPRGS | NKIVRMYSPVSILDIRQGPKE | M:D (Z2/CDC-Z34) |
| O89291 | MQMLKDTINEEAAEWDR | LHPTQAGPIPPGQIREPRGS | NKIVRMYSPVGILDIKQGPKE | M:F1 (93BR020) |
| Q9QSR4 | MQMLKDTINEEAAEWDR | LHPVHAGPAPPGQMREPRGS | NKIVRMYSPVSILDIKQGPKE | M:F1 (VI850) |
| Q9QBZ6 | MQMLKDTINEEAAEWDR | LHPVHAGPIPPGQMREPRGS | NKIVRMYSPVSILDIKQGPKE | M:F2 (MP255) |
| Q9QBZ2 | MQMLKDTINEEAAEWDR | LHPVHAGPIPPGQMREPRGS | NKIVRMYSPVSILDIKQGPKE | M:F2 (MP257) |
| P0C1K7 | MQMLKDTINEEAAEWDR | IHPQQAGPIPPGQMREPRGS | NKIVRMYSPVSILDIKQGPKE | M:G (92NG083) |
| O89939 | MQMLKDTINEEAAEWDR | MHPQQAGPFPPGQIREPRGS | NKIVRMYSPVSILDIKQGPKE | M:G (SE6165) |
| O93182 | MQMLKDTINEEAAEWDR | VHPVHAGPIPPGQMREPRGS | NKIVRMYSPVSILDIKQGPKE | M:H (90CF056) |
| Q9Q721 | MQMLKDTINEEAAEWDR | LHPVHAGPIPPGQMREPRGS | NKIVRMYSPVSILDIKQGPKE | M:H (VI991) |
| Q9WC62 | MQMLKDTINEEAAEWDR | VHPVHAGPVAPGQVREPRGS | NKIVRMYSPVSILDIRQGPKE | M:J (SE9173) |
| Q9WC53 | MQMLKDTINEEAAEWDR | VHPVHAGPVAPGQVREPRGS | NKIVRMYSPVSILDIKQGPKE | M:J (SE9280) |
| Q9QBY4 | MQMLKDTINDEAAEWDR | LHPVHAGPIPPGQMREPRGS | NKIVRMYSPVSILDIRQGPKE | M:K (96CM-MP535) |
| Q9QC00 | MQMLKDTINEEAAEWDR | MHPVQAGPIPPGQIREPRGS | NKIVRMYSPVSILDIRQGPKE | M:K (97ZR-EQTB11) |
| Q9IDV8 | MQMLKEVINEEAAEWDR | THPAPVGPLPPGQMRDPRGS | NRIVRMYSPVSILEIKQGPKE | N (YBF106) |
| O91079 | MQMLKEVINEEAADWDR | THPVPVGPLPPGQLRDPRGS | NRIVRMYSPTSILEIKQGPKE | N (YBF30) |
| Q77372 | LQVLKEVINEEAVEWDR | THPPPVGPLPPGQIREPTGS | NKMVKMYSPVSILDIKQGPKE | O (ANT70) |
| Q79665 | LQVLKEVINEEAAEWDR | THPPAMGPLPPGQIREPTGS | NKMVKMYSPVSILDIRQGPKE | O (MVP5180) |

| HIV2 | PEPTIDE1* (PEPTIDE1-PEPTIDE2) | PEPTIDE3 | GROUP:SUBTYPE (ISOLATE) |
|---|---|---|---|
| P24106 | MQIIREIINEEAADWDA-NHPIP-GPLPAGQLRDPRGS | QKCVRMYNPTNILDIKQGPKE | A (isolate CAM2) |
| P04584 | MQIIREIINEEAAEWDV-QHPIP-GPLPAGQLREPRGS | QKCVRMYNPTNILDIKQGPKE | A (isolate ROD) |
| Q74119 | MQIIREIINEEAADWDQ-QHPIP-GPLPAGQLRDPRGS | QKCVRMYNPTNILDVKQGPKE | A (isolate KR) |
| P20874 | MQIIREIINEEAADWDA-QHPIP-GPLPAGQLREPRGS | QKCVRMYNPTNILDIKQGPKE | A (isolate ST) |
| P17756 | MQIIREIINEEAADWDA-QHPIP-GPLPAGQLRDPRGS | QKCVRMYNPTNILDIKQGPKE | A (isolate D194) |
| P18095 | MQIIREIINEEAADWDS-QHPIP-GPLPAGQLRDPRGS | QKCVRKYNPTNILDIKQGPKE | A (isolate BEN) |
| P18041 | MQIIREIINDEAADWDA-QHPIP-GPLPAGQLRDPRGS | QKCVRMYNPTNILDVKQGPKE | A (isolate Ghana-1) |
| P05891 | MQIIREIINEEAADWDV-AHPIP-GPLPAGQLREPRGS | QKCVRMYNPTNILDINQGPKE | A (isolate NIH-Z) |
| P12450 | MQTIREIINEEAADWDV-QHPIP-GPLPAGQLREPRGS | QKCVRMYNPTNILDIKQGPKE | A (isolate SBLISY) |
| Q76633 | MQIIREIINEEAADWDQ-QHPIP-GPLPAGQLREPRGS | QKCVRMYNPTNILDIKQGPKE | B (isolate UC1) |
| P15832 | MQIIREIINEEAADWDQ-QHPSP-GPMPAGQLRDPRGS | QKCVRMYNPTNILDIKQGPKE | B (isolate D205) |
| Q74230 | MQIIREIINEEAADWDQ-QHPSP-GPMPAGQLREPRGS | QKCVRMYNPTNILDIKQGPKE | B (isolate EHO) |

| SIV2 | PEPTIDE1* (PEPTIDE1-PEPTIDE2) | PEPTIDE3 | GROUP:SUBTYPE (ISOLATE) |
|---|---|---|---|
| P12496 F236/smH4) | MQIIREIINEEAADWDL-QHPQP-GPLPAGQLREPRGS | QKCVRMYNPTNILDVKQGPKE | SIV-mm (isolate |
| P19504 PBj14/BCL-3) | MQTIREIINEEAADWDL-QHPQP-GPIPPGQLREPRGS | QKCVRMYNPTNILDVKQGPKE | SIV-mm (isolate |
| KU892415.1 | MQIIRDIINEEAADWDL-QHPQP-APQ-QGQLREPSGS | QKCVRMYNPTNILDVKQGPKE | SIV-mac (251/32H/L28) |
| D01065.1 | MQTIRDIINEEAADWDL-QHPQP-APQ-QGQLREPSGS | QKCVRMYNPTNILDVKQGPKE | SIV-mac (32H) |
| KF051800.1 | MQTIRDIINEEAADWDL-QHPQP-APQ-QGQLREPSGS | QKCVRMYNPTNILDVKQGPKE | SIV-mac (251) |
| M33262.1 | MQTIRDIINEEAADWDL-QHPQP-APQ-QGQLREPSGS | QKCVRMYNPTNILDVKQGPKE | SIV-mac (239) |
| P05894 | MQIIRDIINEEAADWDL-QHPQQ-APQ-QGQLREPSGS | QKCVRMYNPTNILDVKQGPKE | SIV-mac (Mm142-83) |
| P05897 | MQIIRDIINEEAADWDL-QHPQP-APQ-QGQLREPSGS | QKCVRMYNPTNILDVKQGPKE | SIV-mac (K6W) |
| P05893 | MQTIRDIINEEAADWDL-QHPQP-APQ-QGQLREPSGS | RLQCVYNPINILDVKQPKE | SIV-mac (K6W) |
| P31634 | MQIIREIINEEAADWDV-QHPQP-GPLPAGQLREPSGS | QKCVRMYNPVNILDIKQGPKE | SIV-mac (STM) |

Target peptides are presented with five aa of flanking sequence except where one target peptide abuts another (PEPTIDE1 and PEPTIDE2). A single entry is shown for each isolate. Underlining and bold formatting indicate the highly conserved (bold) and variable (underlined) aa's in each target peptide. Dashes indicate spaces introduced to promote aa sequence alignment.

Table 6 indicates that PEPTIDE1 (ETINEEAAEWDR (SEQ ID NO: 5)) is highly conserved amongst all HIV-1 groups, varying at a single residue (position 1) in all but one of the group M sequence isolates [HIV-1 M:A (MAL)], with both variant positions consisting of conservative D to E substitutions. Additional variants, including one at the same position, are present in individual group N and O isolates, but these minor HIV-1 groups are rare and restricted to very limited geographical areas.

PEPTIDE2 (VHPVHAGPIAPGQMR (SEQ ID NO: 334)) contains multiple sites of amino acid variation spread throughout its length and demonstrates significant variation even within the group M subtypes. Multiple antibodies would be required to capture all the variants of this peptide, making a poor biomarker target.

PEPTIDE1 and PEPTIDE2 would not be generated in HIV-2 or SIV due to a variable amino acid substitution that removes the R reside required to separate these two peptides. An antibody generated to PEPTIDE1, but not PEPTIDE2, might be able to capture this fusion peptide, but it should demonstrate a significantly different elution profile and a would have a much higher mass to charge ratio than PEPTIDE1 isolates from any HIV-1 group and subtype.

PEPTIDE3 (MYSPTSILDIR (SEQ ID NO: 7)) was less conserved than PEPTIDE1 but most of its amino acid variation was restricted to two positions (residues 5 and 11). Most of the HIV-1 group and subtypes, except HIV-1 group M subtype B, had a V residue at position 5 of PEPTIDE3, while a conservative K or R variation at residue 11 was almost equally splits between the various group M subtypes.

PEPTIDE1 antibodies were generated using ETINEEAAEWDR (SEQ ID NO: 5) as the immunogen and they also efficiently detected the DTINEEAAEWDR (SEQ ID NO: 6) peptide. This seems to be a safe choice, particularly since the only other variation was much rarer and was also a conservative E to D substitution. Together these two variants accounted for 96.8% of all the HIV-1 p24 sequences present in the UniProtKB database, implying that we should be able to detect p24 peptides from most groups and subtypes, although this analysis is subject to selection bias in that the deposited sequences may not accurately represent the global distribution of HIV-1 p24 sequence variation.

PEPTIDE3 antibodies were generated using MYSPTSILDIR (SEQ ID NO: 7) as the immunogen and these antibodies efficiently detected the MYSPVSILDIK (SEQ ID NO: 8) peptide, although their performance with any of the other group M subtype B sequence variants was not examined. Due to the sequence variation in group M subtype B at this position, it is possible that these antibodies could have reduced affinity of some of these variants. The analysis indicates that 93.1% of the UniProtKB HIV-1 p24 entries reveal the sequence MYSP[T/V]SILDI[K/R] (SEQ ID NO: 339) at this position, so we should have reasonable coverage of the variation even if a monoclonal antibody raised against MYSPTSILDIR (SEQ ID NO: 7) fails to sensitively bind the MYSPSSILDI[K/R] (SEQ ID NO: 340) and MYSPSSILDI[K/R] (SEQ ID NO: 340) variants of PEPTIDE3, which account for another 4% of the variation of this peptide. However, both these substitutions could be considered conservative to with respect to the amino acid variants already recognized by our current polyclonal antibodies, as each differ be the gain or loss of a single hydrogenated carbon functional group (T to S, terminal loss; V to I, internal gain).

TABLE 7

Estimate of the frequency of specific PEPTIDE1 variants in UniProKB data HIV-1 gag sequence. Table discloses SEQ ID NOS 341, 5, 342-347, and 337, respectively, in order of appearance.

| Short region | Variant1 | Variant2 | Total |
|---|---|---|---|
| *TINEEAAEWDR 55,646 | ETINEEAAEWDR 31,595 | DTINEEAFAEWDR 23,965 | [E/D]TINEEAAEWDR 55,560 (91.3%) |
| *TINEEAADWDR 3,346 | ETINEEAADWDR 2,238 | DTINEEAADWDR 1,099 | [E/D]TINEEAADWDR 3,337 (5.5%) |
|  |  |  | 58,897 (96.8% of 60,829 GSDIAGTTS entries) |

Example 5—Multiplex Serum Detection of HIV-1 and *Mycobacterium tuberculosis* Infections by a Rapid Affinity-Enriched Mass Spectrometry Assay Abstract Co-infection with HIV and *Mycobacterium tuberculosis* (Mtb) significantly contributes to the global morbidity and mortality rates of these diseases. Improving early diagnosis rates and monitoring of the treatment responses of individuals with both infections is essential to improve patient outcomes. PCR-based tests exist for each pathogen but have limitations that hinder their utility for joint screening approaches, particularly since the only United States Food and Drug Administration-approved assay is only approved for sputum specimens. This significantly limits its diagnostic utility in patients co-infected with HIV and Mtb (HIV/Mtb cases), who frequently produce sputum specimens with low Mtb abundance. Herein, we describe the development of a diagnostic assay that directly quantifies the level of single peptides of HIV-1 p24 and Mtb culture filtrate protein 10 (CFP-10) to evaluate the systemic burden of each pathogen and its response to treatment. Results from a case control study found that real-time multiplex quantification p24 and CFP-10 target peptides in patient blood specimens was informative for early HIV and Mtb diagnosis and in assessing patient responses to anti-Mtb and anti-retroviral therapy, indicating this approach can provide clinical information that could facilitate the linkage of Mtb and HIV prevention, diagnosis, treatment and care services to improve patient outcomes.

Introduction

The HIV pandemic presents a significant challenge for global TB control efforts, since people living with HIV (PLHIV) have a 20- to 30-fold increased risk of developing TB, which is the leading cause of morbidity and mortality in this group [1]. PLHIV accounted for 1.2 of the estimated 10.4 million new TB cases in 2016, and 0.4 of the 1.7 million TB deaths [1]. Improving the rate of TB testing in PLHIV and HIV testing in TB patients is a critical step for reducing the prevalence of HIV/TB co-infection by increasing the rate of early treatment to improve patient outcomes. The 2013 Global Tuberculosis Report of the World Health Organization (WHO) recommended regular screening for TB during primary care visits related to HIV screening and treatment [2]. This is required to address the finding that nearly 60% of TB cases in PLHIV are not diagnosed or treated, leading to excess morbidity and mortality [1]. Similarly, the target goal of the Stop TB Partnership's Global Plan to Stop TB was that by 2015 all patients with TB should be tested for HIV [3]. However, in 2016 only 57% of the new and relapsed global TB cases had a documented HIV test. [1].

The primary reasons for this diagnostic gap may include socioeconomic factors associated with HIV/TB, including poverty, poor knowledge of and attitudes about HIV/TB infection, and adverse patient behaviors [4]. However, patients with HIV-associated TB (HIV/TB) often have their TB and HIV managed in separate programs provide treatment for each disease but do not coordinate these therapy regimes. This lack of coordination may be a significant factor in missed or delayed HIV and/or TB diagnosis and treatment, contributing to preventable morbidity and mortality. WHO policy emphasizes the need to establish mechanisms for delivering integrated TB and HIV services, for example at the same time and location [5]. Intensifying TB case-finding in PLHIV and providing HIV testing and counseling to patients with presumptive and diagnosed TB cases are believed to be key requirements to mitigate the burden of TB/HIV in populations at risk of developing, or affected by, both diseases [6].

To further complicate this situation, TB diagnosis in PLHIV presents a major challenge, since PLHIV with TB frequently have "subclinical" TB cases that are often not recognized as TB, delaying their TB diagnosis and treatment. Sputum-based TB diagnostics, including acid-fast bacilli (AFB) smear, Mtb culture, and the GeneXpert® MTB/RIF, exhibit reduced sensitivity with paucibacillary (low bacillary concentration) samples that are frequently associated with HIV/TB cases [7, 8]. New approaches that allow sensitive and specific diagnosis of HIV/TB infections would therefore address an urgent unmet need to improve the integrated management of HIV-1 and TB disease.

Detection and quantification of a pathogen-specific protein in serum or plasma provides direct evidence of infection and can also reflect pathogen burden and thus can be used to both diagnose an infection and monitor its response to treatment. However, conventional immunoassays for such biomarkers are faced with confounding issues. For example, interactions with circulating factors, including antibodies, may significantly attenuate immunoassay sensitivity, while off-target recognition of homologs from related pathogens, such as nontuberculous mycobacteria (NTM), can reduce assay specificity.

Figure 18E:
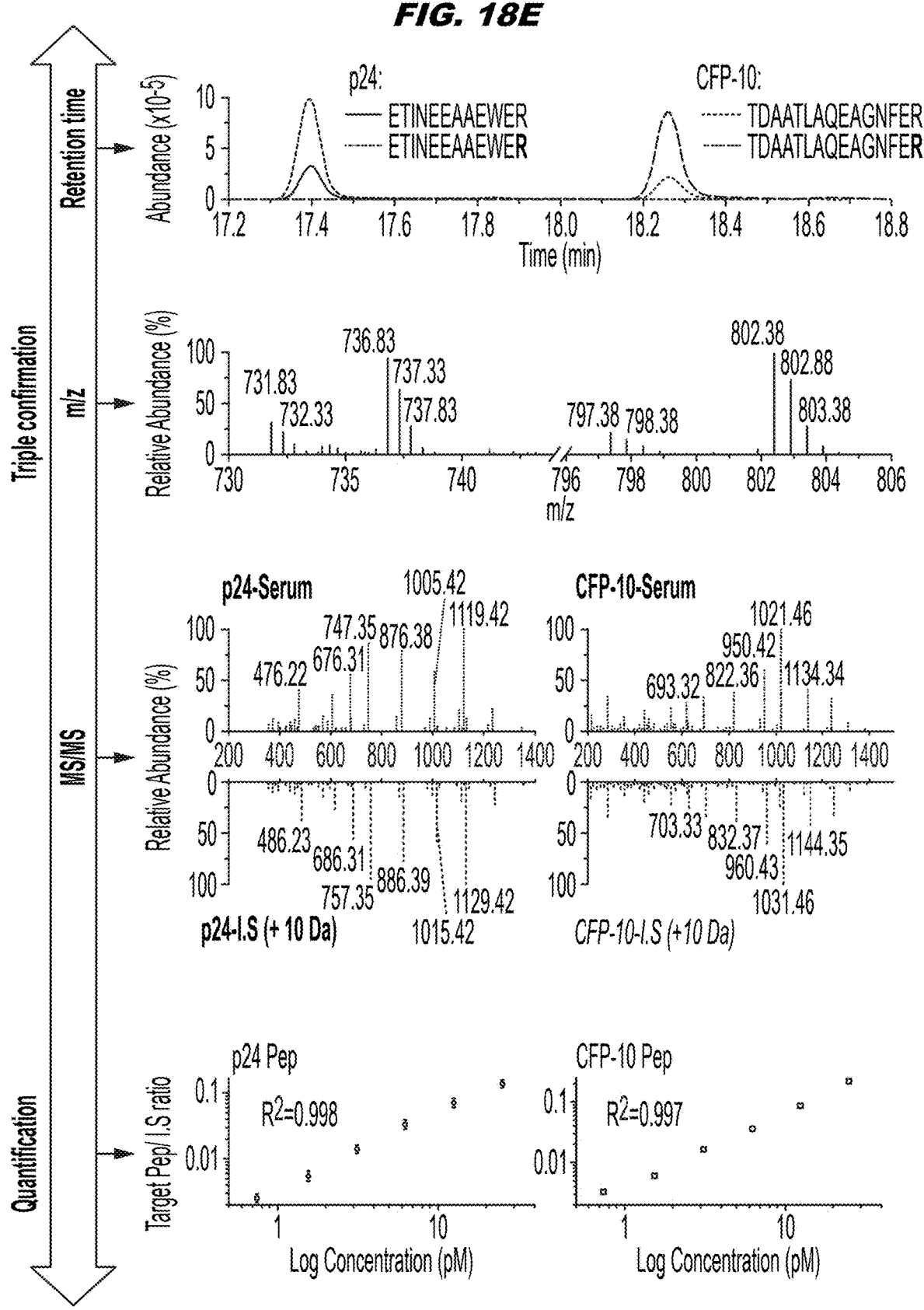
FIG. 18E discloses the "p24" sequences as SEQ ID NO: 13 and the "CFP-10" sequences as SEQ ID NO: 1.

Assays that measure proteotypic biomarker peptides can avoid these issues since the digestion step required to produce these peptides disrupts protein-protein interactions, while the released biomarker peptides can often differentiate between highly similar proteins and their isoforms. We have previously reported that detection of Mtb-derived peptides in patient plasma or serum by mass spectrometry (MS) can diagnose active pulmonary and extrapulmonary TB cases with high sensitivity and specificity in the presence or absence of HIV co-infection [9, 10]. In the current study, we developed a liquid chromatography (LC) MS method that detects and quantifies peptides derived from the Mtb virulence factor culture filtrate protein 10 (CFP-10), and the HIV-1 capsid protein p24 in a single MS spectrum for rapid diagnosis and real-time treatment monitoring of HIV-1/TB co-infections. In this method, target CFP-10 and p24 peptides from trypsin digested plasma or serum samples are analyzed by immunoprecipitation followed by scheduled parallel reaction monitoring (iSPRM) in an LC-iSPRM-MS approach that allows rapid quantification of HIV-1- and Mtb-specific peptides. This assay approach contains multiple features that enhance the sensitivity and specificity of biomarker detection (FIG. 18). Simultaneous and quantitative monitoring of Mtb and HIV-1 infections offered by this assay could open new possibilities for the diagnosis and management of patients with immune reconstitution inflammatory syndrome (IRIS) and facilitate the discrimination of IRIS from TB treatment failure.

We chose CFP-10 as a biomarker of active TB, since it is actively secreted by virulent Mtb strains, detectable soon after infection, attenuates Mtb clearance and can be readily detected in plasma and serum for active TB diagnosis in adults [11]. We selected p24 as a biomarker of HIV-1 infection, since its detection has been shown to be of value in: (i) diagnosing early HIV-1 infections; (ii) screening blood to identify samples from HIV-infected donors; (iii) diagnosing HIV infections in newborns; and (iv) monitoring anti-retroviral therapy (ART) efficacy, provided that the p24 levels is measured with sufficient sensitivity and accuracy [12].

Figure 21A:
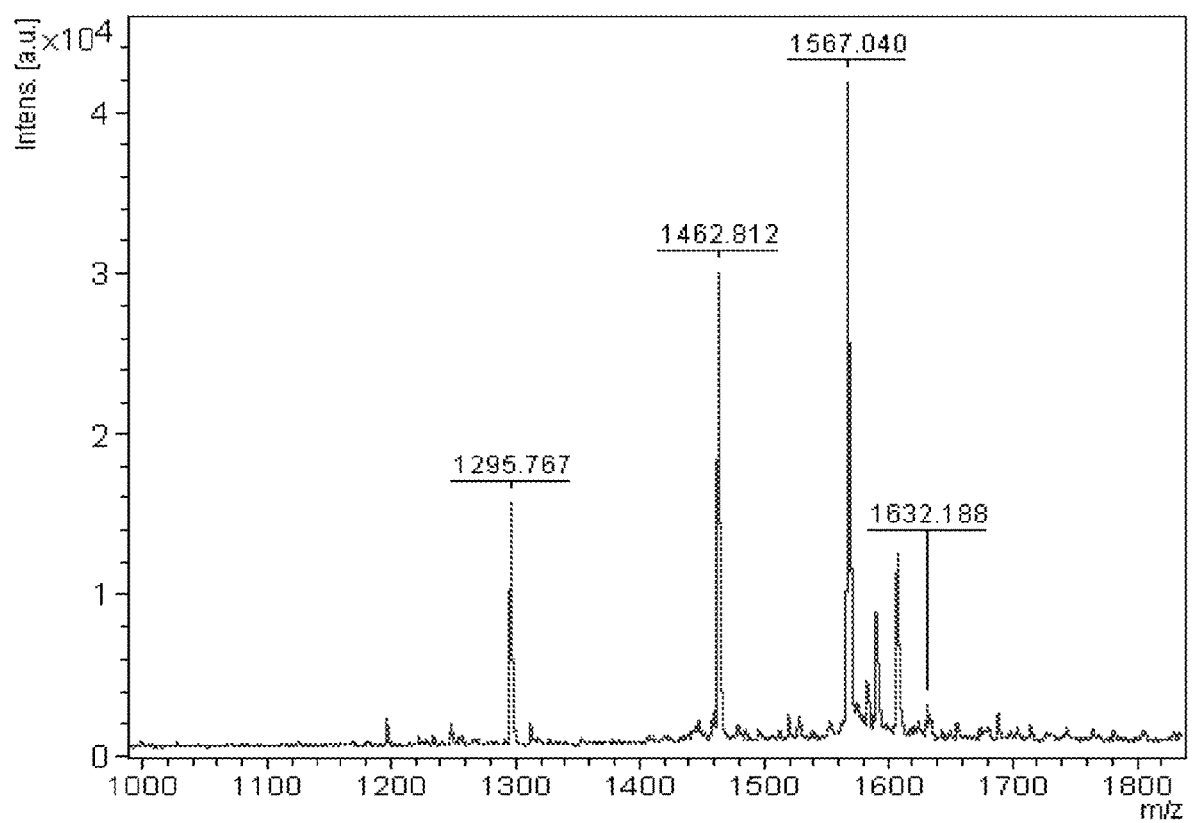
FIG. 21 shows MALDI-TOF MS signals of tryptic digested p24 fragments. A: Mass spectra of recombinant p24 tryptic digestion products. B: Theoretical [M+H]$^+$ values of p24 tryptic digestion products (SEQ ID NOS 334, 5, 335, 7, and 336, respectively, in order of appearance).
Figure 23:
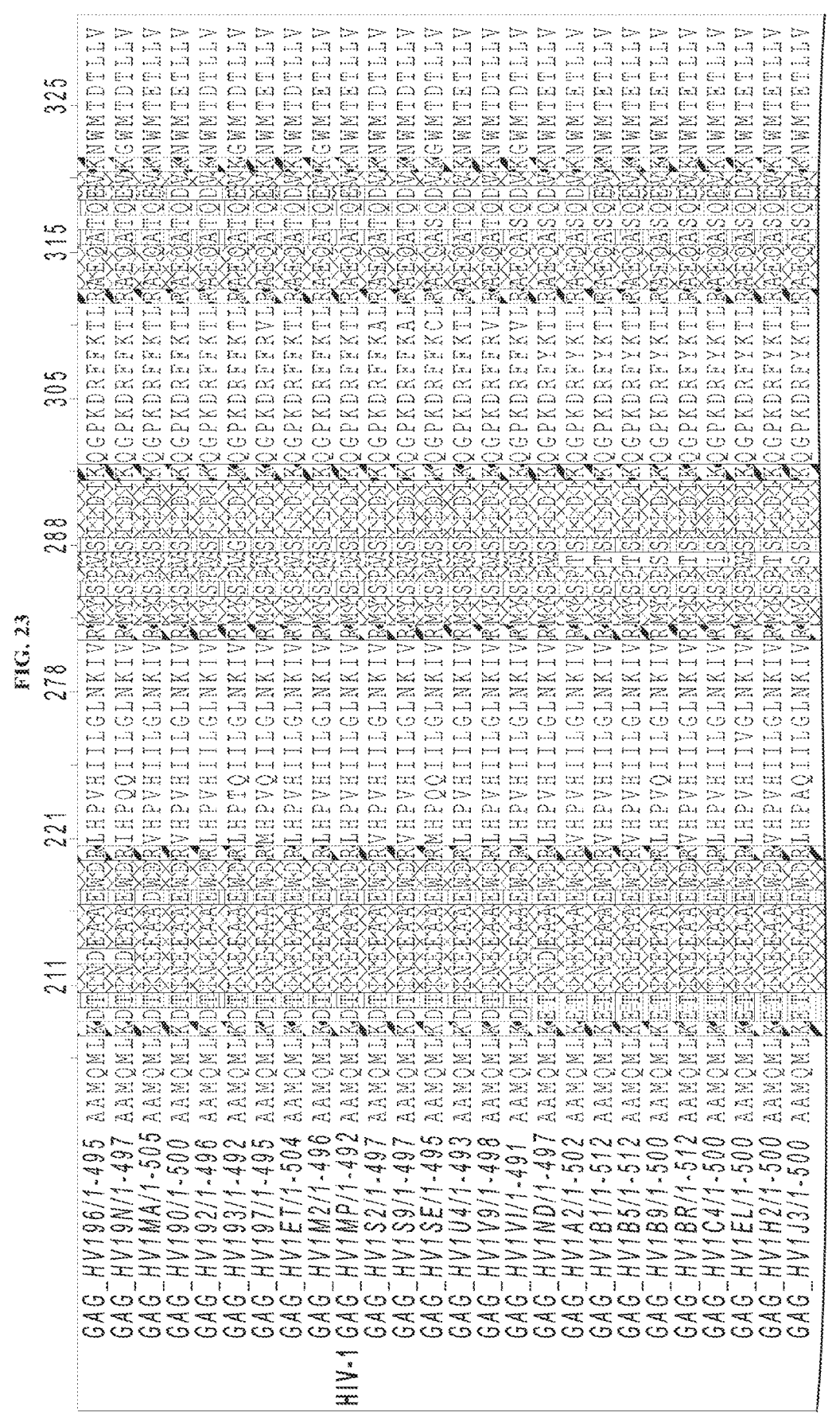
Figure 23:
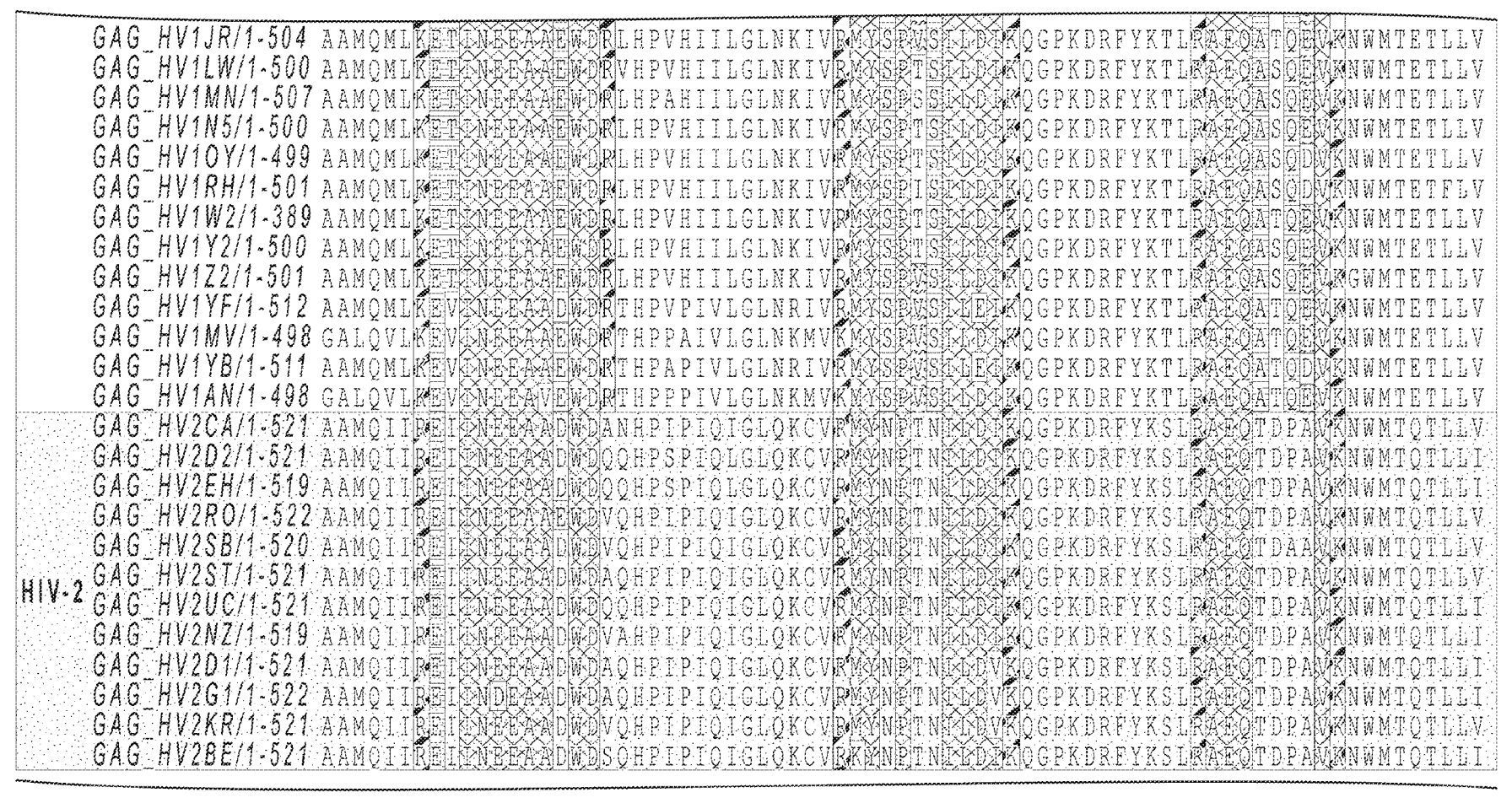

We have previously identified and validated a peptide that can identify and quantitate CFP-10 present in patient serum and plasma samples for TB diagnosis [9, 10]. Proteotypic p24 peptides intended for HIV-1 diagnosis were identified by subjecting tryptic digests of recombinant HIV-1 p24 to matrix-assisted laser desorption/ionization time-of-flight MS and LC electrospray ionization tandem MS analysis. Peptides ETINEEAAEWER (SEQ ID NO: 13) (m/z 1462.83) and MYSPTSILDIR (SEQ ID NO: 7) (m/z 1295.43) detected in this analysis demonstrated signal-to-noise ratios>125 and exhibited HIV-1 specificity when aligned with p24 protein sequence of HIV-1 and HIV-2 (FIGS. 21-23). These peptides, and their variants DTINEE-AAEWER (SEQ ID NO: 348) and MYSPVSILDIR (SEQ ID NO: 9), in aggregate matched the p24 sequence of >95% of the analyzed HIV-1 strains, but not HIV-2 p24 sequence. Antibodies raised against ETINEEAAEWER (SEQ ID NO: 13) and MYSPTSILDIR (SEQ ID NO: 7) also efficiently bound DTINEEAAEWER (SEQ ID NO: 348) and MYSPVSILDIR (SEQ ID NO: 9) (FIG. 24, and not shown).

To evaluate the ability of LC-iSPRM-MS to quantify p24 and CFP-10 in human serum, pooled serum from healthy subjects was spiked with recombinant p24 and CFP-10 protein, trypsin digested, and spiked with stable-isotope-labeled internal standard (IS) peptides matching the sequence of the target p24 and CFP-10 peptides, after which both the target and IS peptides were immunoenriched and quantified by LC-iSPRM-MS at high sensitivity. All peptides were detected with high specificity due to the multiple levels of LC-iSPRM-MS data confirmation: retention time, mass-over-charge (m/z) ratio and the MS/MS spectra of the target and internal standard peptides (FIG. 18b). Standard curves generated by plotting the ratio of the MS peak intensity for a target peptide and its corresponding IS in serum samples spiked with known amounts of p24 and CFP-10 exhibited strong linear correlation ($R^2>0.99$) with the amount of input protein (FIG. 18b) and reproducibility (14-22% within-run and 16-23% between-run coefficients of variation). In this analysis, the p24 ETINEEAAEWER (SEQ ID NO: 13) and CFP-10 TDAATLAQEAGNFER (SEQ ID NO: 1) peptides demonstrated limits of detection (LOD) and quantitation (LOQ) of 0.1 pM and 0.5 pM, respectively, while the p24 MYSPTSILDIR (SEQ ID NO: 7) peptide exhibited a 1.0 pM LOD and 2.5 pM LOQ.

Figure 19A:
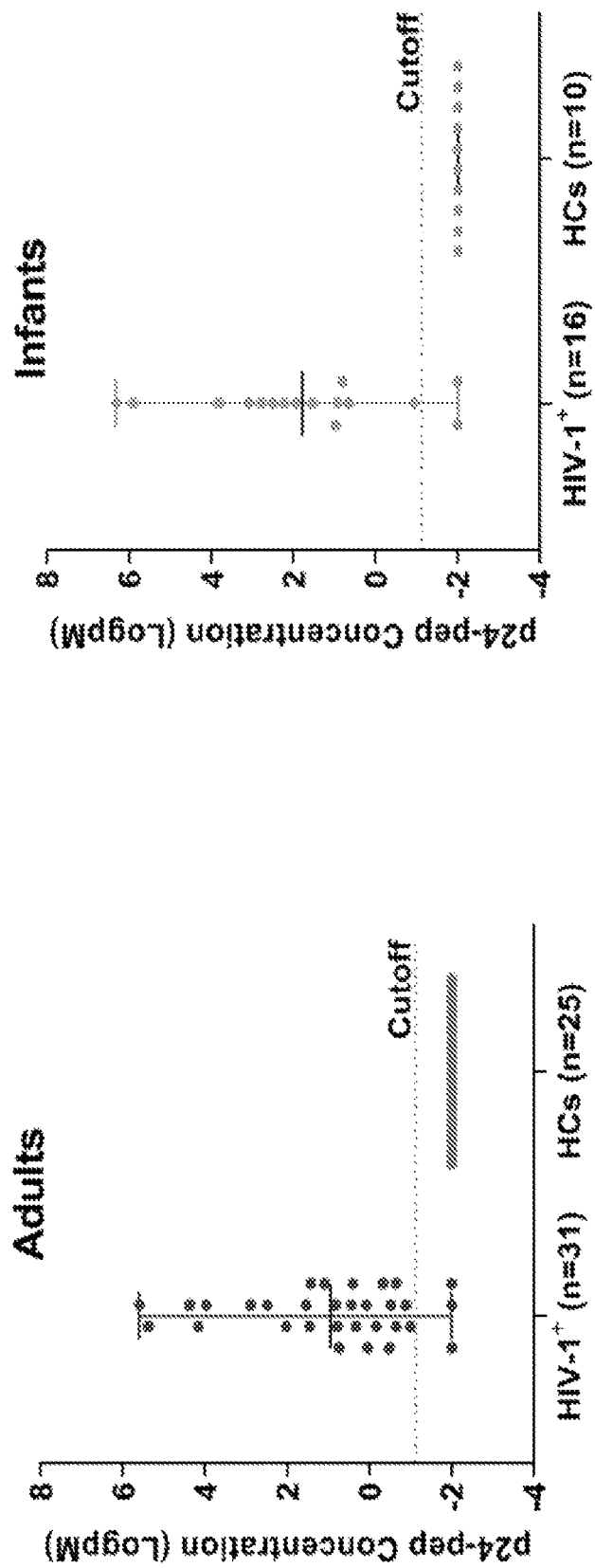
FIG. 19 shows quantitative detection of p24 antigen for diagnosis and treatment monitoring of HIV-1 infection. a. HIV-1 diagnosis using serum from adults and infants. Solid horizontal lines indicate the median and 95% confidence intervals for each group. The red dashed line indicates the p24 cut-off value (0.1 pmol/L) for HIV-1 diagnosis. b. Quantitative monitoring of p24 antigen in seroconversion panels. c. Longitudinal monitoring of p24 in patients receiving antiretroviral therapy from p1041 cohort.
Figure 19B:
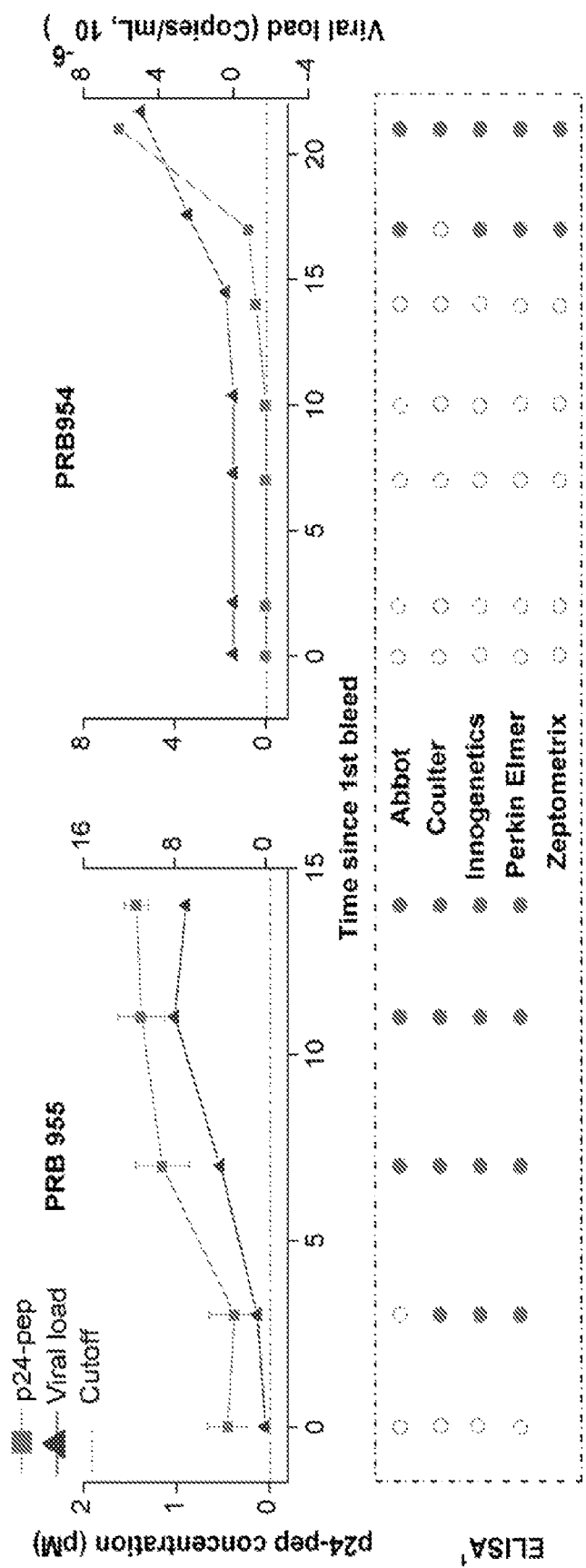

We next evaluated the ability of this assay to diagnose HIV-1 infections in a cohort of adults (31 HIV+ and 25 HIV− individuals) enrolled in the Houston Tuberculosis Initiative (HTI), a large, population-based TB surveillance study. This assay was also applied to diagnose HIV in a group of infants (16 HIV+ and 10 HIV−) enrolled in the International Maternal Pediatric Adolescent AIDS Clinical Trials (IMPAACT) P1041 trial, a TB prevention trial conducted among infants enrolled from 2004 to 2008 during South Africa's roll-out of combination antiretroviral therapy (ART) (Table 8).

sequence variants expressed by different HIV-1 strains. Several factors (e.g., testing method, individual responses and viral characteristics) influence the interval between virus exposure and the earliest reliable detection of HIV RNA, HIV antigens, or anti-HIV antibodies in serum samples. To evaluate LC-iSPRM-MS performance for early HIV diagnosis, we analyzed serum samples obtained from two patients before and after they tested positive for HIV-1 and found that in each case LC-iSPRM-MS detected p24 expression at least one time point earlier than p24 immunoassay (FIG. 19b). LC-iSPRM-MS detected 8 of the 9 HIV+ specimens (88.9% sensitivity) versus the 5 to 6 samples detected by p24 ELISA indicating a range of 55.6% to 66.7% sensitivity. LC-iSPRM-MS detected serum p24 expression one sample earlier than the Innogenetics and Perkin Elmer Alliance ELISAs, and one and two samples earlier than the Coulter or Abbot ELISAs, respectively. Notably, the PRB954 samples analyzed in this study spanned the early

TABLE 8

Demographics and clinical characteristics of the study participants for the diagnosis of HIV-1

|  | Controls | HIV-1 cases | p Value |
| --- | --- | --- | --- |
| Adult (HTI Cohort) | n = 25 | n = 31 |  |
| Sex, male (%)$^a$ | 18 (72) | 23 (74.2) | 0.717$^c$ |
| Age, years (IQR)$^a$ | 46 (40-57) | 37 (36-44) | 0.0025$^c$ |
| Log$^{10}$ CD4 T cells/μL (IQR)$^{a,b}$ | − (−) | 1.8 (1.6-2.2) | — |
| Log$^{10}$ HIV copies/mL (IQR)$^a$ | − (−) | 6.5 (4.6-5.7) | — |
| Infants (p1041 Cohort) | n = 10 | n = 18 |  |
| Age, months | 3-4 | 3-4 |  |
| Log$^{10}$ CD4 T cells/μL (IQR)$^{a,b}$ | − (−) | 3.3 (3-3.4) | — |
| Log$^{10}$ HIV copies/mL (IQR)$^a$ |  | 5.7 (4.6-6) | — |

Data, no. (% or IQR)
IQR interquartile range: n/a not available.
$^a$Percentage or interquartile range of corresponding column population.
$^b$CD4 cell counts were only available for HIV-1 positive subjects.
$^c$p value of Student t test, Mann-Whitney U test, or chi-square test for difference between controls and HIV-1 cases.

The specificity of this assay for diagnosis of HIV-1 infections was assessed by analysis of 12 confirmed HIV-2 antibody-positive plasma samples purchased from SeraCare Life Sciences Inc. (Milford, MA, USA). LC-iSPRM-MS revealed similar diagnostic sensitivity for HIV-1 cases in HTI adults (90.3%; 95% CI: 74.25-97.96%) and P1041 infants (87.5%; 61.65-98.45%), and 100% specificity in both populations (FIG. 19a and Table 10), which would be useful for the diagnosis of infant HIV-1 cases that are often difficult to diagnose using antibody-based assays due to the presence of maternal HIV antibodies during the first year of life [13, 14]. No false positives were found in the tested HIV-2 samples, confirming the specificity of this assay for the diagnosis of HIV-1 infections.

TABLE 10

Sensitivity and specificity of LC-ISPRM-MS for HIV-1 detection

| Cohort | Positive results/ total no. | Sensitivity, % (95% CI) | Specificity, % (95% CI) |
| --- | --- | --- | --- |
| Adult (HTI Cohort) |  |  |  |
| HIV-1+ | 28/31 | 90.3 (74.25-97.96) |  |
| Non-HIV-1 | 0/25 |  | 100 (86.28-100) |
| Infants (p1041 Cohort) |  |  |  |
| HIV-1+ | 14/16 | 87.5 (61.65-98.45) |  |
| Non-HIV-1 | 0/10 |  | 100 (69.15-100) |

Accurate diagnosis of acute HIV-1 infection via a p24 assay depends on its ability to sensitively detect p24 seroconversion interval, as viral RNA was not detected in first three samples of this patient, and that LC-iSPRM-MS detected p24 expression in 3 of the 4 serum samples with detectable HIV RNA.

Regular monitoring of patients on antiretroviral therapy is critical to ensure ongoing viral suppression and, in the case of treatment failure, to detect the emergence of drug-resistant strains as early as possible. Viral load assays are universally recommended for this purpose, and while serum p24 quantification can have applications for HIV prognosis and treatment monitoring [8], it is not yet clear that it can provide useful data for monitoring HIV treatment responses. We therefore analyzed serial blood samples from HIV-1+ infants in the P1041 cohort before and after ART therapy and during long term follow-up and found that there was good correspondence between serum p24 level and viral load, and that these factors tended to decrease and increase in parallel in ART-treated and untreated subjects, respectively (FIG. 19c). LC-iSPRM-MS also identified ART failure in one treated patient (FIG. 19c #5), who demonstrated a p24 increase with a rise in HIV viral load during ART, and a corresponding drop in both p24 level and viral load following a HIV therapy modification. Studies with larger longitudinal cohorts are underway to assess how early changes in antigen level correspond to changes in patient symptoms and treatment outcomes.

WHO recommends integrating clinical services for patients co-infected with TB and HIV as this approach appears to be associated with lower mortality during anti-TB treatment, even in settings where suboptimal fractions of patients initiate ART and complete anti-TB treatment [5]. To provide proof-of-principle evidence for the clinical utility of LC-iSPRM-MS, we analyzed serum from patients with HIV-1, TB, or combined HIV and TB infections, using positive p24 or CFP-10 signal as the diagnostic criteria for an HIV or TB infection. This case-control study (Table 9) analyzed serum from 1 patient infected with HIV-1 alone, 4 infected with Mtb alone, 7 co-infected with HIV-1 and Mtb, and 8 control subjects who were not infected with HIV-1 or Mtb.

TABLE 9

Characteristics of the study population stratified by TB and HIV status

|  | Total | HIV-1 negative | | HIV-1 positive | |
|---|---|---|---|---|---|
|  | patients (n = 20) | TB negative (n = 8) | TB positive (n = 4) | TB negative (n = 1) | TB positive (n = 7) |
| Sex, male (%)[a] | 20 (80) | 8 (62.5) | 4 (75) | 1 (100) | 7 (100) |
| Age, years (IQR)[a] | 52 (41-65) | 59 (37.66) | 59 (41-79) | 46 (–) | 44 (40-54) |
| Culture-positive: no. (%)[a] | 12 (60) | – (–) | 5 (100) | – (–) | 7 (100) |
| AFB smear positive: no. (%)[a] | 5 (25) | – (–) | 1 (20) | – (–) | 4 (80) |

Data, no. (% or IQR)
IQR interquartile range, AFB acid-fast bacilli
[a]Percentage or interquartile range of corresponding column population.

Figure 20A:
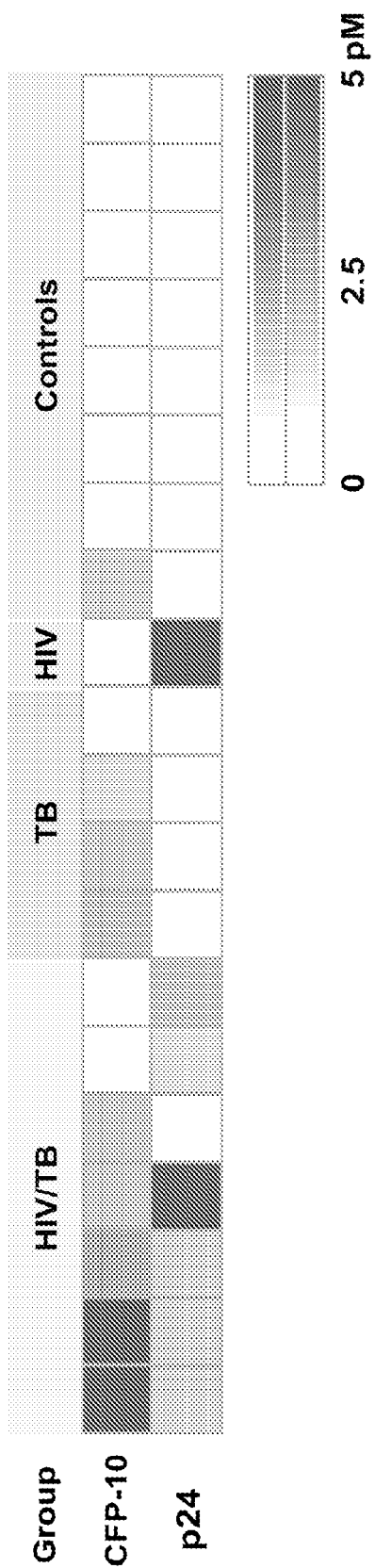
FIG. 20 shows Simultaneous Measurement of p24 and CFP-10 in patient serum samples. a. Heat map of p24 (lower cell, blue) and CFP-10 (upper cell, red) levels in serum from patients with or without HIV, TB or HIV/TB infections, where each column depicts the results from an individual subject, ranked by high to low CFP-10 concentration. Color intensity reflects the triplicate mean of the antigen level and correspond the concentrations in the matching gradient bars. b-f. Longitudinal monitoring of serum p24 and CFP-10 concentration in HIV-1/TB co-infected patients receiving anti-TB treatment.

Blinded LC-iSPRM-MS assays detected CFP-10 and p24 target peptides in the serum samples of 9 of the 11 TB cases (81.8%) and 7 of the 8 HIV-1 cases (87.5%), respectively (FIG. 20a and Table 11).

TABLE 11

Sensitivity and specificity of LC-ISPRMI-MS for active TB and HIV-1

| Group | Positive results/ total no. | Sensitivity, % (95% CI) | Specificity, % (95% CI) |
|---|---|---|---|
| TB detection |  |  |  |
| All TB | 9/11 | 81.82 (48.22-97.72) |  |
| Culture[a], Smear[a] | 4/5 | 80.0 (28.36-99.49) |  |
| Culture[a], Smear[a] | 5/6 | 85.71 (42.13-99.64) |  |
| All Non-TB[a] | 1/9 |  | 88.89 (51.75-99.72) |
| HIV-1 detection |  |  |  |
| HIV-1 | 7/8 | 87.5 (47.35-99.68) |  |
| Non-HIV | 0/12 |  | 100 (73.54-100) |

[a]Non-TB controls are subjects from patients who were judged to not have active TB but at high risk for TB development.

No p24 signals were detected in any of the HIV⁻ subjects (100% specificity), but an apparent false-positive CFP-10 signal was detected in 1 of the 9 at-risk subjects who was judged not to have active TB (88.9% specificity). This degree of diagnostic sensitivity for TB outperformed reported sensitivity values for AFB smear (31%), mycobacteria growth indicator tube (MGIT) culture (69%), and GeneXpert® MTB/RIF (66%) in similar HIV/TB populations [15, 16] and exceeded the WHO-recommended optimal sensitivity (66%) for new high-priority non-sputum diagnostic tests [17]. WHO guidance recommends the use of GeneXpert® MTB/RIF as an initial diagnostic in HIV⁺ patients with suspected TB, but the sensitivity of this test decreases in AFB smear-negative and Mtb culture-negative TB cases that are prevalent in HIV⁺ populations [18]. LC-iSPRM-MS sensitivity in HIV+ smear-negative/culture-positive TB cases (85.7%; 70.5-95.3) also exceeded GeneXpert® sensitivities (47.3%; 29.2-67.0 to 61.1%; 35.7-82.7) reported in other HIV+ adult cohorts [19]. Caution must be exercised in reaching any final conclusions about the performance of LC-iSPRM-MS in this population, however, due to the small sample size of this study.

Figure 20B:
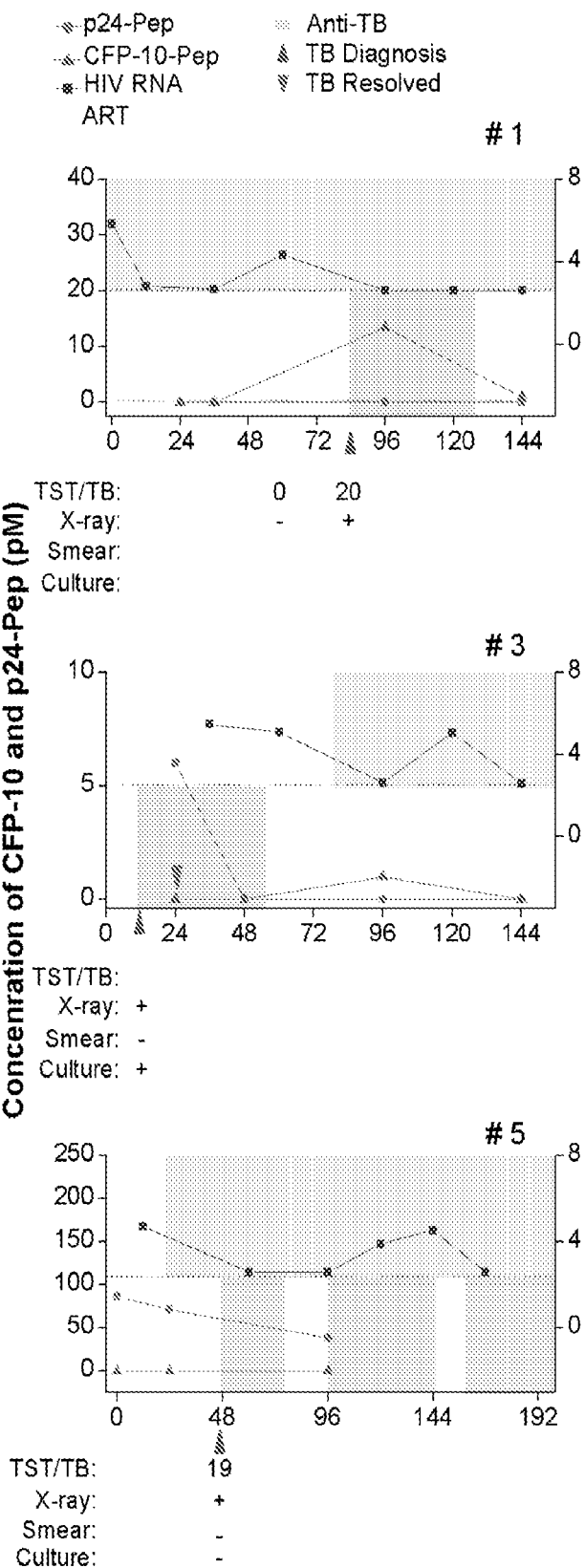
Figure 25:
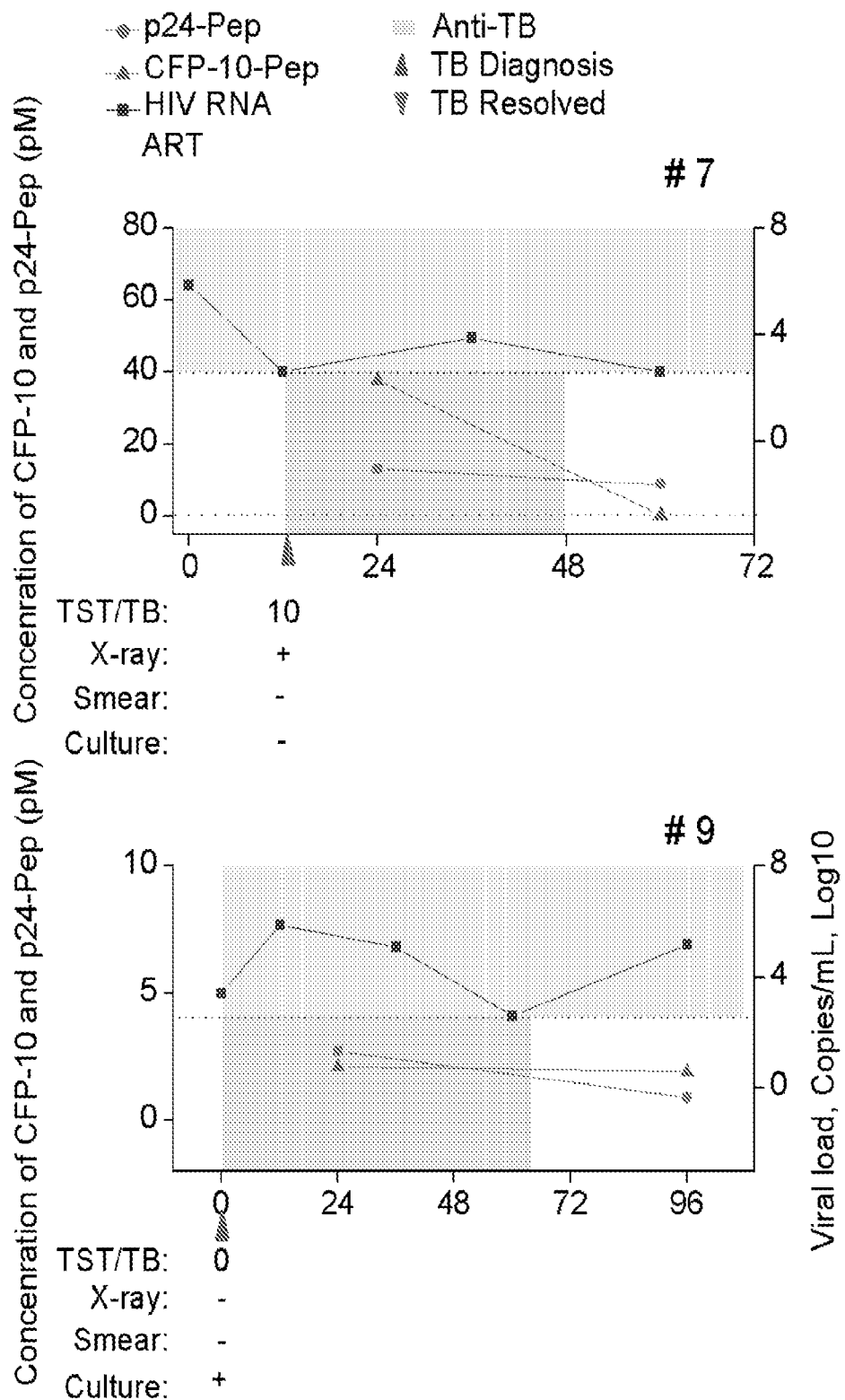
FIG. 25 shows longitudinal monitoring of serum p24 and CFP-10 concentration in HIV-1/TB co-infected patients receiving anti-TB treatment.

The LC-iSPRM-MS assay was also designed to quantify HIV-1 and TB antigens in serum or plasma to monitor responses to anti-TB therapy or ART. This ability is particularly useful for TB therapy, given that most assays used to monitor anti-TB treatment responses provide semi-quantitative results (AFB smear and GeneXpert®) or have significant latency (Mtb culture). Real-time monitoring of HIV-1 and Mtb antigens in serum during anti-TB therapy and/or ART may reflect therapeutic efficacy, which could distinguish treatment failure due to drug-resistant infections from drug toxicity or IRIS. To evaluate LC-iSPRM-MS performance for real-time monitoring of CFP-10 and p24 antigen levels, we analyzed serial blood samples from HIV-1 positive infants in p1041 cohort, who were receiving ART treatment and anti-TB therapy if diagnosed as TB. The results showed that LC-iSPRM-MS can successfully monitor the CFP-10 and p24 levels in real time and provide useful information for TB and HIV diagnosis, as well as for the assessment of anti-TB or ART treatment response (FIG. 20b and FIG. 25). For instance, the turning of CFP-10 signals from positive to negative in patient after completion of anti-TB treatment may reflect a successful anti-TB response (FIG. 20b #1). Similarly, after initiation of ART, the p24 levels in patient #2 showed continued decreases along with a corresponding drop in viral load, which also may represent a positive response of ART (FIG. 20b #2). By contrast, high CFP-10 or p24 levels after completion of anti-TB therapy could represent treatment failure of TB or HIV, respectively. For example, the CFP-10 signals were still very high even after 9-14 months of anti-TB therapy in patient #6 and #9, which could represent two nonresponsive cases. Actually, patient #6 was found to have very high HIV viral load (>1000, 000 copies) but no receiving ART treatment (FIG. 20b #6), while HIV virus rebounded to be very high (750, 000 copies) in patient #9 even though receiving ART (FIG. 25 #9). On the other hand, the positive CFP-10 signals were detected before or shortly after TB diagnosis in several cases (FIG. 20b #1, 4, 6), which indicate that this approach may be also useful for early detection of TB infection.

Intriguingly, when correlated the serum CFP-10 signals with p24 levels or HIV viral loads, the LC-iSPRM-MS can identify TB-IRIS cases. For instance, the CFP-10 levels in patients #3 and #4 were found to be increased shortly after initiation of ART treatment even though whose HIV virus seems to be under controlled by exhibiting undetectable p24 antigen or HIV viral load (FIG. 20b #3, 4). Nonetheless, this proof-of-principle study was not designed to measure rates of decline or to allow comparison with other methods. Future prospective longitudinal studies with frequent sampling are needed to determine how HIV-1 p24 and Mtb CFP-10 serum/plasma changes correspond to patient phenotypes and treatment outcomes. These studies should, in turn, open up new possibilities for the diagnosis and management of patients with IRIS, and facilitate the discrimination of IRIS from TB treatment failure.

Real-time and multiplex LC-iSPRM-MS quantification of p24 and CFP-10 target peptides from patient blood samples was informative for early HIV and TB diagnosis and in assessing patient responses to anti-TB and anti-retroviral therapy in this study. These findings suggest this approach can provide clinical information that could facilitate the linkage of TB and HIV prevention, diagnosis, treatment and care services to improve patient outcomes. Nonetheless, further reductions in operator time and assay cost, along with improvements in instrument portability, are needed to meet WHO guidelines for an optimal noninvasive TB assay.

Materials and Methods

Commercial Plasma and Serum Samples

Confirmed HIV-2 antibody-positive plasma samples (9227022, 9250494, 9227024, 10234820, 10266767, 10276442, 10266768, 10279915, 9226992, 10296579, 10231111 and 10266760) were purchased from SeraCare Life Sciences Inc. (Milford, MA, USA) as well as the HIV-1 seroconversion panels PRB955 and PRB954, which included samples drawn before HIV-1 diagnosis and throughout the immune response to the ongoing HIV-1 infection.

Clinical Samples

The HTI cohort that served as a source of case and control samples for adults in this study was a large, population-based TB surveillance study that performed active surveillance of all confirmed TB cases in Houston/Harris County, Texas between 1995 and 2004. Because of its mandate to collect all active TB cases, the HTI archived samples from a variety of TB disease manifestations, including HIV-negative and -positive pulmonary and extrapulmonary TB cases with both positive and negative culture results. Serum samples were obtained from HTI subjects who were notified of the risks of study participation and provided written informed consent. Demographic, microbiology, and diagnostic data are summarized in (Table 8).

The infant samples used in this study were part of serum samples collected form IMPAACT P1041 cohort, which was a multi-center, Phase randomized, double-blind, placebo-controlled trial evaluating primary isoniazid (INH) prophylaxis in healthy, bacille Calmette-Guérin (BCG) vaccinated, 3- to 4-month-old infants. P1041 enrolled 804 HIV-exposed, uninfected and 547 HIV-infected infants who were followed for up to 4 years. Scheduled visits were quarterly for the first two years for all infants but were reduced to 6-monthly in years 3-4 for those HIV-exposed, uninfected.

Pretreatment of Serum/Plasma

In clinical HIV samples, p24 antigen is present within intact whole HIV viruses and free in solution after viral lysis. However, the availability of analyte is limited by low viral titers in addition to the formation of immune complexes after seroconversion. So to disrupt immune complexes due to maternal antibodies to further improve the trypsin digestion, we employed a heat disruption pretreatment step that denatured the immune-complexing antibodies as well as virus particles by heating the samples to 100° C. for 5 minutes. After allowing the samples to cool to room temperature (25° C.), p24 antigen is available for detection. We empirically tested a range of detergents diluted in phosphate-buffered saline that facilitated heating of plasma to denaturing conditions while precluding the formation of gelled samples. Our chosen buffer, consisting of SDS and NP-40, was robust in allowing a heat spike when a plasma sample is diluted 1:3 in the heat shock buffer (0.4% TritonX-100, 0.2% SDS in PBS, pH=7.4).

LC-iSPRM-MS Analysis

100 µg of the custom polyclonal antibody (GL Biochem) raised against the HIV-1 and Mtb CFP-10 target peptides were coupled to 10 mg of the Dynabeads® M-270 Epoxy (Thermo Fisher Scientific) as described in the manufacturer's instructions, respectively. The final bead concentration is 10 mg/mL antibody coupled beads and stored at 2° C. to 8° C. until use. Serum samples (100 µL) were diluted with 300 µL of heat shock buffer and incubated to 100° C. for 5 minutes. After the samples cooled down to room temperature (25° C.), the samples were diluted with 1100 µL of 100 mM ammonium bicarbonate, then microwave digested [15], spiked with 300 pmol/L stable-isotope-labeled internal standard peptides (m/z of 1472 or 1305 for HIV-1 and m/z of 1603.60 for Mtb; GenScript) matching the p24 and CFP-10 target peptide sequences (m/z of 1462 or 1295 for HIV-1 and m/z of 1593.75 for Mtb), respectively, and mixed with 30 µL prepared anti-1462/1295 and anti-1593 antibody-labeled beads for 1 h at room temperature. Beads were then washed with PBS/0.05% Tween-20 and incubated with 1% formic acid (pH<2.0) to elute bound peptides. Eluates were loaded on a C18 trap column, eluted onto a C18 analytical column, and fractionated with a 0.3 µL/min acetonitrile/formic acid gradient (5-40%) and analyzed using the PRM Mode on a nano-LC UltiMate 3000 high performance liquid chromatography (HPLC) system coupled with an Orbitrap Fusion™ Lumos™ Tribrid™ Mass Spectrometer (Thermo Fisher Scientific). Skyline software version 4.1.0.18169 (MacCoss Lab Software) was used to analyze serum MS and MS/MS spectra against a library produced using recombinant p24 and CFP-10 digests. Standard curves were generated by spiking healthy donor serum with 0-400 pmol/L recombinant p24 or CFP-10 and converting experimental sample MS intensity ratios to absolute molar concentrations by substitution into these calibration curves. Limits of detection (LOD) and quantification (LOQ) were obtained from the mean of each blank plus three times or ten times the standard deviation of their noise, respectively.

Statistical Analysis

Calculation of median, interquartile range (IQR), sensitivity and specificity, data normality, analysis of variance (ANOVA) with post-test correction (Dunn's test), Mann-Whitney, and chi-square tests were performed with GraphPad Prism software (version 7.01).

REFERENCES FOR THIS EXAMPLE

1. World Health Organization (WHO). Global tuberculosis report 2018. https://apps.who.int/iris/bitstream/handle/10665/274453/9789241565646-eng.pdf?ua=1.

2. World Health Organization. Global Tuberculosis Report. Geneva: World Health Organization; (2013).
3. "The Global Plan to Stop TB", WHO, Geneva, 2011, 12 www.stoptb.org/global/plan/4.
4. Kigozi N G, Heunis J C, Engelbrecht M C, Janse van Rensburg A P, van Rensburg H C J D. Tuberculosis knowledge, attitudes and practices of patients at primary health care facilities in a South African metropolitan: research towards improved health education. BMC Public Health. 2017; 17(1):795.
5. WHO Policy on Collaborative TB/HIV Activities. Guidelines for National Programmes and Other Stakeholders. Geneva: World Health Organization; 2012.
6. Boni J, Opravil M, Tomasik Z, et al. Simple monitoring of antiretroviral therapy with a signal-amplification-boosted HIV-1 P24 antigen assay with heat-denatured plasma. AIDS 1997; 1: F47-52.
7. Evans C A. GeneXpert—a game-changer for tuberculosis control? PLoS Med. 2011; 8(7): e1001064.
8. Pai M, Schito M. *Tuberculosis* diagnostics in 2015: landscape, priorities, needs, and prospects. J Infect Dis. 2015; 211 suppl 2: S21-8.
9. Liu C, Zhao Z, Fan J, Lyon C J, Wu H J, Nedelkov D, Zelazny A M, Olivier K N, Cazares L H, Holland S M, et al. Quantification of circulating *Mycobacterium tuberculosis* antigen peptides allows rapid diagnosis of active disease and treatment monitoring. Proc Natl Acad Sci USA. 2017; 114(15): 3969-74.
10. Fan J, Zhang H, Nguyen D T, Lyon C J, Mitchell C D, Zhao Z, Graviss E A, Hu Y. Rapid diagnosis of new and relapse tuberculosis by quantification of a circulating antigen in HIV-infected adults in the Greater Houston metropolitan area. BMC Med. 2017, 15(1):188.
11. Cardona P-J (2012) Understanding Tuberculosis: Deciphering the Secret Life of the Bacilli (In Tech, Rijeka, Croatia).
12. Schüpbach J. Viral RNA and p24 antigen as markers of HIV disease and antiretroviral treatment success. Int Arch Allergy Immunol. 2003; 132(3):196-209
13. Donovan M, Palumbo P. Diagnosis of HIV: challenges and strategies for HIV prevention and detection among pregnant women and their infants. *Clin Perinatal.* 2010; 37(4):751-763, viii.
14. Read J S, Committee on Pediatric AIDS, American Academy of Pediatrics. Diagnosis of HIV-1 infection in children younger than 18 months in the United States. *Pediatrics.* 2007; 120(6): e1547-1562.
15. World Health Organization (2013) Policy Update: Xpert MTB/RIF Assay for the Diagnosis of Pulmonary and Extrapulmonary TB in Adults and Children. (WHO, Geneva).
16. Theron G, Peter J, van Zyl-Smit R, Mishra H, Streicher E, Murray S, Dawson R, Whitelaw A, Hoelscher M, Sharma S, et al. Evaluation of the Xpert MTB/RIF assay for the diagnosis of pulmonary tuberculosis in a high HIV prevalence setting. Am J Respir Crit Care Med. 2011; 184(1): 132-40.
17. Joseph S. Cavanaugh, Surbhi Modi, Susan Musau, Kimberly McCarthy, Heather Alexander, Barbara Burmen, Charles M. Heilig, Ray W. Shiraishi, Kevin Cain. Comparative yield of different diagnostic tests for tuberculosis among people living with HIV in western Kenya. PLoS One. 2016; 11(3): e0152364.
18. Zeka A N, Tasbakan S, Cavusoglu C. Evaluation of the GeneXpert MTB/RIF Assay for Rapid Diagnosis of Tuberculosis and Detection of Rifampin Resistance in Pulmonary and Extrapulmonary Specimens. J Clin Microbiol. 2011; 49(12):4138-41.
19. World Health Organization (2014) High-Priority Target Product Profiles for New Tuberculosis Diagnostics: Report of a Consensus Meeting. (WHO, Geneva).

Example 6—Added Value/Improvements to Protocol for TB-Detection and TB-Diagnostic Kit Using half of the required patient's plasma/serum volume (100 µl instead of 200 µl) which minimize the volume required to be collected from the patient and add facilitate the sample result confirmation by having enough material for repeating the assay.

Figure 26:
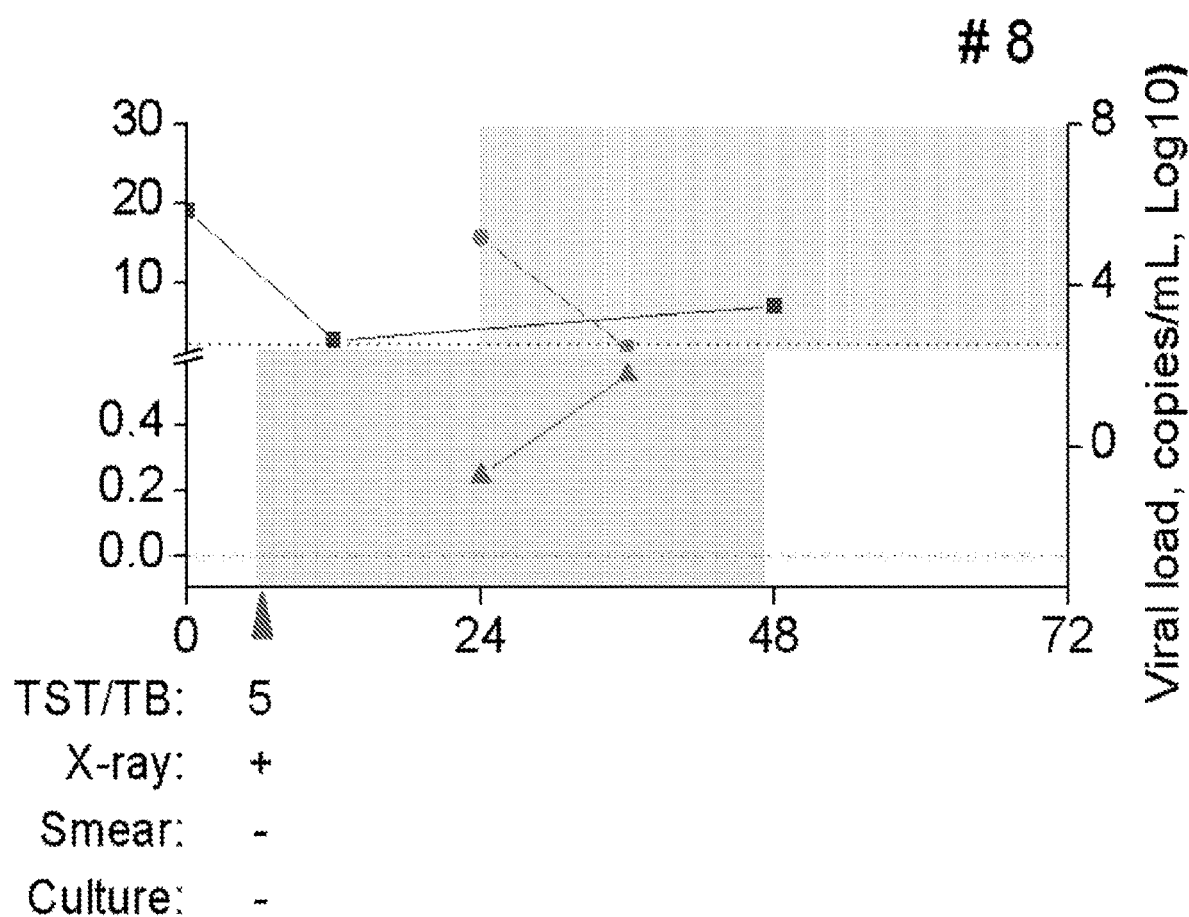
FIG. 26 shows a chart of the values of using immobilized TPCK Trypsin instead of Sequencing grade Trypsin.

Using Immobilized TPCK Trypsin instead of Sequencing grade Trypsin which add multiple values (FIG. 26) including:

Reduce the cost of sample from ($0.4/sample vs $20/sample for the sequencing grade)

(ii) Speeding up the process by allowing automation for high throughput processing Reduce the sample digestion time from overnight to as short as two hours.

Figure 27:
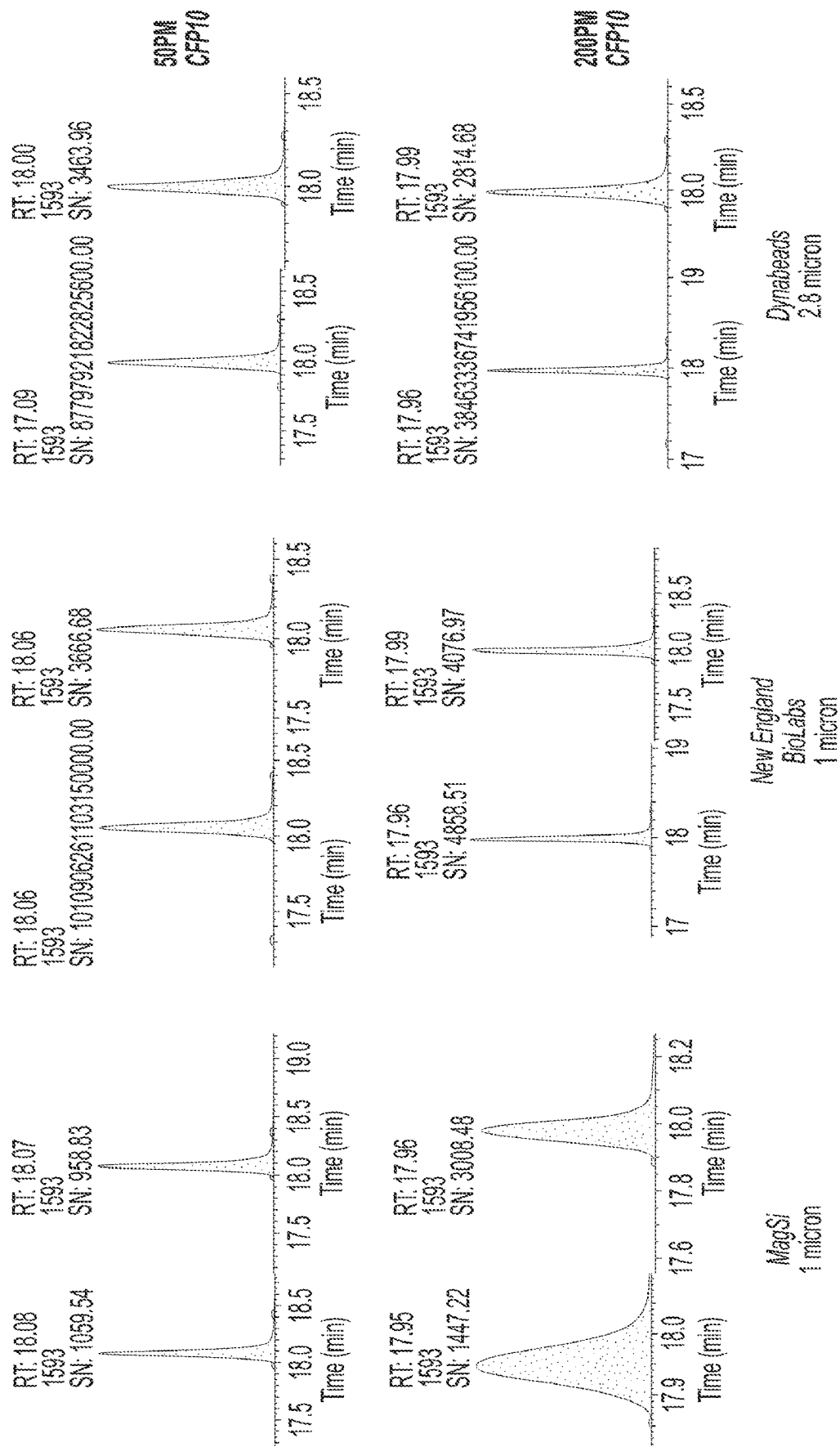
FIG. 27 shows chromatograms resulting from the use of a variety of magnetic nanoparticles from different manufacturers.

Using variety of magnetic nanoparticles from different manufacturers and with various sizes (1 micron and 2.8 micron) not only show the versatility and applicability of our optimized protocol (FIG. 27) but also provide platform for high throughput automation and Secure the supply chain and resources for one of the most value items in the diagnostic kit and in vitro protocol.

Simplifying the protocol by omitting unneeded steps and materials such as 10% TFA in the immunoprecipitation step.

Figure 28:
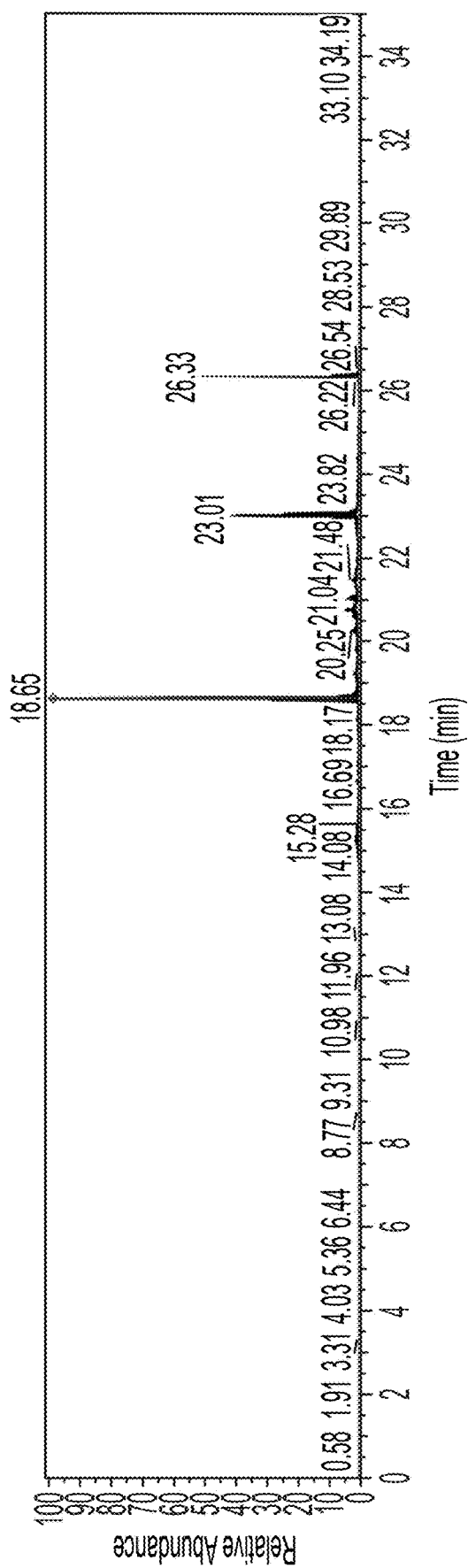
FIG. 28 shows two chromatograms before and after removing unspecific binding.

Improving the purity by removing the unspecific binding using simple was step with 75% acetonitrile/25% PBS for 30 seconds (FIG. 28).

Figure 29:
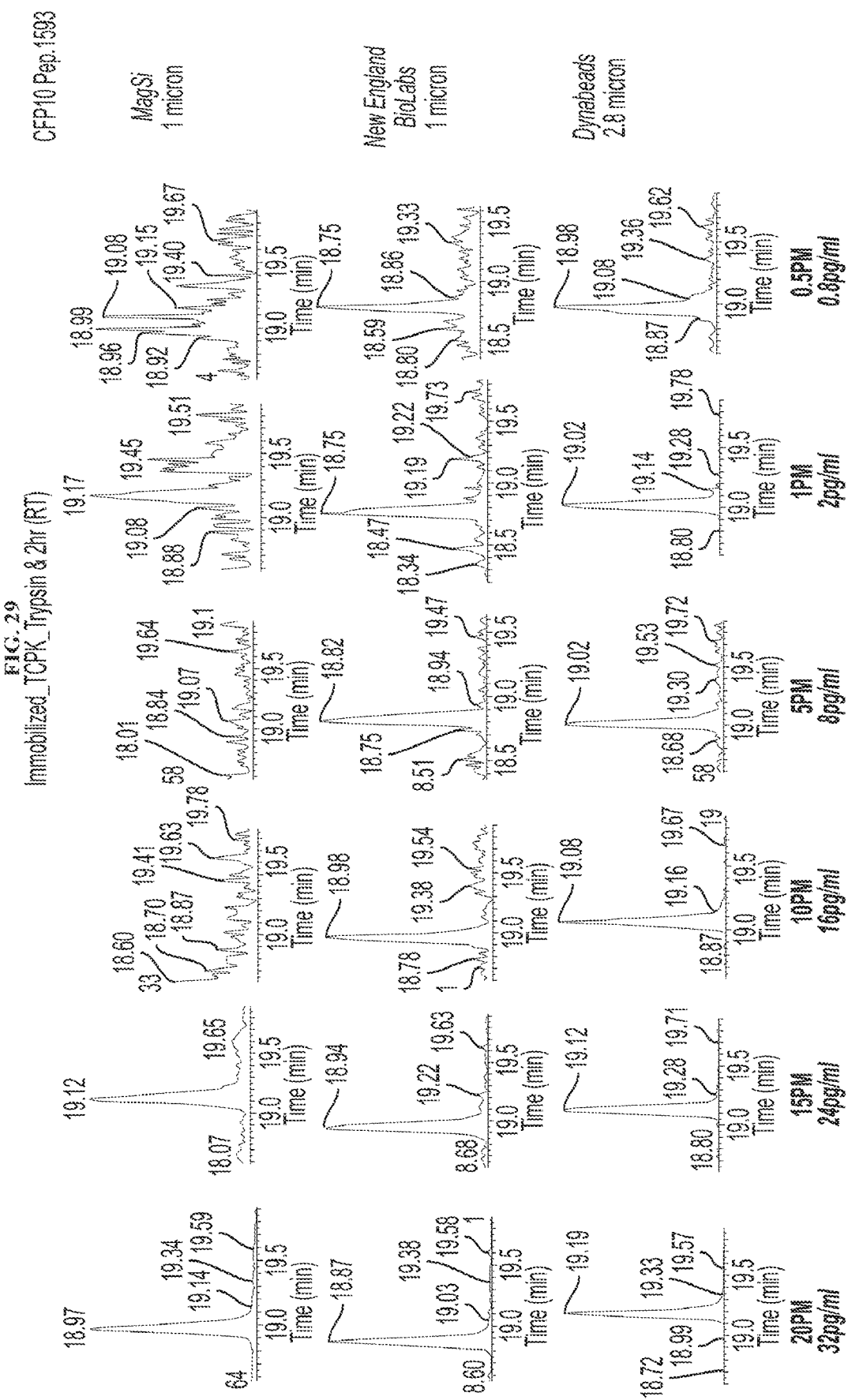
FIG. 29 shows chromatograms resulting from the use of different magnetic bead platforms and varying concentrations of the pathogen target peptide.

Achieving markedly low Limit of Detection (LOD) ~0.8 pg/ml of the pathogen target peptide 1593 in a complex biological serum/plasma samples with at least two different G-Protein magnetic beads platform (FIG. 29).

Figure 30:
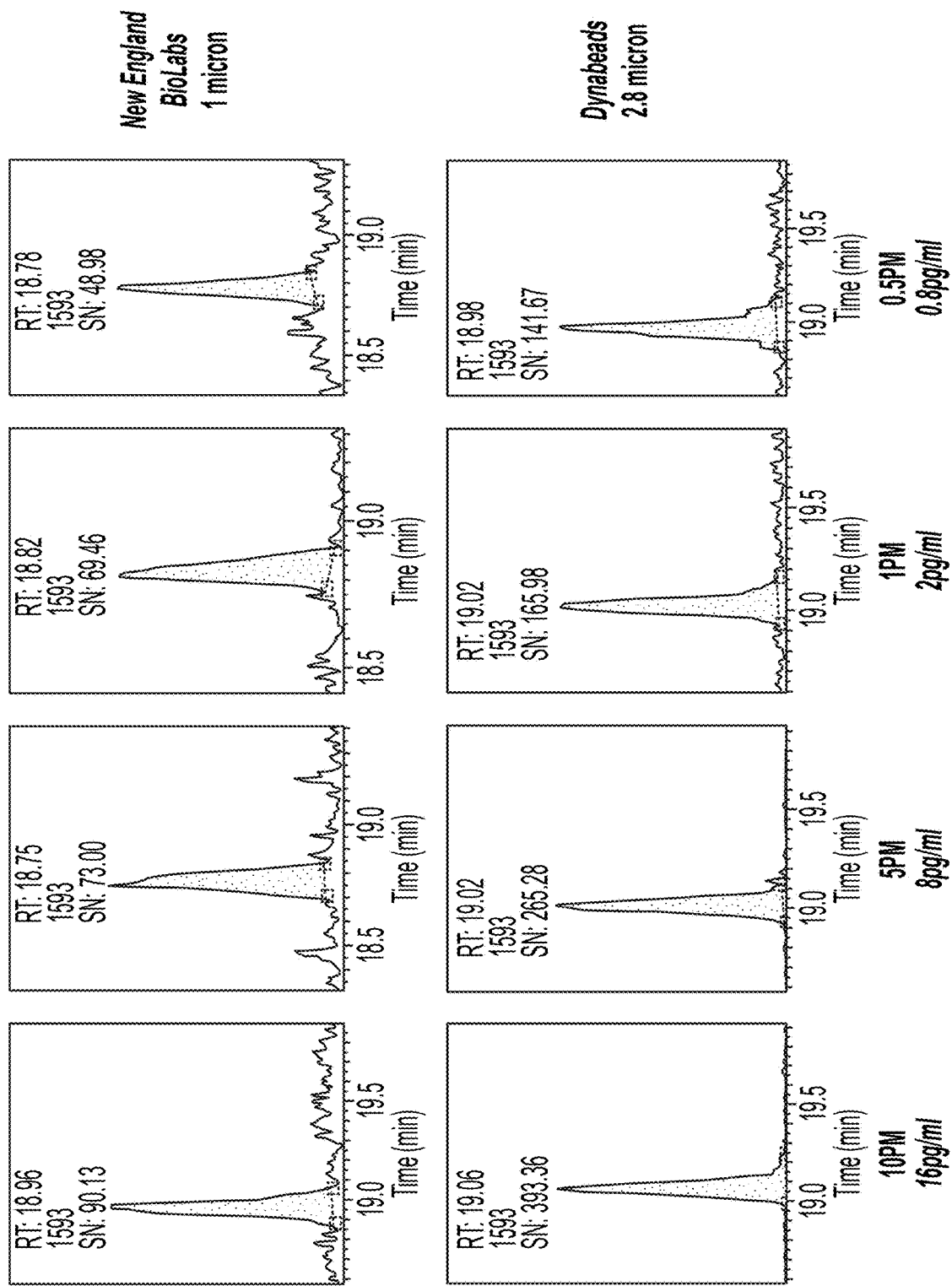
FIG. 30 shows chromatograms resulting from the use of two different magnetic bead platforms and varying concentrations of the pathogen target peptide generated from a Thermo TSQ Altis quadrupole mass spectrometer.

Validating our protocol using top-of-the-line ultra-sensitive Thermo TSQ Altis quadrupole mass spectrometer using nanoflow with that allow us to detect as low concentration as sub-picomolar of the target peptide 1953 (FIG. 30).

The present invention can be used on multiple mass spectrometry platforms. Non-limiting examples include Thermo TSO Altis, Waters XevoTQ-XS, and SCIEX 6500+. For example, analytical validation using ultra-sensitive quadrupole mass spectrometer from two other manufacturers Waters Xevo TQ-XS and SCIEX 6500+ can be used to show the versatility and applicability of the protocols described herein.

Shortening the LCMS analysis time of each sample from 35 min to 10 min or less are undergoing using both nanoflow and microflow platform with multiple manufacturers.

The present invention has been described in terms of one or more preferred embodiments, and it should be appreciated that many equivalents, alternatives, variations, and modifications, aside from those expressly stated, are possible and within the scope of the invention.

Example 7: The Selection Process of the Spectrum Identified by the Spectral Library of the Targeted Peptide in Skyline Database 1. Rank the ions based on the number of interferences they are predicted to have, from the least to the most one.
2. Rank the ions based on their relative abundances in MS spectra, from the highest to the lowest one.
3. Obtain the product ion scans spectra of the peptide target using its synthetic version (MS2 likely sspectra but using triple quadrupole instrument instead of orbitrap or ion trap.) Use the Skyline software to calculate the similarity score rdotp of the spectra by comparing it to the library spectrum and adjusting the ions used for calculation.
4. Select the most abundance ions, if two ions are with identical abundance, the one with less interferences will be kept.
5. Determine the final combination of transitions to achieve the highest rdotp.

Figure 10:
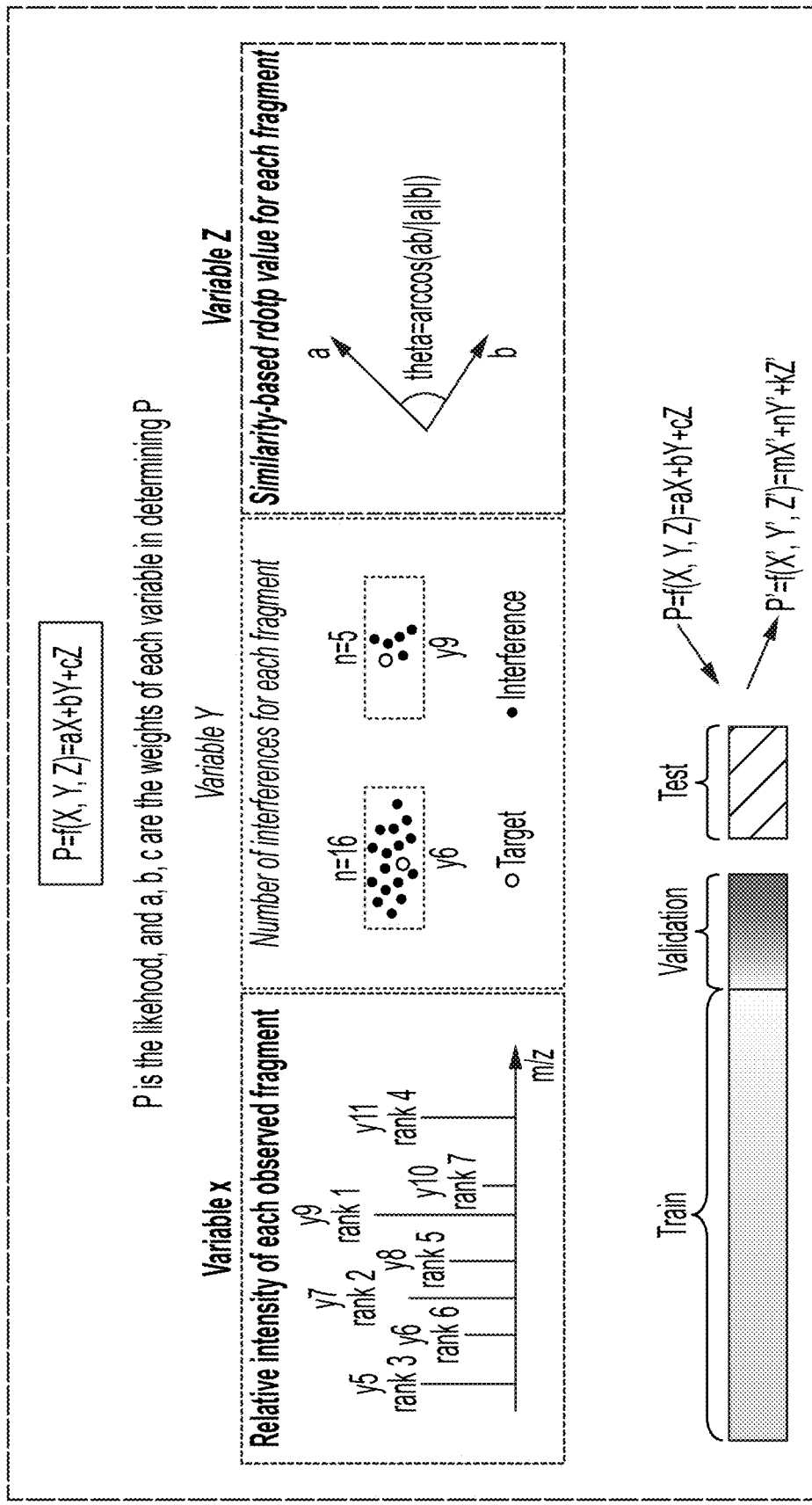
FIG. 10 presents Box 1, a scheme of how to select the MRM transitions via machine based.
Figure 11:
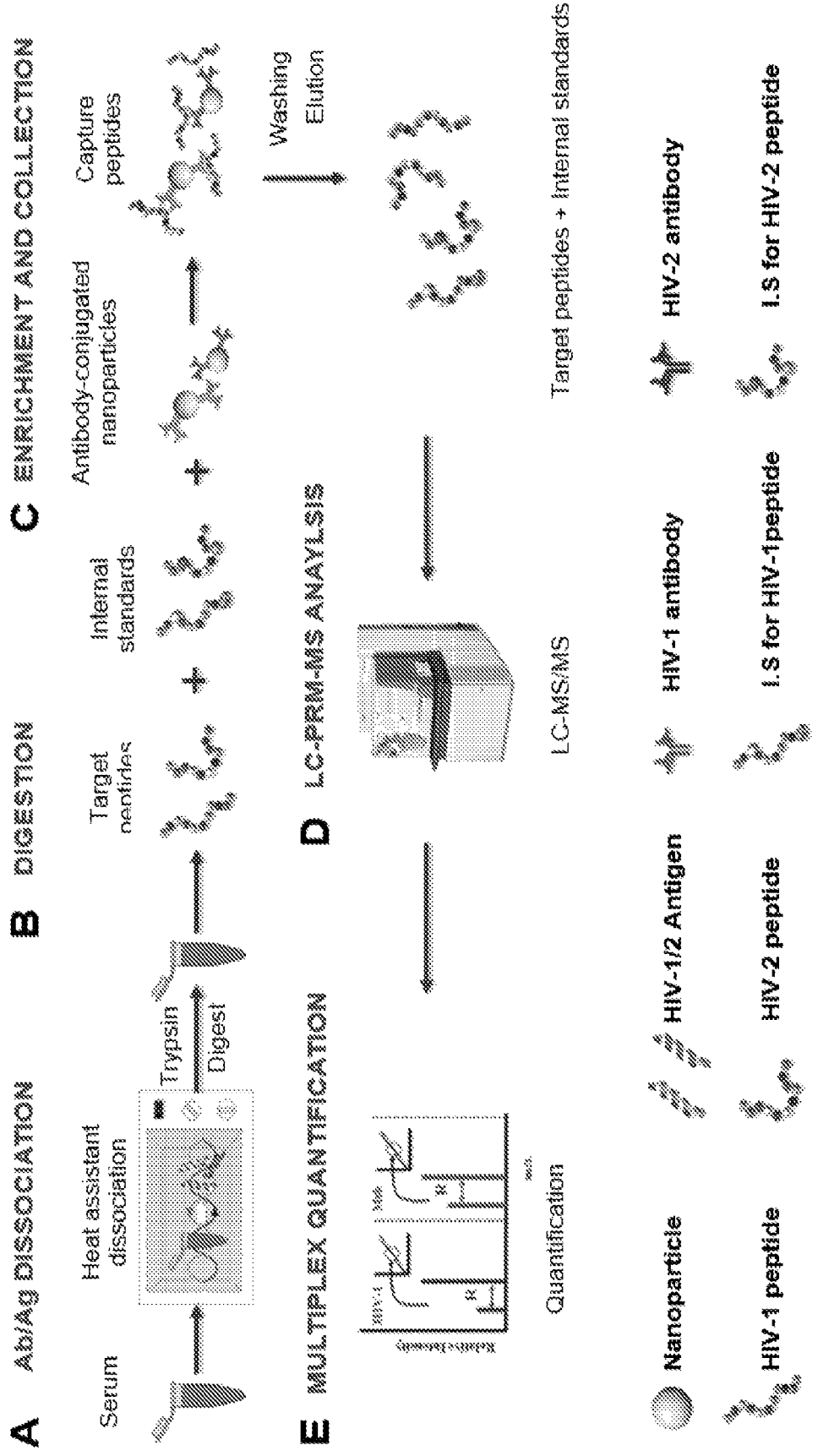
FIG. 11 presents a schematic illustration of the iPRM-MS platform. Serum from HIV were trypsin digested, spiked with stable isotope-labeled internal standards, antibody-enriched for the two target peptides, and analyzed by LC-SPRM-MS. Multiplex quantification of target peptides is determined by MS intensity ratio of target and isotope labeled internal standard peptides.
Figure 13:
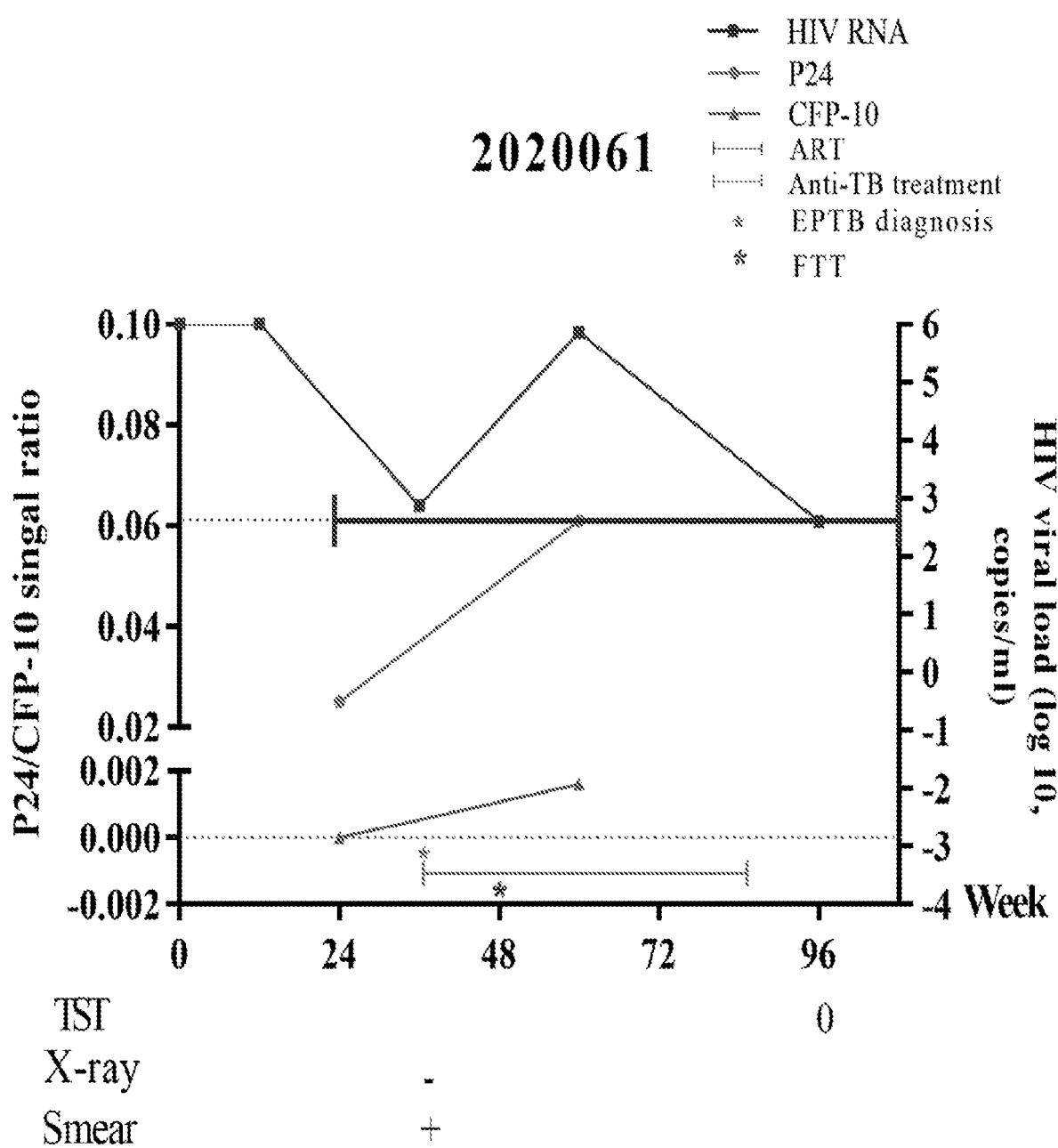
FIG. 13 shows the quantification of both HIV antigen peptides (P24 peptides) and Mtb antigen peptides (CFP-10 peptides) in the same spectrum. This allows for the diagnosis and monitoring of the pathological status of HIV-Tb co-infected patients from a single biological same using the same mass spectrometry quantification spectrum.

Without wishing to be bound by theory, in the FIG. 10, a machine learning based algorithm is used to assist with the selection of MRM transitions. Initially, this algorithm is used for determining the positive result, but it can also be used for MRM transition selection.

What is claimed is:

1. A method for detection and identification of a disease-specific biomarker, the method comprising:
   contacting an enzyme-digested biological sample with an antibody-modified solid support (AMSS) under conditions that promote binding of the AMSS to its target if present in the contacted biological sample, wherein the antibodies bind specifically to a disease-specific biomarker;
   sensing the disease-specific biomarker in a concentration comprising the range of about 0.1 pM to about 200 pM;
   subjecting the sample to an LC-MS/MS based analytical technique;
   detecting m/z peaks in the mass spectrum; and
   identifying the subject from which biological sample was obtained as having the disease based on the m/z peaks in the mass spectrum.

2. A method of detecting and identifying a disease in a subject, the method comprising:
   identifying the disease-specific biomarker according to the method of claim 1;
   identifying the similarities and differences between disease-specific biomarker spectrum and the spectrum obtained from the sample from the subject;
   identifying a subject who has contracted a disease or disorder, or who are at risk of developing an active disease or disorder, based on the m/z peaks in the mass spectrum; and
   treating the subject with a therapeutically effective amount of a medicament.

3. The method of claim 1, wherein the disease is caused by an infectious pathogen comprising a bacterium, a fungus, or a virus.

4. The method of claim 3, wherein the bacterial disease comprises tuberculosis, nontuberculous mycobacterial (NTM) disease, or gut microbial perturbations.

5. The method of claim 3, wherein the viral disease comprises a human immunodeficiency virus (HIV) disease or Ebola disease.

6. The method of claim 1, wherein the disease-specific biomarker comprises a disease-specific antigen, a disease-specific protein, a disease-specific peptide, or a fragment thereof.

7. The method of claim 1, wherein the enzyme-digested biological sample comprises one or more internal reference standards.

8. The method of claim 7, wherein the internal reference standard comprises an isotopically labeled sample.

9. The method of claim 1, wherein the biological sample is obtained from a human subject.

10. The method of claim 1, wherein the biological sample is blood, serum, cerebrospinal fluid, semen, urine, plasma, or a biological culture media.

11. The method of claim 1, further comprising generating a reference mass spectrum in which a peak corresponding to a disease-specific biomarker of interest is present in the reference mass spectrum.

12. The method of claim 6, wherein the disease-specific biomarker has a molecular weight in the range of about 500 Daltons (Da) to about 5000 Da.

13. The method of claim 6, wherein the disease-specific biomarker is a *mycobacterium* peptide comprising the sequence TDAATLAQEAGNFER (SEQ ID NO: 1), TQIDQVESTAGSLQGQWR (SEQ ID NO:2), WDATATELNNALQNLAR (SEQ ID NO:3), TQIDQVESTAASLQAQWR (SEQ ID NO:4), or a combination thereof.

14. The method of claim 6, wherein the disease-specific biomarker is a HIV-1 specific peptide comprising the sequence ETINEEAAEWDR (SEQ ID NO: 5), DTINEEAAEWDR (SEQ ID NO: 6), MYSPTSILDIR (SEQ ID NO: 7), MYSPVSILDIK (SEQ ID NO: 8), MYSPVSILDIR (SEQ ID NO: 9), or a combination thereof.

15. The method of claim 6, wherein the disease-specific biomarker is a HIV-2 specific peptide comprising the sequence MYNPTNILDIK (SEQ ID NO: 10), AEQTDPAVK (SEQ ID NO: 11), or a combination thereof.

16. The method of claim 1, wherein the AMSS is a non-porous support or a porous support.

17. The method of claim 16, wherein the AMSS comprises a bead, a nanodisk, a microdisk, a film, rod, nanoparticle or a microparticle.

18. The method of claim 16, where in the AMSS is etched for structure.

19. The method of claim 16, wherein the AMSS comprises a magnetic bead.

20. The method of claim 1, wherein the LC-MS/MS-based analytical technique is applied to the disease-specific biomarker bound to the AMSS or is applied to an eluted disease-specific biomarker.

21. The method of claim 1, wherein the LC-MS/MS-based analytical technique is selected from a hard ionization technique, a soft ionization technique, or a combination thereof.

22. The method of claim 21, wherein the hard ionization technique comprises electronic ionization (EI).

23. The method of claim 21, wherein the soft ionization technique comprises: matrix-assisted laser desorption/ionization (MALDI), electrospray ionization (ESI), fast atom bombardment (FAB), chemical ionization (CI), atmospheric-pressure chemical ionization (APCI), desorption electrospray ionization (DESI), atmospheric pressure photoionization (APPI), or secondary ion mass spectrometry (SIMS).

24. The method of claim 1, wherein the LC-MS/MS-based analytical technique comprises at least one mass analyzer selected from the group consisting of a quadrupole mass analyzer, a time of flight (TOF) mass analyzer, a magnetic sector mass analyzer, an electrostatic sector mass analyzer, a quadrupole ion trap mass analyzer, an orbitrap mass analyzer, or ion cyclotron resonance mass analyzer.

25. The method of claim 1, wherein the mass spectrometry-based analytical technique is matrix-assisted laser desorption/ionization time-of-flight (MALDI-TOF) mass spectrometry.

26. The method of claim 21, wherein the hard ionization technique or the soft ionization technique is coupled with at least two mass analyzers and at least one technique to induce fragmentation comprises tandem mass spectrometry ($MS^2$).

27. The method of claim 1, wherein the LC-MS/MS-based analytical technique comprises selected reaction monitoring (SRM), single ion monitoring (SIM), parallel reaction monitoring (PRM), scheduled parallel reaction monitoring (sPRM), multiple reaction monitoring (MRM), scheduled multiple reaction monitoring (sMRM), or immunoprecipitation scheduled parallel reaction monitoring (iSPRM).

28. The method of claim 1 further comprising $MS^2/MS^3$ data-dependent neutral loss method.

29. The method of claim 1 further comprising nanoelectrospray-tandem mass spectrometry (iNanoESI-MS/MS).

30. The method of claim 26, wherein at least one technique to induce fragmentation comprises collision-induced dissociation (CID), electron capture dissociation (ECD), electron transfer dissociation (ETD), negative electron transfer dissociation (NETD), electron-detachment dissociation (EDD), charge transfer dissociation (CTD), photodissociation, infrared multiphoton dissociation (IRMPD), blackbody infrared radiative dissociation (BIRD), or surface induced dissociation (SID).

31. The method of claim 26, wherein the tandem mass spectrometry ($MS^2$) technique comprises data-independent acquisition (DIA) or data-dependent acquisition (DDA).

32. The method of claim 1, wherein the LC-MS/MS-based analytical technique is selected from liquid chromatography scheduled parallel reaction monitoring mass spectrometry (LC-sPRM-MS), NanoLC-ESI-MS/MS or immunoprecipitation coupled liquid chromatography scheduled parallel reaction monitoring mass spectrometry (LC-iSPRM-MS).

33. The method of claim 1, wherein m/z peaks $[M+H]^+$ identified by MALDI-TOF MS comprise:
   a m/z peak at 1594 is indicative of a disease-specific target antigen TDAATLAQEAGNFER (SEQ ID NO: 1) associated with co-infection by *Mycobacterium tuberculosis* complex subspecies and one or more of *M. kansasii, M. marinum*, and *M. ulcerans* infection;
   a m/z peak at 1901 (ESAT-6) is indicative of a disease-specific target antigen WDATATELNNALQNLAR (SEQ ID NO: 3) associated with infection by *Mycobacterium tuberculosis* complex species;
   a m/z peak at 2004 is indicative of a disease-specific target antigen TQIDQVESTAGSLQGQWR (SEQ ID NO: 2) associated with infection by *Mycobacterium tuberculosis* complex subspecies;
   a m/z peak at 2032 is indicative of a disease-specific target antigen associated with infection by *M. kansasii*; or a combination thereof.

34. The method of claim 1, wherein m/z peaks $[M+H]^+$ identified by MALDI-TOF MS comprise:
   a m/z peak at 1463 Da is indicative of a disease-specific peptide ETINEEAAEWDR (SEQ ID NO: 5) of HIV-1 infection;
   a m/z peak at 1448 Da is indicative of a disease-specific peptide DTINEEAAEWDR (SEQ ID NO: 6) of HIV-1 infection;
   a m/z peak at 1294 Da is indicative of a disease-specific peptide MYSPVSILDIR (SEQ ID NO: 9) of HIV-1 infection;
   a m/z peak at 1296 Da is indicative of a disease-specific peptide MYSPTSILDIR (SEQ ID NO: 7) of HIV-1 infection;
   or a combination thereof.

35. The method of claim 1, wherein m/z peaks $[M+H]^+$ identified by MALDI-TOF MS comprise:
   a m/z peak at 1322 Da is indicative of a disease specific peptide MYNPTNILDIK (SEQ ID NO: 10) of HIV-2 infection;
   a m/z peak at 958 Da is indicative of a disease specific peptide AEQTDPAVK (SEQ ID NO: 11) indicative of HIV-2 infection;
   or a combination thereof.

* * * * *

```
                        SEQUENCE LISTING

<160> NUMBER OF SEQ ID NOS: 757

<210> SEQ ID NO 1
<211> LENGTH: 15
<212> TYPE: PRT
<213> ORGANISM: Mycobacterium tuberculosis

<400> SEQUENCE: 1

Thr Asp Ala Ala Thr Leu Ala Gln Glu Ala Gly Asn Phe Glu Arg
1               5                   10                  15

<210> SEQ ID NO 2
<211> LENGTH: 18
<212> TYPE: PRT
<213> ORGANISM: Mycobacterium tuberculosis

<400> SEQUENCE: 2

Thr Gln Ile Asp Gln Val Glu Ser Thr Ala Gly Ser Leu Gln Gly Gln
1               5                   10                  15

Trp Arg

<210> SEQ ID NO 3
<211> LENGTH: 17
<212> TYPE: PRT
<213> ORGANISM: Mycobacterium tuberculosis

<400> SEQUENCE: 3

Trp Asp Ala Thr Ala Thr Glu Leu Asn Asn Ala Leu Gln Asn Leu Ala
1               5                   10                  15

Arg

<210> SEQ ID NO 4
<211> LENGTH: 18
<212> TYPE: PRT
<213> ORGANISM: Mycobacterium tuberculosis

<400> SEQUENCE: 4

Thr Gln Ile Asp Gln Val Glu Ser Thr Ala Ala Ser Leu Gln Ala Gln
1               5                   10                  15

Trp Arg

<210> SEQ ID NO 5
<211> LENGTH: 12
<212> TYPE: PRT
<213> ORGANISM: Human immunodeficiency virus 1

<400> SEQUENCE: 5

Glu Thr Ile Asn Glu Glu Ala Ala Glu Trp Asp Arg
1               5                   10
```

```
<210> SEQ ID NO 6
<211> LENGTH: 12
<212> TYPE: PRT
<213> ORGANISM: Human immunodeficiency virus 1

<400> SEQUENCE: 6

Asp Thr Ile Asn Glu Glu Ala Ala Glu Trp Asp Arg
1               5                   10

<210> SEQ ID NO 7
<211> LENGTH: 11
<212> TYPE: PRT
<213> ORGANISM: Human immunodeficiency virus 1

<400> SEQUENCE: 7

Met Tyr Ser Pro Thr Ser Ile Leu Asp Ile Arg
1               5                   10

<210> SEQ ID NO 8
<211> LENGTH: 11
<212> TYPE: PRT
<213> ORGANISM: Human immunodeficiency virus 1

<400> SEQUENCE: 8

Met Tyr Ser Pro Val Ser Ile Leu Asp Ile Lys
1               5                   10

<210> SEQ ID NO 9
<211> LENGTH: 11
<212> TYPE: PRT
<213> ORGANISM: Human immunodeficiency virus 1

<400> SEQUENCE: 9

Met Tyr Ser Pro Val Ser Ile Leu Asp Ile Arg
1               5                   10

<210> SEQ ID NO 10
<211> LENGTH: 11
<212> TYPE: PRT
<213> ORGANISM: Human immunodeficiency virus 2

<400> SEQUENCE: 10

Met Tyr Asn Pro Thr Asn Ile Leu Asp Ile Lys
1               5                   10

<210> SEQ ID NO 11
<211> LENGTH: 9
<212> TYPE: PRT
<213> ORGANISM: Human immunodeficiency virus 2

<400> SEQUENCE: 11

Ala Glu Gln Thr Asp Pro Ala Val Lys
1               5

<210> SEQ ID NO 12
<211> LENGTH: 12
<212> TYPE: PRT
<213> ORGANISM: Human immunodeficiency virus 2

<400> SEQUENCE: 12

Met Tyr Asn Pro Pro Thr Asn Ile Leu Asp Ile Lys
1               5                   10

<210> SEQ ID NO 13
```

```
<211> LENGTH: 12
<212> TYPE: PRT
<213> ORGANISM: Human immunodeficiency virus 1

<400> SEQUENCE: 13

Glu Thr Ile Asn Glu Glu Ala Ala Glu Trp Glu Arg
1               5                   10

<210> SEQ ID NO 14
<211> LENGTH: 15
<212> TYPE: PRT
<213> ORGANISM: Human immunodeficiency virus 1

<400> SEQUENCE: 14

Val His Pro Val His Ala Gly Pro Ile Pro Pro Gly Gln Met Arg
1               5                   10                  15

<210> SEQ ID NO 15
<211> LENGTH: 12
<212> TYPE: PRT
<213> ORGANISM: Human immunodeficiency virus 1
<220> FEATURE:
<221> NAME/KEY: MOD_RES
<222> LOCATION: (1)..(1)
<223> OTHER INFORMATION: Glu or Asp

<400> SEQUENCE: 15

Xaa Thr Ile Asn Glu Glu Ala Ala Glu Trp Asp Arg
1               5                   10

<210> SEQ ID NO 16
<211> LENGTH: 11
<212> TYPE: PRT
<213> ORGANISM: Human immunodeficiency virus 1
<220> FEATURE:
<221> NAME/KEY: MOD_RES
<222> LOCATION: (11)..(11)
<223> OTHER INFORMATION: Arg or Lys

<400> SEQUENCE: 16

Met Tyr Ser Pro Thr Ser Ile Leu Asp Ile Xaa
1               5                   10

<210> SEQ ID NO 17
<211> LENGTH: 11
<212> TYPE: PRT
<213> ORGANISM: Ebola virus

<400> SEQUENCE: 17

Leu Gly Pro Gly Ile Pro Asp His Pro Leu Arg
1               5                   10

<210> SEQ ID NO 18
<211> LENGTH: 11
<212> TYPE: PRT
<213> ORGANISM: Ebola virus

<400> SEQUENCE: 18

Leu Gly Gln Gly Ile Pro Asp His Pro Leu Arg
1               5                   10

<210> SEQ ID NO 19
<211> LENGTH: 9
<212> TYPE: PRT
<213> ORGANISM: Ebola virus

<400> SEQUENCE: 19
```

```
Leu Arg Pro Ile Leu Leu Pro Asn Lys
1               5

<210> SEQ ID NO 20
<211> LENGTH: 9
<212> TYPE: PRT
<213> ORGANISM: Ebola virus

<400> SEQUENCE: 20

Leu Arg Pro Ile Leu Leu Pro Gly Lys
1               5

<210> SEQ ID NO 21
<211> LENGTH: 9
<212> TYPE: PRT
<213> ORGANISM: Ebola virus

<400> SEQUENCE: 21

Leu Arg Pro Ile Leu Leu Pro Gly Arg
1               5

<210> SEQ ID NO 22
<211> LENGTH: 9
<212> TYPE: PRT
<213> ORGANISM: Ebola virus

<400> SEQUENCE: 22

Leu Arg Pro Val Leu Leu Pro Gly Lys
1               5

<210> SEQ ID NO 23
<211> LENGTH: 11
<212> TYPE: PRT
<213> ORGANISM: Human immunodeficiency virus 2

<400> SEQUENCE: 23

Met Tyr Asn Pro Thr Asn Ile Leu Asp Ile Lys
1               5                   10

<210> SEQ ID NO 24
<211> LENGTH: 11
<212> TYPE: PRT
<213> ORGANISM: Mycobacterium tuberculosis

<400> SEQUENCE: 24

Leu Tyr Ala Ser Ala Glu Ala Thr Asp Ser Lys
1               5                   10

<210> SEQ ID NO 25
<211> LENGTH: 9
<212> TYPE: PRT
<213> ORGANISM: Mycobacterium tuberculosis

<400> SEQUENCE: 25

Asn Asp Pro Thr Gln Gln Ile Pro Lys
1               5

<210> SEQ ID NO 26
<211> LENGTH: 15
<212> TYPE: PRT
<213> ORGANISM: Mycobacterium tuberculosis

<400> SEQUENCE: 26

Ala Gln Ala Ala Ser Leu Glu Ala Glu His Gln Ala Ile Val Arg
```

```
<210> SEQ ID NO 27
<211> LENGTH: 11
<212> TYPE: PRT
<213> ORGANISM: Mycobacterium tuberculosis

<400> SEQUENCE: 27

Phe Leu Ser Ala Ala Thr Ser Ser Thr Pro Arg
1               5                   10

<210> SEQ ID NO 28
<211> LENGTH: 7
<212> TYPE: PRT
<213> ORGANISM: Mycobacterium tuberculosis

<400> SEQUENCE: 28

Val Glu Tyr Val Asp Val Arg
1               5

<210> SEQ ID NO 29
<211> LENGTH: 15
<212> TYPE: PRT
<213> ORGANISM: Mycobacterium tuberculosis

<400> SEQUENCE: 29

Ile Glu Ser Glu Asn Pro Asp Ala Val Ala Asn Val Gln Ala Arg
1               5                   10                  15

<210> SEQ ID NO 30
<211> LENGTH: 12
<212> TYPE: PRT
<213> ORGANISM: Mycobacterium tuberculosis

<400> SEQUENCE: 30

Gly Val Thr Glu Glu Thr Thr Thr Gly Val Leu Arg
1               5                   10

<210> SEQ ID NO 31
<211> LENGTH: 13
<212> TYPE: PRT
<213> ORGANISM: Mycobacterium tuberculosis

<400> SEQUENCE: 31

Leu Glu Glu Glu Asn Pro Glu Ala Ala Gln Ala Leu Arg
1               5                   10

<210> SEQ ID NO 32
<211> LENGTH: 12
<212> TYPE: PRT
<213> ORGANISM: Mycobacterium tuberculosis

<400> SEQUENCE: 32

Asn Gln Ala Glu Thr Leu Val Tyr Gln Thr Glu Lys
1               5                   10

<210> SEQ ID NO 33
<211> LENGTH: 14
<212> TYPE: PRT
<213> ORGANISM: Mycobacterium tuberculosis

<400> SEQUENCE: 33

Gly Ser Leu Val Glu Gly Gly Ile Gly Gly Thr Glu Ala Arg
1               5                   10
```

<210> SEQ ID NO 34
<211> LENGTH: 15
<212> TYPE: PRT
<213> ORGANISM: Mycobacterium tuberculosis

<400> SEQUENCE: 34

Ala Gln Ala Gly Leu Leu Glu Ala Glu His Gln Ala Ile Val Arg
1               5                   10                  15

<210> SEQ ID NO 35
<211> LENGTH: 12
<212> TYPE: PRT
<213> ORGANISM: Mycobacterium tuberculosis

<400> SEQUENCE: 35

Ser Leu Ala Asp Pro Asn Val Ser Phe Ala Asn Lys
1               5                   10

<210> SEQ ID NO 36
<211> LENGTH: 10
<212> TYPE: PRT
<213> ORGANISM: Mycobacterium tuberculosis

<400> SEQUENCE: 36

Ile Ala Leu Phe Gly Asn His Ala Pro Lys
1               5                   10

<210> SEQ ID NO 37
<211> LENGTH: 11
<212> TYPE: PRT
<213> ORGANISM: Mycobacterium tuberculosis

<400> SEQUENCE: 37

Gln Glu Leu Asp Glu Ile Ser Thr Asn Ile Arg
1               5                   10

<210> SEQ ID NO 38
<211> LENGTH: 10
<212> TYPE: PRT
<213> ORGANISM: Mycobacterium tuberculosis

<400> SEQUENCE: 38

Ser Leu Glu Asn Tyr Ile Ala Gln Thr Arg
1               5                   10

<210> SEQ ID NO 39
<211> LENGTH: 19
<212> TYPE: PRT
<213> ORGANISM: Mycobacterium tuberculosis

<400> SEQUENCE: 39

Thr Thr Gly Asp Pro Pro Phe Pro Gly Gln Pro Pro Pro Val Ala Asn
1               5                   10                  15

Asp Thr Arg

<210> SEQ ID NO 40
<211> LENGTH: 10
<212> TYPE: PRT
<213> ORGANISM: Mycobacterium tuberculosis

<400> SEQUENCE: 40

Ile Pro Asp Glu Asp Leu Ala Gly Leu Arg
1               5                   10

<210> SEQ ID NO 41
<211> LENGTH: 13
<212> TYPE: PRT
<213> ORGANISM: Mycobacterium tuberculosis

<400> SEQUENCE: 41

Thr Val Ala Asn Phe Val Gly Leu Ala Gln Gly Thr Lys
1               5                   10

<210> SEQ ID NO 42
<211> LENGTH: 8
<212> TYPE: PRT
<213> ORGANISM: Mycobacterium tuberculosis

<400> SEQUENCE: 42

Leu Val Phe Leu Thr Gly Pro Lys
1               5

<210> SEQ ID NO 43
<211> LENGTH: 9
<212> TYPE: PRT
<213> ORGANISM: Mycobacterium tuberculosis

<400> SEQUENCE: 43

Met Pro Ala Val Thr Asp Leu Val Lys
1               5

<210> SEQ ID NO 44
<211> LENGTH: 9
<212> TYPE: PRT
<213> ORGANISM: Mycobacterium tuberculosis

<400> SEQUENCE: 44

Ala Phe Asp Trp Asp Gln Ala Tyr Arg
1               5

<210> SEQ ID NO 45
<211> LENGTH: 11
<212> TYPE: PRT
<213> ORGANISM: Mycobacterium tuberculosis

<400> SEQUENCE: 45

Thr Val Gly Asp Val Val Ala Tyr Ile Gln Lys
1               5                   10

<210> SEQ ID NO 46
<211> LENGTH: 15
<212> TYPE: PRT
<213> ORGANISM: Mycobacterium tuberculosis

<400> SEQUENCE: 46

Thr Asp Ala Ala Thr Leu Ala Gln Glu Ala Gly Asn Phe Glu Arg
1               5                   10                  15

<210> SEQ ID NO 47
<211> LENGTH: 8
<212> TYPE: PRT
<213> ORGANISM: Mycobacterium tuberculosis

<400> SEQUENCE: 47

Val Val Asp Trp Leu Val Asp Lys
1               5

<210> SEQ ID NO 48

```
<211> LENGTH: 18
<212> TYPE: PRT
<213> ORGANISM: Mycobacterium tuberculosis

<400> SEQUENCE: 48

Thr Gln Ile Asp Gln Val Glu Ser Thr Ala Gly Ser Leu Gln Gly Gln
1               5                   10                  15

Trp Arg

<210> SEQ ID NO 49
<211> LENGTH: 15
<212> TYPE: PRT
<213> ORGANISM: Mycobacterium tuberculosis

<400> SEQUENCE: 49

Ala Ala Asp Met Trp Gly Pro Ser Ser Asp Pro Ala Trp Glu Arg
1               5                   10                  15

<210> SEQ ID NO 50
<211> LENGTH: 15
<212> TYPE: PRT
<213> ORGANISM: Mycobacterium tuberculosis

<400> SEQUENCE: 50

Ile Pro Leu Asp Val Ala Glu Gly Asp Thr Val Ile Tyr Ser Lys
1               5                   10                  15

<210> SEQ ID NO 51
<211> LENGTH: 31
<212> TYPE: PRT
<213> ORGANISM: Mycobacterium tuberculosis

<400> SEQUENCE: 51

Phe Ser Asp Pro Ser Lys Pro Asn Gly Gln Ile Trp Thr Gly Val Ile
1               5                   10                  15

Gly Ser Pro Ala Ala Asn Ala Pro Asp Ala Gly Pro Pro Gln Arg
            20                  25                  30

<210> SEQ ID NO 52
<211> LENGTH: 12
<212> TYPE: PRT
<213> ORGANISM: Mycobacterium tuberculosis

<400> SEQUENCE: 52

Phe Leu Leu Asp Gln Ala Ile Thr Ser Ala Gly Arg
1               5                   10

<210> SEQ ID NO 53
<211> LENGTH: 20
<212> TYPE: PRT
<213> ORGANISM: Mycobacterium tuberculosis

<400> SEQUENCE: 53

Glu Ala Pro Tyr Glu Leu Asn Ile Thr Ser Ala Thr Tyr Gln Ser Ala
1               5                   10                  15

Ile Pro Pro Arg
            20

<210> SEQ ID NO 54
<211> LENGTH: 20
<212> TYPE: PRT
<213> ORGANISM: Mycobacterium tuberculosis

<400> SEQUENCE: 54
```

```
Gly Phe Gln Ser Ile His Glu Ser Asp Met Leu Leu Pro Asp Pro
1               5                   10                  15

Glu Thr Ala Arg
            20

<210> SEQ ID NO 55
<211> LENGTH: 15
<212> TYPE: PRT
<213> ORGANISM: Mycobacterium tuberculosis

<400> SEQUENCE: 55

Ser Val Phe Asp Asp Gly Leu Ala Phe Asp Gly Ser Ser Ile Arg
1               5                   10                  15

<210> SEQ ID NO 56
<211> LENGTH: 17
<212> TYPE: PRT
<213> ORGANISM: Mycobacterium tuberculosis

<400> SEQUENCE: 56

Pro Gly Leu Pro Val Glu Tyr Leu Gln Val Pro Ser Pro Ser Met Gly
1               5                   10                  15

Arg

<210> SEQ ID NO 57
<211> LENGTH: 17
<212> TYPE: PRT
<213> ORGANISM: Mycobacterium tuberculosis

<400> SEQUENCE: 57

Trp Asp Ala Thr Ala Thr Glu Leu Asn Asn Ala Leu Gln Asn Leu Ala
1               5                   10                  15

Arg

<210> SEQ ID NO 58
<211> LENGTH: 14
<212> TYPE: PRT
<213> ORGANISM: Mycobacterium tuberculosis

<400> SEQUENCE: 58

Ala Gly Ala Asn Leu Phe Glu Leu Glu Asn Phe Val Ala Arg
1               5                   10

<210> SEQ ID NO 59
<211> LENGTH: 17
<212> TYPE: PRT
<213> ORGANISM: Mycobacterium tuberculosis

<400> SEQUENCE: 59

Trp Glu Thr Phe Leu Thr Ser Glu Leu Pro Gly Trp Leu Gln Ala Asn
1               5                   10                  15

Arg

<210> SEQ ID NO 60
<211> LENGTH: 31
<212> TYPE: PRT
<213> ORGANISM: Mycobacterium tuberculosis

<400> SEQUENCE: 60

Asp Pro Ala Ser Ala Pro Asp Val Pro Thr Ala Ala Gln Leu Thr Ser
1               5                   10                  15
```

Leu Leu Asn Ser Leu Ala Asp Pro Asn Val Ser Phe Ala Asn Lys
            20                  25                  30

<210> SEQ ID NO 61
<211> LENGTH: 14
<212> TYPE: PRT
<213> ORGANISM: Mycobacterium tuberculosis

<400> SEQUENCE: 61

Thr Asn Leu Thr Thr Glu Gln Ile Ala Asn Tyr Val Ala Arg
1               5                   10

<210> SEQ ID NO 62
<211> LENGTH: 21
<212> TYPE: PRT
<213> ORGANISM: Mycobacterium tuberculosis

<400> SEQUENCE: 62

Asp Pro Ala Leu Cys Gln His Lys Pro Leu Thr Pro Gln Gly Asp Glu
1               5                   10                  15

Leu Ser Lys Pro Arg
            20

<210> SEQ ID NO 63
<211> LENGTH: 15
<212> TYPE: PRT
<213> ORGANISM: Mycobacterium tuberculosis

<400> SEQUENCE: 63

Leu Gly Gly Leu Ser Ala Pro Pro Trp Ala Lys Pro Glu Asp Arg
1               5                   10                  15

<210> SEQ ID NO 64
<211> LENGTH: 15
<212> TYPE: PRT
<213> ORGANISM: Mycobacterium tuberculosis

<400> SEQUENCE: 64

Asp Leu Glu Val Glu Thr Leu Thr Ala Ser Ser Glu Gly Asn Lys
1               5                   10                  15

<210> SEQ ID NO 65
<211> LENGTH: 16
<212> TYPE: PRT
<213> ORGANISM: Mycobacterium tuberculosis

<400> SEQUENCE: 65

Thr Thr Leu Pro Gly Val Val Asn Gly Ala Asn Asn Pro Ala Ile Arg
1               5                   10                  15

<210> SEQ ID NO 66
<211> LENGTH: 15
<212> TYPE: PRT
<213> ORGANISM: Mycobacterium tuberculosis

<400> SEQUENCE: 66

Tyr Ser Asp Ile Glu Pro Ser Thr Gly Gly Glu Val Val Leu Lys
1               5                   10                  15

<210> SEQ ID NO 67
<211> LENGTH: 13
<212> TYPE: PRT
<213> ORGANISM: Mycobacterium tuberculosis

<400> SEQUENCE: 67

```
<210> SEQ ID NO 68
<211> LENGTH: 14
<212> TYPE: PRT
<213> ORGANISM: Mycobacterium tuberculosis

<400> SEQUENCE: 68

Gln Tyr His Val Gln Phe Phe Gly Asp Ala Pro Glu Arg
1               5                   10

<210> SEQ ID NO 68
<211> LENGTH: 14
<212> TYPE: PRT
<213> ORGANISM: Mycobacterium tuberculosis

<400> SEQUENCE: 68

Met Thr Ser Glu Ile Glu Thr Asn Ile Val Ala Val Glu Arg
1               5                   10

<210> SEQ ID NO 69
<211> LENGTH: 17
<212> TYPE: PRT
<213> ORGANISM: Mycobacterium tuberculosis

<400> SEQUENCE: 69

Met Glu Pro Gly Pro Asp Gly Pro Ala Ala Ser Gly Pro Ala Ala Ile
1               5                   10                  15

Arg

<210> SEQ ID NO 70
<211> LENGTH: 22
<212> TYPE: PRT
<213> ORGANISM: Mycobacterium tuberculosis

<400> SEQUENCE: 70

Val Asn Asp Pro Thr Glu Ser Gln Gln Glu Asp Gln Leu Ile Ala Gly
1               5                   10                  15

Ala Gln Asp Glu Ala Lys
            20

<210> SEQ ID NO 71
<211> LENGTH: 14
<212> TYPE: PRT
<213> ORGANISM: Mycobacterium tuberculosis

<400> SEQUENCE: 71

Glu Gln Val Gln Ile Gly Ala His Ser Pro Pro Gln Phe Arg
1               5                   10

<210> SEQ ID NO 72
<211> LENGTH: 14
<212> TYPE: PRT
<213> ORGANISM: Mycobacterium tuberculosis

<400> SEQUENCE: 72

Thr Glu Gln Glu Val Val Glu Gly Met Asp Ile Ser Thr Arg
1               5                   10

<210> SEQ ID NO 73
<211> LENGTH: 13
<212> TYPE: PRT
<213> ORGANISM: Mycobacterium tuberculosis

<400> SEQUENCE: 73

Val Val Cys Thr Glu Ser Trp Pro Leu Ala His His Arg
1               5                   10

<210> SEQ ID NO 74
<211> LENGTH: 16
<212> TYPE: PRT
```

```
<213> ORGANISM: Mycobacterium tuberculosis

<400> SEQUENCE: 74

Glu Pro Gly Pro Ile Ala Pro Ser Thr Asn Ser Ser Pro Val Leu Lys
1               5                   10                  15

<210> SEQ ID NO 75
<211> LENGTH: 14
<212> TYPE: PRT
<213> ORGANISM: Mycobacterium tuberculosis

<400> SEQUENCE: 75

Ala His Phe Asn Ala Met Phe Gln Pro Ser Ser Pro Thr Arg
1               5                   10

<210> SEQ ID NO 76
<211> LENGTH: 14
<212> TYPE: PRT
<213> ORGANISM: Mycobacterium tuberculosis

<400> SEQUENCE: 76

Met Asp Gln Phe Gly Asn Gly Leu Glu Ile Asp Gln Ala Arg
1               5                   10

<210> SEQ ID NO 77
<211> LENGTH: 21
<212> TYPE: PRT
<213> ORGANISM: Mycobacterium tuberculosis

<400> SEQUENCE: 77

Asp Pro Ala Leu Cys Gln His Lys Pro Leu Thr Pro Gln Gly Asp Glu
1               5                   10                  15

Leu Ser Glu Pro Arg
            20

<210> SEQ ID NO 78
<211> LENGTH: 25
<212> TYPE: PRT
<213> ORGANISM: Mycobacterium tuberculosis

<400> SEQUENCE: 78

Met Glu Thr Arg Pro Thr Ala Leu Met Ser Ser Thr Val Ala Ala Ala
1               5                   10                  15

Ala Pro Ala Ala Gly Ala Ala Ser Arg
            20                  25

<210> SEQ ID NO 79
<211> LENGTH: 14
<212> TYPE: PRT
<213> ORGANISM: Mycobacterium tuberculosis

<400> SEQUENCE: 79

Thr Arg Pro Thr Asp Leu Val Phe Val Val Asp Ser Ser Arg
1               5                   10

<210> SEQ ID NO 80
<211> LENGTH: 15
<212> TYPE: PRT
<213> ORGANISM: Mycobacterium tuberculosis

<400> SEQUENCE: 80

Glu Leu Gly Phe Val Gln Pro Ser Gly Val Thr Asp Gly Met Arg
1               5                   10                  15
```

<210> SEQ ID NO 81
<211> LENGTH: 13
<212> TYPE: PRT
<213> ORGANISM: Mycobacterium tuberculosis

<400> SEQUENCE: 81

Met Leu Thr Asp Pro Asp Leu Pro Gln Glu Phe Glu Arg
1               5                   10

<210> SEQ ID NO 82
<211> LENGTH: 13
<212> TYPE: PRT
<213> ORGANISM: Mycobacterium tuberculosis

<400> SEQUENCE: 82

Cys Ser Thr Pro Leu Leu His Gln Gln Tyr Thr Ser Arg
1               5                   10

<210> SEQ ID NO 83
<211> LENGTH: 15
<212> TYPE: PRT
<213> ORGANISM: Mycobacterium tuberculosis

<400> SEQUENCE: 83

Ile Ser Cys Gly Pro Pro Ala His Val Glu Asn Ala Ile Ala Arg
1               5                   10                  15

<210> SEQ ID NO 84
<211> LENGTH: 17
<212> TYPE: PRT
<213> ORGANISM: Mycobacterium tuberculosis

<400> SEQUENCE: 84

Leu Leu Glu Ala Val Gly Ser Ser Ser Gly Thr Pro Asn Ala Pro Pro
1               5                   10                  15

Pro

<210> SEQ ID NO 85
<211> LENGTH: 22
<212> TYPE: PRT
<213> ORGANISM: Mycobacterium tuberculosis

<400> SEQUENCE: 85

Thr Pro Thr Gln His Ser Pro Val Pro Pro Glu Glu Val Thr Gly Pro
1               5                   10                  15

Ser Gln Met Asp Thr Arg
            20

<210> SEQ ID NO 86
<211> LENGTH: 15
<212> TYPE: PRT
<213> ORGANISM: Mycobacterium tuberculosis

<400> SEQUENCE: 86

Thr Thr Tyr Val Ser Gln Ser Gly Gln Val Ile Ser Ala Pro Arg
1               5                   10                  15

<210> SEQ ID NO 87
<211> LENGTH: 14
<212> TYPE: PRT
<213> ORGANISM: Mycobacterium tuberculosis

<400> SEQUENCE: 87

```
Ser Phe Pro Gln Ser Ser Gln Leu Ser Gln Glu Thr Val Arg
1               5                   10
```

<210> SEQ ID NO 88
<211> LENGTH: 15
<212> TYPE: PRT
<213> ORGANISM: Mycobacterium tuberculosis

<400> SEQUENCE: 88

```
Met Asn Gly Asp His Met Val Leu Gly Ser Ser Val Thr Asp Lys
1               5                   10                  15
```

<210> SEQ ID NO 89
<211> LENGTH: 12
<212> TYPE: PRT
<213> ORGANISM: Mycobacterium tuberculosis

<400> SEQUENCE: 89

```
Glu Tyr Pro Leu Tyr Ile Asn Gln Thr Cys His Arg
1               5                   10
```

<210> SEQ ID NO 90
<211> LENGTH: 15
<212> TYPE: PRT
<213> ORGANISM: Mycobacterium tuberculosis

<400> SEQUENCE: 90

```
Gly Glu Gly Ala Ile Gly Ser Leu Asp Tyr Thr Pro Glu Glu Arg
1               5                   10                  15
```

<210> SEQ ID NO 91
<211> LENGTH: 15
<212> TYPE: PRT
<213> ORGANISM: Mycobacterium tuberculosis

<400> SEQUENCE: 91

```
Asp Val Val His Pro Leu Gly Gly Glu Glu Pro Ser Met Ala Arg
1               5                   10                  15
```

<210> SEQ ID NO 92
<211> LENGTH: 13
<212> TYPE: PRT
<213> ORGANISM: Mycobacterium tuberculosis

<400> SEQUENCE: 92

```
Val Tyr Gln Pro Phe Leu Thr Thr Cys Asp Gly His Arg
1               5                   10
```

<210> SEQ ID NO 93
<211> LENGTH: 13
<212> TYPE: PRT
<213> ORGANISM: Mycobacterium tuberculosis

<400> SEQUENCE: 93

```
Ala Phe Asp Cys Pro Ser Ser Phe Gln Ile His Glu Arg
1               5                   10
```

<210> SEQ ID NO 94
<211> LENGTH: 15
<212> TYPE: PRT
<213> ORGANISM: Mycobacterium tuberculosis

<400> SEQUENCE: 94

```
Thr Leu Ala Pro Gln Val Cys Ser Ser Phe Ala Thr Gly Pro Arg
1               5                   10                  15
```

<210> SEQ ID NO 95
<211> LENGTH: 21
<212> TYPE: PRT
<213> ORGANISM: Mycobacterium tuberculosis

<400> SEQUENCE: 95

Ser Glu Pro Cys Asp Asp Leu Gln Ile Pro Asn Thr Asn Val His Leu
1               5                   10                  15

Ser His Asp Ala Lys
            20

<210> SEQ ID NO 96
<211> LENGTH: 13
<212> TYPE: PRT
<213> ORGANISM: Mycobacterium tuberculosis

<400> SEQUENCE: 96

Phe Asn Asn Val Gln Leu Asn Leu Thr Asp Glu Glu Arg
1               5                   10

<210> SEQ ID NO 97
<211> LENGTH: 15
<212> TYPE: PRT
<213> ORGANISM: Mycobacterium tuberculosis

<400> SEQUENCE: 97

Gln Leu Val Asp Glu Phe Gln Ala Ser Gly Gly Val Gly Glu Arg
1               5                   10                  15

<210> SEQ ID NO 98
<211> LENGTH: 23
<212> TYPE: PRT
<213> ORGANISM: Mycobacterium tuberculosis

<400> SEQUENCE: 98

Glu Asp Ala Ser Gly Gln Leu Ser Cys Ile Gln Leu Pro Val Asp Ser
1               5                   10                  15

Gln Gly Gly Asp Ala Asn Lys
            20

<210> SEQ ID NO 99
<211> LENGTH: 13
<212> TYPE: PRT
<213> ORGANISM: Mycobacterium tuberculosis

<400> SEQUENCE: 99

Phe Thr Ser Asp Met Ser Asn Thr Glu Trp Gly Tyr Arg
1               5                   10

<210> SEQ ID NO 100
<211> LENGTH: 14
<212> TYPE: PRT
<213> ORGANISM: Mycobacterium tuberculosis

<400> SEQUENCE: 100

Met Ala Phe Met Ala Ala Thr Asp His Ser Asp Gln Leu Arg
1               5                   10

<210> SEQ ID NO 101
<211> LENGTH: 15
<212> TYPE: PRT
<213> ORGANISM: Mycobacterium tuberculosis

```
<400> SEQUENCE: 101

Leu Glu Ile Gly Pro Val Tyr Ser Ser Val Ser Ser Glu Ala Arg
1               5                  10                  15

<210> SEQ ID NO 102
<211> LENGTH: 14
<212> TYPE: PRT
<213> ORGANISM: Mycobacterium tuberculosis

<400> SEQUENCE: 102

Thr Ile Gly Met Pro Ala Thr Glu Glu Val Asp Cys Ile Arg
1               5                  10

<210> SEQ ID NO 103
<211> LENGTH: 14
<212> TYPE: PRT
<213> ORGANISM: Mycobacterium tuberculosis

<400> SEQUENCE: 103

Leu Leu Glu Thr Val Glu Tyr Asn Ile Ser Gly Ala Glu Arg
1               5                  10

<210> SEQ ID NO 104
<211> LENGTH: 14
<212> TYPE: PRT
<213> ORGANISM: Mycobacterium tuberculosis

<400> SEQUENCE: 104

Ser Gln Gly Asp Asn Asn Val Ser Leu Val Glu Glu Phe Arg
1               5                  10

<210> SEQ ID NO 105
<211> LENGTH: 15
<212> TYPE: PRT
<213> ORGANISM: Mycobacterium tuberculosis

<400> SEQUENCE: 105

Thr Ile Gln Ala Pro Thr Gln Val Pro Val Val Ser Pro Arg
1               5                  10                  15

<210> SEQ ID NO 106
<211> LENGTH: 14
<212> TYPE: PRT
<213> ORGANISM: Mycobacterium tuberculosis

<400> SEQUENCE: 106

Cys Thr Leu His Leu Gly Ile Glu Pro Pro Asp Ser Val Arg
1               5                  10

<210> SEQ ID NO 107
<211> LENGTH: 23
<212> TYPE: PRT
<213> ORGANISM: Mycobacterium tuberculosis

<400> SEQUENCE: 107

Ser Glu Ile Thr Asn Gln Leu Ser Val Ser Asp Ile Asn Ser Gln Ser
1               5                  10                  15

Val Gly Gly Ala Arg Pro Lys
            20

<210> SEQ ID NO 108
<211> LENGTH: 24
<212> TYPE: PRT
<213> ORGANISM: Mycobacterium tuberculosis
```

```
<400> SEQUENCE: 108

Trp Ala Gly Gly Pro Pro Gly Thr Gly His Gly Pro Leu Ser Leu
1               5                   10                  15

Asn Ser Pro Asp Pro Tyr Glu Lys
            20

<210> SEQ ID NO 109
<211> LENGTH: 14
<212> TYPE: PRT
<213> ORGANISM: Mycobacterium tuberculosis

<400> SEQUENCE: 109

Gly Cys Phe Thr Pro Val Val Thr Asp Pro Ile Thr Glu Arg
1               5                   10

<210> SEQ ID NO 110
<211> LENGTH: 14
<212> TYPE: PRT
<213> ORGANISM: Mycobacterium tuberculosis

<400> SEQUENCE: 110

Gly Ser Ile Asp Asp Val Phe Asn Cys Asn Leu Ser Pro Arg
1               5                   10

<210> SEQ ID NO 111
<211> LENGTH: 22
<212> TYPE: PRT
<213> ORGANISM: Mycobacterium tuberculosis

<400> SEQUENCE: 111

Thr Phe Ile Ser Leu Ser Ser Thr Asp Val Ser Pro Asn Gln Ser Asn
1               5                   10                  15

Thr Ser Asn Glu Met Lys
            20

<210> SEQ ID NO 112
<211> LENGTH: 21
<212> TYPE: PRT
<213> ORGANISM: Mycobacterium tuberculosis

<400> SEQUENCE: 112

His Val Leu Thr Ser His Ile Asp Glu Pro Pro Thr Gln Asn Gln Ser
1               5                   10                  15

Asp Leu Leu Asn Lys
            20

<210> SEQ ID NO 113
<211> LENGTH: 16
<212> TYPE: PRT
<213> ORGANISM: Mycobacterium tuberculosis

<400> SEQUENCE: 113

Ser Thr Leu Gly Pro Ala Leu Glu Ala Val Ser Met Asp Gly Asp Lys
1               5                   10                  15

<210> SEQ ID NO 114
<211> LENGTH: 13
<212> TYPE: PRT
<213> ORGANISM: Mycobacterium tuberculosis

<400> SEQUENCE: 114

Val Trp Thr His Cys Gln Thr Gln His Gly Ile Val Lys
1               5                   10
```

-continued

```
<210> SEQ ID NO 115
<211> LENGTH: 15
<212> TYPE: PRT
<213> ORGANISM: Mycobacterium tuberculosis

<400> SEQUENCE: 115

Gln Ser Gly Gln Cys Leu Asp Gly Val Ser Leu Ser Ser Pro Arg
1               5                   10                  15

<210> SEQ ID NO 116
<211> LENGTH: 14
<212> TYPE: PRT
<213> ORGANISM: Mycobacterium tuberculosis

<400> SEQUENCE: 116

Glu Asn Tyr Gly Ser Ile Thr Ser Met Gly Tyr Glu Ser Arg
1               5                   10

<210> SEQ ID NO 117
<211> LENGTH: 14
<212> TYPE: PRT
<213> ORGANISM: Mycobacterium tuberculosis

<400> SEQUENCE: 117

Glu Gly Asp Tyr Ile Val Ser Val Asn Gly Gln Pro Cys Arg
1               5                   10

<210> SEQ ID NO 118
<211> LENGTH: 15
<212> TYPE: PRT
<213> ORGANISM: Mycobacterium tuberculosis

<400> SEQUENCE: 118

Glu Gly Tyr Leu Gln Ile Gly Ala Asn Thr Gln Ala Ala Gln Lys
1               5                   10                  15

<210> SEQ ID NO 119
<211> LENGTH: 14
<212> TYPE: PRT
<213> ORGANISM: Mycobacterium tuberculosis

<400> SEQUENCE: 119

Thr Asn Gly Val Pro Thr Thr Glu Glu Val Asp Cys Ile Arg
1               5                   10

<210> SEQ ID NO 120
<211> LENGTH: 15
<212> TYPE: PRT
<213> ORGANISM: Mycobacterium tuberculosis

<400> SEQUENCE: 120

Val Gln Thr Asp Lys Pro His Leu Val Ser Leu Gly Ser Gly Arg
1               5                   10                  15

<210> SEQ ID NO 121
<211> LENGTH: 13
<212> TYPE: PRT
<213> ORGANISM: Mycobacterium tuberculosis

<400> SEQUENCE: 121

Tyr Ser Ser Asn Leu Gly Asn Phe Asn Tyr Glu Gln Arg
1               5                   10
```

<210> SEQ ID NO 122
<211> LENGTH: 22
<212> TYPE: PRT
<213> ORGANISM: Mycobacterium tuberculosis

<400> SEQUENCE: 122

Val Val Ala Gly Asp His Asn Leu Ser Gln Asn Asp Gly Thr Glu Gln
1               5                   10                  15

Tyr Val Ser Val Gln Lys
            20

<210> SEQ ID NO 123
<211> LENGTH: 13
<212> TYPE: PRT
<213> ORGANISM: Mycobacterium tuberculosis

<400> SEQUENCE: 123

Ile Leu Asp Glu Thr Gln Glu Ala Val Glu Tyr Gln Arg
1               5                   10

<210> SEQ ID NO 124
<211> LENGTH: 23
<212> TYPE: PRT
<213> ORGANISM: Mycobacterium tuberculosis

<400> SEQUENCE: 124

Asp Asp Ser Cys Ser Gly Asp Ser Ser Ala Gln Leu Ser Ser Gly Glu
1               5                   10                  15

His Leu Leu Gly Pro Asn Arg
            20

<210> SEQ ID NO 125
<211> LENGTH: 14
<212> TYPE: PRT
<213> ORGANISM: Mycobacterium tuberculosis

<400> SEQUENCE: 125

Ser Val Gln Trp Cys Ala Val Ser Gln Pro Glu Ala Thr Lys
1               5                   10

<210> SEQ ID NO 126
<211> LENGTH: 14
<212> TYPE: PRT
<213> ORGANISM: Mycobacterium tuberculosis

<400> SEQUENCE: 126

Asn Thr Ser Ser Glu Gln Glu Glu Val Val Glu Ala Leu Arg
1               5                   10

<210> SEQ ID NO 127
<211> LENGTH: 13
<212> TYPE: PRT
<213> ORGANISM: Mycobacterium tuberculosis

<400> SEQUENCE: 127

Thr Thr Thr Trp Gln Arg Pro Thr Met Glu Ser Val Arg
1               5                   10

<210> SEQ ID NO 128
<211> LENGTH: 16
<212> TYPE: PRT
<213> ORGANISM: Mycobacterium tuberculosis

<400> SEQUENCE: 128

```
Thr Ala Ser Glu Ser Ile Ser Asn Leu Ser Glu Ala Gly Ser Ile Lys
1               5                   10                  15
```

<210> SEQ ID NO 129
<211> LENGTH: 15
<212> TYPE: PRT
<213> ORGANISM: Mycobacterium tuberculosis

<400> SEQUENCE: 129

```
Thr Pro Ser Thr Thr Thr Ser Ser His Tyr Leu Gly Thr Leu Lys
1               5                   10                  15
```

<210> SEQ ID NO 130
<211> LENGTH: 14
<212> TYPE: PRT
<213> ORGANISM: Mycobacterium tuberculosis

<400> SEQUENCE: 130

```
Thr Val Gly Phe Asn His Leu Thr Leu Gly His Asn Gln Arg
1               5                   10
```

<210> SEQ ID NO 131
<211> LENGTH: 14
<212> TYPE: PRT
<213> ORGANISM: Mycobacterium tuberculosis

<400> SEQUENCE: 131

```
Gly Gly His Ile Asn Asp Ala Phe Met Thr Glu Asp Glu Arg
1               5                   10
```

<210> SEQ ID NO 132
<211> LENGTH: 13
<212> TYPE: PRT
<213> ORGANISM: Mycobacterium tuberculosis

<400> SEQUENCE: 132

```
Gly Phe Gly Cys Cys Phe Pro Cys Cys Ser Val Asp Lys
1               5                   10
```

<210> SEQ ID NO 133
<211> LENGTH: 13
<212> TYPE: PRT
<213> ORGANISM: Mycobacterium tuberculosis

<400> SEQUENCE: 133

```
Trp Thr Cys Ser Lys Pro Lys Pro Ser Thr Met Leu Arg
1               5                   10
```

<210> SEQ ID NO 134
<211> LENGTH: 14
<212> TYPE: PRT
<213> ORGANISM: Mycobacterium tuberculosis

<400> SEQUENCE: 134

```
Met Pro Ala Tyr His Ser Ser Leu Met Asp Pro Asp Thr Lys
1               5                   10
```

<210> SEQ ID NO 135
<211> LENGTH: 23
<212> TYPE: PRT
<213> ORGANISM: Mycobacterium tuberculosis

<400> SEQUENCE: 135

```
Ser Ser Leu Gly Leu Asp Asn Ser Leu Ser Thr Ser Ser Glu Asp Pro
```

-continued

```
                1               5                  10                 15
His Ser Gly Cys Pro Ser Arg
            20

<210> SEQ ID NO 136
<211> LENGTH: 23
<212> TYPE: PRT
<213> ORGANISM: Mycobacterium tuberculosis

<400> SEQUENCE: 136

Gly Ser Glu Cys Trp His Leu Ser Ser Gly Ser Val His Pro Ser Pro
1               5                  10                 15

Gly Ser Ala Pro Ala Gln Arg
            20

<210> SEQ ID NO 137
<211> LENGTH: 15
<212> TYPE: PRT
<213> ORGANISM: Mycobacterium tuberculosis

<400> SEQUENCE: 137

Cys Gln Pro Leu Gly Ser Ala Leu Pro Pro Gln Ala Pro Thr Arg
1               5                  10                 15

<210> SEQ ID NO 138
<211> LENGTH: 13
<212> TYPE: PRT
<213> ORGANISM: Mycobacterium tuberculosis

<400> SEQUENCE: 138

Asn Ile Gln His Leu Asn Ser Gln Ile His Ser Phe Arg
1               5                  10

<210> SEQ ID NO 139
<211> LENGTH: 15
<212> TYPE: PRT
<213> ORGANISM: Mycobacterium tuberculosis

<400> SEQUENCE: 139

Val Thr Thr Ser Asp Glu Asp Ile Gly Ile Asn Ala Ile Ser Arg
1               5                  10                 15

<210> SEQ ID NO 140
<211> LENGTH: 12
<212> TYPE: PRT
<213> ORGANISM: Mycobacterium tuberculosis

<400> SEQUENCE: 140

Phe Val Glu Leu Gln Val Cys Asp His Tyr Gln Arg
1               5                  10

<210> SEQ ID NO 141
<211> LENGTH: 20
<212> TYPE: PRT
<213> ORGANISM: Mycobacterium tuberculosis

<400> SEQUENCE: 141

His Phe Ile Thr Ser Ser Ser Ser Lys Pro Cys Glu Pro Glu Glu His
1               5                  10                 15

Tyr Val Gln Lys
            20

<210> SEQ ID NO 142
```

```
<211> LENGTH: 14
<212> TYPE: PRT
<213> ORGANISM: Mycobacterium tuberculosis

<400> SEQUENCE: 142

Thr Thr Gly Ser Thr Gln Ser Asn Phe Asn Phe Tyr Val Lys
1               5                   10

<210> SEQ ID NO 143
<211> LENGTH: 24
<212> TYPE: PRT
<213> ORGANISM: Mycobacterium tuberculosis

<400> SEQUENCE: 143

Gly Leu His Gly Ala Ala Thr Val Val Leu Gly Gln Gly Gln His Gly
1               5                   10                  15

Gly Cys Ala Pro Glu Glu Glu Asp
            20

<210> SEQ ID NO 144
<211> LENGTH: 13
<212> TYPE: PRT
<213> ORGANISM: Mycobacterium tuberculosis

<400> SEQUENCE: 144

Thr Leu Thr Ala Glu Glu Ala Glu Glu Glu Trp Glu Arg
1               5                   10

<210> SEQ ID NO 145
<211> LENGTH: 15
<212> TYPE: PRT
<213> ORGANISM: Mycobacterium tuberculosis

<400> SEQUENCE: 145

Phe Gly Gly Thr Pro Ile His Phe Pro Gly Gly Arg Pro Pro Arg
1               5                   10                  15

<210> SEQ ID NO 146
<211> LENGTH: 14
<212> TYPE: PRT
<213> ORGANISM: Mycobacterium tuberculosis

<400> SEQUENCE: 146

Thr Leu Asp Glu Asn Ser Asp Ser Ala Gly Leu Trp Gln Arg
1               5                   10

<210> SEQ ID NO 147
<211> LENGTH: 29
<212> TYPE: PRT
<213> ORGANISM: Mycobacterium tuberculosis

<400> SEQUENCE: 147

Leu Asn Val Ala Gly Ala Gly Gly Gly Gly Asp Ser Gly Gly Gly Pro
1               5                   10                  15

Gly Ala Ala Thr Asp Gly Asn Phe Thr Ala Gly Leu Ala
            20                  25

<210> SEQ ID NO 148
<211> LENGTH: 13
<212> TYPE: PRT
<213> ORGANISM: Mycobacterium tuberculosis

<400> SEQUENCE: 148

Val Phe Ser Gln Asn Ala Tyr Leu Ile Asp His Gln Arg
```

```
                         1               5                   10
```

<210> SEQ ID NO 149
<211> LENGTH: 16
<212> TYPE: PRT
<213> ORGANISM: Mycobacterium tuberculosis

<400> SEQUENCE: 149

```
Glu Gly Ser Gly Asn Pro Thr Pro Leu Ile Asn Pro Leu Ala Gly Arg
1               5                   10                  15
```

<210> SEQ ID NO 150
<211> LENGTH: 13
<212> TYPE: PRT
<213> ORGANISM: Mycobacterium tuberculosis

<400> SEQUENCE: 150

```
Thr Phe Ala Gln Thr Thr Tyr Leu Ile Asp His Gln Arg
1               5                   10
```

<210> SEQ ID NO 151
<211> LENGTH: 15
<212> TYPE: PRT
<213> ORGANISM: Mycobacterium tuberculosis

<400> SEQUENCE: 151

```
Val Ala Ser Met Ala Pro Val Thr Ala Glu Gly Phe Gln Glu Arg
1               5                   10                  15
```

<210> SEQ ID NO 152
<211> LENGTH: 16
<212> TYPE: PRT
<213> ORGANISM: Mycobacterium tuberculosis

<400> SEQUENCE: 152

```
Ser Val Leu Pro Pro Asp Gly Asn Gly Ser Pro Val Leu Pro Asp Lys
1               5                   10                  15
```

<210> SEQ ID NO 153
<211> LENGTH: 14
<212> TYPE: PRT
<213> ORGANISM: Mycobacterium tuberculosis

<400> SEQUENCE: 153

```
Val Asn Pro Asp Leu Gln Val Glu Val Lys Pro Ser Ile Arg
1               5                   10
```

<210> SEQ ID NO 154
<211> LENGTH: 21
<212> TYPE: PRT
<213> ORGANISM: Mycobacterium tuberculosis

<400> SEQUENCE: 154

```
Thr Ser Glu Thr Asn Thr Pro Gln Gly Asn Gln Glu Gln Leu Val Thr
1               5                   10                  15

Val Met Glu Glu Arg
            20
```

<210> SEQ ID NO 155
<211> LENGTH: 14
<212> TYPE: PRT
<213> ORGANISM: Mycobacterium tuberculosis

<400> SEQUENCE: 155

```
Gln Ile Gln Gly Thr Glu Thr Glu Phe Asn Ser Leu Val Lys
1               5                   10
```

<210> SEQ ID NO 156
<211> LENGTH: 13
<212> TYPE: PRT
<213> ORGANISM: Mycobacterium tuberculosis

<400> SEQUENCE: 156

```
Asp Glu Ile Tyr Ile Pro Leu Gln Glu Glu Asp Thr Lys
1               5                   10
```

<210> SEQ ID NO 157
<211> LENGTH: 13
<212> TYPE: PRT
<213> ORGANISM: Mycobacterium tuberculosis

<400> SEQUENCE: 157

```
Val Glu Asp Glu Ser Leu Asp Asn Thr Trp Leu Asn Arg
1               5                   10
```

<210> SEQ ID NO 158
<211> LENGTH: 22
<212> TYPE: PRT
<213> ORGANISM: Mycobacterium tuberculosis

<400> SEQUENCE: 158

```
Cys Val Pro Arg Pro Gly Gly Ala Val Cys Glu Cys Pro Gly Gly Phe
1               5                   10                  15

Gln Leu Asp Ala Ser Arg
                20
```

<210> SEQ ID NO 159
<211> LENGTH: 16
<212> TYPE: PRT
<213> ORGANISM: Mycobacterium tuberculosis

<400> SEQUENCE: 159

```
Met Gly Gly Gly Gly Ala Leu Gln Trp Asn Cys Ser Gly Gly Ile Gln
1               5                   10                  15
```

<210> SEQ ID NO 160
<211> LENGTH: 22
<212> TYPE: PRT
<213> ORGANISM: Mycobacterium tuberculosis

<400> SEQUENCE: 160

```
Asp Val Glu Glu Lys Pro Ala His Ala Pro Ala Arg Pro Glu Ala Pro
1               5                   10                  15

Val Asp Ser Met Leu Lys
                20
```

<210> SEQ ID NO 161
<211> LENGTH: 16
<212> TYPE: PRT
<213> ORGANISM: Mycobacterium tuberculosis

<400> SEQUENCE: 161

```
Met Ala Gly Ser Tyr Pro Glu Gly Ala Pro Ala Ile Leu Ala Asp Lys
1               5                   10                  15
```

<210> SEQ ID NO 162
<211> LENGTH: 23
<212> TYPE: PRT

<213> ORGANISM: Mycobacterium tuberculosis

<400> SEQUENCE: 162

Leu Asp Cys Ala Ser Ala Ile Gln Asn Tyr Leu Ser Gly Thr His Gly
1 5 10 15

Gly Ser Pro Gly Pro Glu Arg
20

<210> SEQ ID NO 163
<211> LENGTH: 15
<212> TYPE: PRT
<213> ORGANISM: Mycobacterium tuberculosis

<400> SEQUENCE: 163

His Ala Leu Pro Ser Pro Leu Glu Gly Ser Phe Gln Pro Gly Arg
1 5 10 15

<210> SEQ ID NO 164
<211> LENGTH: 14
<212> TYPE: PRT
<213> ORGANISM: Mycobacterium tuberculosis

<400> SEQUENCE: 164

His Cys Pro Ser Thr Phe Phe Ser Ser Pro Gly Leu Thr Arg
1 5 10

<210> SEQ ID NO 165
<211> LENGTH: 14
<212> TYPE: PRT
<213> ORGANISM: Mycobacterium tuberculosis

<400> SEQUENCE: 165

Ile Ser Asp Asp Thr Pro Leu Glu Met Met Thr Ser Pro Arg
1 5 10

<210> SEQ ID NO 166
<211> LENGTH: 19
<212> TYPE: PRT
<213> ORGANISM: Mycobacterium tuberculosis

<400> SEQUENCE: 166

Glu Leu Cys Asp Cys Glu Gln Cys Gly Glu Val Phe Ser Glu His Ser
1 5 10 15

Cys Leu Lys

<210> SEQ ID NO 167
<211> LENGTH: 15
<212> TYPE: PRT
<213> ORGANISM: Mycobacterium tuberculosis

<400> SEQUENCE: 167

Glu Gly Val Tyr Glu Ile Ser Leu Ser Pro Thr Gly Val Ser Arg
1 5 10 15

<210> SEQ ID NO 168
<211> LENGTH: 14
<212> TYPE: PRT
<213> ORGANISM: Mycobacterium tuberculosis

<400> SEQUENCE: 168

Ser Glu Ser Glu Val His Phe Asp Val Glu Thr Ala Ile Lys
1 5 10

```
<210> SEQ ID NO 169
<211> LENGTH: 14
<212> TYPE: PRT
<213> ORGANISM: Mycobacterium tuberculosis

<400> SEQUENCE: 169

Leu Ile Gly Thr Asn Cys Ile Ile Tyr Pro Val Asn Ser Lys
1               5                   10

<210> SEQ ID NO 170
<211> LENGTH: 17
<212> TYPE: PRT
<213> ORGANISM: Mycobacterium tuberculosis

<400> SEQUENCE: 170

Cys Asp Val Val Val Gly Gly Gly Ile Ser Gly Met Ala Ala Ala
1               5                   10                  15

Lys

<210> SEQ ID NO 171
<211> LENGTH: 14
<212> TYPE: PRT
<213> ORGANISM: Mycobacterium tuberculosis

<400> SEQUENCE: 171

Glu Glu Val Tyr Ile Val Gln Ala Ser Asn Val Asp Val Lys
1               5                   10

<210> SEQ ID NO 172
<211> LENGTH: 24
<212> TYPE: PRT
<213> ORGANISM: Mycobacterium tuberculosis

<400> SEQUENCE: 172

Gln Glu Ala Ala Ser Thr Gly Pro Gly Met Glu Pro Glu Thr Thr Ala
1               5                   10                  15

Thr Thr Ile Leu Ala Ser Val Lys
            20

<210> SEQ ID NO 173
<211> LENGTH: 14
<212> TYPE: PRT
<213> ORGANISM: Mycobacterium tuberculosis

<400> SEQUENCE: 173

Val Val Glu Thr Met Gln Ser Thr Leu Asp Ala Glu Ile Arg
1               5                   10

<210> SEQ ID NO 174
<211> LENGTH: 14
<212> TYPE: PRT
<213> ORGANISM: Mycobacterium tuberculosis

<400> SEQUENCE: 174

Ile Asn Ser Glu Leu Gln Val Pro Pro Thr Gln Val Leu Arg
1               5                   10

<210> SEQ ID NO 175
<211> LENGTH: 23
<212> TYPE: PRT
<213> ORGANISM: Mycobacterium tuberculosis

<400> SEQUENCE: 175

Gln Gln Asn Ala Gln Gly Gly Phe Ser Ser Thr Gln Asp Thr Val Val
```

```
1               5                   10                  15
Ala Leu His Ala Leu Ser Lys
            20

<210> SEQ ID NO 176
<211> LENGTH: 14
<212> TYPE: PRT
<213> ORGANISM: Mycobacterium tuberculosis

<400> SEQUENCE: 176

Phe Pro Ser Leu Leu Thr Gln Asn Glu Asn Met Val Ala Lys
1               5                   10

<210> SEQ ID NO 177
<211> LENGTH: 21
<212> TYPE: PRT
<213> ORGANISM: Mycobacterium tuberculosis

<400> SEQUENCE: 177

Gln His His His Gln Ser Ser Phe Pro Gly Ser Leu Pro Gln Glu Thr
1               5                   10                  15

Asn Leu Thr Leu Lys
            20

<210> SEQ ID NO 178
<211> LENGTH: 24
<212> TYPE: PRT
<213> ORGANISM: Mycobacterium tuberculosis

<400> SEQUENCE: 178

Ser Gly Gly Glu Ala Leu Ala Val Ala Asn Asp Ser Thr Ser Thr Pro
1               5                   10                  15

Gln Asn Ala Asn Gly Leu Trp Lys
            20

<210> SEQ ID NO 179
<211> LENGTH: 13
<212> TYPE: PRT
<213> ORGANISM: Mycobacterium tuberculosis

<400> SEQUENCE: 179

Ser Ser Cys Ser Asp Met Asp Leu Leu His Ser Trp Arg
1               5                   10

<210> SEQ ID NO 180
<211> LENGTH: 14
<212> TYPE: PRT
<213> ORGANISM: Mycobacterium tuberculosis

<400> SEQUENCE: 180

Ala Gly Ser Val His Tyr Gly His Tyr Thr Ala Leu Cys Arg
1               5                   10

<210> SEQ ID NO 181
<211> LENGTH: 14
<212> TYPE: PRT
<213> ORGANISM: Mycobacterium tuberculosis

<400> SEQUENCE: 181

Cys Asn Thr Gln Ala Glu Leu Leu Ala Ala Gly Cys Gln Arg
1               5                   10

<210> SEQ ID NO 182
```

-continued

<210> SEQ ID NO 182
<211> LENGTH: 13
<212> TYPE: PRT
<213> ORGANISM: Mycobacterium tuberculosis

<400> SEQUENCE: 182

Gly Val Leu Val Cys Asp Glu Cys Cys Ser Val His Arg
1               5                   10

<210> SEQ ID NO 183
<211> LENGTH: 13
<212> TYPE: PRT
<213> ORGANISM: Mycobacterium tuberculosis

<400> SEQUENCE: 183

Thr Phe Met Asp Met Asp Gln Asp Ser Glu Asp Glu Lys
1               5                   10

<210> SEQ ID NO 184
<211> LENGTH: 13
<212> TYPE: PRT
<213> ORGANISM: Mycobacterium tuberculosis

<400> SEQUENCE: 184

Leu Thr Trp His Ser Tyr Pro Ser Glu Asp Asp Asp Lys
1               5                   10

<210> SEQ ID NO 185
<211> LENGTH: 15
<212> TYPE: PRT
<213> ORGANISM: Mycobacterium tuberculosis

<400> SEQUENCE: 185

Phe Ala Val Val Glu Asn Asn Ser Ser Ala Val Thr Ala Gln Arg
1               5                   10                  15

<210> SEQ ID NO 186
<211> LENGTH: 14
<212> TYPE: PRT
<213> ORGANISM: Mycobacterium tuberculosis

<400> SEQUENCE: 186

Val Glu Asp Thr Cys Val Glu Trp Asp Pro Thr Gly Gly Lys
1               5                   10

<210> SEQ ID NO 187
<211> LENGTH: 13
<212> TYPE: PRT
<213> ORGANISM: Mycobacterium tuberculosis

<400> SEQUENCE: 187

Ala Phe Ser Gln Asn Ser Gln Phe Ile Gln His Gln Arg
1               5                   10

<210> SEQ ID NO 188
<211> LENGTH: 16
<212> TYPE: PRT
<213> ORGANISM: Mycobacterium tuberculosis

<400> SEQUENCE: 188

Cys Leu Pro Asn Pro Thr Pro Glu Gly Gly Ala Val Pro Gly Pro Lys
1               5                   10                  15

<210> SEQ ID NO 189
<211> LENGTH: 14
<212> TYPE: PRT

<213> ORGANISM: Mycobacterium tuberculosis

<400> SEQUENCE: 189

Gly Glu Gly Gln Gly Leu Val Cys Asp Leu Cys Asn Asp Arg
1 5 10

<210> SEQ ID NO 190
<211> LENGTH: 15
<212> TYPE: PRT
<213> ORGANISM: Mycobacterium tuberculosis

<400> SEQUENCE: 190

Ser Ser Thr Asn Thr Ser Leu Pro Asp Asp Asn Gly Ala Trp Lys
1 5 10 15

<210> SEQ ID NO 191
<211> LENGTH: 15
<212> TYPE: PRT
<213> ORGANISM: Mycobacterium tuberculosis

<400> SEQUENCE: 191

Leu Gly Glu Val Val Asn Thr His Gly Pro Val Glu Pro Asp Lys
1 5 10 15

<210> SEQ ID NO 192
<211> LENGTH: 22
<212> TYPE: PRT
<213> ORGANISM: Mycobacterium tuberculosis

<400> SEQUENCE: 192

Gln Ser Ser Asn Arg Pro Ala His Asn Ile Ser His Ile Leu Gly His
1 5 10 15

Asp Cys Ser Ser Ala Val
20

<210> SEQ ID NO 193
<211> LENGTH: 27
<212> TYPE: PRT
<213> ORGANISM: Mycobacterium tuberculosis

<400> SEQUENCE: 193

Gly Pro Gln Gly Pro Thr Gly Ser Glu Gly Thr Pro Gly Leu Pro Gly
1 5 10 15

Gly Val Gly Gln Pro Gly Ala Val Gly Glu Lys
20 25

<210> SEQ ID NO 194
<211> LENGTH: 23
<212> TYPE: PRT
<213> ORGANISM: Mycobacterium tuberculosis

<400> SEQUENCE: 194

Gln Gly Thr Leu Ser Thr Ala Ala Pro Thr Thr Ser Pro Ala Pro Cys
1 5 10 15

Leu Ser Asn His His Asn Lys
20

<210> SEQ ID NO 195
<211> LENGTH: 14
<212> TYPE: PRT
<213> ORGANISM: Mycobacterium tuberculosis

<400> SEQUENCE: 195

```
Glu Asn Ser Glu Asn Thr Thr Ala Pro Glu Val Phe Pro Arg
1               5                   10
```

<210> SEQ ID NO 196
<211> LENGTH: 15
<212> TYPE: PRT
<213> ORGANISM: Mycobacterium tuberculosis

<400> SEQUENCE: 196

```
Glu Gln Gln Met Val Pro Gly Ile Pro Gln Gly Ala His Glu Ala
1               5                   10                  15
```

<210> SEQ ID NO 197
<211> LENGTH: 14
<212> TYPE: PRT
<213> ORGANISM: Mycobacterium tuberculosis

<400> SEQUENCE: 197

```
Leu Val Ala Ala Cys Pro Glu Ser Cys Val Val Cys Thr Lys
1               5                   10
```

<210> SEQ ID NO 198
<211> LENGTH: 15
<212> TYPE: PRT
<213> ORGANISM: Mycobacterium tuberculosis

<400> SEQUENCE: 198

```
Ala Ser Cys Gly Gln Asp Gln Ala Ala Ala Glu Thr Leu Leu Arg
1               5                   10                  15
```

<210> SEQ ID NO 199
<211> LENGTH: 14
<212> TYPE: PRT
<213> ORGANISM: Mycobacterium tuberculosis

<400> SEQUENCE: 199

```
Ser Met Asn Asp Ile Ser Leu Thr Pro Asn Thr Asp Gln Arg
1               5                   10
```

<210> SEQ ID NO 200
<211> LENGTH: 24
<212> TYPE: PRT
<213> ORGANISM: Mycobacterium tuberculosis

<400> SEQUENCE: 200

```
Glu Asp Gly Thr Val Ser Thr Ala Asn Gln Asn Gly Val Ser Ser Asn
1               5                   10                  15

Gly Pro Gly Glu Ile Leu Asn Lys
            20
```

<210> SEQ ID NO 201
<211> LENGTH: 13
<212> TYPE: PRT
<213> ORGANISM: Mycobacterium tuberculosis

<400> SEQUENCE: 201

```
Ser Asn Pro Glu Asp Gln Ile Leu Tyr Gln Thr Glu Arg
1               5                   10
```

<210> SEQ ID NO 202
<211> LENGTH: 14
<212> TYPE: PRT
<213> ORGANISM: Mycobacterium tuberculosis

<400> SEQUENCE: 202

```
Leu Glu Gly Met Asn Glu Thr Val Ser Asn Leu Thr Gln Arg
1               5                   10
```

<210> SEQ ID NO 203
<211> LENGTH: 14
<212> TYPE: PRT
<213> ORGANISM: Mycobacterium tuberculosis

<400> SEQUENCE: 203

```
Lys Pro Ser Ser Glu Thr Asp Ile Glu Asn Trp Ala Ser Lys
1               5                   10
```

<210> SEQ ID NO 204
<211> LENGTH: 16
<212> TYPE: PRT
<213> ORGANISM: Mycobacterium tuberculosis

<400> SEQUENCE: 204

```
Met Ser Glu Ser Leu Asp Thr Ala Asp Pro Ala Val Thr Gly Ala Lys
1               5                   10                  15
```

<210> SEQ ID NO 205
<211> LENGTH: 13
<212> TYPE: PRT
<213> ORGANISM: Mycobacterium tuberculosis

<400> SEQUENCE: 205

```
Val Thr Leu Tyr Glu Cys His Ser Gln Gly Glu Ile Arg
1               5                   10
```

<210> SEQ ID NO 206
<211> LENGTH: 15
<212> TYPE: PRT
<213> ORGANISM: Mycobacterium tuberculosis

<400> SEQUENCE: 206

```
Val His Ser His Glu Val Ala Ala Tyr Leu Ala Ser Pro Gly Arg
1               5                   10                  15
```

<210> SEQ ID NO 207
<211> LENGTH: 15
<212> TYPE: PRT
<213> ORGANISM: Mycobacterium tuberculosis

<400> SEQUENCE: 207

```
Ala Gly Cys Gln Val Val Ala Pro Ser Asp Met Met Asp Gly Arg
1               5                   10                  15
```

<210> SEQ ID NO 208
<211> LENGTH: 23
<212> TYPE: PRT
<213> ORGANISM: Mycobacterium tuberculosis

<400> SEQUENCE: 208

```
Ser Ile Ser Gly Thr Ser Thr Ser Glu Lys Pro Asn Ser Met Asp Thr
1               5                   10                  15

Ala Asn Thr Ser Pro Phe Lys
            20
```

<210> SEQ ID NO 209
<211> LENGTH: 15
<212> TYPE: PRT
<213> ORGANISM: Mycobacterium tuberculosis

```
<400> SEQUENCE: 209

Asn Phe Gln Ser Glu Ser Val Pro Ala Leu Gly Gly Gln Glu Lys
1               5                   10                  15

<210> SEQ ID NO 210
<211> LENGTH: 14
<212> TYPE: PRT
<213> ORGANISM: Mycobacterium tuberculosis

<400> SEQUENCE: 210

Asp Ser Pro Val Cys Pro Ser Tyr Ser Pro Thr Met Pro Arg
1               5                   10

<210> SEQ ID NO 211
<211> LENGTH: 13
<212> TYPE: PRT
<213> ORGANISM: Mycobacterium tuberculosis

<400> SEQUENCE: 211

Asp Arg Pro Ser Leu Pro Gln Glu Arg Pro Gly Trp Arg
1               5                   10

<210> SEQ ID NO 212
<211> LENGTH: 21
<212> TYPE: PRT
<213> ORGANISM: Mycobacterium tuberculosis

<400> SEQUENCE: 212

Glu Asp Gly Glu Val Val Gln Glu Glu Val Cys Ala Lys Pro Ser
1               5                   10                  15

Val Thr Glu Glu Lys
            20

<210> SEQ ID NO 213
<211> LENGTH: 14
<212> TYPE: PRT
<213> ORGANISM: Mycobacterium tuberculosis

<400> SEQUENCE: 213

Asp Ala Glu Thr Gly Glu Glu Val Thr His Tyr Leu Val Lys
1               5                   10

<210> SEQ ID NO 214
<211> LENGTH: 15
<212> TYPE: PRT
<213> ORGANISM: Mycobacterium tuberculosis

<400> SEQUENCE: 214

Thr Gly Ser Leu Pro His Ser Ser Glu Gln Leu Leu Gly His Lys
1               5                   10                  15

<210> SEQ ID NO 215
<211> LENGTH: 14
<212> TYPE: PRT
<213> ORGANISM: Mycobacterium tuberculosis

<400> SEQUENCE: 215

Ala Ser Ser Val Leu Pro Glu His His Glu Ala Phe Asn Arg
1               5                   10

<210> SEQ ID NO 216
<211> LENGTH: 22
<212> TYPE: PRT
<213> ORGANISM: Mycobacterium tuberculosis
```

<400> SEQUENCE: 216

Leu Ser Gly Ala Met Cys Thr Ser Cys Ala Ser Gln Thr Thr Ala Asn
1               5                   10                  15

Asp Pro Tyr Thr Val Arg
            20

<210> SEQ ID NO 217
<211> LENGTH: 14
<212> TYPE: PRT
<213> ORGANISM: Mycobacterium tuberculosis

<400> SEQUENCE: 217

Val Ser Thr Ala Gln Asp Val Ile Gln Gln Thr Leu Cys Lys
1               5                   10

<210> SEQ ID NO 218
<211> LENGTH: 15
<212> TYPE: PRT
<213> ORGANISM: Mycobacterium tuberculosis

<400> SEQUENCE: 218

Val Ser Ser Ser Ser Glu Ser Glu Pro Glu Leu Ala Gln Leu Lys
1               5                   10                  15

<210> SEQ ID NO 219
<211> LENGTH: 20
<212> TYPE: PRT
<213> ORGANISM: Mycobacterium tuberculosis

<400> SEQUENCE: 219

Thr Ser Cys Ser Asn Cys Thr Ser Asn Gly Met Glu Cys Met Trp Cys
1               5                   10                  15

Ser Ser Thr Lys
            20

<210> SEQ ID NO 220
<211> LENGTH: 15
<212> TYPE: PRT
<213> ORGANISM: Mycobacterium tuberculosis

<400> SEQUENCE: 220

Glu Ser Ser Gln Pro Pro Val Ala Phe Ser Ser Ser Ile Glu Lys
1               5                   10                  15

<210> SEQ ID NO 221
<211> LENGTH: 21
<212> TYPE: PRT
<213> ORGANISM: Mycobacterium tuberculosis

<400> SEQUENCE: 221

Asn Cys Gln Thr Val Leu Ala Pro Cys Ser Pro Asn Pro Cys Glu Asn
1               5                   10                  15

Ala Ala Val Cys Lys
            20

<210> SEQ ID NO 222
<211> LENGTH: 14
<212> TYPE: PRT
<213> ORGANISM: Mycobacterium tuberculosis

<400> SEQUENCE: 222

Gly Gln Asp Thr Gln Phe Trp Ala Gly His Tyr Gly Ala Arg

```
<210> SEQ ID NO 223
<211> LENGTH: 15
<212> TYPE: PRT
<213> ORGANISM: Mycobacterium tuberculosis

<400> SEQUENCE: 223

Met Thr Glu Asn Val Val Cys Thr Gly Ala Val Asn Ala Val Lys
1               5                   10                  15

<210> SEQ ID NO 224
<211> LENGTH: 15
<212> TYPE: PRT
<213> ORGANISM: Mycobacterium tuberculosis

<400> SEQUENCE: 224

Tyr Pro Ser Thr Ser Glu Ala Val Asn Ile Gln Gly Ile Ser Lys
1               5                   10                  15

<210> SEQ ID NO 225
<211> LENGTH: 15
<212> TYPE: PRT
<213> ORGANISM: Mycobacterium tuberculosis

<400> SEQUENCE: 225

Ala Gly Phe Pro Cys Phe Lys Pro Ser Gly Ala Ala Pro Gln Arg
1               5                   10                  15

<210> SEQ ID NO 226
<211> LENGTH: 14
<212> TYPE: PRT
<213> ORGANISM: Mycobacterium tuberculosis

<400> SEQUENCE: 226

Ser Thr Leu Glu Glu Gln Gly Leu His Val His Ser Val Arg
1               5                   10

<210> SEQ ID NO 227
<211> LENGTH: 16
<212> TYPE: PRT
<213> ORGANISM: Mycobacterium tuberculosis

<400> SEQUENCE: 227

Gly Thr Ala Asn Thr Cys Ile Pro Ser Ile Ser Ser Ile Gly Ser Lys
1               5                   10                  15

<210> SEQ ID NO 228
<211> LENGTH: 13
<212> TYPE: PRT
<213> ORGANISM: Mycobacterium tuberculosis

<400> SEQUENCE: 228

Ser Phe Asn Gln Asn Ser His Leu Ile Ile His Gln Arg
1               5                   10

<210> SEQ ID NO 229
<211> LENGTH: 13
<212> TYPE: PRT
<213> ORGANISM: Mycobacterium tuberculosis

<400> SEQUENCE: 229

Ile Pro Ile Asp Asn Met Thr Asn Glu Met Glu Gln Arg
1               5                   10
```

<210> SEQ ID NO 230
<211> LENGTH: 15
<212> TYPE: PRT
<213> ORGANISM: Mycobacterium tuberculosis

<400> SEQUENCE: 230

Ile Asn Leu Pro Ala Pro Asn Pro Asp His Val Gly Gly Tyr Lys
1               5                   10                  15

<210> SEQ ID NO 231
<211> LENGTH: 16
<212> TYPE: PRT
<213> ORGANISM: Mycobacterium tuberculosis

<400> SEQUENCE: 231

Ser Pro Gly Thr His Leu Gly Ala Leu Ala Gln Thr Val Gln Gly Arg
1               5                   10                  15

<210> SEQ ID NO 232
<211> LENGTH: 21
<212> TYPE: PRT
<213> ORGANISM: Mycobacterium tuberculosis

<400> SEQUENCE: 232

Leu Ser Asn Cys Asp Pro Pro Thr Tyr Glu Glu Ala Thr Gly Gln
1               5                   10                  15

Val Asn Leu Gln Arg
            20

<210> SEQ ID NO 233
<211> LENGTH: 14
<212> TYPE: PRT
<213> ORGANISM: Mycobacterium tuberculosis

<400> SEQUENCE: 233

Glu Asp Ile Ser Ala Cys Leu Gln Gly Thr His Gly Phe Arg
1               5                   10

<210> SEQ ID NO 234
<211> LENGTH: 13
<212> TYPE: PRT
<213> ORGANISM: Mycobacterium tuberculosis

<400> SEQUENCE: 234

Glu Asp Cys Cys Pro Gly Lys Pro Leu Asn Val Phe Arg
1               5                   10

<210> SEQ ID NO 235
<211> LENGTH: 13
<212> TYPE: PRT
<213> ORGANISM: Mycobacterium tuberculosis

<400> SEQUENCE: 235

Glu Cys Asp Met Cys Phe Ser Gln Ala Ser Ser Leu Arg
1               5                   10

<210> SEQ ID NO 236
<211> LENGTH: 14
<212> TYPE: PRT
<213> ORGANISM: Mycobacterium tuberculosis

<400> SEQUENCE: 236

Asp Cys Ala Ala Asn Thr Phe Ile Glu Asp Ser Gly Tyr Lys
1               5                   10

<210> SEQ ID NO 237
<211> LENGTH: 14
<212> TYPE: PRT
<213> ORGANISM: Mycobacterium tuberculosis

<400> SEQUENCE: 237

Leu Gln Glu Ser Gly Gln Val Thr Ile Ser Glu Leu Cys Lys
1               5                   10

<210> SEQ ID NO 238
<211> LENGTH: 15
<212> TYPE: PRT
<213> ORGANISM: Mycobacterium tuberculosis

<400> SEQUENCE: 238

Ser Gln Ala Cys Gly Gly Asn Leu Gly Ser Ile Glu Glu Leu Arg
1               5                   10                  15

<210> SEQ ID NO 239
<211> LENGTH: 27
<212> TYPE: PRT
<213> ORGANISM: Mycobacterium tuberculosis

<400> SEQUENCE: 239

Gly Pro His Pro Gln Ala Leu Pro Gly His Leu Pro Gly Ala Gly Asp
1               5                   10                  15

Ser Gly Ala Gly Ala Gly Gly Val Val Arg
            20                  25

<210> SEQ ID NO 240
<211> LENGTH: 14
<212> TYPE: PRT
<213> ORGANISM: Mycobacterium tuberculosis

<400> SEQUENCE: 240

Leu Glu Tyr Ser Gly Ala Ile Ser Ala His Cys Asn Leu Arg
1               5                   10

<210> SEQ ID NO 241
<211> LENGTH: 15
<212> TYPE: PRT
<213> ORGANISM: Mycobacterium tuberculosis

<400> SEQUENCE: 241

Met Gly Val Thr Cys Val Ser Gln Met Pro Val Ala Glu Gly Lys
1               5                   10                  15

<210> SEQ ID NO 242
<211> LENGTH: 13
<212> TYPE: PRT
<213> ORGANISM: Mycobacterium tuberculosis

<400> SEQUENCE: 242

Thr Cys Asp Phe Phe Ser Pro Tyr Glu Asn Gly Glu Lys
1               5                   10

<210> SEQ ID NO 243
<211> LENGTH: 13
<212> TYPE: PRT
<213> ORGANISM: Mycobacterium tuberculosis

<400> SEQUENCE: 243

Phe Gly Tyr Tyr Gly Asp Ala Leu Gln Gln Asp Cys Arg

<210> SEQ ID NO 244
<211> LENGTH: 14
<212> TYPE: PRT
<213> ORGANISM: Mycobacterium tuberculosis

<400> SEQUENCE: 244

Leu Leu Ser Leu His Ser Pro Asn Ser Tyr Tyr Gly Ser Arg
1               5                   10

<210> SEQ ID NO 245
<211> LENGTH: 15
<212> TYPE: PRT
<213> ORGANISM: Mycobacterium tuberculosis

<400> SEQUENCE: 245

Tyr Gln Val Ser Glu Glu Val Pro Ser Gly Thr Val Ile Gly Lys
1               5                   10                  15

<210> SEQ ID NO 246
<211> LENGTH: 15
<212> TYPE: PRT
<213> ORGANISM: Mycobacterium tuberculosis

<400> SEQUENCE: 246

Glu Ser Thr Ala Thr Leu Leu Gly Cys Asn Ala Ser Ile Gln Lys
1               5                   10                  15

<210> SEQ ID NO 247
<211> LENGTH: 14
<212> TYPE: PRT
<213> ORGANISM: Mycobacterium tuberculosis

<400> SEQUENCE: 247

Thr Ser Val Thr Thr Ser Ile Ser Glu Pro Trp Thr Gln Arg
1               5                   10

<210> SEQ ID NO 248
<211> LENGTH: 13
<212> TYPE: PRT
<213> ORGANISM: Mycobacterium tuberculosis

<400> SEQUENCE: 248

Met Ser Tyr Ser Cys Cys Leu Pro Ser Leu Gly Cys Arg
1               5                   10

<210> SEQ ID NO 249
<211> LENGTH: 13
<212> TYPE: PRT
<213> ORGANISM: Mycobacterium tuberculosis

<400> SEQUENCE: 249

Ser Glu Tyr Ser Ser Tyr Pro Asp Ile Asn Phe Asn Arg
1               5                   10

<210> SEQ ID NO 250
<211> LENGTH: 15
<212> TYPE: PRT
<213> ORGANISM: Mycobacterium tuberculosis

<400> SEQUENCE: 250

His Ser His Gly Leu Ala Leu Gln Pro Ser Phe Pro Gly Ser Arg
1               5                   10                  15

-continued

<210> SEQ ID NO 251
<211> LENGTH: 17
<212> TYPE: PRT
<213> ORGANISM: Mycobacterium tuberculosis

<400> SEQUENCE: 251

Leu Pro Tyr Ser Gly Arg Pro Ala Pro Ala Pro Ala Ala Ala Pro Gly
1               5                   10                  15

Val

<210> SEQ ID NO 252
<211> LENGTH: 14
<212> TYPE: PRT
<213> ORGANISM: Mycobacterium tuberculosis

<400> SEQUENCE: 252

Ala Glu Gln Asp Ile Thr Thr Leu Glu Gln Ser Ile Ser Arg
1 5 10

<210> SEQ ID NO 253
<211> LENGTH: 15
<212> TYPE: PRT
<213> ORGANISM: Mycobacterium tuberculosis

<400> SEQUENCE: 253

Val Met Ser Pro Glu Asn Phe Pro Thr Ala Ser Val Glu Gly Lys
1 5 10 15

<210> SEQ ID NO 254
<211> LENGTH: 16
<212> TYPE: PRT
<213> ORGANISM: Mycobacterium tuberculosis

<400> SEQUENCE: 254

Gly Gly Asn Gln Glu Ile Gly Pro Leu Pro Pro Thr Gly Asn Leu Lys
1 5 10 15

<210> SEQ ID NO 255
<211> LENGTH: 14
<212> TYPE: PRT
<213> ORGANISM: Mycobacterium tuberculosis

<400> SEQUENCE: 255

Gly Ala Glu Val Thr Tyr Met Asn Met Thr Ala Tyr Asn Lys
1 5 10

<210> SEQ ID NO 256
<211> LENGTH: 16
<212> TYPE: PRT
<213> ORGANISM: Mycobacterium tuberculosis

<400> SEQUENCE: 256

Ser Pro Ala Ala Arg Pro Pro Val Pro Ala Pro Pro Ala Leu Pro Arg
1 5 10 15

<210> SEQ ID NO 257
<211> LENGTH: 13
<212> TYPE: PRT
<213> ORGANISM: Mycobacterium tuberculosis

<400> SEQUENCE: 257

Cys Leu Val Pro Gly Tyr Tyr Ser Thr His Leu Gln Arg
1 5 10

<210> SEQ ID NO 258
<211> LENGTH: 15
<212> TYPE: PRT
<213> ORGANISM: Mycobacterium tuberculosis

<400> SEQUENCE: 258

Leu Ala Pro Ile Ser Glu Glu Gly Lys Pro Gln Leu Val Gly Arg
1               5                   10                  15

<210> SEQ ID NO 259
<211> LENGTH: 13
<212> TYPE: PRT
<213> ORGANISM: Mycobacterium tuberculosis

<400> SEQUENCE: 259

Asp Glu Asp Leu Gln Glu Met Glu Asn Leu Ala Gln Arg
1               5                   10

<210> SEQ ID NO 260
<211> LENGTH: 14
<212> TYPE: PRT
<213> ORGANISM: Mycobacterium tuberculosis

<400> SEQUENCE: 260

Trp Ile His Phe Gly Thr Glu Val Thr Asn Ser Ser Gly Arg
1               5                   10

<210> SEQ ID NO 261
<211> LENGTH: 17
<212> TYPE: PRT
<213> ORGANISM: Mycobacterium tuberculosis

<400> SEQUENCE: 261

Val Leu Pro Met Val Pro Ala Pro Pro Gly Ser Ser Ala Ala Ala
1               5                   10                  15

Arg

<210> SEQ ID NO 262
<211> LENGTH: 14
<212> TYPE: PRT
<213> ORGANISM: Mycobacterium tuberculosis

<400> SEQUENCE: 262

Ser Asn Phe Ser Pro His Phe Ala Ser Ser Asn Gln Leu Arg
1               5                   10

<210> SEQ ID NO 263
<211> LENGTH: 11
<212> TYPE: PRT
<213> ORGANISM: Mycobacterium tuberculosis

<400> SEQUENCE: 263

Cys Leu His Cys Leu Tyr Ser Cys His Trp Arg
1               5                   10

<210> SEQ ID NO 264
<211> LENGTH: 14
<212> TYPE: PRT
<213> ORGANISM: Mycobacterium tuberculosis

<400> SEQUENCE: 264

Val Gly Asn Ile Pro Tyr Glu Ala Thr Glu Glu Gln Leu Lys
1               5                   10

```
<210> SEQ ID NO 265
<211> LENGTH: 15
<212> TYPE: PRT
<213> ORGANISM: Mycobacterium tuberculosis

<400> SEQUENCE: 265

His Pro Asp Glu Ala Ala Phe Phe Asp Thr Ala Ser Thr Gly Lys
1               5                   10                  15

<210> SEQ ID NO 266
<211> LENGTH: 14
<212> TYPE: PRT
<213> ORGANISM: Mycobacterium tuberculosis

<400> SEQUENCE: 266

Ser Ser Leu Thr Gln Glu Glu Ala Pro Val Ser Trp Glu Lys
1               5                   10

<210> SEQ ID NO 267
<211> LENGTH: 13
<212> TYPE: PRT
<213> ORGANISM: Mycobacterium tuberculosis

<400> SEQUENCE: 267

Val Leu Asn Gln Tyr Thr Asp Thr Ile Ile Gln Glu Arg
1               5                   10

<210> SEQ ID NO 268
<211> LENGTH: 14
<212> TYPE: PRT
<213> ORGANISM: Mycobacterium tuberculosis

<400> SEQUENCE: 268

Leu Glu Gln Gly Glu Asn Val Phe Leu Gln Ala Thr Asp Lys
1               5                   10

<210> SEQ ID NO 269
<211> LENGTH: 14
<212> TYPE: PRT
<213> ORGANISM: Mycobacterium tuberculosis

<400> SEQUENCE: 269

Met Ala Phe Met Ala Ala Thr Asp His Ser Asn Gln Leu Arg
1               5                   10

<210> SEQ ID NO 270
<211> LENGTH: 23
<212> TYPE: PRT
<213> ORGANISM: Mycobacterium tuberculosis

<400> SEQUENCE: 270

Met Asn Ser Pro Ser Gln Ser Ser Pro Gly Met Asn Pro Gly Gln Pro
1               5                   10                  15

Thr Ser Met Leu Ser Pro Arg
            20

<210> SEQ ID NO 271
<211> LENGTH: 13
<212> TYPE: PRT
<213> ORGANISM: Mycobacterium tuberculosis

<400> SEQUENCE: 271

Phe Val Tyr Pro Val Pro Tyr Thr Thr Arg Pro Pro Arg
1               5                   10
```

<210> SEQ ID NO 272
<211> LENGTH: 12
<212> TYPE: PRT
<213> ORGANISM: Mycobacterium tuberculosis

<400> SEQUENCE: 272

Trp Asp Ser Asn Ile Cys Glu Leu His Tyr Thr Arg
1               5                   10

<210> SEQ ID NO 273
<211> LENGTH: 23
<212> TYPE: PRT
<213> ORGANISM: Mycobacterium tuberculosis

<400> SEQUENCE: 273

Tyr Pro Ala Glu Glu Pro Ala Ser Ala Trp Thr Pro Ser Pro Pro Pro
1               5                   10                  15

Val Thr Thr Ser Ser Ser Lys
            20

<210> SEQ ID NO 274
<211> LENGTH: 15
<212> TYPE: PRT
<213> ORGANISM: Mycobacterium tuberculosis

<400> SEQUENCE: 274

Thr Ser Ala Asn Pro Glu Thr Leu Leu Gly Glu Met Glu Ala Lys
1               5                   10                  15

<210> SEQ ID NO 275
<211> LENGTH: 14
<212> TYPE: PRT
<213> ORGANISM: Mycobacterium tuberculosis

<400> SEQUENCE: 275

Met Thr Gln Pro Phe Pro Thr Gln Phe Ala Pro Gln Ala Lys
1               5                   10

<210> SEQ ID NO 276
<211> LENGTH: 13
<212> TYPE: PRT
<213> ORGANISM: Mycobacterium tuberculosis

<400> SEQUENCE: 276

Thr Phe Ser Gln Met Ser Ser Leu Val Tyr His His Arg
1               5                   10

<210> SEQ ID NO 277
<211> LENGTH: 15
<212> TYPE: PRT
<213> ORGANISM: Mycobacterium tuberculosis

<400> SEQUENCE: 277

Val Gly Gln Cys Val Val Val Phe Ser Gln Ala Pro Ser Gly Arg
1               5                   10                  15

<210> SEQ ID NO 278
<211> LENGTH: 15
<212> TYPE: PRT
<213> ORGANISM: Mycobacterium tuberculosis

<400> SEQUENCE: 278

Asn Pro Ser Thr Asn Val Ser Val Val Val Phe Asp Ser Thr Lys

<210> SEQ ID NO 279
<211> LENGTH: 13
<212> TYPE: PRT
<213> ORGANISM: Mycobacterium tuberculosis

<400> SEQUENCE: 279

Val Leu Met Val Glu Thr His Asn Glu Ile Tyr Asp Lys
1               5                   10

<210> SEQ ID NO 280
<211> LENGTH: 15
<212> TYPE: PRT
<213> ORGANISM: Mycobacterium tuberculosis

<400> SEQUENCE: 280

Met Asp Asn Cys Leu Ala Ala Ala Ala Leu Asn Gly Val Asp Arg
1               5                   10                  15

<210> SEQ ID NO 281
<211> LENGTH: 14
<212> TYPE: PRT
<213> ORGANISM: Mycobacterium tuberculosis

<400> SEQUENCE: 281

Leu Val Ile Glu Cys Gly Ala Asp Cys Asn Ile Leu Ser Lys
1               5                   10

<210> SEQ ID NO 282
<211> LENGTH: 13
<212> TYPE: PRT
<213> ORGANISM: Mycobacterium tuberculosis

<400> SEQUENCE: 282

Phe Cys Cys Glu Asp Gly Thr Thr Ile Val Asn Phe Lys
1               5                   10

<210> SEQ ID NO 283
<211> LENGTH: 14
<212> TYPE: PRT
<213> ORGANISM: Mycobacterium tuberculosis

<400> SEQUENCE: 283

Tyr His Tyr Ala Glu Ile Ser Ser Gln Val Pro Leu Gly Lys
1               5                   10

<210> SEQ ID NO 284
<211> LENGTH: 13
<212> TYPE: PRT
<213> ORGANISM: Mycobacterium tuberculosis

<400> SEQUENCE: 284

Leu Gln Thr Leu Ser Ile Gln Gln Cys Leu Pro His Arg
1               5                   10

<210> SEQ ID NO 285
<211> LENGTH: 15
<212> TYPE: PRT
<213> ORGANISM: Mycobacterium tuberculosis

<400> SEQUENCE: 285

Leu Val Met Val Ser Thr Leu Asp Thr Ser Ser Gln Pro Gly Arg
1               5                   10                  15

<210> SEQ ID NO 286
<211> LENGTH: 16
<212> TYPE: PRT
<213> ORGANISM: Mycobacterium tuberculosis

<400> SEQUENCE: 286

Gln Pro Pro Pro Gly Ile Val Ala Pro Ala Ala Met Leu Ser Ser Arg
1               5                   10                  15

<210> SEQ ID NO 287
<211> LENGTH: 15
<212> TYPE: PRT
<213> ORGANISM: Mycobacterium tuberculosis

<400> SEQUENCE: 287

Ser Pro Leu Gln Ala Val Glu Pro Ile Ser Thr Ser Val His Lys
1               5                   10                  15

<210> SEQ ID NO 288
<211> LENGTH: 14
<212> TYPE: PRT
<213> ORGANISM: Mycobacterium tuberculosis

<400> SEQUENCE: 288

Ile Val Glu Thr Asp Glu Ser Gln Gly Ile Phe Val Glu Lys
1               5                   10

<210> SEQ ID NO 289
<211> LENGTH: 14
<212> TYPE: PRT
<213> ORGANISM: Mycobacterium tuberculosis

<400> SEQUENCE: 289

Leu Ser Trp Pro Gln Ser Thr Gly Ile Cys Ser Asn Ile Lys
1               5                   10

<210> SEQ ID NO 290
<211> LENGTH: 17
<212> TYPE: PRT
<213> ORGANISM: Mycobacterium tuberculosis

<400> SEQUENCE: 290

Ser Val Leu Asp Leu Gly Ser Gly Cys Gly Ala Thr Ala Ile Ala Ala
1               5                   10                  15

Lys

<210> SEQ ID NO 291
<211> LENGTH: 14
<212> TYPE: PRT
<213> ORGANISM: Mycobacterium tuberculosis

<400> SEQUENCE: 291

Ala Ala Gly Phe Asp Glu Ile Glu Gln Asp Leu Thr Gln Arg
1               5                   10

<210> SEQ ID NO 292
<211> LENGTH: 14
<212> TYPE: PRT
<213> ORGANISM: Mycobacterium tuberculosis

<400> SEQUENCE: 292

Gln Thr Val Met Thr Ser Ala Thr Trp Pro Asp Thr Val Arg
1               5                   10

```
<210> SEQ ID NO 293
<211> LENGTH: 13
<212> TYPE: PRT
<213> ORGANISM: Mycobacterium tuberculosis

<400> SEQUENCE: 293

Thr Ala Phe Thr Asn His Gln Ile Tyr Glu Leu Glu Lys
1               5                   10

<210> SEQ ID NO 294
<211> LENGTH: 17
<212> TYPE: PRT
<213> ORGANISM: Mycobacterium tuberculosis

<400> SEQUENCE: 294

Ala Pro Ser Ser Pro Ala Leu Gln Ala Leu Ala Gly Gln Ala Gly Val
1               5                   10                  15

Arg

<210> SEQ ID NO 295
<211> LENGTH: 16
<212> TYPE: PRT
<213> ORGANISM: Mycobacterium tuberculosis

<400> SEQUENCE: 295

Met Glu Pro Ala Val Gly Gly Pro Gly Pro Leu Ile Val Asn Asn Lys
1               5                   10                  15

<210> SEQ ID NO 296
<211> LENGTH: 13
<212> TYPE: PRT
<213> ORGANISM: Mycobacterium tuberculosis

<400> SEQUENCE: 296

Gln Val His Ile Leu Gln Gln Asn Cys Ile Ala Leu Arg
1               5                   10

<210> SEQ ID NO 297
<211> LENGTH: 22
<212> TYPE: PRT
<213> ORGANISM: Mycobacterium tuberculosis

<400> SEQUENCE: 297

Val Glu Val Ser Gly Asp Ala Ser Cys Cys Ser Pro Asp Pro Ile Ser
1               5                   10                  15

Pro Glu Asp Leu Pro Arg
            20

<210> SEQ ID NO 298
<211> LENGTH: 15
<212> TYPE: PRT
<213> ORGANISM: Mycobacterium tuberculosis

<400> SEQUENCE: 298

Glu Gly Phe Pro Thr Asp Ala Pro Tyr Pro Thr Thr Leu Gly Lys
1               5                   10                  15

<210> SEQ ID NO 299
<211> LENGTH: 16
<212> TYPE: PRT
<213> ORGANISM: Mycobacterium tuberculosis

<400> SEQUENCE: 299
```

```
Ser Ala Tyr Ala Leu Gly Gly Leu Gly Ser Gly Ile Cys Pro Asn Arg
1               5                   10                  15
```

<210> SEQ ID NO 300
<211> LENGTH: 14
<212> TYPE: PRT
<213> ORGANISM: Mycobacterium tuberculosis

<400> SEQUENCE: 300

```
Ala Ser Ser Leu Cys His His Ala Ser Leu Pro Trp Val Lys
1               5                   10
```

<210> SEQ ID NO 301
<211> LENGTH: 13
<212> TYPE: PRT
<213> ORGANISM: Mycobacterium tuberculosis

<400> SEQUENCE: 301

```
Phe Leu Asn Asp Thr Ser Leu Pro His Ser Cys Phe Arg
1               5                   10
```

<210> SEQ ID NO 302
<211> LENGTH: 14
<212> TYPE: PRT
<213> ORGANISM: Mycobacterium tuberculosis

<400> SEQUENCE: 302

```
Phe Leu Ile Asp Ser Asn Gly Gln Val Ile Thr Thr Glu Arg
1               5                   10
```

<210> SEQ ID NO 303
<211> LENGTH: 13
<212> TYPE: PRT
<213> ORGANISM: Mycobacterium tuberculosis

<400> SEQUENCE: 303

```
Ile Glu Gly Glu Asn Tyr Leu Pro Gln Pro Ile Tyr Arg
1               5                   10
```

<210> SEQ ID NO 304
<211> LENGTH: 13
<212> TYPE: PRT
<213> ORGANISM: Mycobacterium tuberculosis

<400> SEQUENCE: 304

```
Val Thr Gly Leu Ile Glu Asn His Asp Tyr Glu Phe Arg
1               5                   10
```

<210> SEQ ID NO 305
<211> LENGTH: 15
<212> TYPE: PRT
<213> ORGANISM: Mycobacterium tuberculosis

<400> SEQUENCE: 305

```
Ile Leu Phe Val Ser Gln Gly Ser Glu Ile Ala Ser Gln Gly Arg
1               5                   10                  15
```

<210> SEQ ID NO 306
<211> LENGTH: 13
<212> TYPE: PRT
<213> ORGANISM: Mycobacterium tuberculosis

<400> SEQUENCE: 306

```
Asp Leu Asp Gln Val Gln Leu His Leu Glu Glu Val Arg
1               5                   10
```

<210> SEQ ID NO 307
<211> LENGTH: 13
<212> TYPE: PRT
<213> ORGANISM: Mycobacterium tuberculosis

<400> SEQUENCE: 307

Phe Asn Asp Ile Thr Ala Asp Val Tyr Ser Glu Tyr Arg
1               5                   10

<210> SEQ ID NO 308
<211> LENGTH: 15
<212> TYPE: PRT
<213> ORGANISM: Mycobacterium tuberculosis

<400> SEQUENCE: 308

Leu Cys Val Pro Gly Ile Val Ala Leu Gln Ser Pro Pro Asn Lys
1               5                   10                  15

<210> SEQ ID NO 309
<211> LENGTH: 22
<212> TYPE: PRT
<213> ORGANISM: Mycobacterium tuberculosis

<400> SEQUENCE: 309

Ile Glu Glu Thr Cys Gln Val Gly Met Lys Pro Pro Val Pro Gly Gly
1               5                   10                  15

Tyr Thr Leu Gln Gly Lys
            20

<210> SEQ ID NO 310
<211> LENGTH: 22
<212> TYPE: PRT
<213> ORGANISM: Mycobacterium tuberculosis

<400> SEQUENCE: 310

Val Trp Pro Gln Ala Thr Ala Pro Glu Gln Ala Pro Ala Pro Ala Arg
1               5                   10                  15

Pro Tyr Gln Gly Val Arg
            20

<210> SEQ ID NO 311
<211> LENGTH: 15
<212> TYPE: PRT
<213> ORGANISM: Mycobacterium tuberculosis

<400> SEQUENCE: 311

Leu Gly Val Glu Met Leu Ser Glu Ser Gln Leu Ser Asp Gly Lys
1               5                   10                  15

<210> SEQ ID NO 312
<211> LENGTH: 23
<212> TYPE: PRT
<213> ORGANISM: Mycobacterium tuberculosis

<400> SEQUENCE: 312

Gln Asn Glu His His Leu Glu Gly Gly Phe Ser Ile Gly Ser Val Gly
1               5                   10                  15

Pro Asp Gly Gln Leu Gly Arg
            20

<210> SEQ ID NO 313
<211> LENGTH: 14

```
<212> TYPE: PRT
<213> ORGANISM: Mycobacterium tuberculosis

<400> SEQUENCE: 313

Asn Phe Leu Glu Thr Asp Asn Glu Gly Asn Gly Ile Leu Arg
1 5 10

<210> SEQ ID NO 314
<211> LENGTH: 17
<212> TYPE: PRT
<213> ORGANISM: Mycobacterium tuberculosis

<400> SEQUENCE: 314

Gly Ile Leu Phe Val Gly Ser Gly Val Ser Gly Gly Glu Glu Gly Ala
1 5 10 15

Arg

<210> SEQ ID NO 315
<211> LENGTH: 14
<212> TYPE: PRT
<213> ORGANISM: Mycobacterium tuberculosis

<400> SEQUENCE: 315

Val Thr Asp Ala Thr Glu Thr Thr Ile Thr Ile Ser Trp Arg
1 5 10

<210> SEQ ID NO 316
<211> LENGTH: 12
<212> TYPE: PRT
<213> ORGANISM: Mycobacterium tuberculosis

<400> SEQUENCE: 316

Glu Trp Asp Ile Leu Glu Thr Glu Glu His Tyr Lys
1 5 10

<210> SEQ ID NO 317
<211> LENGTH: 21
<212> TYPE: PRT
<213> ORGANISM: Mycobacterium tuberculosis

<400> SEQUENCE: 317

Gln Val Arg Pro Pro Ser Cys Pro Val Pro Phe Pro Glu Thr Phe Asn
1 5 10 15

Gly Glu Ser Ser Arg
20

<210> SEQ ID NO 318
<211> LENGTH: 13
<212> TYPE: PRT
<213> ORGANISM: Mycobacterium tuberculosis

<400> SEQUENCE: 318

Val Val Phe His Leu His Glu Ser Phe Pro Arg Pro Lys
1 5 10

<210> SEQ ID NO 319
<211> LENGTH: 14
<212> TYPE: PRT
<213> ORGANISM: Mycobacterium tuberculosis

<400> SEQUENCE: 319

Met Tyr Gln Gly His Met Gln Val Val Gly Val Thr Leu Lys
1 5 10

<210> SEQ ID NO 320
<211> LENGTH: 23
<212> TYPE: PRT
<213> ORGANISM: Mycobacterium tuberculosis

<400> SEQUENCE: 320

Ser Pro Gly Asp Gly Gly Pro His Asp Val Phe Thr Ser Leu Pro Ser
1               5                   10                  15

Asp Cys Gln Leu Gly Ser Arg
            20

<210> SEQ ID NO 321
<211> LENGTH: 15
<212> TYPE: PRT
<213> ORGANISM: Mycobacterium tuberculosis

<400> SEQUENCE: 321

Trp Ala Ala Gly Ala Met Ala Ala Pro Glu Pro Leu Arg Pro Arg
1               5                   10                  15

<210> SEQ ID NO 322
<211> LENGTH: 13
<212> TYPE: PRT
<213> ORGANISM: Mycobacterium tuberculosis

<400> SEQUENCE: 322

Ala Gln Leu Glu Glu Glu Ile Ile Ala Tyr Glu Glu Arg
1               5                   10

<210> SEQ ID NO 323
<211> LENGTH: 14
<212> TYPE: PRT
<213> ORGANISM: Mycobacterium tuberculosis

<400> SEQUENCE: 323

Met Ser Glu Asp Ser Ser Ala Leu Pro Trp Ser Ile Asn Arg
1               5                   10

<210> SEQ ID NO 324
<211> LENGTH: 13
<212> TYPE: PRT
<213> ORGANISM: Mycobacterium tuberculosis

<400> SEQUENCE: 324

Leu Met Asn Glu Asp Pro Met Tyr Ser Met Tyr Ala Lys
1               5                   10

<210> SEQ ID NO 325
<211> LENGTH: 15
<212> TYPE: PRT
<213> ORGANISM: Mycobacterium tuberculosis

<400> SEQUENCE: 325

Gly Leu Gly Ala Phe Val Ile Asp Ser Asp His Leu Gly His Arg
1               5                   10                  15

<210> SEQ ID NO 326
<211> LENGTH: 15
<212> TYPE: PRT
<213> ORGANISM: Mycobacterium tuberculosis

<400> SEQUENCE: 326

Ala Asp Ala Asn Thr Ala Ala Ile Gln Ala Val Leu Tyr Asn Arg
1               5                   10                  15

```
<210> SEQ ID NO 327
<211> LENGTH: 14
<212> TYPE: PRT
<213> ORGANISM: Mycobacterium tuberculosis

<400> SEQUENCE: 327

Glu Asp Ile Val Thr Glu Gln Ile Asp Phe Ser Ala Ala Arg
1               5                   10

<210> SEQ ID NO 328
<211> LENGTH: 20
<212> TYPE: PRT
<213> ORGANISM: Mycobacterium tuberculosis

<400> SEQUENCE: 328

Met Val Arg Pro Gln Asp Thr Val Ala Tyr Glu Asp Leu Ser Glu Asp
1               5                   10                  15

Tyr Thr Gln Lys
            20

<210> SEQ ID NO 329
<211> LENGTH: 12
<212> TYPE: PRT
<213> ORGANISM: Mycobacterium tuberculosis

<400> SEQUENCE: 329

Asp Tyr Phe Gln His Pro His Phe Ser Thr Trp Lys
1               5                   10

<210> SEQ ID NO 330
<211> LENGTH: 14
<212> TYPE: PRT
<213> ORGANISM: Mycobacterium tuberculosis

<400> SEQUENCE: 330

Ile Val Glu Ser Met Gln Ser Thr Leu Asp Ala Glu Ile Arg
1               5                   10

<210> SEQ ID NO 331
<211> LENGTH: 22
<212> TYPE: PRT
<213> ORGANISM: Mycobacterium tuberculosis

<400> SEQUENCE: 331

Ser Leu Ser Asn Glu Asn Tyr Gly Val Tyr Asn Cys Ser Ile Ile Asn
1               5                   10                  15

Glu Ala Gly Ala Gly Arg
            20

<210> SEQ ID NO 332
<211> LENGTH: 13
<212> TYPE: PRT
<213> ORGANISM: Mycobacterium tuberculosis

<400> SEQUENCE: 332

Gln Ser Trp Asn Pro Phe Pro Asp Phe Thr Pro Gln Lys
1               5                   10

<210> SEQ ID NO 333
<211> LENGTH: 23
<212> TYPE: PRT
<213> ORGANISM: Mycobacterium tuberculosis
```

```
<400> SEQUENCE: 333

Leu Thr Trp Pro Thr Asp Ala Gly Pro Asp Asp Ala Ala Val Asp Thr
1               5                   10                  15

Ser Ser Glu Ile Thr Thr Lys
            20

<210> SEQ ID NO 334
<211> LENGTH: 15
<212> TYPE: PRT
<213> ORGANISM: Human immunodeficiency virus 1

<400> SEQUENCE: 334

Val His Pro Val His Ala Gly Pro Ile Ala Pro Gly Gln Met Arg
1               5                   10                  15

<210> SEQ ID NO 335
<211> LENGTH: 12
<212> TYPE: PRT
<213> ORGANISM: Human immunodeficiency virus 1

<400> SEQUENCE: 335

Pro Glu Pro Thr Ala Pro Pro Glu Glu Ser Phe Arg
1               5                   10

<210> SEQ ID NO 336
<211> LENGTH: 11
<212> TYPE: PRT
<213> ORGANISM: Human immunodeficiency virus 1

<400> SEQUENCE: 336

Ser Gly Val Glu Thr Thr Thr Pro Pro Gln Lys
1               5                   10

<210> SEQ ID NO 337
<211> LENGTH: 9
<212> TYPE: PRT
<213> ORGANISM: Human immunodeficiency virus 1

<400> SEQUENCE: 337

Gly Ser Asp Ile Ala Gly Thr Thr Ser
1               5

<210> SEQ ID NO 338
<211> LENGTH: 14
<212> TYPE: PRT
<213> ORGANISM: Human immunodeficiency virus 1

<400> SEQUENCE: 338

Gln Gly Pro Lys Glu Pro Phe Arg Asp Tyr Val Asp Arg Phe
1               5                   10

<210> SEQ ID NO 339
<211> LENGTH: 11
<212> TYPE: PRT
<213> ORGANISM: Human immunodeficiency virus 1
<220> FEATURE:
<221> NAME/KEY: MOD_RES
<222> LOCATION: (5)..(5)
<223> OTHER INFORMATION: Thr or Val
<220> FEATURE:
<221> NAME/KEY: MOD_RES
<222> LOCATION: (11)..(11)
<223> OTHER INFORMATION: Lys or Arg

<400> SEQUENCE: 339
```

```
Met Tyr Ser Pro Xaa Ser Ile Leu Asp Ile Xaa
1               5                   10
```

<210> SEQ ID NO 340
<211> LENGTH: 11
<212> TYPE: PRT
<213> ORGANISM: Human immunodeficiency virus 1
<220> FEATURE:
<221> NAME/KEY: MOD_RES
<222> LOCATION: (11)..(11)
<223> OTHER INFORMATION: Lys or Arg

<400> SEQUENCE: 340

```
Met Tyr Ser Pro Ser Ser Ile Leu Asp Ile Xaa
1               5                   10
```

<210> SEQ ID NO 341
<211> LENGTH: 11
<212> TYPE: PRT
<213> ORGANISM: Human immunodeficiency virus 1

<400> SEQUENCE: 341

```
Thr Ile Asn Glu Glu Ala Ala Glu Trp Asp Arg
1               5                   10
```

<210> SEQ ID NO 342
<211> LENGTH: 13
<212> TYPE: PRT
<213> ORGANISM: Human immunodeficiency virus 1

<400> SEQUENCE: 342

```
Asp Thr Ile Asn Glu Glu Ala Phe Ala Glu Trp Asp Arg
1               5                   10
```

<210> SEQ ID NO 343
<211> LENGTH: 12
<212> TYPE: PRT
<213> ORGANISM: Human immunodeficiency virus 1
<220> FEATURE:
<221> NAME/KEY: MOD_RES
<222> LOCATION: (1)..(1)
<223> OTHER INFORMATION: Glu or Asp

<400> SEQUENCE: 343

```
Xaa Thr Ile Asn Glu Glu Ala Ala Glu Trp Asp Arg
1               5                   10
```

<210> SEQ ID NO 344
<211> LENGTH: 11
<212> TYPE: PRT
<213> ORGANISM: Human immunodeficiency virus 1

<400> SEQUENCE: 344

```
Thr Ile Asn Glu Glu Ala Ala Asp Trp Asp Arg
1               5                   10
```

<210> SEQ ID NO 345
<211> LENGTH: 12
<212> TYPE: PRT
<213> ORGANISM: Human immunodeficiency virus 1

<400> SEQUENCE: 345

```
Glu Thr Ile Asn Glu Glu Ala Ala Asp Trp Asp Arg
1               5                   10
```

<210> SEQ ID NO 346

```
<211> LENGTH: 12
<212> TYPE: PRT
<213> ORGANISM: Human immunodeficiency virus 1

<400> SEQUENCE: 346

Asp Thr Ile Asn Glu Glu Ala Ala Asp Trp Asp Arg
1               5                   10

<210> SEQ ID NO 347
<211> LENGTH: 12
<212> TYPE: PRT
<213> ORGANISM: Human immunodeficiency virus 1
<220> FEATURE:
<221> NAME/KEY: MOD_RES
<222> LOCATION: (1)..(1)
<223> OTHER INFORMATION: Glu or Asp

<400> SEQUENCE: 347

Xaa Thr Ile Asn Glu Glu Ala Ala Asp Trp Asp Arg
1               5                   10

<210> SEQ ID NO 348
<211> LENGTH: 12
<212> TYPE: PRT
<213> ORGANISM: Human immunodeficiency virus 1

<400> SEQUENCE: 348

Asp Thr Ile Asn Glu Glu Ala Ala Glu Trp Glu Arg
1               5                   10

<210> SEQ ID NO 349
<211> LENGTH: 17
<212> TYPE: PRT
<213> ORGANISM: Human immunodeficiency virus 1

<400> SEQUENCE: 349

Met Gln Met Leu Lys Asp Thr Ile Asn Glu Glu Ala Ala Asp Trp Asp
1               5                   10                  15

Arg

<210> SEQ ID NO 350
<211> LENGTH: 20
<212> TYPE: PRT
<213> ORGANISM: Human immunodeficiency virus 1

<400> SEQUENCE: 350

Val His Pro Val His Ala Gly Pro Ile Pro Pro Gly Gln Met Arg Glu
1               5                   10                  15

Pro Arg Gly Ser
            20

<210> SEQ ID NO 351
<211> LENGTH: 21
<212> TYPE: PRT
<213> ORGANISM: Human immunodeficiency virus 1

<400> SEQUENCE: 351

Asn Lys Ile Val Arg Met Tyr Ser Pro Val Ser Ile Leu Asp Ile Arg
1               5                   10                  15

Gln Gly Pro Lys Glu
            20

<210> SEQ ID NO 352
<211> LENGTH: 17
```

```
<212> TYPE: PRT
<213> ORGANISM: Human immunodeficiency virus 1

<400> SEQUENCE: 352

Met Gln Met Leu Lys Asp Thr Ile Asn Glu Glu Ala Ala Glu Trp Asp
1               5                   10                  15

Arg

<210> SEQ ID NO 353
<211> LENGTH: 20
<212> TYPE: PRT
<213> ORGANISM: Human immunodeficiency virus 1

<400> SEQUENCE: 353

Leu His Pro Val His Ala Gly Pro Ile Pro Pro Gly Gln Met Arg Glu
1               5                   10                  15

Pro Arg Gly Ser
            20

<210> SEQ ID NO 354
<211> LENGTH: 21
<212> TYPE: PRT
<213> ORGANISM: Human immunodeficiency virus 1

<400> SEQUENCE: 354

Asn Lys Ile Val Arg Met Tyr Ser Pro Val Ser Ile Leu Asp Ile Arg
1               5                   10                  15

Gln Gly Pro Lys Glu
            20

<210> SEQ ID NO 355
<211> LENGTH: 17
<212> TYPE: PRT
<213> ORGANISM: Human immunodeficiency virus 1

<400> SEQUENCE: 355

Met Gln Met Leu Lys Glu Thr Ile Asn Glu Glu Ala Ala Glu Trp Asp
1               5                   10                  15

Arg

<210> SEQ ID NO 356
<211> LENGTH: 20
<212> TYPE: PRT
<213> ORGANISM: Human immunodeficiency virus 1

<400> SEQUENCE: 356

Leu His Pro Val Gln Ala Gly Pro Val Ala Pro Gly Gln Met Arg Glu
1               5                   10                  15

Pro Arg Gly Ser
            20

<210> SEQ ID NO 357
<211> LENGTH: 21
<212> TYPE: PRT
<213> ORGANISM: Human immunodeficiency virus 1

<400> SEQUENCE: 357

Asn Lys Ile Val Arg Met Tyr Ser Pro Ser Ser Ile Leu Asp Ile Lys
1               5                   10                  15

Gln Gly Pro Lys Glu
            20
```

```
<210> SEQ ID NO 358
<211> LENGTH: 17
<212> TYPE: PRT
<213> ORGANISM: Human immunodeficiency virus 1

<400> SEQUENCE: 358

Met Gln Met Leu Lys Asp Thr Ile Asn Glu Glu Ala Ala Glu Trp Asp
1               5                   10                  15

Arg

<210> SEQ ID NO 359
<211> LENGTH: 20
<212> TYPE: PRT
<213> ORGANISM: Human immunodeficiency virus 1

<400> SEQUENCE: 359

Leu His Pro Val His Ala Gly Pro Val Ala Pro Gly Gln Met Arg Glu
1               5                   10                  15

Pro Arg Gly Ser
            20

<210> SEQ ID NO 360
<211> LENGTH: 21
<212> TYPE: PRT
<213> ORGANISM: Human immunodeficiency virus 1

<400> SEQUENCE: 360

Asn Lys Ile Val Arg Met Tyr Ser Pro Val Ser Ile Leu Asp Ile Lys
1               5                   10                  15

Gln Gly Pro Lys Glu
            20

<210> SEQ ID NO 361
<211> LENGTH: 17
<212> TYPE: PRT
<213> ORGANISM: Human immunodeficiency virus 1

<400> SEQUENCE: 361

Met Gln Met Leu Lys Glu Thr Ile Asn Glu Glu Ala Ala Glu Trp Asp
1               5                   10                  15

Arg

<210> SEQ ID NO 362
<211> LENGTH: 20
<212> TYPE: PRT
<213> ORGANISM: Human immunodeficiency virus 1

<400> SEQUENCE: 362

Val His Pro Val His Ala Gly Pro Ile Ala Pro Gly Gln Met Arg Glu
1               5                   10                  15

Pro Arg Gly Ser
            20

<210> SEQ ID NO 363
<211> LENGTH: 21
<212> TYPE: PRT
<213> ORGANISM: Human immunodeficiency virus 1

<400> SEQUENCE: 363

Asn Lys Ile Val Arg Met Tyr Ser Pro Thr Ser Ile Leu Asp Ile Arg
1               5                   10                  15
```

Gln Gly Pro Lys Glu
            20

<210> SEQ ID NO 364
<211> LENGTH: 17
<212> TYPE: PRT
<213> ORGANISM: Human immunodeficiency virus 1

<400> SEQUENCE: 364

Met Gln Met Leu Lys Glu Thr Ile Asn Glu Glu Ala Ala Glu Trp Asp
1               5                   10                  15

Arg

<210> SEQ ID NO 365
<211> LENGTH: 20
<212> TYPE: PRT
<213> ORGANISM: Human immunodeficiency virus 1

<400> SEQUENCE: 365

Val His Pro Val His Ala Gly Pro Ile Ala Pro Gly Gln Met Arg Glu
1               5                   10                  15

Pro Arg Gly Ser
            20

<210> SEQ ID NO 366
<211> LENGTH: 21
<212> TYPE: PRT
<213> ORGANISM: Human immunodeficiency virus 1

<400> SEQUENCE: 366

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 367
<211> LENGTH: 17
<212> TYPE: PRT
<213> ORGANISM: Human immunodeficiency virus 1

<400> SEQUENCE: 367

Met Gln Met Leu Lys Glu Thr Ile Asn Glu Glu Ala Ala Glu Trp Asp
1               5                   10                  15

Arg

<210> SEQ ID NO 368
<211> LENGTH: 20
<212> TYPE: PRT
<213> ORGANISM: Human immunodeficiency virus 1

<400> SEQUENCE: 368

Val His Pro Val His Ala Gly Pro Ile Ala Pro Gly Gln Met Arg Glu
1               5                   10                  15

Pro Arg Gly Ser
            20

<210> SEQ ID NO 369
<211> LENGTH: 21
<212> TYPE: PRT
<213> ORGANISM: Human immunodeficiency virus 1

<400> SEQUENCE: 369

```
Asn Lys Ile Val Arg Met Tyr Ser Pro Thr Ser Ile Leu Asp Ile Arg
1               5                   10                  15

Gln Gly Pro Lys Glu
            20

<210> SEQ ID NO 370
<211> LENGTH: 17
<212> TYPE: PRT
<213> ORGANISM: Human immunodeficiency virus 1

<400> SEQUENCE: 370

Met Gln Met Leu Lys Glu Thr Ile Asn Glu Glu Ala Ala Glu Trp Asp
1               5                   10                  15

Arg

<210> SEQ ID NO 371
<211> LENGTH: 20
<212> TYPE: PRT
<213> ORGANISM: Human immunodeficiency virus 1

<400> SEQUENCE: 371

Val His Pro Val His Ala Gly Pro Ile Ala Pro Gly Gln Met Arg Glu
1               5                   10                  15

Pro Arg Gly Ser
            20

<210> SEQ ID NO 372
<211> LENGTH: 21
<212> TYPE: PRT
<213> ORGANISM: Human immunodeficiency virus 1

<400> SEQUENCE: 372

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 373
<211> LENGTH: 17
<212> TYPE: PRT
<213> ORGANISM: Human immunodeficiency virus 1

<400> SEQUENCE: 373

Met Gln Met Leu Lys Glu Thr Ile Asn Glu Glu Ala Ala Glu Trp Asp
1               5                   10                  15

Arg

<210> SEQ ID NO 374
<211> LENGTH: 20
<212> TYPE: PRT
<213> ORGANISM: Human immunodeficiency virus 1

<400> SEQUENCE: 374

Leu His Pro Val His Ala Gly Pro Ile Ala Pro Gly Gln Met Arg Glu
1               5                   10                  15

Pro Arg Gly Ser
            20

<210> SEQ ID NO 375
<211> LENGTH: 21
<212> TYPE: PRT
<213> ORGANISM: Human immunodeficiency virus 1
```

<400> SEQUENCE: 375

Asn Lys Ile Val Arg Met Tyr Ser Pro Ile Ser Ile Leu Asp Ile Arg
1               5                   10                  15

Gln Gly Pro Lys Glu
            20

<210> SEQ ID NO 376
<211> LENGTH: 17
<212> TYPE: PRT
<213> ORGANISM: Human immunodeficiency virus 1

<400> SEQUENCE: 376

Met Gln Met Leu Lys Asp Thr Ile Asn Glu Glu Ala Ala Glu Trp Asp
1               5                   10                  15

Arg

<210> SEQ ID NO 377
<211> LENGTH: 20
<212> TYPE: PRT
<213> ORGANISM: Human immunodeficiency virus 1

<400> SEQUENCE: 377

Leu His Pro Val His Ala Gly Pro Val Ala Pro Gly Gln Met Arg Asp
1               5                   10                  15

Pro Arg Gly Ser
            20

<210> SEQ ID NO 378
<211> LENGTH: 21
<212> TYPE: PRT
<213> ORGANISM: Human immunodeficiency virus 1

<400> SEQUENCE: 378

Asn Lys Ile Val Arg Met Tyr Ser Pro Val Ser Ile Leu Asp Ile Lys
1               5                   10                  15

Gln Gly Pro Lys Glu
            20

<210> SEQ ID NO 379
<211> LENGTH: 17
<212> TYPE: PRT
<213> ORGANISM: Human immunodeficiency virus 1

<400> SEQUENCE: 379

Met Gln Met Leu Lys Glu Thr Ile Asn Glu Glu Ala Ala Glu Trp Asp
1               5                   10                  15

Arg

<210> SEQ ID NO 380
<211> LENGTH: 20
<212> TYPE: PRT
<213> ORGANISM: Human immunodeficiency virus 1

<400> SEQUENCE: 380

Val His Pro Val His Ala Gly Pro Ile Ala Pro Gly Gln Met Arg Glu
1               5                   10                  15

Pro Arg Gly Ser
            20

<210> SEQ ID NO 381

-continued

```
<210> SEQ ID NO 381
<211> LENGTH: 21
<212> TYPE: PRT
<213> ORGANISM: Human immunodeficiency virus 1

<400> SEQUENCE: 381

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 382
<211> LENGTH: 17
<212> TYPE: PRT
<213> ORGANISM: Human immunodeficiency virus 1

<400> SEQUENCE: 382

Met Gln Met Leu Lys Glu Thr Ile Asn Glu Glu Ala Ala Glu Trp Asp
1               5                   10                  15

Arg

<210> SEQ ID NO 383
<211> LENGTH: 20
<212> TYPE: PRT
<213> ORGANISM: Human immunodeficiency virus 1

<400> SEQUENCE: 383

Leu His Pro Ala Gln Ala Gly Pro Ile Ala Pro Gly Gln Met Arg Glu
1               5                   10                  15

Pro Arg Gly Ser
            20

<210> SEQ ID NO 384
<211> LENGTH: 21
<212> TYPE: PRT
<213> ORGANISM: Human immunodeficiency virus 1

<400> SEQUENCE: 384

Asn Lys Ile Val Arg Met Tyr Ser Pro Ser Ser Ile Leu Asp Ile Arg
1               5                   10                  15

Gln Gly Pro Lys Glu
            20

<210> SEQ ID NO 385
<211> LENGTH: 17
<212> TYPE: PRT
<213> ORGANISM: Human immunodeficiency virus 1

<400> SEQUENCE: 385

Met Gln Met Leu Lys Glu Thr Ile Asn Glu Glu Ala Ala Glu Trp Asp
1               5                   10                  15

Arg

<210> SEQ ID NO 386
<211> LENGTH: 20
<212> TYPE: PRT
<213> ORGANISM: Human immunodeficiency virus 1

<400> SEQUENCE: 386

Leu His Pro Val His Ala Gly Pro Ile Ala Pro Gly Gln Met Arg Glu
1               5                   10                  15

Pro Arg Gly Ser
            20
```

<210> SEQ ID NO 387
<211> LENGTH: 21
<212> TYPE: PRT
<213> ORGANISM: Human immunodeficiency virus 1

<400> SEQUENCE: 387

Asn Lys Ile Val Arg Met Tyr Ser Pro Val Ser Ile Leu Asp Ile Arg
1               5                   10                  15

Gln Gly Pro Lys Glu
            20

<210> SEQ ID NO 388
<211> LENGTH: 17
<212> TYPE: PRT
<213> ORGANISM: Human immunodeficiency virus 1

<400> SEQUENCE: 388

Met Gln Met Leu Lys Glu Thr Ile Asn Glu Glu Ala Ala Glu Trp Asp
1               5                   10                  15

Arg

<210> SEQ ID NO 389
<211> LENGTH: 20
<212> TYPE: PRT
<213> ORGANISM: Human immunodeficiency virus 1

<400> SEQUENCE: 389

Val His Pro Val His Ala Gly Pro Ile Ala Pro Gly Gln Met Arg Glu
1               5                   10                  15

Pro Arg Gly Ser
            20

<210> SEQ ID NO 390
<211> LENGTH: 21
<212> TYPE: PRT
<213> ORGANISM: Human immunodeficiency virus 1

<400> SEQUENCE: 390

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 391
<211> LENGTH: 17
<212> TYPE: PRT
<213> ORGANISM: Human immunodeficiency virus 1

<400> SEQUENCE: 391

Met Gln Met Leu Lys Glu Thr Ile Asn Glu Glu Ala Ala Glu Trp Asp
1               5                   10                  15

Arg

<210> SEQ ID NO 392
<211> LENGTH: 20
<212> TYPE: PRT
<213> ORGANISM: Human immunodeficiency virus 1

<400> SEQUENCE: 392

Leu His Pro Ala His Ala Gly Pro Ile Ala Pro Gly Gln Met Arg Glu
1               5                   10                  15

```
Pro Arg Gly Ser
        20

<210> SEQ ID NO 393
<211> LENGTH: 21
<212> TYPE: PRT
<213> ORGANISM: Human immunodeficiency virus 1

<400> SEQUENCE: 393

Asn Lys Ile Val Arg Met Tyr Ser Pro Ser Ser Ile Leu Asp Ile Arg
1               5                   10                  15

Gln Gly Pro Lys Glu
        20

<210> SEQ ID NO 394
<211> LENGTH: 17
<212> TYPE: PRT
<213> ORGANISM: Human immunodeficiency virus 1

<400> SEQUENCE: 394

Met Gln Met Leu Lys Glu Thr Ile Asn Glu Glu Ala Ala Glu Trp Asp
1               5                   10                  15

Arg

<210> SEQ ID NO 395
<211> LENGTH: 20
<212> TYPE: PRT
<213> ORGANISM: Human immunodeficiency virus 1

<400> SEQUENCE: 395

Leu His Pro Val His Ala Gly Pro Ile Ala Pro Gly Gln Met Arg Glu
1               5                   10                  15

Pro Arg Gly Ser
        20

<210> SEQ ID NO 396
<211> LENGTH: 21
<212> TYPE: PRT
<213> ORGANISM: Human immunodeficiency virus 1

<400> SEQUENCE: 396

Asn Lys Ile Val Arg Met Tyr Ser Pro Thr Ser Ile Leu Asp Ile Arg
1               5                   10                  15

Gln Gly Pro Lys Glu
        20

<210> SEQ ID NO 397
<211> LENGTH: 17
<212> TYPE: PRT
<213> ORGANISM: Human immunodeficiency virus 1

<400> SEQUENCE: 397

Met Gln Met Leu Lys Glu Thr Ile Asn Glu Glu Ala Ala Glu Trp Asp
1               5                   10                  15

Arg

<210> SEQ ID NO 398
<211> LENGTH: 20
<212> TYPE: PRT
<213> ORGANISM: Human immunodeficiency virus 1

<400> SEQUENCE: 398
```

```
Leu His Pro Val His Ala Gly Pro Ile Ala Pro Gly Gln Met Arg Glu
1               5                   10                  15

Pro Arg Gly Ser
            20

<210> SEQ ID NO 399
<211> LENGTH: 21
<212> TYPE: PRT
<213> ORGANISM: Human immunodeficiency virus 1

<400> SEQUENCE: 399

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 400
<211> LENGTH: 17
<212> TYPE: PRT
<213> ORGANISM: Human immunodeficiency virus 1

<400> SEQUENCE: 400

Met Gln Met Leu Lys Glu Thr Ile Asn Glu Glu Ala Ala Glu Trp Asp
1               5                   10                  15

Arg

<210> SEQ ID NO 401
<211> LENGTH: 20
<212> TYPE: PRT
<213> ORGANISM: Human immunodeficiency virus 1

<400> SEQUENCE: 401

Leu His Pro Val His Ala Gly Pro Ile Ala Pro Gly Gln Met Arg Glu
1               5                   10                  15

Pro Arg Gly Ser
            20

<210> SEQ ID NO 402
<211> LENGTH: 21
<212> TYPE: PRT
<213> ORGANISM: Human immunodeficiency virus 1

<400> SEQUENCE: 402

Asn Lys Ile Val Arg Met Tyr Ser Pro Ile Ser Ile Leu Asp Ile Arg
1               5                   10                  15

Gln Gly Pro Lys Glu
            20

<210> SEQ ID NO 403
<211> LENGTH: 17
<212> TYPE: PRT
<213> ORGANISM: Human immunodeficiency virus 1

<400> SEQUENCE: 403

Met Gln Met Leu Lys Asp Thr Ile Asn Glu Glu Ala Ala Glu Trp Asp
1               5                   10                  15

Arg

<210> SEQ ID NO 404
<211> LENGTH: 20
<212> TYPE: PRT
```

<213> ORGANISM: Human immunodeficiency virus 1

<400> SEQUENCE: 404

Leu His Pro Val His Ala Gly Pro Ile Pro Pro Gly Gln Met Arg Glu
1               5                   10                  15

Pro Arg Gly Ser
            20

<210> SEQ ID NO 405
<211> LENGTH: 21
<212> TYPE: PRT
<213> ORGANISM: Human immunodeficiency virus 1

<400> SEQUENCE: 405

Asn Lys Ile Val Arg Met Tyr Ser Pro Val Ser Ile Leu Asp Ile Arg
1               5                   10                  15

Gln Gly Pro Lys Glu
            20

<210> SEQ ID NO 406
<211> LENGTH: 17
<212> TYPE: PRT
<213> ORGANISM: Human immunodeficiency virus 1

<400> SEQUENCE: 406

Met Gln Met Leu Lys Glu Thr Ile Asn Glu Glu Ala Ala Glu Trp Asp
1               5                   10                  15

Arg

<210> SEQ ID NO 407
<211> LENGTH: 20
<212> TYPE: PRT
<213> ORGANISM: Human immunodeficiency virus 1

<400> SEQUENCE: 407

Leu His Pro Val His Ala Gly Pro Ile Ala Pro Gly Gln Met Arg Glu
1               5                   10                  15

Pro Arg Gly Ser
            20

<210> SEQ ID NO 408
<211> LENGTH: 21
<212> TYPE: PRT
<213> ORGANISM: Human immunodeficiency virus 1

<400> SEQUENCE: 408

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 409
<211> LENGTH: 17
<212> TYPE: PRT
<213> ORGANISM: Human immunodeficiency virus 1

<400> SEQUENCE: 409

Met Gln Met Leu Lys Glu Thr Ile Asn Glu Glu Ala Ala Glu Trp Asp
1               5                   10                  15

Arg

```
<210> SEQ ID NO 410
<211> LENGTH: 20
<212> TYPE: PRT
<213> ORGANISM: Human immunodeficiency virus 1

<400> SEQUENCE: 410

Leu His Pro Val His Ala Gly Pro Ile Ala Pro Gly Gln Met Arg Glu
1               5                   10                  15

Pro Arg Gly Ser
            20

<210> SEQ ID NO 411
<211> LENGTH: 21
<212> TYPE: PRT
<213> ORGANISM: Human immunodeficiency virus 1

<400> SEQUENCE: 411

Asn Lys Ile Val Arg Met Tyr Ser Pro Thr Ser Ile Leu Asp Ile Arg
1               5                   10                  15

Gln Gly Pro Lys Glu
            20

<210> SEQ ID NO 412
<211> LENGTH: 17
<212> TYPE: PRT
<213> ORGANISM: Human immunodeficiency virus 1

<400> SEQUENCE: 412

Met Gln Met Leu Lys Asp Thr Ile Asn Glu Glu Ala Ala Glu Trp Asp
1               5                   10                  15

Arg

<210> SEQ ID NO 413
<211> LENGTH: 20
<212> TYPE: PRT
<213> ORGANISM: Human immunodeficiency virus 1

<400> SEQUENCE: 413

Leu His Pro Val His Ala Gly Pro Val Ala Pro Gly Gln Met Arg Glu
1               5                   10                  15

Pro Arg Gly Ser
            20

<210> SEQ ID NO 414
<211> LENGTH: 21
<212> TYPE: PRT
<213> ORGANISM: Human immunodeficiency virus 1

<400> SEQUENCE: 414

Asn Lys Ile Val Arg Met Tyr Ser Pro Val Ser Ile Leu Asp Ile Lys
1               5                   10                  15

Gln Gly Pro Lys Glu
            20

<210> SEQ ID NO 415
<211> LENGTH: 17
<212> TYPE: PRT
<213> ORGANISM: Human immunodeficiency virus 1

<400> SEQUENCE: 415

Met Gln Met Leu Lys Asp Thr Ile Asn Glu Glu Ala Ala Glu Trp Asp
1               5                   10                  15
```

Arg

<210> SEQ ID NO 416
<211> LENGTH: 20
<212> TYPE: PRT
<213> ORGANISM: Human immunodeficiency virus 1

<400> SEQUENCE: 416

Leu His Pro Val His Ala Gly Pro Val Ala Pro Gly Gln Met Arg Asp
1               5                   10                  15

Pro Arg Gly Ser
            20

<210> SEQ ID NO 417
<211> LENGTH: 21
<212> TYPE: PRT
<213> ORGANISM: Human immunodeficiency virus 1

<400> SEQUENCE: 417

Asn Lys Ile Val Arg Met Tyr Ser Pro Val Ser Ile Leu Asp Ile Lys
1               5                   10                  15

Gln Gly Pro Lys Glu
            20

<210> SEQ ID NO 418
<211> LENGTH: 17
<212> TYPE: PRT
<213> ORGANISM: Human immunodeficiency virus 1

<400> SEQUENCE: 418

Met Gln Met Leu Lys Glu Thr Ile Asn Glu Glu Ala Ala Glu Trp Asp
1               5                   10                  15

Arg

<210> SEQ ID NO 419
<211> LENGTH: 20
<212> TYPE: PRT
<213> ORGANISM: Human immunodeficiency virus 1

<400> SEQUENCE: 419

Leu His Pro Val His Ala Gly Pro Ile Ala Pro Gly Gln Met Arg Glu
1               5                   10                  15

Pro Arg Gly Ser
            20

<210> SEQ ID NO 420
<211> LENGTH: 21
<212> TYPE: PRT
<213> ORGANISM: Human immunodeficiency virus 1

<400> SEQUENCE: 420

Asn Lys Ile Val Arg Met Tyr Ser Pro Val Ser Ile Leu Asp Ile Arg
1               5                   10                  15

Gln Gly Pro Lys Glu
            20

<210> SEQ ID NO 421
<211> LENGTH: 17
<212> TYPE: PRT
<213> ORGANISM: Human immunodeficiency virus 1

<400> SEQUENCE: 421

```
Met Gln Met Leu Lys Glu Thr Ile Asn Asp Glu Ala Ala Glu Trp Asp
1               5                   10                  15

Arg
```

<210> SEQ ID NO 422
<211> LENGTH: 20
<212> TYPE: PRT
<213> ORGANISM: Human immunodeficiency virus 1

<400> SEQUENCE: 422

```
Leu His Pro Val His Ala Gly Pro Val Ala Pro Gly Gln Met Arg Glu
1               5                   10                  15

Pro Arg Gly Ser
            20
```

<210> SEQ ID NO 423
<211> LENGTH: 21
<212> TYPE: PRT
<213> ORGANISM: Human immunodeficiency virus 1

<400> SEQUENCE: 423

```
Asn Lys Ile Val Arg Met Tyr Ser Pro Val Ser Ile Leu Asp Ile Arg
1               5                   10                  15

Gln Gly Pro Lys Glu
            20
```

<210> SEQ ID NO 424
<211> LENGTH: 17
<212> TYPE: PRT
<213> ORGANISM: Human immunodeficiency virus 1

<400> SEQUENCE: 424

```
Met Gln Met Leu Lys Glu Thr Ile Asn Glu Glu Ala Ala Glu Trp Asp
1               5                   10                  15

Arg
```

<210> SEQ ID NO 425
<211> LENGTH: 20
<212> TYPE: PRT
<213> ORGANISM: Human immunodeficiency virus 1

<400> SEQUENCE: 425

```
Leu His Pro Val His Ala Gly Pro Ile Ala Pro Gly Gln Met Arg Glu
1               5                   10                  15

Pro Arg Gly Ser
            20
```

<210> SEQ ID NO 426
<211> LENGTH: 21
<212> TYPE: PRT
<213> ORGANISM: Human immunodeficiency virus 1

<400> SEQUENCE: 426

```
Asn Lys Ile Val Arg Met Tyr Ser Pro Val Ser Ile Leu Asp Ile Arg
1               5                   10                  15

Gln Gly Pro Lys Glu
            20
```

<210> SEQ ID NO 427
<211> LENGTH: 17
<212> TYPE: PRT
<213> ORGANISM: Human immunodeficiency virus 1

<400> SEQUENCE: 427

Met Gln Met Leu Lys Asp Thr Ile Asn Glu Glu Ala Ala Glu Trp Asp
1               5                   10                  15

Arg

<210> SEQ ID NO 428
<211> LENGTH: 20
<212> TYPE: PRT
<213> ORGANISM: Human immunodeficiency virus 1

<400> SEQUENCE: 428

Leu His Pro Thr Gln Ala Gly Pro Ile Pro Pro Gly Gln Ile Arg Glu
1               5                   10                  15

Pro Arg Gly Ser
            20

<210> SEQ ID NO 429
<211> LENGTH: 21
<212> TYPE: PRT
<213> ORGANISM: Human immunodeficiency virus 1

<400> SEQUENCE: 429

Asn Lys Ile Val Arg Met Tyr Ser Pro Val Gly Ile Leu Asp Ile Arg
1               5                   10                  15

Gln Gly Pro Lys Glu
            20

<210> SEQ ID NO 430
<211> LENGTH: 17
<212> TYPE: PRT
<213> ORGANISM: Human immunodeficiency virus 1

<400> SEQUENCE: 430

Met Gln Met Leu Lys Asp Thr Ile Asn Glu Glu Ala Ala Glu Trp Asp
1               5                   10                  15

Arg

<210> SEQ ID NO 431
<211> LENGTH: 20
<212> TYPE: PRT
<213> ORGANISM: Human immunodeficiency virus 1

<400> SEQUENCE: 431

Leu His Pro Val His Ala Gly Pro Ala Pro Pro Gly Gln Met Arg Glu
1               5                   10                  15

Pro Arg Gly Ser
            20

<210> SEQ ID NO 432
<211> LENGTH: 21
<212> TYPE: PRT
<213> ORGANISM: Human immunodeficiency virus 1

<400> SEQUENCE: 432

Asn Lys Ile Val Arg Met Tyr Ser Pro Val Ser Ile Leu Asp Ile Lys
1               5                   10                  15

Gln Gly Pro Lys Glu
            20

<210> SEQ ID NO 433

```
<211> LENGTH: 17
<212> TYPE: PRT
<213> ORGANISM: Human immunodeficiency virus 1

<400> SEQUENCE: 433

Met Gln Met Leu Lys Asp Thr Ile Asn Glu Glu Ala Ala Glu Trp Asp
1               5                   10                  15

Arg

<210> SEQ ID NO 434
<211> LENGTH: 20
<212> TYPE: PRT
<213> ORGANISM: Human immunodeficiency virus 1

<400> SEQUENCE: 434

Leu His Pro Val His Ala Gly Pro Ile Pro Pro Gly Gln Met Arg Glu
1               5                   10                  15

Pro Arg Gly Ser
            20

<210> SEQ ID NO 435
<211> LENGTH: 21
<212> TYPE: PRT
<213> ORGANISM: Human immunodeficiency virus 1

<400> SEQUENCE: 435

Asn Lys Ile Val Arg Met Tyr Ser Pro Val Ser Ile Leu Asp Ile Lys
1               5                   10                  15

Gln Gly Pro Lys Glu
            20

<210> SEQ ID NO 436
<211> LENGTH: 17
<212> TYPE: PRT
<213> ORGANISM: Human immunodeficiency virus 1

<400> SEQUENCE: 436

Met Gln Met Leu Lys Asp Thr Ile Asn Glu Glu Ala Ala Glu Trp Asp
1               5                   10                  15

Arg

<210> SEQ ID NO 437
<211> LENGTH: 20
<212> TYPE: PRT
<213> ORGANISM: Human immunodeficiency virus 1

<400> SEQUENCE: 437

Leu His Pro Val His Ala Gly Pro Ile Pro Pro Gly Gln Met Arg Glu
1               5                   10                  15

Pro Arg Gly Ser
            20

<210> SEQ ID NO 438
<211> LENGTH: 21
<212> TYPE: PRT
<213> ORGANISM: Human immunodeficiency virus 1

<400> SEQUENCE: 438

Asn Lys Ile Val Arg Met Tyr Ser Pro Val Ser Ile Leu Asp Ile Lys
1               5                   10                  15

Gln Gly Pro Lys Glu
            20
```

<210> SEQ ID NO 439
<211> LENGTH: 17
<212> TYPE: PRT
<213> ORGANISM: Human immunodeficiency virus 1

<400> SEQUENCE: 439

Met Gln Met Leu Lys Asp Thr Ile Asn Asp Glu Ala Ala Glu Trp Asp
1               5                   10                  15

Arg

<210> SEQ ID NO 440
<211> LENGTH: 20
<212> TYPE: PRT
<213> ORGANISM: Human immunodeficiency virus 1

<400> SEQUENCE: 440

Ile His Pro Gln Gln Ala Gly Pro Ile Pro Pro Gly Gln Ile Arg Glu
1               5                   10                  15

Pro Ser Gly Ser
            20

<210> SEQ ID NO 441
<211> LENGTH: 21
<212> TYPE: PRT
<213> ORGANISM: Human immunodeficiency virus 1

<400> SEQUENCE: 441

Asn Lys Ile Val Arg Met Tyr Ser Pro Val Ser Ile Leu Asp Ile Arg
1               5                   10                  15

Gln Gly Pro Lys Glu
            20

<210> SEQ ID NO 442
<211> LENGTH: 17
<212> TYPE: PRT
<213> ORGANISM: Human immunodeficiency virus 1

<400> SEQUENCE: 442

Met Gln Met Leu Lys Asp Thr Ile Asn Glu Glu Ala Ala Glu Trp Asp
1               5                   10                  15

Arg

<210> SEQ ID NO 443
<211> LENGTH: 20
<212> TYPE: PRT
<213> ORGANISM: Human immunodeficiency virus 1

<400> SEQUENCE: 443

Met His Pro Gln Gln Ala Gly Pro Phe Pro Pro Gly Gln Ile Arg Glu
1               5                   10                  15

Pro Arg Gly Ser
            20

<210> SEQ ID NO 444
<211> LENGTH: 21
<212> TYPE: PRT
<213> ORGANISM: Human immunodeficiency virus 1

<400> SEQUENCE: 444

Asn Lys Ile Val Arg Met Tyr Ser Pro Val Ser Ile Leu Asp Ile Arg
1               5                   10                  15

```
Gln Gly Pro Lys Glu
        20

<210> SEQ ID NO 445
<211> LENGTH: 17
<212> TYPE: PRT
<213> ORGANISM: Human immunodeficiency virus 1

<400> SEQUENCE: 445

Met Gln Met Leu Lys Asp Thr Ile Asn Glu Glu Ala Ala Glu Trp Asp
1               5                   10                  15

Arg

<210> SEQ ID NO 446
<211> LENGTH: 20
<212> TYPE: PRT
<213> ORGANISM: Human immunodeficiency virus 1

<400> SEQUENCE: 446

Val His Pro Val His Ala Gly Pro Ile Pro Pro Gly Gln Met Arg Glu
1               5                   10                  15

Pro Arg Gly Ser
        20

<210> SEQ ID NO 447
<211> LENGTH: 21
<212> TYPE: PRT
<213> ORGANISM: Human immunodeficiency virus 1

<400> SEQUENCE: 447

Asn Lys Ile Val Arg Met Tyr Ser Pro Val Ser Ile Leu Asp Ile Lys
1               5                   10                  15

Gln Gly Pro Lys Glu
        20

<210> SEQ ID NO 448
<211> LENGTH: 17
<212> TYPE: PRT
<213> ORGANISM: Human immunodeficiency virus 1

<400> SEQUENCE: 448

Met Gln Met Leu Lys Asp Thr Ile Asn Glu Glu Ala Ala Glu Trp Asp
1               5                   10                  15

Arg

<210> SEQ ID NO 449
<211> LENGTH: 20
<212> TYPE: PRT
<213> ORGANISM: Human immunodeficiency virus 1

<400> SEQUENCE: 449

Leu His Pro Val His Ala Gly Pro Ile Pro Pro Gly Gln Met Arg Glu
1               5                   10                  15

Pro Arg Gly Ser
        20

<210> SEQ ID NO 450
<211> LENGTH: 21
<212> TYPE: PRT
<213> ORGANISM: Human immunodeficiency virus 1

<400> SEQUENCE: 450
```

-continued

Asn Lys Ile Val Arg Met Tyr Ser Pro Val Ser Ile Leu Asp Ile Lys
1               5                   10                  15

Gln Gly Pro Lys Glu
            20

<210> SEQ ID NO 451
<211> LENGTH: 17
<212> TYPE: PRT
<213> ORGANISM: Human immunodeficiency virus 1

<400> SEQUENCE: 451

Met Gln Met Leu Lys Asp Thr Ile Asn Glu Glu Ala Ala Glu Trp Asp
1               5                   10                  15

Arg

<210> SEQ ID NO 452
<211> LENGTH: 20
<212> TYPE: PRT
<213> ORGANISM: Human immunodeficiency virus 1

<400> SEQUENCE: 452

Val His Pro Val His Ala Gly Pro Val Ala Pro Gly Gln Val Arg Glu
1               5                   10                  15

Pro Arg Gly Ser
            20

<210> SEQ ID NO 453
<211> LENGTH: 21
<212> TYPE: PRT
<213> ORGANISM: Human immunodeficiency virus 1

<400> SEQUENCE: 453

Asn Lys Ile Val Arg Met Tyr Ser Pro Val Ser Ile Leu Asp Ile Arg
1               5                   10                  15

Gln Gly Pro Lys Glu
            20

<210> SEQ ID NO 454
<211> LENGTH: 17
<212> TYPE: PRT
<213> ORGANISM: Human immunodeficiency virus 1

<400> SEQUENCE: 454

Met Gln Met Leu Lys Asp Thr Ile Asn Glu Glu Ala Ala Glu Trp Asp
1               5                   10                  15

Arg

<210> SEQ ID NO 455
<211> LENGTH: 20
<212> TYPE: PRT
<213> ORGANISM: Human immunodeficiency virus 1

<400> SEQUENCE: 455

Val His Pro Val His Ala Gly Pro Ile Ala Pro Gly Gln Val Arg Glu
1               5                   10                  15

Pro Arg Gly Ser
            20

<210> SEQ ID NO 456
<211> LENGTH: 21
<212> TYPE: PRT

<213> ORGANISM: Human immunodeficiency virus 1

<400> SEQUENCE: 456

Asn Lys Ile Val Arg Met Tyr Ser Pro Val Ser Ile Leu Asp Ile Arg
1               5                   10                  15

Gln Gly Pro Lys Glu
            20

<210> SEQ ID NO 457
<211> LENGTH: 17
<212> TYPE: PRT
<213> ORGANISM: Human immunodeficiency virus 1

<400> SEQUENCE: 457

Met Gln Met Leu Lys Asp Thr Ile Asn Asp Glu Ala Ala Glu Trp Asp
1               5                   10                  15

Arg

<210> SEQ ID NO 458
<211> LENGTH: 20
<212> TYPE: PRT
<213> ORGANISM: Human immunodeficiency virus 1

<400> SEQUENCE: 458

Leu His Pro Val His Ala Gly Pro Ile Pro Pro Gly Gln Met Arg Glu
1               5                   10                  15

Pro Arg Gly Ser
            20

<210> SEQ ID NO 459
<211> LENGTH: 21
<212> TYPE: PRT
<213> ORGANISM: Human immunodeficiency virus 1

<400> SEQUENCE: 459

Asn Lys Ile Val Arg Met Tyr Ser Pro Val Ser Ile Leu Asp Ile Arg
1               5                   10                  15

Gln Gly Pro Lys Glu
            20

<210> SEQ ID NO 460
<211> LENGTH: 17
<212> TYPE: PRT
<213> ORGANISM: Human immunodeficiency virus 1

<400> SEQUENCE: 460

Met Gln Met Leu Lys Asp Thr Ile Asn Glu Glu Ala Ala Glu Trp Asp
1               5                   10                  15

Arg

<210> SEQ ID NO 461
<211> LENGTH: 20
<212> TYPE: PRT
<213> ORGANISM: Human immunodeficiency virus 1

<400> SEQUENCE: 461

Met His Pro Val Gln Ala Gly Pro Ile Pro Pro Gly Gln Ile Arg Glu
1               5                   10                  15

Pro Arg Gly Ser
            20

<210> SEQ ID NO 462
<211> LENGTH: 21
<212> TYPE: PRT
<213> ORGANISM: Human immunodeficiency virus 1

<400> SEQUENCE: 462

Asn Lys Ile Val Arg Met Tyr Ser Pro Val Ser Ile Leu Asp Ile Arg
1               5                   10                  15

Gln Gly Pro Lys Glu
            20

<210> SEQ ID NO 463
<211> LENGTH: 17
<212> TYPE: PRT
<213> ORGANISM: Human immunodeficiency virus 1

<400> SEQUENCE: 463

Met Gln Met Leu Lys Glu Val Ile Asn Glu Glu Ala Ala Glu Trp Asp
1               5                   10                  15

Arg

<210> SEQ ID NO 464
<211> LENGTH: 20
<212> TYPE: PRT
<213> ORGANISM: Human immunodeficiency virus 1

<400> SEQUENCE: 464

Thr His Pro Ala Pro Val Gly Pro Leu Pro Pro Gly Gln Met Arg Asp
1               5                   10                  15

Pro Arg Gly Ser
            20

<210> SEQ ID NO 465
<211> LENGTH: 21
<212> TYPE: PRT
<213> ORGANISM: Human immunodeficiency virus 1

<400> SEQUENCE: 465

Asn Arg Ile Val Arg Met Tyr Ser Pro Val Ser Ile Leu Glu Ile Lys
1               5                   10                  15

Gln Gly Pro Lys Glu
            20

<210> SEQ ID NO 466
<211> LENGTH: 17
<212> TYPE: PRT
<213> ORGANISM: Human immunodeficiency virus 1

<400> SEQUENCE: 466

Met Gln Met Leu Lys Glu Val Ile Asn Glu Glu Ala Ala Asp Trp Asp
1               5                   10                  15

Arg

<210> SEQ ID NO 467
<211> LENGTH: 20
<212> TYPE: PRT
<213> ORGANISM: Human immunodeficiency virus 1

<400> SEQUENCE: 467

Thr His Pro Val Pro Val Gly Pro Leu Pro Pro Gly Gln Leu Arg Asp
1               5                   10                  15

Pro Arg Gly Ser

<210> SEQ ID NO 468
<211> LENGTH: 21
<212> TYPE: PRT
<213> ORGANISM: Human immunodeficiency virus 1

<400> SEQUENCE: 468

Asn Arg Ile Val Arg Met Tyr Ser Pro Val Ser Ile Leu Glu Ile Lys
1               5                   10                  15

Gln Gly Pro Lys Glu
            20

<210> SEQ ID NO 469
<211> LENGTH: 17
<212> TYPE: PRT
<213> ORGANISM: Human immunodeficiency virus 1

<400> SEQUENCE: 469

Leu Gln Val Leu Lys Glu Val Ile Asn Glu Glu Ala Val Glu Trp Asp
1               5                   10                  15

Arg

<210> SEQ ID NO 470
<211> LENGTH: 20
<212> TYPE: PRT
<213> ORGANISM: Human immunodeficiency virus 1

<400> SEQUENCE: 470

Thr His Pro Pro Pro Val Gly Pro Leu Pro Pro Gly Gln Ile Arg Glu
1               5                   10                  15

Pro Thr Gly Ser
            20

<210> SEQ ID NO 471
<211> LENGTH: 21
<212> TYPE: PRT
<213> ORGANISM: Human immunodeficiency virus 1

<400> SEQUENCE: 471

Asn Lys Met Val Lys Met Tyr Ser Pro Val Ser Ile Leu Asp Ile Lys
1               5                   10                  15

Gln Gly Pro Lys Glu
            20

<210> SEQ ID NO 472
<211> LENGTH: 17
<212> TYPE: PRT
<213> ORGANISM: Human immunodeficiency virus 1

<400> SEQUENCE: 472

Leu Gln Val Leu Lys Glu Val Ile Asn Glu Glu Ala Ala Glu Trp Asp
1               5                   10                  15

Arg

<210> SEQ ID NO 473
<211> LENGTH: 20
<212> TYPE: PRT
<213> ORGANISM: Human immunodeficiency virus 1

<400> SEQUENCE: 473

Thr His Pro Pro Ala Met Gly Pro Leu Pro Pro Gly Gln Ile Arg Glu

```
1               5                   10                  15

Pro Thr Gly Ser
            20

<210> SEQ ID NO 474
<211> LENGTH: 21
<212> TYPE: PRT
<213> ORGANISM: Human immunodeficiency virus 1

<400> SEQUENCE: 474

Asn Lys Met Val Lys Met Tyr Ser Pro Val Ser Ile Leu Asp Ile Arg
1               5                   10                  15

Gln Gly Pro Lys Glu
            20

<210> SEQ ID NO 475
<211> LENGTH: 17
<212> TYPE: PRT
<213> ORGANISM: Human immunodeficiency virus 2

<400> SEQUENCE: 475

Met Gln Ile Ile Arg Glu Ile Ile Asn Glu Glu Ala Ala Asp Trp Asp
1               5                   10                  15

Ala

<210> SEQ ID NO 476
<211> LENGTH: 19
<212> TYPE: PRT
<213> ORGANISM: Human immunodeficiency virus 2

<400> SEQUENCE: 476

Asn His Pro Ile Pro Gly Pro Leu Pro Ala Gly Gln Leu Arg Asp Pro
1               5                   10                  15

Arg Gly Ser

<210> SEQ ID NO 477
<211> LENGTH: 21
<212> TYPE: PRT
<213> ORGANISM: Human immunodeficiency virus 2

<400> SEQUENCE: 477

Gln Lys Cys Val Arg Met Tyr Asn Pro Thr Asn Ile Leu Asp Ile Lys
1               5                   10                  15

Gln Gly Pro Lys Glu
            20

<210> SEQ ID NO 478
<211> LENGTH: 17
<212> TYPE: PRT
<213> ORGANISM: Human immunodeficiency virus 2

<400> SEQUENCE: 478

Met Gln Ile Ile Arg Glu Ile Ile Asn Glu Glu Ala Ala Glu Trp Asp
1               5                   10                  15

Val

<210> SEQ ID NO 479
<211> LENGTH: 19
<212> TYPE: PRT
<213> ORGANISM: Human immunodeficiency virus 2

<400> SEQUENCE: 479
```

```
Gln His Pro Ile Pro Gly Pro Leu Pro Ala Gly Gln Leu Arg Glu Pro
1               5                   10                  15

Arg Gly Ser

<210> SEQ ID NO 480
<211> LENGTH: 21
<212> TYPE: PRT
<213> ORGANISM: Human immunodeficiency virus 2

<400> SEQUENCE: 480

Gln Lys Cys Val Arg Met Tyr Asn Pro Thr Asn Ile Leu Asp Ile Lys
1               5                   10                  15

Gln Gly Pro Lys Glu
            20

<210> SEQ ID NO 481
<211> LENGTH: 17
<212> TYPE: PRT
<213> ORGANISM: Human immunodeficiency virus 2

<400> SEQUENCE: 481

Met Gln Ile Ile Arg Glu Ile Ile Asn Glu Glu Ala Ala Asp Trp Asp
1               5                   10                  15

Val

<210> SEQ ID NO 482
<211> LENGTH: 19
<212> TYPE: PRT
<213> ORGANISM: Human immunodeficiency virus 2

<400> SEQUENCE: 482

Gln His Pro Ile Pro Gly Pro Leu Pro Ala Gly Gln Leu Arg Glu Pro
1               5                   10                  15

Arg Gly Ser

<210> SEQ ID NO 483
<211> LENGTH: 21
<212> TYPE: PRT
<213> ORGANISM: Human immunodeficiency virus 2

<400> SEQUENCE: 483

Gln Lys Cys Val Arg Met Tyr Asn Pro Thr Asn Ile Leu Asp Val Lys
1               5                   10                  15

Gln Gly Pro Lys Glu
            20

<210> SEQ ID NO 484
<211> LENGTH: 17
<212> TYPE: PRT
<213> ORGANISM: Human immunodeficiency virus 2

<400> SEQUENCE: 484

Met Gln Ile Ile Arg Glu Ile Ile Asn Glu Glu Ala Ala Asp Trp Asp
1               5                   10                  15

Ala

<210> SEQ ID NO 485
<211> LENGTH: 19
<212> TYPE: PRT
<213> ORGANISM: Human immunodeficiency virus 2
```

<400> SEQUENCE: 485

Gln His Pro Ile Pro Gly Pro Leu Pro Ala Gly Gln Leu Arg Glu Pro
1               5                   10                  15

Arg Gly Ser

<210> SEQ ID NO 486
<211> LENGTH: 21
<212> TYPE: PRT
<213> ORGANISM: Human immunodeficiency virus 2

<400> SEQUENCE: 486

Gln Lys Cys Val Arg Met Tyr Asn Pro Thr Asn Ile Leu Asp Ile Lys
1               5                   10                  15

Gln Gly Pro Lys Glu
            20

<210> SEQ ID NO 487
<211> LENGTH: 17
<212> TYPE: PRT
<213> ORGANISM: Human immunodeficiency virus 2

<400> SEQUENCE: 487

Met Gln Ile Ile Arg Glu Ile Ile Asn Glu Glu Ala Ala Asp Trp Asp
1               5                   10                  15

Ala

<210> SEQ ID NO 488
<211> LENGTH: 19
<212> TYPE: PRT
<213> ORGANISM: Human immunodeficiency virus 2

<400> SEQUENCE: 488

Gln His Pro Ile Pro Gly Pro Leu Pro Ala Gly Gln Leu Arg Asp Pro
1               5                   10                  15

Arg Gly Ser

<210> SEQ ID NO 489
<211> LENGTH: 21
<212> TYPE: PRT
<213> ORGANISM: Human immunodeficiency virus 2

<400> SEQUENCE: 489

Gln Lys Cys Val Arg Met Tyr Asn Pro Thr Asn Ile Leu Asp Val Lys
1               5                   10                  15

Gln Gly Pro Lys Glu
            20

<210> SEQ ID NO 490
<211> LENGTH: 17
<212> TYPE: PRT
<213> ORGANISM: Human immunodeficiency virus 2

<400> SEQUENCE: 490

Met Gln Ile Ile Arg Glu Ile Ile Asn Glu Glu Ala Ala Asp Trp Asp
1               5                   10                  15

Ser

<210> SEQ ID NO 491
<211> LENGTH: 19
<212> TYPE: PRT

-continued

<400> SEQUENCE: 491

Gln His Pro Ile Pro Gly Pro Leu Pro Ala Gly Gln Leu Arg Asp Pro
1               5                   10                  15

Arg Gly Ser

<210> SEQ ID NO 492
<211> LENGTH: 21
<212> TYPE: PRT
<213> ORGANISM: Human immunodeficiency virus 2

<400> SEQUENCE: 492

Gln Lys Cys Val Arg Lys Tyr Asn Pro Thr Asn Ile Leu Asp Ile Lys
1               5                   10                  15

Gln Gly Pro Lys Glu
            20

<210> SEQ ID NO 493
<211> LENGTH: 17
<212> TYPE: PRT
<213> ORGANISM: Human immunodeficiency virus 2

<400> SEQUENCE: 493

Met Gln Ile Ile Arg Glu Ile Ile Asn Asp Glu Ala Ala Asp Trp Asp
1               5                   10                  15

Ala

<210> SEQ ID NO 494
<211> LENGTH: 19
<212> TYPE: PRT
<213> ORGANISM: Human immunodeficiency virus 2

<400> SEQUENCE: 494

Gln His Pro Ile Pro Gly Pro Leu Pro Ala Gly Gln Leu Arg Asp Pro
1               5                   10                  15

Arg Gly Ser

<210> SEQ ID NO 495
<211> LENGTH: 21
<212> TYPE: PRT
<213> ORGANISM: Human immunodeficiency virus 2

<400> SEQUENCE: 495

Gln Lys Cys Val Arg Met Tyr Asn Pro Thr Asn Ile Leu Asp Val Lys
1               5                   10                  15

Gln Gly Pro Lys Glu
            20

<210> SEQ ID NO 496
<211> LENGTH: 17
<212> TYPE: PRT
<213> ORGANISM: Human immunodeficiency virus 2

<400> SEQUENCE: 496

Met Gln Ile Ile Arg Glu Ile Ile Asn Glu Glu Ala Ala Asp Trp Asp
1               5                   10                  15

Val

<210> SEQ ID NO 497
<211> LENGTH: 19
<212> TYPE: PRT

<213> ORGANISM: Human immunodeficiency virus 2

<400> SEQUENCE: 497

Ala His Pro Ile Pro Gly Pro Leu Pro Ala Gly Gln Leu Ar

<212> TYPE: PRT
<213> ORGANISM: Human immunodeficiency virus 2

<400> SEQUENCE: 503

Gln His Pro Ile Pro Gly Pro Leu Pro Ala Gly Gln Leu Arg Asp Pro
1               5                   10                  15

Arg Gly Ser

<210> SEQ ID NO 504
<211> LENGTH: 21
<212> TYPE: PRT
<213> ORGANISM: Human immunodeficiency virus 2

<400> SEQUENCE: 504

Gln Lys Cys Val Arg Met Tyr Asn Pro Thr Asn Ile Leu Asp Ile Lys
1               5                   10                  15

Gln Gly Pro Lys Glu
            20

<210> SEQ ID NO 505
<211> LENGTH: 17
<212> TYPE: PRT
<213> ORGANISM: Human immunodeficiency virus 2

<400> SEQUENCE: 505

Met Gln Ile Ile Arg Glu Ile Ile Asn Glu Glu Ala Ala Asp Trp Asp
1               5                   10                  15

Gln

<210> SEQ ID NO 506
<211> LENGTH: 19
<212> TYPE: PRT
<213> ORGANISM: Human immunodeficiency virus 2

<400> SEQUENCE: 506

Gln His Pro Ser Pro Gly Pro Met Pro Ala Gly Gln Leu Arg Asp Pro
1               5                   10                  15

Arg Gly Ser

<210> SEQ ID NO 507
<211> LENGTH: 21
<212> TYPE: PRT
<213> ORGANISM: Human immunodeficiency virus 2

<400> SEQUENCE: 507

Gln Lys Cys Val Arg Met Tyr Asn Pro Thr Asn Ile Leu Asp Ile Lys
1               5                   10                  15

Gln Gly Pro Lys Glu
            20

<210> SEQ ID NO 508
<211> LENGTH: 17
<212> TYPE: PRT
<213> ORGANISM: Human immunodeficiency virus 2

<400> SEQUENCE: 508

Met Gln Ile Ile Arg Glu Ile Ile Asn Glu Glu Ala Ala Asp Trp Asp
1               5                   10                  15

Gln

<210> SEQ ID NO 509

```
<211> LENGTH: 19
<212> TYPE: PRT
<213> ORGANISM: Human immunodeficiency virus 2

<400> SEQUENCE: 509

Gln His Pro Ser Pro Gly Pro Met Pro Ala Gly Gln Leu Arg Glu Pro
1               5                   10                  15

Arg Gly Ser

<210> SEQ ID NO 510
<211> LENGTH: 21
<212> TYPE: PRT
<213> ORGANISM: Human immunodeficiency virus 2

<400> SEQUENCE: 510

Gln Lys Cys Val Arg Met Tyr Asn Pro Thr Asn Ile Leu Asp Ile Lys
1               5                   10                  15

Gln Gly Pro Lys Glu
            20

<210> SEQ ID NO 511
<211> LENGTH: 17
<212> TYPE: PRT
<213> ORGANISM: Simian immunodeficiency virus

<400> SEQUENCE: 511

Met Gln Ile Ile Arg Glu Ile Ile Asn Glu Glu Ala Ala Asp Trp Asp
1               5                   10                  15

Leu

<210> SEQ ID NO 512
<211> LENGTH: 19
<212> TYPE: PRT
<213> ORGANISM: Simian immunodeficiency virus

<400> SEQUENCE: 512

Gln His Pro Gln Pro Gly Pro Leu Pro Ala Gly Gln Leu Arg Glu Pro
1               5                   10                  15

Arg Gly Ser

<210> SEQ ID NO 513
<211> LENGTH: 21
<212> TYPE: PRT
<213> ORGANISM: Simian immunodeficiency virus

<400> SEQUENCE: 513

Gln Lys Cys Val Arg Met Tyr Asn Pro Thr Asn Ile Leu Asp Val Lys
1               5                   10                  15

Gln Gly Pro Lys Glu
            20

<210> SEQ ID NO 514
<211> LENGTH: 17
<212> TYPE: PRT
<213> ORGANISM: Simian immunodeficiency virus

<400> SEQUENCE: 514

Met Gln Ile Ile Arg Glu Ile Ile Asn Glu Glu Ala Ala Asp Trp Asp
1               5                   10                  15

Leu
```

```
<210> SEQ ID NO 515
<211> LENGTH: 19
<212> TYPE: PRT
<213> ORGANISM: Simian immunodeficiency virus

<400> SEQUENCE: 515

Gln His Pro Gln Pro Gly Pro Ile Pro Pro Gly Gln Leu Arg Glu Pro
1               5                   10                  15

Arg Gly Ser

<210> SEQ ID NO 516
<211> LENGTH: 21
<212> TYPE: PRT
<213> ORGANISM: Simian immunodeficiency virus

<400> SEQUENCE: 516

Gln Lys Cys Val Arg Met Tyr Asn Pro Thr Asn Ile Leu Asp Val Lys
1               5                   10                  15

Gln Gly Pro Lys Glu
            20

<210> SEQ ID NO 517
<211> LENGTH: 17
<212> TYPE: PRT
<213> ORGANISM: Simian immunodeficiency virus

<400> SEQUENCE: 517

Met Gln Ile Ile Arg Asp Ile Ile Asn Glu Glu Ala Ala Asp Trp Asp
1               5                   10                  15

Leu

<210> SEQ ID NO 518
<211> LENGTH: 18
<212> TYPE: PRT
<213> ORGANISM: Simian immunodeficiency virus

<400> SEQUENCE: 518

Gln His Pro Gln Pro Ala Pro Gln Gln Gly Gln Leu Arg Glu Pro Ser
1               5                   10                  15

Gly Ser

<210> SEQ ID NO 519
<211> LENGTH: 21
<212> TYPE: PRT
<213> ORGANISM: Simian immunodeficiency virus

<400> SEQUENCE: 519

Gln Lys Cys Val Arg Met Tyr Asn Pro Thr Asn Ile Leu Asp Val Lys
1               5                   10                  15

Gln Gly Pro Lys Glu
            20

<210> SEQ ID NO 520
<211> LENGTH: 17
<212> TYPE: PRT
<213> ORGANISM: Simian immunodeficiency virus

<400> SEQUENCE: 520

Met Gln Ile Ile Arg Asp Ile Ile Asn Glu Glu Ala Ala Asp Trp Asp
1               5                   10                  15

Leu
```

<210> SEQ ID NO 521
<211> LENGTH: 18
<212> TYPE: PRT
<213> ORGANISM: Simian immunodeficiency virus

<400> SEQUENCE: 521

Gln His Pro Gln Pro Ala Pro Gln Gln Gly Gln Leu Arg Glu Pro Ser
1               5                   10                  15

Gly Ser

<210> SEQ ID NO 522
<211> LENGTH: 21
<212> TYPE: PRT
<213> ORGANISM: Simian immunodeficiency virus

<400> SEQUENCE: 522

Gln Lys Cys Val Arg Met Tyr Asn Pro Thr Asn Ile Leu Asp Val Lys
1               5                   10                  15

Gln Gly Pro Lys Glu
            20

<210> SEQ ID NO 523
<211> LENGTH: 17
<212> TYPE: PRT
<213> ORGANISM: Simian immunodeficiency virus

<400> SEQUENCE: 523

Met Gln Ile Ile Arg Asp Ile Ile Asn Glu Glu Ala Ala Asp Trp Asp
1               5                   10                  15

Leu

<210> SEQ ID NO 524
<211> LENGTH: 18
<212> TYPE: PRT
<213> ORGANISM: Simian immunodeficiency virus

<400> SEQUENCE: 524

Gln His Pro Gln Pro Ala Pro Gln Gln Gly Gln Leu Arg Glu Pro Ser
1               5                   10                  15

Gly Ser

<210> SEQ ID NO 525
<211> LENGTH: 21
<212> TYPE: PRT
<213> ORGANISM: Simian immunodeficiency virus

<400> SEQUENCE: 525

Gln Lys Cys Val Arg Met Tyr Asn Pro Thr Asn Ile Leu Asp Val Lys
1               5                   10                  15

Gln Gly Pro Lys Glu
            20

<210> SEQ ID NO 526
<211> LENGTH: 17
<212> TYPE: PRT
<213> ORGANISM: Simian immunodeficiency virus

<400> SEQUENCE: 526

Met Gln Ile Ile Arg Asp Ile Ile Asn Glu Glu Ala Ala Asp Trp Asp
1               5                   10                  15

Leu

<210> SEQ ID NO 527
<211> LENGTH: 18
<212> TYPE: PRT
<213> ORGANISM: Simian immunodeficiency virus

<400> SEQUENCE: 527

Gln His Pro Gln Pro Ala Pro Gln Gln Gly Gln Leu Arg Glu Pro Ser
1               5                   10                  15

Gly Ser

<210> SEQ ID NO 528
<211> LENGTH: 21
<212> TYPE: PRT
<213> ORGANISM: Simian immunodeficiency virus

<400> SEQUENCE: 528

Gln Lys Cys Val Arg Met Tyr Asn Pro Thr Asn Ile Leu Asp Val Lys
1               5                   10                  15

Gln Gly Pro Lys Glu
            20

<210> SEQ ID NO 529
<211> LENGTH: 17
<212> TYPE: PRT
<213> ORGANISM: Simian immunodeficiency virus

<400> SEQUENCE: 529

Met Gln Ile Ile Arg Asp Ile Ile Asn Glu Glu Ala Ala Asp Trp Asp
1               5                   10                  15

Leu

<210> SEQ ID NO 530
<211> LENGTH: 18
<212> TYPE: PRT
<213> ORGANISM: Simian immunodeficiency virus

<400> SEQUENCE: 530

Gln His Pro Gln Gln Ala Pro Gln Gln Gly Gln Leu Arg Glu Pro Ser
1               5                   10                  15

Gly Ser

<210> SEQ ID NO 531
<211> LENGTH: 21
<212> TYPE: PRT
<213> ORGANISM: Simian immunodeficiency virus

<400> SEQUENCE: 531

Gln Lys Cys Val Arg Met Tyr Asn Pro Thr Asn Ile Leu Asp Val Lys
1               5                   10                  15

Gln Gly Pro Lys Glu
            20

<210> SEQ ID NO 532
<211> LENGTH: 17
<212> TYPE: PRT
<213> ORGANISM: Simian immunodeficiency virus

<400> SEQUENCE: 532

Met Gln Ile Ile Arg Asp Ile Ile Asn Glu Glu Ala Ala Asp Trp Asp
1               5                   10                  15

Leu

<210> SEQ ID NO 533
<211> LENGTH: 18
<212> TYPE: PRT
<213> ORGANISM: Simian immunodeficiency virus

<400> SEQUENCE: 533

Gln His Pro Gln Pro Ala Pro Gln Gln Gly Gln Leu Arg Glu Pro Ser
1               5                   10                  15

Gly Ser

<210> SEQ ID NO 534
<211> LENGTH: 21
<212> TYPE: PRT
<213> ORGANISM: Simian immunodeficiency virus

<400> SEQUENCE: 534

Gln Lys Cys Val Arg Met Tyr Asn Pro Thr Asn Ile Leu Asp Val Lys
1               5                   10                  15

Gln Gly Pro Lys Glu
            20

<210> SEQ ID NO 535
<211> LENGTH: 17
<212> TYPE: PRT
<213> ORGANISM: Simian immunodeficiency virus

<400> SEQUENCE: 535

Met Gln Ile Ile Arg Asp Ile Ile Asn Glu Glu Ala Ala Asp Trp Asp
1               5                   10                  15

Leu

<210> SEQ ID NO 536
<211> LENGTH: 18
<212> TYPE: PRT
<213> ORGANISM: Simian immunodeficiency virus

<400> SEQUENCE: 536

Gln His Pro Gln Pro Ala Pro Gln Gln Gly Gln Leu Arg Glu Pro Ser
1               5                   10                  15

Gly Ser

<210> SEQ ID NO 537
<211> LENGTH: 21
<212> TYPE: PRT
<213> ORGANISM: Simian immunodeficiency virus

<400> SEQUENCE: 537

Arg Leu Gln Lys Cys Val Tyr Asn Pro Ile Asn Ile Leu Asp Val Lys
1               5                   10                  15

Gln Arg Pro Lys Glu
            20

<210> SEQ ID NO 538
<211> LENGTH: 17
<212> TYPE: PRT
<213> ORGANISM: Simian immunodeficiency virus

<400> SEQUENCE: 538

Met Gln Ile Ile Arg Glu Ile Ile Asn Glu Glu Ala Ala Asp Trp Asp
1               5                   10                  15

Val

<210> SEQ ID NO 539
<211> LENGTH: 19
<212> TYPE: PRT
<213> ORGANISM: Simian immunodeficiency virus

<400> SEQUENCE: 539

Gln His Pro Gln Pro Gly Pro Leu Pro Ala Gly Gln Leu Arg Glu Pro
1               5                   10                  15

Ser Gly Ser

<210> SEQ ID NO 540
<211> LENGTH: 21
<212> TYPE: PRT
<213> ORGANISM: Simian immunodeficiency virus

<400> SEQUENCE: 540

Gln Lys Cys Val Arg Met Tyr Asn Pro Val Asn Ile Leu Asp Ile Lys
1               5                   10                  15

Gln Gly Pro Lys Glu
            20

<210> SEQ ID NO 541
<211> LENGTH: 37
<212> TYPE: PRT
<213> ORGANISM: Human immunodeficiency virus 1

<400> SEQUENCE: 541

Met Gln Met Leu Lys Asp Thr Ile Asn Glu Glu Ala Ala Asp Trp Asp
1               5                   10                  15

Arg Val His Pro Val His Ala Gly Pro Ile Pro Pro Gly Gln Met Arg
            20                  25                  30

Glu Pro Arg Gly Ser
        35

<210> SEQ ID NO 542
<211> LENGTH: 37
<212> TYPE: PRT
<213> ORGANISM: Human immunodeficiency virus 1

<400> SEQUENCE: 542

Met Gln Met Leu Lys Asp Thr Ile Asn Glu Glu Ala Ala Glu Trp Asp
1               5                   10                  15

Arg Leu His Pro Val His Ala Gly Pro Ile Pro Pro Gly Gln Met Arg
            20                  25                  30

Glu Pro Arg Gly Ser
        35

<210> SEQ ID NO 543
<211> LENGTH: 37
<212> TYPE: PRT
<213> ORGANISM: Human immunodeficiency virus 1

<400> SEQUENCE: 543

Met Gln Met Leu Lys Glu Thr Ile Asn Glu Glu Ala Ala Glu Trp Asp
1               5                   10                  15

Arg Leu His Pro Val Gln Ala Gly Pro Val Ala Pro Gly Gln Met Arg
            20                  25                  30

Glu Pro Arg Gly Ser

35

<210> SEQ ID NO 544
<211> LENGTH: 37
<212> TYPE: PRT
<213> ORGANISM: Human immunodeficiency virus 1

<400> SEQUENCE: 544

Met Gln Met Leu Lys Asp Thr Ile Asn Glu Glu Ala Ala Glu Trp Asp
1               5                   10                  15

Arg Leu His Pro Val His Ala Gly Pro Val Ala Pro Gly Gln Met Arg
            20                  25                  30

Glu Pro Arg Gly Ser
        35

<210> SEQ ID NO 545
<211> LENGTH: 37
<212> TYPE: PRT
<213> ORGANISM: Human immunodeficiency virus 1

<400> SEQUENCE: 545

Met Gln Met Leu Lys Glu Thr Ile Asn Glu Glu Ala Ala Glu Trp Asp
1               5                   10                  15

Arg Val His Pro Val His Ala Gly Pro Ile Ala Pro Gly Gln Met Arg
            20                  25                  30

Glu Pro Arg Gly Ser
        35

<210> SEQ ID NO 546
<211> LENGTH: 37
<212> TYPE: PRT
<213> ORGANISM: Human immunodeficiency virus 1

<400> SEQUENCE: 546

Met Gln Met Leu Lys Glu Thr Ile Asn Glu Glu Ala Ala Glu Trp Asp
1               5                   10                  15

Arg Val His Pro Val His Ala Gly Pro Ile Ala Pro Gly Gln Met Arg
            20                  25                  30

Glu Pro Arg Gly Ser
        35

<210> SEQ ID NO 547
<211> LENGTH: 37
<212> TYPE: PRT
<213> ORGANISM: Human immunodeficiency virus 1

<400> SEQUENCE: 547

Met Gln Met Leu Lys Glu Thr Ile Asn Glu Glu Ala Ala Glu Trp Asp
1               5                   10                  15

Arg Val His Pro Val His Ala Gly Pro Ile Ala Pro Gly Gln Met Arg
            20                  25                  30

Glu Pro Arg Gly Ser
        35

<210> SEQ ID NO 548
<211> LENGTH: 37
<212> TYPE: PRT
<213> ORGANISM: Human immunodeficiency virus 1

<400> SEQUENCE: 548

Met Gln Met Leu Lys Glu Thr Ile Asn Glu Glu Ala Ala Glu Trp Asp

```
1               5                   10                  15
Arg Val His Pro Val His Ala Gly Pro Ile Ala Pro Gly Gln Met Arg
            20                  25                  30

Glu Pro Arg Gly Ser
        35

<210> SEQ ID NO 549
<211> LENGTH: 37
<212> TYPE: PRT
<213> ORGANISM: Human immunodeficiency virus 1

<400> SEQUENCE: 549

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
        35

<210> SEQ ID NO 550
<211> LENGTH: 37
<212> TYPE: PRT
<213> ORGANISM: Human immunodeficiency virus 1

<400> SEQUENCE: 550

Met Gln Met Leu Lys Asp Thr Ile Asn Glu Glu Ala Ala Glu Trp Asp
1               5                   10                  15

Arg Leu His Pro Val His Ala Gly Pro Val Ala Pro Gly Gln Met Arg
            20                  25                  30

Asp Pro Arg Gly Ser
        35

<210> SEQ ID NO 551
<211> LENGTH: 37
<212> TYPE: PRT
<213> ORGANISM: Human immunodeficiency virus 1

<400> SEQUENCE: 551

Met Gln Met Leu Lys Glu Thr Ile Asn Glu Glu Ala Ala Glu Trp Asp
1               5                   10                  15

Arg Val His Pro Val His Ala Gly Pro Ile Ala Pro Gly Gln Met Arg
            20                  25                  30

Glu Pro Arg Gly Ser
        35

<210> SEQ ID NO 552
<211> LENGTH: 37
<212> TYPE: PRT
<213> ORGANISM: Human immunodeficiency virus 1

<400> SEQUENCE: 552

Met Gln Met Leu Lys Glu Thr Ile Asn Glu Glu Ala Ala Glu Trp Asp
1               5                   10                  15

Arg Leu His Pro Ala Gln Ala Gly Pro Ile Ala Pro Gly Gln Met Arg
            20                  25                  30

Glu Pro Arg Gly Ser
        35

<210> SEQ ID NO 553
<211> LENGTH: 37
```

```
<212> TYPE: PRT
<213> ORGANISM: Human immunodeficiency virus 1

<400> SEQUENCE: 553

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
        35

<210> SEQ ID NO 554
<211> LENGTH: 37
<212> TYPE: PRT
<213> ORGANISM: Human immunodeficiency virus 1

<400> SEQUENCE: 554

Met Gln Met Leu Lys Glu Thr Ile Asn Glu Glu Ala Ala Glu Trp Asp
1               5                   10                  15

Arg Val His Pro Val His Ala Gly Pro Ile Ala Pro Gly Gln Met Arg
            20                  25                  30

Glu Pro Arg Gly Ser
        35

<210> SEQ ID NO 555
<211> LENGTH: 37
<212> TYPE: PRT
<213> ORGANISM: Human immunodeficiency virus 1

<400> SEQUENCE: 555

Met Gln Met Leu Lys Glu Thr Ile Asn Glu Glu Ala Ala Glu Trp Asp
1               5                   10                  15

Arg Leu His Pro Ala His Ala Gly Pro Ile Ala Pro Gly Gln Met Arg
            20                  25                  30

Glu Pro Arg Gly Ser
        35

<210> SEQ ID NO 556
<211> LENGTH: 37
<212> TYPE: PRT
<213> ORGANISM: Human immunodeficiency virus 1

<400> SEQUENCE: 556

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
        35

<210> SEQ ID NO 557
<211> LENGTH: 37
<212> TYPE: PRT
<213> ORGANISM: Human immunodeficiency virus 1

<400> SEQUENCE: 557

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30
```

-continued

Glu Pro Arg Gly Ser
        35

<210> SEQ ID NO 558
<211> LENGTH: 37
<212> TYPE: PRT
<213> ORGANISM: Human immunodeficiency virus 1

<400> SEQUENCE: 558

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
        35

<210> SEQ ID NO 559
<211> LENGTH: 37
<212> TYPE: PRT
<213> ORGANISM: Human immunodeficiency virus 1

<400> SEQUENCE: 559

Met Gln Met Leu Lys Asp Thr Ile Asn Glu Glu Ala Ala Glu Trp Asp
1               5                   10                  15

Arg Leu His Pro Val His Ala Gly Pro Ile Pro Pro Gly Gln Met Arg
            20                  25                  30

Glu Pro Arg Gly Ser
        35

<210> SEQ ID NO 560
<211> LENGTH: 37
<212> TYPE: PRT
<213> ORGANISM: Human immunodeficiency virus 1

<400> SEQUENCE: 560

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
        35

<210> SEQ ID NO 561
<211> LENGTH: 37
<212> TYPE: PRT
<213> ORGANISM: Human immunodeficiency virus 1

<400> SEQUENCE: 561

Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
        35

<210> SEQ ID NO 562
<211> LENGTH: 37
<212> TYPE: PRT
<213> ORGANISM: Human immunodeficiency virus 1

<400> SEQUENCE: 562

```
Met Gln Met Leu Lys Asp Thr Ile Asn Glu Glu Ala Ala Glu Trp Asp
1               5                   10                  15

Arg Leu His Pro Val His Ala Gly Pro Val Ala Pro Gly Gln Met Arg
            20                  25                  30

Glu Pro Arg Gly Ser
            35
```

<210> SEQ ID NO 563
<211> LENGTH: 37
<212> TYPE: PRT
<213> ORGANISM: Human immunodeficiency virus 1

<400> SEQUENCE: 563

```
Met Gln Met Leu Lys Asp Thr Ile Asn Glu Glu Ala Ala Glu Trp Asp
1               5                   10                  15

Arg Leu His Pro Val His Ala Gly Pro Val Ala Pro Gly Gln Met Arg
            20                  25                  30

Asp Pro Arg Gly Ser
            35
```

<210> SEQ ID NO 564
<211> LENGTH: 37
<212> TYPE: PRT
<213> ORGANISM: Human immunodeficiency virus 1

<400> SEQUENCE: 564

```
Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
            35
```

<210> SEQ ID NO 565
<211> LENGTH: 37
<212> TYPE: PRT
<213> ORGANISM: Human immunodeficiency virus 1

<400> SEQUENCE: 565

```
Met Gln Met Leu Lys Glu Thr Ile Asn Asp Glu Ala Ala Glu Trp Asp
1               5                   10                  15

Arg Leu His Pro Val His Ala Gly Pro Val Ala Pro Gly Gln Met Arg
            20                  25                  30

Glu Pro Arg Gly Ser
            35
```

<210> SEQ ID NO 566
<211> LENGTH: 37
<212> TYPE: PRT
<213> ORGANISM: Human immunodeficiency virus 1

<400> SEQUENCE: 566

```
Met Gln Met Leu Lys Glu Thr Ile Asn Glu Glu Ala Ala Glu Trp Asp
1               5                   10                  15

Arg Leu His Pro Val His Ala Gly Pro Ile Ala Pro Gly Gln Met Arg
            20                  25                  30

Glu Pro Arg Gly Ser
            35
```

<210> SEQ ID NO 567

```
<210> SEQ ID NO 567
<211> LENGTH: 37
<212> TYPE: PRT
<213> ORGANISM: Human immunodeficiency virus 1

<400> SEQUENCE: 567

Met Gln Met Leu Lys Asp Thr Ile Asn Glu Glu Ala Ala Glu Trp Asp
1               5                   10                  15

Arg Leu His Pro Thr Gln Ala Gly Pro Ile Pro Pro Gly Gln Ile Arg
            20                  25                  30

Glu Pro Arg Gly Ser
        35

<210> SEQ ID NO 568
<211> LENGTH: 37
<212> TYPE: PRT
<213> ORGANISM: Human immunodeficiency virus 1

<400> SEQUENCE: 568

Met Gln Met Leu Lys Asp Thr Ile Asn Glu Glu Ala Ala Glu Trp Asp
1               5                   10                  15

Arg Leu His Pro Val His Ala Gly Pro Ala Pro Pro Gly Gln Met Arg
            20                  25                  30

Glu Pro Arg Gly Ser
        35

<210> SEQ ID NO 569
<211> LENGTH: 37
<212> TYPE: PRT
<213> ORGANISM: Human immunodeficiency virus 1

<400> SEQUENCE: 569

Met Gln Met Leu Lys Asp Thr Ile Asn Glu Glu Ala Ala Glu Trp Asp
1               5                   10                  15

Arg Leu His Pro Val His Ala Gly Pro Ile Pro Pro Gly Gln Met Arg
            20                  25                  30

Glu Pro Arg Gly Ser
        35

<210> SEQ ID NO 570
<211> LENGTH: 37
<212> TYPE: PRT
<213> ORGANISM: Human immunodeficiency virus 1

<400> SEQUENCE: 570

Met Gln Met Leu Lys Asp Thr Ile Asn Glu Glu Ala Ala Glu Trp Asp
1               5                   10                  15

Arg Leu His Pro Val His Ala Gly Pro Ile Pro Pro Gly Gln Met Arg
            20                  25                  30

Glu Pro Arg Gly Ser
        35

<210> SEQ ID NO 571
<211> LENGTH: 37
<212> TYPE: PRT
<213> ORGANISM: Human immunodeficiency virus 1

<400> SEQUENCE: 571

Met Gln Met Leu Lys Asp Thr Ile Asn Asp Glu Ala Ala Glu Trp Asp
1               5                   10                  15

Arg Ile His Pro Gln Gln Ala Gly Pro Ile Pro Pro Gly Gln Ile Arg
            20                  25                  30
```

-continued

```
Glu Pro Ser Gly Ser
        35

<210> SEQ ID NO 572
<211> LENGTH: 37
<212> TYPE: PRT
<213> ORGANISM: Human immunodeficiency virus 1

<400> SEQUENCE: 572

Met Gln Met Leu Lys Asp Thr Ile Asn Glu Glu Ala Ala Glu Trp Asp
1               5                   10                  15

Arg Met His Pro Gln Gln Ala Gly Pro Phe Pro Pro Gly Gln Ile Arg
            20                  25                  30

Glu Pro Arg Gly Ser
        35

<210> SEQ ID NO 573
<211> LENGTH: 37
<212> TYPE: PRT
<213> ORGANISM: Human immunodeficiency virus 1

<400> SEQUENCE: 573

Met Gln Met Leu Lys Asp Thr Ile Asn Glu Glu Ala Ala Glu Trp Asp
1               5                   10                  15

Arg Val His Pro Val His Ala Gly Pro Ile Pro Pro Gly Gln Met Arg
            20                  25                  30

Glu Pro Arg Gly Ser
        35

<210> SEQ ID NO 574
<211> LENGTH: 37
<212> TYPE: PRT
<213> ORGANISM: Human immunodeficiency virus 1

<400> SEQUENCE: 574

Met Gln Met Leu Lys Asp Thr Ile Asn Glu Glu Ala Ala Glu Trp Asp
1               5                   10                  15

Arg Leu His Pro Val His Ala Gly Pro Ile Pro Pro Gly Gln Met Arg
            20                  25                  30

Glu Pro Arg Gly Ser
        35

<210> SEQ ID NO 575
<211> LENGTH: 37
<212> TYPE: PRT
<213> ORGANISM: Human immunodeficiency virus 1

<400> SEQUENCE: 575

Met Gln Met Leu Lys Asp Thr Ile Asn Glu Glu Ala Ala Glu Trp Asp
1               5                   10                  15

Arg Val His Pro Val His Ala Gly Pro Val Ala Pro Gly Gln Val Arg
            20                  25                  30

Glu Pro Arg Gly Ser
        35

<210> SEQ ID NO 576
<211> LENGTH: 37
<212> TYPE: PRT
<213> ORGANISM: Human immunodeficiency virus 1

<400> SEQUENCE: 576
```

-continued

Met Gln Met Leu Lys Asp Thr Ile Asn Glu Glu Ala Ala Glu Trp Asp
1               5                   10                  15

Arg Val His Pro Val His Ala Gly Pro Ile Ala Pro Gly Gln Val Arg
            20                  25                  30

Glu Pro Arg Gly Ser
            35

<210> SEQ ID NO 577
<211> LENGTH: 37
<212> TYPE: PRT
<213> ORGANISM: Human immunodeficiency virus 1

<400> SEQUENCE: 577

Met Gln Met Leu Lys Asp Thr Ile Asn Asp Glu Ala Ala Glu Trp Asp
1               5                   10                  15

Arg Leu His Pro Val His Ala Gly Pro Ile Pro Pro Gly Gln Met Arg
            20                  25                  30

Glu Pro Arg Gly Ser
            35

<210> SEQ ID NO 578
<211> LENGTH: 37
<212> TYPE: PRT
<213> ORGANISM: Human immunodeficiency virus 1

<400> SEQUENCE: 578

Met Gln Met Leu Lys Asp Thr Ile Asn Glu Glu Ala Ala Glu Trp Asp
1               5                   10                  15

Arg Met His Pro Val Gln Ala Gly Pro Ile Pro Pro Gly Gln Ile Arg
            20                  25                  30

Glu Pro Arg Gly Ser
            35

<210> SEQ ID NO 579
<211> LENGTH: 37
<212> TYPE: PRT
<213> ORGANISM: Human immunodeficiency virus 1

<400> SEQUENCE: 579

Met Gln Met Leu Lys Glu Val Ile Asn Glu Glu Ala Ala Glu Trp Asp
1               5                   10                  15

Arg Thr His Pro Ala Pro Val Gly Pro Leu Pro Pro Gly Gln Met Arg
            20                  25                  30

Asp Pro Arg Gly Ser
            35

<210> SEQ ID NO 580
<211> LENGTH: 37
<212> TYPE: PRT
<213> ORGANISM: Human immunodeficiency virus 1

<400> SEQUENCE: 580

Met Gln Met Leu Lys Glu Val Ile Asn Glu Glu Ala Ala Asp Trp Asp
1               5                   10                  15

Arg Thr His Pro Val Pro Val Gly Pro Leu Pro Pro Gly Gln Leu Arg
            20                  25                  30

Asp Pro Arg Gly Ser
            35

```
<210> SEQ ID NO 581
<211> LENGTH: 37
<212> TYPE: PRT
<213> ORGANISM: Human immunodeficiency virus 1

<400> SEQUENCE: 581

Leu Gln Val Leu Lys Glu Val Ile Asn Glu Glu Ala Val Glu Trp Asp
1               5                   10                  15

Arg Thr His Pro Pro Val Gly Pro Leu Pro Pro Gly Gln Ile Arg
            20                  25                  30

Glu Pro Thr Gly Ser
        35

<210> SEQ ID NO 582
<211> LENGTH: 37
<212> TYPE: PRT
<213> ORGANISM: Human immunodeficiency virus 1

<400> SEQUENCE: 582

Leu Gln Val Leu Lys Glu Val Ile Asn Glu Glu Ala Ala Glu Trp Asp
1               5                   10                  15

Arg Thr His Pro Pro Ala Met Gly Pro Leu Pro Pro Gly Gln Ile Arg
            20                  25                  30

Glu Pro Thr Gly Ser
        35

<210> SEQ ID NO 583
<211> LENGTH: 36
<212> TYPE: PRT
<213> ORGANISM: Human immunodeficiency virus 2

<400> SEQUENCE: 583

Met Gln Ile Ile Arg Glu Ile Ile Asn Glu Glu Ala Ala Asp Trp Asp
1               5                   10                  15

Ala Asn His Pro Ile Pro Gly Pro Leu Pro Ala Gly Gln Leu Arg Asp
            20                  25                  30

Pro Arg Gly Ser
        35

<210> SEQ ID NO 584
<211> LENGTH: 36
<212> TYPE: PRT
<213> ORGANISM: Human immunodeficiency virus 2

<400> SEQUENCE: 584

Met Gln Ile Ile Arg Glu Ile Ile Asn Glu Glu Ala Ala Glu Trp Asp
1               5                   10                  15

Val Gln His Pro Ile Pro Gly Pro Leu Pro Ala Gly Gln Leu Arg Glu
            20                  25                  30

Pro Arg Gly Ser
        35

<210> SEQ ID NO 585
<211> LENGTH: 36
<212> TYPE: PRT
<213> ORGANISM: Human immunodeficiency virus 2

<400> SEQUENCE: 585

Met Gln Ile Ile Arg Glu Ile Ile Asn Glu Glu Ala Ala Asp Trp Asp
1               5                   10                  15

Val Gln His Pro Ile Pro Gly Pro Leu Pro Ala Gly Gln Leu Arg Glu
```

```
                20                  25                  30

Pro Arg Gly Ser
        35

<210> SEQ ID NO 586
<211> LENGTH: 36
<212> TYPE: PRT
<213> ORGANISM: Human immunodeficiency virus 2

<400> SEQUENCE: 586

Met Gln Ile Ile Arg Glu Ile Ile Asn Glu Glu Ala Ala Asp Trp Asp
1               5                   10                  15

Ala Gln His Pro Ile Pro Gly Pro Leu Pro Ala Gly Gln Leu Arg Glu
                20                  25                  30

Pro Arg Gly Ser
        35

<210> SEQ ID NO 587
<211> LENGTH: 36
<212> TYPE: PRT
<213> ORGANISM: Human immunodeficiency virus 2

<400> SEQUENCE: 587

Met Gln Ile Ile Arg Glu Ile Ile Asn Glu Glu Ala Ala Asp Trp Asp
1               5                   10                  15

Ala Gln His Pro Ile Pro Gly Pro Leu Pro Ala Gly Gln Leu Arg Asp
                20                  25                  30

Pro Arg Gly Ser
        35

<210> SEQ ID NO 588
<211> LENGTH: 36
<212> TYPE: PRT
<213> ORGANISM: Human immunodeficiency virus 2

<400> SEQUENCE: 588

Met Gln Ile Ile Arg Glu Ile Ile Asn Glu Glu Ala Ala Asp Trp Asp
1               5                   10                  15

Ser Gln His Pro Ile Pro Gly Pro Leu Pro Ala Gly Gln Leu Arg Asp
                20                  25                  30

Pro Arg Gly Ser
        35

<210> SEQ ID NO 589
<211> LENGTH: 36
<212> TYPE: PRT
<213> ORGANISM: Human immunodeficiency virus 2

<400> SEQUENCE: 589

Met Gln Ile Ile Arg Glu Ile Ile Asn Asp Glu Ala Ala Asp Trp Asp
1               5                   10                  15

Ala Gln His Pro Ile Pro Gly Pro Leu Pro Ala Gly Gln Leu Arg Asp
                20                  25                  30

Pro Arg Gly Ser
        35

<210> SEQ ID NO 590
<211> LENGTH: 36
<212> TYPE: PRT
<213> ORGANISM: Human immunodeficiency virus 2
```

```
<400> SEQUENCE: 590

Met Gln Ile Ile Arg Glu Ile Ile Asn Glu Glu Ala Ala Asp Trp Asp
1               5                   10                  15

Val Ala His Pro Ile Pro Gly Pro Leu Pro Ala Gly Gln Leu Arg Glu
            20                  25                  30

Pro Arg Gly Ser
            35

<210> SEQ ID NO 591
<211> LENGTH: 36
<212> TYPE: PRT
<213> ORGANISM: Human immunodeficiency virus 2

<400> SEQUENCE: 591

Met Gln Ile Ile Arg Glu Ile Ile Asn Glu Glu Ala Ala Asp Trp Asp
1               5                   10                  15

Val Gln His Pro Ile Pro Gly Pro Leu Pro Ala Gly Gln Leu Arg Asp
            20                  25                  30

Pro Arg Gly Ser
            35

<210> SEQ ID NO 592
<211> LENGTH: 36
<212> TYPE: PRT
<213> ORGANISM: Human immunodeficiency virus 2

<400> SEQUENCE: 592

Met Gln Ile Ile Arg Glu Ile Ile Asn Glu Glu Ala Ala Asp Trp Asp
1               5                   10                  15

Gln Gln His Pro Ile Pro Gly Pro Leu Pro Ala Gly Gln Leu Arg Asp
            20                  25                  30

Pro Arg Gly Ser
            35

<210> SEQ ID NO 593
<211> LENGTH: 36
<212> TYPE: PRT
<213> ORGANISM: Human immunodeficiency virus 2

<400> SEQUENCE: 593

Met Gln Ile Ile Arg Glu Ile Ile Asn Glu Glu Ala Ala Asp Trp Asp
1               5                   10                  15

Gln Gln His Pro Ser Pro Gly Pro Met Pro Ala Gly Gln Leu Arg Asp
            20                  25                  30

Pro Arg Gly Ser
            35

<210> SEQ ID NO 594
<211> LENGTH: 36
<212> TYPE: PRT
<213> ORGANISM: Human immunodeficiency virus 2

<400> SEQUENCE: 594

Met Gln Ile Ile Arg Glu Ile Ile Asn Glu Glu Ala Ala Asp Trp Asp
1               5                   10                  15

Gln Gln His Pro Ser Pro Gly Pro Met Pro Ala Gly Gln Leu Arg Glu
            20                  25                  30

Pro Arg Gly Ser
            35
```

<210> SEQ ID NO 595
<211> LENGTH: 36
<212> TYPE: PRT
<213> ORGANISM: Simian immunodeficiency virus

<400> SEQUENCE: 595

Met Gln Ile Ile Arg Glu Ile Ile Asn Glu Glu Ala Ala Asp Trp Asp
1               5                   10                  15

Leu Gln His Pro Gln Pro Gly Pro Leu Pro Ala Gly Gln Leu Arg Glu
            20                  25                  30

Pro Arg Gly Ser
        35

<210> SEQ ID NO 596
<211> LENGTH: 36
<212> TYPE: PRT
<213> ORGANISM: Simian immunodeficiency virus

<400> SEQUENCE: 596

Met Gln Ile Ile Arg Glu Ile Ile Asn Glu Glu Ala Ala Asp Trp Asp
1               5                   10                  15

Leu Gln His Pro Gln Pro Gly Pro Ile Pro Pro Gly Gln Leu Arg Glu
            20                  25                  30

Pro Arg Gly Ser
        35

<210> SEQ ID NO 597
<211> LENGTH: 35
<212> TYPE: PRT
<213> ORGANISM: Simian immunodeficiency virus

<400> SEQUENCE: 597

Met Gln Ile Ile Arg Asp Ile Ile Asn Glu Glu Ala Ala Asp Trp Asp
1               5                   10                  15

Leu Gln His Pro Gln Pro Ala Pro Gln Gln Gly Gln Leu Arg Glu Pro
            20                  25                  30

Ser Gly Ser
        35

<210> SEQ ID NO 598
<211> LENGTH: 35
<212> TYPE: PRT
<213> ORGANISM: Simian immunodeficiency virus

<400> SEQUENCE: 598

Met Gln Ile Ile Arg Asp Ile Ile Asn Glu Glu Ala Ala Asp Trp Asp
1               5                   10                  15

Leu Gln His Pro Gln Pro Ala Pro Gln Gln Gly Gln Leu Arg Glu Pro
            20                  25                  30

Ser Gly Ser
        35

<210> SEQ ID NO 599
<211> LENGTH: 35
<212> TYPE: PRT
<213> ORGANISM: Simian immunodeficiency virus

<400> SEQUENCE: 599

Met Gln Ile Ile Arg Asp Ile Ile Asn Glu Glu Ala Ala Asp Trp Asp
1               5                   10                  15

Leu Gln His Pro Gln Pro Ala Pro Gln Gln Gly Gln Leu Arg Glu Pro
            20                  25                  30

Ser Gly Ser
        35

<210> SEQ ID NO 600
<211> LENGTH: 35
<212> TYPE: PRT
<213> ORGANISM: Simian immunodeficiency virus

<400> SEQUENCE: 600

Met Gln Ile Ile Arg Asp Ile Ile Asn Glu Glu Ala Ala Asp Trp Asp
1               5                   10                  15

Leu Gln His Pro Gln Pro Ala Pro Gln Gln Gly Gln Leu Arg Glu Pro
            20                  25                  30

Ser Gly Ser
        35

<210> SEQ ID NO 601
<211> LENGTH: 35
<212> TYPE: PRT
<213> ORGANISM: Simian immunodeficiency virus

<400> SEQUENCE: 601

Met Gln Ile Ile Arg Asp Ile Ile Asn Glu Glu Ala Ala Asp Trp Asp
1               5                   10                  15

Leu Gln His Pro Gln Gln Ala Pro Gln Gln Gly Gln Leu Arg Glu Pro
            20                  25                  30

Ser Gly Ser
        35

<210> SEQ ID NO 602
<211> LENGTH: 35
<212> TYPE: PRT
<213> ORGANISM: Simian immunodeficiency virus

<400> SEQUENCE: 602

Met Gln Ile Ile Arg Asp Ile Ile Asn Glu Glu Ala Ala Asp Trp Asp
1               5                   10                  15

Leu Gln His Pro Gln Pro Ala Pro Gln Gln Gly Gln Leu Arg Glu Pro
            20                  25                  30

Ser Gly Ser
        35

<210> SEQ ID NO 603
<211> LENGTH: 35
<212> TYPE: PRT
<213> ORGANISM: Simian immunodeficiency virus

<400> SEQUENCE: 603

Met Gln Ile Ile Arg Asp Ile Ile Asn Glu Glu Ala Ala Asp Trp Asp
1               5                   10                  15

Leu Gln His Pro Gln Pro Ala Pro Gln Gln Gly Gln Leu Arg Glu Pro
            20                  25                  30

Ser Gly Ser
        35

<210> SEQ ID NO 604
<211> LENGTH: 36
<212> TYPE: PRT
<213> ORGANISM: Simian immunodeficiency virus

<400> SEQUENCE: 604

Met Gln Ile Ile Arg Glu Ile Asn Glu Glu Ala Ala Asp Trp Asp
1               5                   10                  15

Val Gln His Pro Gln Pro Gly Pro Leu Pro Ala Gly Gln Leu Arg Glu
            20                  25                  30

Pro Ser Gly Ser
        35

<210> SEQ ID NO 605
<211> LENGTH: 24
<212> TYPE: PRT
<213> ORGANISM: Human immunodeficiency virus 1

<400> SEQUENCE: 605

Ala Ala Met Gln Met Leu Lys Asp Thr Ile Asn Asp Glu Ala Ala Glu
1               5                   10                  15

Trp Asp Arg Leu His Pro Val His
            20

<210> SEQ ID NO 606
<211> LENGTH: 25
<212> TYPE: PRT
<213> ORGANISM: Human immunodeficiency virus 1

<400> SEQUENCE: 606

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 607
<211> LENGTH: 26
<212> TYPE: PRT
<213> ORGANISM: Human immunodeficiency virus 1

<400> SEQUENCE: 607

Asp Arg Phe Phe Lys Thr Leu Arg Ala Glu Gln Ala Thr Gln Glu Val
1               5                   10                  15

Lys Asn Trp Met Thr Asp Thr Leu Leu Val
            20                  25

<210> SEQ ID NO 608
<211> LENGTH: 24
<212> TYPE: PRT
<213> ORGANISM: Human immunodeficiency virus 1

<400> SEQUENCE: 608

Ala Ala Met Gln Met Leu Lys Asp Thr Ile Asn Asp Glu Ala Ala Glu
1               5                   10                  15

Trp Asp Arg Ile His Pro Gln Gln
            20

<210> SEQ ID NO 609
<211> LENGTH: 25
<212> TYPE: PRT
<213> ORGANISM: Human immunodeficiency virus 1

<400> SEQUENCE: 609

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 610
<211> LENGTH: 26
<212> TYPE: PRT
<213> ORGANISM: Human immunodeficiency virus 1

<400> SEQUENCE: 610

Asp Arg Phe Phe Lys Thr Leu Arg Ala Glu Gln Ala Thr Gln Glu Val
1               5                   10                  15

Lys Gly Trp Met Thr Asp Thr Leu Leu Val
            20                  25

<210> SEQ ID NO 611
<211> LENGTH: 24
<212> TYPE: PRT
<213> ORGANISM: Human immunodeficiency virus 1

<400> SEQUENCE: 611

Ala Ala Met Gln Met Leu Lys Asp Thr Ile Asn Glu Glu Ala Ala Asp
1               5                   10                  15

Trp Asp Arg Val His Pro Val His
            20

<210> SEQ ID NO 612
<211> LENGTH: 25
<212> TYPE: PRT
<213> ORGANISM: Human immunodeficiency virus 1

<400> SEQUENCE: 612

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 613
<211> LENGTH: 26
<212> TYPE: PRT
<213> ORGANISM: Human immunodeficiency virus 1

<400> SEQUENCE: 613

Asp Arg Phe Phe Lys Thr Leu Arg Ala Glu Gln Ala Thr Gln Glu Val
1               5                   10                  15

Lys Asn Trp Met Thr Glu Thr Leu Leu Val
            20                  25

<210> SEQ ID NO 614
<211> LENGTH: 24
<212> TYPE: PRT
<213> ORGANISM: Human immunodeficiency virus 1

<400> SEQUENCE: 614

Ala Ala Met Gln Met Leu Lys Asp Thr Ile Asn Glu Glu Ala Ala Glu
1               5                   10                  15

Trp Asp Arg Val His Pro Val His
            20

<210> SEQ ID NO 615
<211> LENGTH: 25
<212> TYPE: PRT
<213> ORGANISM: Human immunodeficiency virus 1

```
<400> SEQUENCE: 615

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 616
<211> LENGTH: 26
<212> TYPE: PRT
<213> ORGANISM: Human immunodeficiency virus 1

<400> SEQUENCE: 616

Asp Arg Phe Phe Lys Thr Leu Arg Ala Glu Gln Ala Thr Gln Asp Val
1               5                   10                  15

Lys Asn Trp Met Thr Glu Thr Leu Leu Val
            20                  25

<210> SEQ ID NO 617
<211> LENGTH: 24
<212> TYPE: PRT
<213> ORGANISM: Human immunodeficiency virus 1

<400> SEQUENCE: 617

Ala Ala Met Gln Met Leu Lys Asp Thr Ile Asn Glu Glu Ala Ala Glu
1               5                   10                  15

Trp Asp Arg Leu His Pro Val His
            20

<210> SEQ ID NO 618
<211> LENGTH: 25
<212> TYPE: PRT
<213> ORGANISM: Human immunodeficiency virus 1

<400> SEQUENCE: 618

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 619
<211> LENGTH: 26
<212> TYPE: PRT
<213> ORGANISM: Human immunodeficiency virus 1

<400> SEQUENCE: 619

Asp Arg Phe Phe Lys Thr Leu Arg Ala Glu Gln Ala Thr Gln Asp Val
1               5                   10                  15

Lys Asn Trp Met Thr Asp Thr Leu Leu Val
            20                  25

<210> SEQ ID NO 620
<211> LENGTH: 24
<212> TYPE: PRT
<213> ORGANISM: Human immunodeficiency virus 1

<400> SEQUENCE: 620

Ala Ala Met Gln Met Leu Lys Asp Thr Ile Asn Glu Glu Ala Ala Glu
1               5                   10                  15

Trp Asp Arg Leu His Pro Thr Gln
            20
```

```
<210> SEQ ID NO 621
<211> LENGTH: 25
<212> TYPE: PRT
<213> ORGANISM: Human immunodeficiency virus 1

<400> SEQUENCE: 621

Ile Ile Leu Gly Leu Asn Lys Ile Val Arg Met Tyr Ser Pro Val Gly
1               5                   10                  15

Ile Leu Asp Ile Lys Gln Gly Pro Lys
            20                  25

<210> SEQ ID NO 622
<211> LENGTH: 26
<212> TYPE: PRT
<213> ORGANISM: Human immunodeficiency virus 1

<400> SEQUENCE: 622

Asp Arg Phe Phe Lys Thr Leu Arg Ala Glu Gln Ala Thr Gln Glu Val
1               5                   10                  15

Lys Gly Trp Met Thr Asp Thr Leu Leu Val
            20                  25

<210> SEQ ID NO 623
<211> LENGTH: 24
<212> TYPE: PRT
<213> ORGANISM: Human immunodeficiency virus 1

<400> SEQUENCE: 623

Ala Ala Met Gln Met Leu Lys Asp Thr Ile Asn Glu Glu Ala Ala Glu
1               5                   10                  15

Trp Asp Arg Met His Pro Val Gln
            20

<210> SEQ ID NO 624
<211> LENGTH: 25
<212> TYPE: PRT
<213> ORGANISM: Human immunodeficiency virus 1

<400> SEQUENCE: 624

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 625
<211> LENGTH: 26
<212> TYPE: PRT
<213> ORGANISM: Human immunodeficiency virus 1

<400> SEQUENCE: 625

Asp Arg Phe Phe Arg Val Leu Arg Ala Glu Gln Ala Thr Gln Glu Val
1               5                   10                  15

Lys Asn Trp Met Thr Glu Thr Leu Leu Val
            20                  25

<210> SEQ ID NO 626
<211> LENGTH: 24
<212> TYPE: PRT
<213> ORGANISM: Human immunodeficiency virus 1

<400> SEQUENCE: 626

Ala Ala Met Gln Met Leu Lys Asp Thr Ile Asn Glu Glu Ala Ala Glu
1               5                   10                  15
```

Trp Asp Arg Leu His Pro Val His
            20

<210> SEQ ID NO 627
<211> LENGTH: 25
<212> TYPE: PRT
<213> ORGANISM: Human immunodeficiency virus 1

<400> SEQUENCE: 627

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 628
<211> LENGTH: 26
<212> TYPE: PRT
<213> ORGANISM: Human immunodeficiency virus 1

<400> SEQUENCE: 628

Asp Arg Phe Phe Lys Thr Leu Arg Ala Glu Gln Ala Thr Gln Asp Val
1               5                   10                  15

Lys Asn Trp Met Thr Asp Thr Leu Leu Val
            20                  25

<210> SEQ ID NO 629
<211> LENGTH: 24
<212> TYPE: PRT
<213> ORGANISM: Human immunodeficiency virus 1

<400> SEQUENCE: 629

Ala Ala Met Gln Met Leu Lys Asp Thr Ile Asn Glu Glu Ala Ala Glu
1               5                   10                  15

Trp Asp Arg Leu His Pro Val His
            20

<210> SEQ ID NO 630
<211> LENGTH: 25
<212> TYPE: PRT
<213> ORGANISM: Human immunodeficiency virus 1

<400> SEQUENCE: 630

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 631
<211> LENGTH: 26
<212> TYPE: PRT
<213> ORGANISM: Human immunodeficiency virus 1

<400> SEQUENCE: 631

Asp Arg Phe Phe Lys Thr Leu Arg Ala Glu Gln Ala Thr Gln Glu Val
1               5                   10                  15

Lys Gly Trp Met Thr Glu Thr Leu Leu Val
            20                  25

<210> SEQ ID NO 632
<211> LENGTH: 24
<212> TYPE: PRT
<213> ORGANISM: Human immunodeficiency virus 1

<400> SEQUENCE: 632

Ala Ala Met Gln Met Leu Lys Asp Thr Ile Asn Glu Glu Ala Ala Glu
1               5                   10                  15

Trp Asp Arg Leu His Pro Val His
            20

<210> SEQ ID NO 633
<211> LENGTH: 25
<212> TYPE: PRT
<213> ORGANISM: Human immunodeficiency virus 1

<400> SEQUENCE: 633

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 634
<211> LENGTH: 26
<212> TYPE: PRT
<213> ORGANISM: Human immunodeficiency virus 1

<400> SEQUENCE: 634

Asp Arg Phe Phe Lys Thr Leu Arg Ala Glu Gln Ala Thr Gln Glu Val
1               5                   10                  15

Lys Asn Trp Met Thr Glu Thr Leu Leu Val
            20                  25

<210> SEQ ID NO 635
<211> LENGTH: 24
<212> TYPE: PRT
<213> ORGANISM: Human immunodeficiency virus 1

<400> SEQUENCE: 635

Ala Ala Met Gln Met Leu Lys Asp Thr Ile Asn Glu Glu Ala Ala Glu
1               5                   10                  15

Trp Asp Arg Val His Pro Val His
            20

<210> SEQ ID NO 636
<211> LENGTH: 25
<212> TYPE: PRT
<213> ORGANISM: Human immunodeficiency virus 1

<400> SEQUENCE: 636

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 637
<211> LENGTH: 26
<212> TYPE: PRT
<213> ORGANISM: Human immunodeficiency virus 1

<400> SEQUENCE: 637

Asp Arg Phe Phe Lys Ala Leu Arg Ala Glu Gln Ala Thr Gln Asp Val
1               5                   10                  15

Lys Asn Trp Met Thr Asp Thr Leu Leu Val
            20                  25

<210> SEQ ID NO 638
<211> LENGTH: 24
<212> TYPE: PRT
<213> ORGANISM: Human immunodeficiency virus 1

<400> SEQUENCE: 638

Ala Ala Met Gln Met Leu Lys Asp Thr Ile Asn Glu Glu Ala Ala Glu
1               5                   10                  15

Trp Asp Arg Val His Pro Val His
            20

<210> SEQ ID NO 639
<211> LENGTH: 25
<212> TYPE: PRT
<213> ORGANISM: Human immunodeficiency virus 1

<400> SEQUENCE: 639

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 640
<211> LENGTH: 26
<212> TYPE: PRT
<213> ORGANISM: Human immunodeficiency virus 1

<400> SEQUENCE: 640

Asp Arg Phe Phe Lys Ala Leu Arg Ala Glu Gln Ala Thr Gln Asp Val
1               5                   10                  15

Lys Asn Trp Met Thr Asp Thr Leu Leu Val
            20                  25

<210> SEQ ID NO 641
<211> LENGTH: 24
<212> TYPE: PRT
<213> ORGANISM: Human immunodeficiency virus 1

<400> SEQUENCE: 641

Ala Ala Met Gln Met Leu Lys Asp Thr Ile Asn Glu Glu Ala Ala Glu
1               5                   10                  15

Trp Asp Arg Met His Pro Gln Gln
            20

<210> SEQ ID NO 642
<211> LENGTH: 25
<212> TYPE: PRT
<213> ORGANISM: Human immunodeficiency virus 1

<400> SEQUENCE: 642

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 643
<211> LENGTH: 26
<212> TYPE: PRT
<213> ORGANISM: Human immunodeficiency virus 1

<400> SEQUENCE: 643

Asp Arg Phe Phe Lys Cys Leu Arg Ala Glu Gln Ala Ser Gln Asp Val

Lys Gly Trp Met Thr Asp Thr Leu Leu Val
            20                  25

<210> SEQ ID NO 644
<211> LENGTH: 24
<212> TYPE: PRT
<213> ORGANISM: Human immunodeficiency virus 1

<400> SEQUENCE: 644

Ala Ala Met Gln Met Leu Lys Asp Thr Ile Asn Glu Glu Ala Ala Glu
1               5                   10                  15

Trp Asp Arg Leu His Pro Val His
            20

<210> SEQ ID NO 645
<211> LENGTH: 25
<212> TYPE: PRT
<213> ORGANISM: Human immunodeficiency virus 1

<400> SEQUENCE: 645

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 646
<211> LENGTH: 26
<212> TYPE: PRT
<213> ORGANISM: Human immunodeficiency virus 1

<400> SEQUENCE: 646

Asp Arg Phe Phe Lys Thr Leu Arg Ala Glu Gln Ala Thr Gln Asp Val
1               5                   10                  15

Lys Asn Trp Met Thr Glu Thr Leu Leu Val
            20                  25

<210> SEQ ID NO 647
<211> LENGTH: 24
<212> TYPE: PRT
<213> ORGANISM: Human immunodeficiency virus 1

<400> SEQUENCE: 647

Ala Ala Met Gln Met Leu Lys Asp Thr Ile Asn Glu Glu Ala Ala Glu
1               5                   10                  15

Trp Asp Arg Leu His Pro Val His
            20

<210> SEQ ID NO 648
<211> LENGTH: 25
<212> TYPE: PRT
<213> ORGANISM: Human immunodeficiency virus 1

<400> SEQUENCE: 648

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 649
<211> LENGTH: 26
<212> TYPE: PRT

<213> ORGANISM: Human immunodeficiency virus 1

<400> SEQUENCE: 649

Asp Arg Phe Phe Arg Val Leu Arg Ala Glu Gln Ala Thr Gln Asp Val
1               5                   10                  15

Lys Asn Trp Met Thr Asp Thr Leu Leu Val
            20                  25

<210> SEQ ID NO 650
<211> LENGTH: 24
<212> TYPE: PRT
<213> ORGANISM: Human immunodeficiency virus 1

<400> SEQUENCE: 650

Ala Ala Met Gln Met Leu Lys Asp Thr Ile Asn Glu Glu Ala Ala Glu
1               5                   10                  15

Trp Asp Arg Leu His Pro Val His
            20

<210> SEQ ID NO 651
<211> LENGTH: 25
<212> TYPE: PRT
<213> ORGANISM: Human immunodeficiency virus 1

<400> SEQUENCE: 651

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 652
<211> LENGTH: 26
<212> TYPE: PRT
<213> ORGANISM: Human immunodeficiency virus 1

<400> SEQUENCE: 652

Asp Arg Phe Phe Lys Val Leu Arg Ala Glu Gln Ala Ser Gln Asp Val
1               5                   10                  15

Lys Gly Trp Met Thr Asp Thr Leu Leu Val
            20                  25

<210> SEQ ID NO 653
<211> LENGTH: 24
<212> TYPE: PRT
<213> ORGANISM: Human immunodeficiency virus 1

<400> SEQUENCE: 653

Ala Ala Met Gln Met Leu Lys Glu Thr Ile Asn Asp Glu Ala Ala Glu
1               5                   10                  15

Trp Asp Arg Leu His Pro Val His
            20

<210> SEQ ID NO 654
<211> LENGTH: 25
<212> TYPE: PRT
<213> ORGANISM: Human immunodeficiency virus 1

<400> SEQUENCE: 654

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 655
<211> LENGTH: 26
<212> TYPE: PRT
<213> ORGANISM: Human immunodeficiency virus 1

<400> SEQUENCE: 655

Asp Arg Phe Tyr Lys Thr Leu Arg Ala Glu Gln Ala Ser Gln Asp Val
1               5                   10                  15

Lys Asn Trp Met Thr Glu Thr Leu Leu Val
            20                  25

<210> SEQ ID NO 656
<211> LENGTH: 24
<212> TYPE: PRT
<213> ORGANISM: Human immunodeficiency virus 1

<400> SEQUENCE: 656

Ala Ala Met Gln Met Leu Lys Glu Thr Ile Asn Glu Glu Ala Ala Glu
1               5                   10                  15

Trp Asp Arg Val His Pro Val His
            20

<210> SEQ ID NO 657
<211> LENGTH: 25
<212> TYPE: PRT
<213> ORGANISM: Human immunodeficiency virus 1

<400> SEQUENCE: 657

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 658
<211> LENGTH: 26
<212> TYPE: PRT
<213> ORGANISM: Human immunodeficiency virus 1

<400> SEQUENCE: 658

Asp Arg Phe Tyr Lys Thr Leu Arg Ala Glu Gln Ala Ser Gln Asp Val
1               5                   10                  15

Lys Asn Trp Met Thr Glu Thr Leu Leu Val
            20                  25

<210> SEQ ID NO 659
<211> LENGTH: 24
<212> TYPE: PRT
<213> ORGANISM: Human immunodeficiency virus 1

<400> SEQUENCE: 659

Ala Ala Met Gln Met Leu Lys Glu Thr Ile Asn Glu Glu Ala Ala Glu
1               5                   10                  15

Trp Asp Arg Val His Pro Val His
            20

<210> SEQ ID NO 660
<211> LENGTH: 25
<212> TYPE: PRT
<213> ORGANISM: Human immunodeficiency virus 1

<400> SEQUENCE: 660

```
Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25
```

<210> SEQ ID NO 661
<211> LENGTH: 26
<212> TYPE: PRT
<213> ORGANISM: Human immunodeficiency virus 1

<400> SEQUENCE: 661

```
Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25
```

<210> SEQ ID NO 662
<211> LENGTH: 24
<212> TYPE: PRT
<213> ORGANISM: Human immunodeficiency virus 1

<400> SEQUENCE: 662

```
Ala Ala Met Gln Met Leu Lys Glu Thr Ile Asn Glu Glu Ala Ala Glu
1               5                   10                  15

Trp Asp Arg Val His Pro Val His
            20
```

<210> SEQ ID NO 663
<211> LENGTH: 25
<212> TYPE: PRT
<213> ORGANISM: Human immunodeficiency virus 1

<400> SEQUENCE: 663

```
Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25
```

<210> SEQ ID NO 664
<211> LENGTH: 26
<212> TYPE: PRT
<213> ORGANISM: Human immunodeficiency virus 1

<400> SEQUENCE: 664

```
Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25
```

<210> SEQ ID NO 665
<211> LENGTH: 24
<212> TYPE: PRT
<213> ORGANISM: Human immunodeficiency virus 1

<400> SEQUENCE: 665

```
Ala Ala Met Gln Met Leu Lys Glu Thr Ile Asn Glu Glu Ala Ala Glu
1               5                   10                  15

Trp Asp Arg Leu His Pro Val Gln
            20
```

<210> SEQ ID NO 666
<211> LENGTH: 25

```
<212> TYPE: PRT
<213> ORGANISM: Human immunodeficiency virus 1

<400> SEQUENCE: 666

Ile Ile Leu Gly Leu Asn Lys Ile Val Arg Met Tyr Ser Pro Ser Ser
1               5                   10                  15

Ile Leu Asp Ile Lys Gln Gly Pro Lys
            20                  25

<210> SEQ ID NO 667
<211> LENGTH: 26
<212> TYPE: PRT
<213> ORGANISM: Human immunodeficiency virus 1

<400> SEQUENCE: 667

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 668
<211> LENGTH: 24
<212> TYPE: PRT
<213> ORGANISM: Human immunodeficiency virus 1

<400> SEQUENCE: 668

Ala Ala Met Gln Met Leu Lys Glu Thr Ile Asn Glu Glu Ala Ala Glu
1               5                   10                  15

Trp Asp Arg Val His Pro Val His
            20

<210> SEQ ID NO 669
<211> LENGTH: 25
<212> TYPE: PRT
<213> ORGANISM: Human immunodeficiency virus 1

<400> SEQUENCE: 669

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 670
<211> LENGTH: 26
<212> TYPE: PRT
<213> ORGANISM: Human immunodeficiency virus 1

<400> SEQUENCE: 670

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 671
<211> LENGTH: 24
<212> TYPE: PRT
<213> ORGANISM: Human immunodeficiency virus 1

<400> SEQUENCE: 671

Ala Ala Met Gln Met Leu Lys Glu Thr Ile Asn Glu Glu Ala Ala Glu
1               5                   10                  15

Trp Asp Arg Leu His Pro Val His
```

<210> SEQ ID NO 672
<211> LENGTH: 25
<212> TYPE: PRT
<213> ORGANISM: Human immunodeficiency virus 1

<400> SEQUENCE: 672

Ile Ile Leu Gly Leu Asn Lys Ile Val Arg Met Tyr Ser Pro Ile Ser
1               5                   10                  15

Ile Leu Asp Ile Lys Gln Gly Pro Lys
            20                  25

<210> SEQ ID NO 673
<211> LENGTH: 26
<212> TYPE: PRT
<213> ORGANISM: Human immunodeficiency virus 1

<400> SEQUENCE: 673

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 674
<211> LENGTH: 24
<212> TYPE: PRT
<213> ORGANISM: Human immunodeficiency virus 1

<400> SEQUENCE: 674

Ala Ala Met Gln Met Leu Lys Glu Thr Ile Asn Glu Glu Ala Ala Glu
1               5                   10                  15

Trp Asp Arg Leu His Pro Val His
            20

<210> SEQ ID NO 675
<211> LENGTH: 25
<212> TYPE: PRT
<213> ORGANISM: Human immunodeficiency virus 1

<400> SEQUENCE: 675

Ile Ile Val Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 676
<211> LENGTH: 26
<212> TYPE: PRT
<213> ORGANISM: Human immunodeficiency virus 1

<400> SEQUENCE: 676

Asp Arg Phe Tyr Lys Thr Leu Arg Ala Glu Gln Ala Ser Gln Asp Val
1               5                   10                  15

Lys Asn Trp Met Thr Glu Thr Leu Leu Val
            20                  25

<210> SEQ ID NO 677
<211> LENGTH: 24
<212> TYPE: PRT
<213> ORGANISM: Human immunodeficiency virus 1

<400> SEQUENCE: 677

-continued

Ala Ala Met Gln Met Leu Lys Glu Thr Ile Asn Glu Glu Ala Ala Glu
1               5                   10                  15

Trp Asp Arg Val His Pro Val His
            20

<210> SEQ ID NO 678
<211> LENGTH: 25
<212> TYPE: PRT
<213> ORGANISM: Human immunodeficiency virus 1

<400> SEQUENCE: 678

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 679
<211> LENGTH: 26
<212> TYPE: PRT
<213> ORGANISM: Human immunodeficiency virus 1

<400> SEQUENCE: 679

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 680
<211> LENGTH: 24
<212> TYPE: PRT
<213> ORGANISM: Human immunodeficiency virus 1

<400> SEQUENCE: 680

Ala Ala Met Gln Met Leu Lys Glu Thr Ile Asn Glu Glu Ala Ala Glu
1               5                   10                  15

Trp Asp Arg Leu His Pro Ala Gln
            20

<210> SEQ ID NO 681
<211> LENGTH: 25
<212> TYPE: PRT
<213> ORGANISM: Human immunodeficiency virus 1

<400> SEQUENCE: 681

Ile Ile Leu Gly Leu Asn Lys Ile Val Arg Met Tyr Ser Pro Ser Ser
1               5                   10                  15

Ile Leu Asp Ile Lys Gln Gly Pro Lys
            20                  25

<210> SEQ ID NO 682
<211> LENGTH: 26
<212> TYPE: PRT
<213> ORGANISM: Human immunodeficiency virus 1

<400> SEQUENCE: 682

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 683

```
<211> LENGTH: 24
<212> TYPE: PRT
<213> ORGANISM: Human immunodeficiency virus 1

<400> SEQUENCE: 683

Ala Ala Met Gln Met Leu Lys Glu Thr Ile Asn Glu Glu Ala Ala Glu
1               5                   10                  15

Trp Asp Arg Leu His Pro Val His
            20

<210> SEQ ID NO 684
<211> LENGTH: 25
<212> TYPE: PRT
<213> ORGANISM: Human immunodeficiency virus 1

<400> SEQUENCE: 684

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 685
<211> LENGTH: 26
<212> TYPE: PRT
<213> ORGANISM: Human immunodeficiency virus 1

<400> SEQUENCE: 685

Asp Arg Phe Tyr Lys Thr Leu Arg Ala Glu Gln Ala Thr Gln Glu Val
1               5                   10                  15

Lys Asn Trp Met Thr Glu Thr Leu Leu Val
            20                  25

<210> SEQ ID NO 686
<211> LENGTH: 24
<212> TYPE: PRT
<213> ORGANISM: Human immunodeficiency virus 1

<400> SEQUENCE: 686

Ala Ala Met Gln Met Leu Lys Glu Thr Ile Asn Glu Glu Ala Ala Glu
1               5                   10                  15

Trp Asp Arg Val His Pro Val His
            20

<210> SEQ ID NO 687
<211> LENGTH: 25
<212> TYPE: PRT
<213> ORGANISM: Human immunodeficiency virus 1

<400> SEQUENCE: 687

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 688
<211> LENGTH: 26
<212> TYPE: PRT
<213> ORGANISM: Human immunodeficiency virus 1

<400> SEQUENCE: 688

Asp Arg Phe Tyr Lys Thr Leu Arg Ala Glu Gln Ala Ser Gln Glu Val
1               5                   10                  15
```

```
Lys Asn Trp Met Thr Glu Thr Leu Leu Val
            20                  25

<210> SEQ ID NO 689
<211> LENGTH: 24
<212> TYPE: PRT
<213> ORGANISM: Human immunodeficiency virus 1

<400> SEQUENCE: 689

Ala Ala Met Gln Met Leu Lys Glu Thr Ile Asn Glu Glu Ala Ala Glu
1               5                   10                  15

Trp Asp Arg Leu His Pro Ala His
            20

<210> SEQ ID NO 690
<211> LENGTH: 25
<212> TYPE: PRT
<213> ORGANISM: Human immunodeficiency virus 1

<400> SEQUENCE: 690

Ile Ile Leu Gly Leu Asn Lys Ile Val Arg Met Tyr Ser Pro Ser Ser
1               5                   10                  15

Ile Leu Asp Ile Lys Gln Gly Pro Lys
            20                  25

<210> SEQ ID NO 691
<211> LENGTH: 26
<212> TYPE: PRT
<213> ORGANISM: Human immunodeficiency virus 1

<400> SEQUENCE: 691

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 692
<211> LENGTH: 24
<212> TYPE: PRT
<213> ORGANISM: Human immunodeficiency virus 1

<400> SEQUENCE: 692

Ala Ala Met Gln Met Leu Lys Glu Thr Ile Asn Glu Glu Ala Ala Glu
1               5                   10                  15

Trp Asp Arg Leu His Pro Val His
            20

<210> SEQ ID NO 693
<211> LENGTH: 25
<212> TYPE: PRT
<213> ORGANISM: Human immunodeficiency virus 1

<400> SEQUENCE: 693

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 694
<211> LENGTH: 26
<212> TYPE: PRT
<213> ORGANISM: Human immunodeficiency virus 1
```

```
<400> SEQUENCE: 694

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 695
<211> LENGTH: 24
<212> TYPE: PRT
<213> ORGANISM: Human immunodeficiency virus 1

<400> SEQUENCE: 695

Ala Ala Met Gln Met Leu Lys Glu Thr Ile Asn Glu Glu Ala Ala Glu
1               5                   10                  15

Trp Asp Arg Leu His Pro Val His
            20

<210> SEQ ID NO 696
<211> LENGTH: 25
<212> TYPE: PRT
<213> ORGANISM: Human immunodeficiency virus 1

<400> SEQUENCE: 696

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 697
<211> LENGTH: 26
<212> TYPE: PRT
<213> ORGANISM: Human immunodeficiency virus 1

<400> SEQUENCE: 697

Asp Arg Phe Tyr Lys Thr Leu Arg Ala Glu Gln Ala Ser Gln Asp Val
1               5                   10                  15

Lys Asn Trp Met Thr Glu Thr Leu Leu Val
            20                  25

<210> SEQ ID NO 698
<211> LENGTH: 24
<212> TYPE: PRT
<213> ORGANISM: Human immunodeficiency virus 1

<400> SEQUENCE: 698

Ala Ala Met Gln Met Leu Lys Glu Thr Ile Asn Glu Glu Ala Ala Glu
1               5                   10                  15

Trp Asp Arg Leu His Pro Val His
            20

<210> SEQ ID NO 699
<211> LENGTH: 25
<212> TYPE: PRT
<213> ORGANISM: Human immunodeficiency virus 1

<400> SEQUENCE: 699

Ile Ile Leu Gly Leu Asn Lys Ile Val Arg Met Tyr Ser Pro Ile Ser
1               5                   10                  15

Ile Leu Asp Ile Lys Gln Gly Pro Lys
            20                  25
```

<210> SEQ ID NO 700
<211> LENGTH: 26
<212> TYPE: PRT
<213> ORGANISM: Human immunodeficiency virus 1

<400> SEQUENCE: 700

Asp Arg Phe Tyr Lys Thr Leu Arg Ala Glu Gln Ala Ser Gln Asp Val
1               5                   10                  15
Lys Asn Trp Met Thr Glu Thr Phe Leu Val
            20                  25

<210> SEQ ID NO 701
<211> LENGTH: 24
<212> TYPE: PRT
<213> ORGANISM: Human immunodeficiency virus 1

<400> SEQUENCE: 701

Ala Ala Met Gln Met Leu Lys Glu Thr Ile Asn Glu Glu Ala Ala Glu
1               5                   10                  15
Trp Asp Arg Leu His Pro Val His
            20

<210> SEQ ID NO 702
<211> LENGTH: 25
<212> TYPE: PRT
<213> ORGANISM: Human immunodeficiency virus 1

<400> SEQUENCE: 702

Ile Ile Leu Gly Leu Asn Lys Ile Val Arg Met Tyr Ser Pro Thr Ser
1               5                   10                  15
Ile Leu Asp Ile Lys Gln Gly Pro Lys
            20                  25

<210> SEQ ID NO 703
<211> LENGTH: 26
<212> TYPE: PRT
<213> ORGANISM: Human immunodeficiency virus 1

<400> SEQUENCE: 703

Asp Arg Phe Tyr Lys Thr Leu Arg Ala Glu Gln Ala Thr Gln Glu Val
1               5                   10                  15
Lys Asn Trp Met Thr Glu Thr Leu Leu Val
            20                  25

<210> SEQ ID NO 704
<211> LENGTH: 24
<212> TYPE: PRT
<213> ORGANISM: Human immunodeficiency virus 1

<400> SEQUENCE: 704

Ala Ala Met Gln Met Leu Lys Glu Thr Ile Asn Glu Glu Ala Ala Glu
1               5                   10                  15
Trp Asp Arg Leu His Pro Val His
            20

<210> SEQ ID NO 705
<211> LENGTH: 25
<212> TYPE: PRT
<213> ORGANISM: Human immunodeficiency virus 1

<400> SEQUENCE: 705

Ile Ile Leu Gly Leu Asn Lys Ile Val Arg Met Tyr Ser Pro Thr Ser
1               5                   10                  15

Ile Leu Asp Ile Lys Gln Gly Pro Lys
            20                  25

<210> SEQ ID NO 706
<211> LENGTH: 26
<212> TYPE: PRT
<213> ORGANISM: Human immunodeficiency virus 1

<400> SEQUENCE: 706

Asp Arg Phe Tyr Lys Thr Leu Arg Ala Glu Gln Ala Ser Gln Glu Val
1               5                   10                  15

Lys Asn Trp Met Thr Glu Thr Leu Leu Val
            20                  25

<210> SEQ ID NO 707
<211> LENGTH: 24
<212> TYPE: PRT
<213> ORGANISM: Human immunodeficiency virus 1

<400> SEQUENCE: 707

Ala Ala Met Gln Met Leu Lys Glu Thr Ile Asn Glu Glu Ala Ala Glu
1               5                   10                  15

Trp Asp Arg Leu His Pro Val His
            20

<210> SEQ ID NO 708
<211> LENGTH: 25
<212> TYPE: PRT
<213> ORGANISM: Human immunodeficiency virus 1

<400> SEQUENCE: 708

Ile Ile Leu Gly Leu Asn Lys Ile Val Arg Met Tyr Ser Pro Val Ser
1               5                   10                  15

Ile Leu Asp Ile Lys Gln Gly Pro Lys
            20                  25

<210> SEQ ID NO 709
<211> LENGTH: 26
<212> TYPE: PRT
<213> ORGANISM: Human immunodeficiency virus 1

<400> SEQUENCE: 709

Asp Arg Phe Tyr Lys Thr Leu Arg Ala Glu Gln Ala Ser Gln Glu Val
1               5                   10                  15

Lys Gly Trp Met Thr Glu Thr Leu Leu Val
            20                  25

<210> SEQ ID NO 710
<211> LENGTH: 24
<212> TYPE: PRT
<213> ORGANISM: Human immunodeficiency virus 1

<400> SEQUENCE: 710

Ala Ala Met Gln Met Leu Lys Glu Val Ile Asn Glu Glu Ala Ala Asp
1               5                   10                  15

Trp Asp Arg Thr His Pro Val Pro
            20

<210> SEQ ID NO 711
<211> LENGTH: 25
<212> TYPE: PRT
<213> ORGANISM: Human immunodeficiency virus 1

```
<400> SEQUENCE: 711

Ile Val Leu Gly Leu Asn Arg Ile Val Arg Met Tyr Ser Pro Val Ser
1               5                   10                  15

Ile Leu Glu Ile Lys Gln Gly Pro Lys
            20                  25

<210> SEQ ID NO 712
<211> LENGTH: 26
<212> TYPE: PRT
<213> ORGANISM: Human immunodeficiency virus 1

<400> SEQUENCE: 712

Asp Arg Phe Tyr Lys Thr Leu Arg Ala Glu Gln Ala Thr Gln Glu Val
1               5                   10                  15

Lys Asn Trp Met Thr Glu Thr Leu Leu Val
            20                  25

<210> SEQ ID NO 713
<211> LENGTH: 24
<212> TYPE: PRT
<213> ORGANISM: Human immunodeficiency virus 1

<400> SEQUENCE: 713

Gly Ala Leu Gln Val Leu Lys Glu Val Ile Asn Glu Glu Ala Ala Glu
1               5                   10                  15

Trp Asp Arg Thr His Pro Pro Ala
            20

<210> SEQ ID NO 714
<211> LENGTH: 25
<212> TYPE: PRT
<213> ORGANISM: Human immunodeficiency virus 1

<400> SEQUENCE: 714

Ile Val Leu Gly Leu Asn Lys Met Val Lys Met Tyr Ser Pro Val Ser
1               5                   10                  15

Ile Leu Asp Ile Lys Gln Gly Pro Lys
            20                  25

<210> SEQ ID NO 715
<211> LENGTH: 26
<212> TYPE: PRT
<213> ORGANISM: Human immunodeficiency virus 1

<400> SEQUENCE: 715

Asp Arg Phe Tyr Lys Thr Leu Arg Ala Glu Gln Ala Thr Gln Glu Val
1               5                   10                  15

Lys Asn Trp Met Thr Glu Thr Leu Leu Val
            20                  25

<210> SEQ ID NO 716
<211> LENGTH: 24
<212> TYPE: PRT
<213> ORGANISM: Human immunodeficiency virus 1

<400> SEQUENCE: 716

Ala Ala Met Gln Met Leu Lys Glu Val Ile Asn Glu Glu Ala Ala Glu
1               5                   10                  15

Trp Asp Arg Thr His Pro Ala Pro
            20
```

<210> SEQ ID NO 717
<211> LENGTH: 25
<212> TYPE: PRT
<213> ORGANISM: Human immunodeficiency virus 1

<400> SEQUENCE: 717

Ile Val Leu Gly Leu Asn Arg Ile Val Arg Met Tyr Ser Pro Val Ser
1               5                   10                  15

Ile Leu Glu Ile Lys Gln Gly Pro Lys
            20                  25

<210> SEQ ID NO 718
<211> LENGTH: 26
<212> TYPE: PRT
<213> ORGANISM: Human immunodeficiency virus 1

<400> SEQUENCE: 718

Asp Arg Phe Tyr Lys Thr Leu Arg Ala Glu Gln Ala Thr Gln Asp Val
1               5                   10                  15

Lys Asn Trp Met Thr Glu Thr Leu Leu Val
            20                  25

<210> SEQ ID NO 719
<211> LENGTH: 24
<212> TYPE: PRT
<213> ORGANISM: Human immunodeficiency virus 1

<400> SEQUENCE: 719

Gly Ala Leu Gln Val Leu Lys Glu Val Ile Asn Glu Glu Ala Val Glu
1               5                   10                  15

Trp Asp Arg Thr His Pro Pro Pro
            20

<210> SEQ ID NO 720
<211> LENGTH: 25
<212> TYPE: PRT
<213> ORGANISM: Human immunodeficiency virus 1

<400> SEQUENCE: 720

Ile Val Leu Gly Leu Asn Lys Met Val Lys Met Tyr Ser Pro Val Ser
1               5                   10                  15

Ile Leu Asp Ile Lys Gln Gly Pro Lys
            20                  25

<210> SEQ ID NO 721
<211> LENGTH: 26
<212> TYPE: PRT
<213> ORGANISM: Human immunodeficiency virus 1

<400> SEQUENCE: 721

Asp Arg Phe Tyr Lys Thr Leu Arg Ala Glu Gln Ala Thr Gln Glu Val
1               5                   10                  15

Lys Asn Trp Met Thr Glu Thr Leu Leu Val
            20                  25

<210> SEQ ID NO 722
<211> LENGTH: 24
<212> TYPE: PRT
<213> ORGANISM: Human immunodeficiency virus 2

<400> SEQUENCE: 722

Ala Ala Met Gln Ile Ile Arg Glu Ile Ile Asn Glu Glu Ala Ala Asp

```
1               5                   10                  15

Trp Asp Ala Asn His Pro Ile Pro
            20
```

<210> SEQ ID NO 723
<211> LENGTH: 25
<212> TYPE: PRT
<213> ORGANISM: Human immunodeficiency virus 2

<400> SEQUENCE: 723

```
Ile Gln Ile Gly Leu Gln Lys Cys Val Arg Met Tyr Asn Pro Thr Asn
1               5                   10                  15

Ile Leu Asp Ile Lys Gln Gly Pro Lys
            20                  25
```

<210> SEQ ID NO 724
<211> LENGTH: 26
<212> TYPE: PRT
<213> ORGANISM: Human immunodeficiency virus 2

<400> SEQUENCE: 724

```
Asp Arg Phe Tyr Lys Ser Leu Arg Ala Glu Gln Thr Asp Pro Ala Val
1               5                   10                  15

Lys Asn Trp Met Thr Gln Thr Leu Leu Val
            20                  25
```

<210> SEQ ID NO 725
<211> LENGTH: 24
<212> TYPE: PRT
<213> ORGANISM: Human immunodeficiency virus 2

<400> SEQUENCE: 725

```
Ala Ala Met Gln Ile Ile Arg Glu Ile Ile Asn Glu Glu Ala Ala Asp
1               5                   10                  15

Trp Asp Gln Gln His Pro Ser Pro
            20
```

<210> SEQ ID NO 726
<211> LENGTH: 25
<212> TYPE: PRT
<213> ORGANISM: Human immunodeficiency virus 2

<400> SEQUENCE: 726

```
Ile Gln Leu Gly Leu Gln Lys Cys Val Arg Met Tyr Asn Pro Thr Asn
1               5                   10                  15

Ile Leu Asp Ile Lys Gln Gly Pro Lys
            20                  25
```

<210> SEQ ID NO 727
<211> LENGTH: 26
<212> TYPE: PRT
<213> ORGANISM: Human immunodeficiency virus 2

<400> SEQUENCE: 727

```
Asp Arg Phe Tyr Lys Ser Leu Arg Ala Glu Gln Thr Asp Pro Ala Val
1               5                   10                  15

Lys Asn Trp Met Thr Gln Thr Leu Leu Ile
            20                  25
```

<210> SEQ ID NO 728
<211> LENGTH: 24
<212> TYPE: PRT

```
<213> ORGANISM: Human immunodeficiency virus 2

<400> SEQUENCE: 728

Ala Ala Met Gln Ile Ile Arg Glu Ile Ile Asn Glu Glu Ala

<210> SEQ ID NO 734
<211> LENGTH: 24
<212> TYPE: PRT
<213> ORGANISM: Human immunodeficiency virus 2

<400> SEQUENCE: 734

Ala Ala Met Gln Ile Ile Arg Glu Ile Ile Asn Glu Glu Ala Ala Asp
1               5                   10                  15

Trp Asp Val Gln His Pro Ile Pro
            20

<210> SEQ ID NO 735
<211> LENGTH: 25
<212> TYPE: PRT
<213> ORGANISM: Human immunodeficiency virus 2

<400> SEQUENCE: 735

Ile Gln Ile Gly Leu Gln Lys Cys Val Arg Met Tyr Asn Pro Thr Asn
1               5                   10                  15

Ile Leu Asp Ile Lys Gln Gly Pro Lys
            20                  25

<210> SEQ ID NO 736
<211> LENGTH: 26
<212> TYPE: PRT
<213> ORGANISM: Human immunodeficiency virus 2

<400> SEQUENCE: 736

Asp Arg Phe Tyr Lys Ser Leu Arg Ala Glu Gln Thr Asp Ala Ala Val
1               5                   10                  15

Lys Asn Trp Met Thr Gln Thr Leu Leu Val
            20                  25

<210> SEQ ID NO 737
<211> LENGTH: 24
<212> TYPE: PRT
<213> ORGANISM: Human immunodeficiency virus 2

<400> SEQUENCE: 737

Ala Ala Met Gln Ile Ile Arg Glu Ile Ile Asn Glu Glu Ala Ala Asp
1               5                   10                  15

Trp Asp Ala Gln His Pro Ile Pro
            20

<210> SEQ ID NO 738
<211> LENGTH: 25
<212> TYPE: PRT
<213> ORGANISM: Human immunodeficiency virus 2

<400> SEQUENCE: 738

Ile Gln Ile Gly Leu Gln Lys Cys Val Arg Met Tyr Asn Pro Thr Asn
1               5                   10                  15

Ile Leu Asp Ile Lys Gln Gly Pro Lys
            20                  25

<210> SEQ ID NO 739
<211> LENGTH: 26
<212> TYPE: PRT
<213> ORGANISM: Human immunodeficiency virus 2

<400> SEQUENCE: 739

-continued

Asp Arg Phe Tyr Lys Ser Leu Arg Ala Glu Gln Thr Asp Pro Ala Val
1               5                   10                  15

Lys Asn Trp Met Thr Gln Thr Leu Leu Val
            20                  25

<210> SEQ ID NO 740
<211> LENGTH: 24
<212> TYPE: PRT
<213> ORGANISM: Human immunodeficiency virus 2

<400> SEQUENCE: 740

Ala Ala Met Gln Ile Ile Arg Glu Ile Ile Asn Glu Glu Ala Ala Asp
1               5                   10                  15

Trp Asp Gln Gln His Pro Ile Pro
            20

<210> SEQ ID NO 741
<211> LENGTH: 25
<212> TYPE: PRT
<213> ORGANISM: Human immunodeficiency virus 2

<400> SEQUENCE: 741

Ile Gln Ile Gly Leu Gln Lys Cys Val Arg Met Tyr Asn Pro Thr Asn
1               5                   10                  15

Ile Leu Asp Ile Lys Gln Gly Pro Lys
            20                  25

<210> SEQ ID NO 742
<211> LENGTH: 26
<212> TYPE: PRT
<213> ORGANISM: Human immunodeficiency virus 2

<400> SEQUENCE: 742

Asp Arg Phe Tyr Lys Ser Leu Arg Ala Glu Gln Thr Asp Pro Ala Val
1               5                   10                  15

Lys Asn Trp Met Thr Gln Thr Leu Leu Ile
            20                  25

<210> SEQ ID NO 743
<211> LENGTH: 24
<212> TYPE: PRT
<213> ORGANISM: Human immunodeficiency virus 2

<400> SEQUENCE: 743

Ala Ala Met Gln Ile Ile Arg Glu Ile Ile Asn Glu Glu Ala Ala Asp
1               5                   10                  15

Trp Asp Val Ala His Pro Ile Pro
            20

<210> SEQ ID NO 744
<211> LENGTH: 25
<212> TYPE: PRT
<213> ORGANISM: Human immunodeficiency virus 2

<400> SEQUENCE: 744

Ile Gln Ile Gly Leu Gln Lys Cys Val Arg Met Tyr Asn Pro Thr Asn
1               5                   10                  15

Ile Leu Asp Ile Lys Gln Gly Pro Lys
            20                  25

<210> SEQ ID NO 745
<211> LENGTH: 26

```
<212> TYPE: PRT
<213> ORGANISM: Human immunodeficiency virus 2

<400> SEQUENCE: 745

Asp Arg Phe Tyr Lys Ser Leu Arg Ala Glu Gln Thr Asp Pro Ala Val
1               5                   10                  15

Lys Asn Trp Met Thr Gln Thr Leu Leu Ile
            20                  25

<210> SEQ ID NO 746
<211> LENGTH: 24
<212> TYPE: PRT
<213> ORGANISM: Human immunodeficiency virus 2

<400> SEQUENCE: 746

Ala Ala Met Gln Ile Ile Arg Glu Ile Ile Asn Glu Glu Ala Ala Asp
1               5                   10                  15

Trp Asp Ala Gln His Pro Ile Pro
            20

<210> SEQ ID NO 747
<211> LENGTH: 25
<212> TYPE: PRT
<213> ORGANISM: Human immunodeficiency virus 2

<400> SEQUENCE: 747

Ile Gln Ile Gly Leu Gln Lys Cys Val Arg Met Tyr Asn Pro Thr Asn
1               5                   10                  15

Ile Leu Asp Val Lys Gln Gly Pro Lys
            20                  25

<210> SEQ ID NO 748
<211> LENGTH: 26
<212> TYPE: PRT
<213> ORGANISM: Human immunodeficiency virus 2

<400> SEQUENCE: 748

Asp Arg Phe Tyr Lys Ser Leu Arg Ala Glu Gln Thr Asp Pro Ala Val
1               5                   10                  15

Lys Asn Trp Met Thr Gln Thr Leu Leu Ile
            20                  25

<210> SEQ ID NO 749
<211> LENGTH: 24
<212> TYPE: PRT
<213> ORGANISM: Human immunodeficiency virus 2

<400> SEQUENCE: 749

Ala Ala Met Gln Ile Ile Arg Glu Ile Ile Asn Asp Glu Ala Ala Asp
1               5                   10                  15

Trp Asp Ala Gln His Pro Ile Pro
            20

<210> SEQ ID NO 750
<211> LENGTH: 25
<212> TYPE: PRT
<213> ORGANISM: Human immunodeficiency virus 2

<400> SEQUENCE: 750

Ile Gln Ile Gly Leu Gln Lys Cys Val Arg Met Tyr Asn Pro Thr Asn
1               5                   10                  15

Ile Leu Asp Val Lys Gln Gly Pro Lys
```

<210> SEQ ID NO 751
<211> LENGTH: 26
<212> TYPE: PRT
<213> ORGANISM: Human immunodeficiency virus 2

<400> SEQUENCE: 751

Asp Arg Phe Tyr Lys Ser Leu Arg Ala Glu Gln Thr Asp Pro Ala Val
1               5                   10                  15
Lys Asn Trp Met Thr Gln Thr Leu Leu Ile
            20                  25

<210> SEQ ID NO 752
<211> LENGTH: 24
<212> TYPE: PRT
<213> ORGANISM: Human immunodeficiency virus 2

<400> SEQUENCE: 752

Ala Ala Met Gln Ile Ile Arg Glu Ile Ile Asn Glu Glu Ala Ala Asp
1               5                   10                  15
Trp Asp Val Gln His Pro Ile Pro
            20

<210> SEQ ID NO 753
<211> LENGTH: 25
<212> TYPE: PRT
<213> ORGANISM: Human immunodeficiency virus 2

<400> SEQUENCE: 753

Ile Gln Ile Gly Leu Gln Lys Cys Val Arg Met Tyr Asn Pro Thr Asn
1               5                   10                  15
Ile Leu Asp Val Lys Gln Gly Pro Lys
            20                  25

<210> SEQ ID NO 754
<211> LENGTH: 26
<212> TYPE: PRT
<213> ORGANISM: Human immunodeficiency virus 2

<400> SEQUENCE: 754

Asp Arg Phe Tyr Lys Ser Leu Arg Ala Glu Gln Thr Asp Pro Ala Val
1               5                   10                  15
Lys Asn Trp Met Thr Gln Thr Leu Leu Val
            20                  25

<210> SEQ ID NO 755
<211> LENGTH: 24
<212> TYPE: PRT
<213> ORGANISM: Human immunodeficiency virus 2

<400> SEQUENCE: 755

Ala Ala Met Gln Ile Ile Arg Glu Ile Ile Asn Glu Glu Ala Ala Asp
1               5                   10                  15
Trp Asp Ser Gln His Pro Ile Pro
            20

<210> SEQ ID NO 756
<211> LENGTH: 25
<212> TYPE: PRT
<213> ORGANISM: Human immunodeficiency virus 2

<400> SEQUENCE: 756

```
Ile Gln Ile Gly Leu Gln Lys Cys Val Arg Lys Tyr Asn Pro Thr Asn
1               5                   10                  15

Ile Leu Asp Ile Lys Gln Gly Pro Lys
            20              25

<210> SEQ ID NO 757
<211> LENGTH: 26
<212> TYPE: PRT
<213> ORGANISM: Human immunodeficiency virus 2

<400> SEQUENCE: 757

Asp Arg Phe Tyr Lys Ser Leu Arg Ala Glu Gln Thr Asp Pro Ala Val
1               5                   10                  15

Lys Asn Trp Met Thr Gln Thr Leu Leu Ile
            20              25
```